US012594393B2

(12) United States Patent
Spear et al.

(10) Patent No.: US 12,594,393 B2
(45) Date of Patent: Apr. 7, 2026

(54) HEADGEAR CONNECTORS AND HEADGEAR FOR USE WITH OR COMPRISING PART OF A USER INTERFACE ASSEMBLY

(71) Applicant: Fisher & Paykel Healthcare Limited, Auckland (NZ)

(72) Inventors: Tony William Spear, Auckland (NZ); Andrew Chun Mon Fan, Auckland (NZ); Mark Richard Tomlinson, Auckland (NZ); Mark Arvind McLaren, Auckland (NZ); Carsten Ma On Wong Corazza, Auckland (NZ); Ryan Anthony Graham, Auckland (NZ); Katie Fyfe, Auckland (NZ); Neil Gray Duthie, Auckland (NZ); Matthew Joseph Lucas, Auckland (NZ); Jeroen Hammer, Auckland (NZ)

(73) Assignee: Fisher & Paykel Healthcare Limited, Auckland (NZ)

( * ) Notice: Subject to any disclaimer, the term of this patent is extended or adjusted under 35 U.S.C. 154(b) by 1081 days.

(21) Appl. No.: 17/250,721

(22) PCT Filed: Aug. 27, 2019

(86) PCT No.: PCT/NZ2019/050109
§ 371 (c)(1),
(2) Date: Feb. 24, 2021

(87) PCT Pub. No.: WO2020/046141
PCT Pub. Date: Mar. 5, 2020

(65) Prior Publication Data
US 2021/0213231 A1     Jul. 15, 2021

Related U.S. Application Data

(60) Provisional application No. 62/840,943, filed on Apr. 30, 2019, provisional application No. 62/723,198, filed on Aug. 27, 2018.

(51) Int. Cl.
*A61M 16/06*      (2006.01)

(52) U.S. Cl.
CPC .... *A61M 16/0683* (2013.01); *A61M 16/0666* (2013.01); *A61M 2209/088* (2013.01); *A61M 2210/06* (2013.01)

(58) Field of Classification Search
CPC ..... A62B 18/084; A41D 13/1161; A41F 1/06; A63B 71/141; A63B 71/143;
(Continued)

(56)         References Cited

U.S. PATENT DOCUMENTS

| | | | |
|---|---|---|---|
| 2,097,676 A | 11/1937 | Shindel et al. | |
| 2,970,593 A | 2/1961 | Seeler | |

(Continued)

FOREIGN PATENT DOCUMENTS

| | | |
|---|---|---|
| EP | 1001830 | 12/1997 |
| EP | 0958841 | 11/1999 |

(Continued)

OTHER PUBLICATIONS

Patent Cooperation Treaty, International Search Report, Application No. PCT/NZ2019/050109, dated Dec. 4, 2019, in 6 pages.

*Primary Examiner* — Joseph D. Boecker
*Assistant Examiner* — Jaeick Jang
(74) *Attorney, Agent, or Firm* — VIA LLP

(57)          ABSTRACT

A headgear connector is provided for connecting a user interface to a headgear strap. The headgear connector comprises a headgear receiving passage configured to receive a headgear strap from a first direction and to enable the headgear strap to loop back onto itself in a second direction substantially opposed to the first direction, and a gripping element configured to grip a portion of the headgear strap to secure the headgear strap with respect to the user interface. Headgear is also provided.

12 Claims, 75 Drawing Sheets

(58) Field of Classification Search

CPC ..... A61M 16/0683–0694; A61M 16/06–0677; A61M 16/0497; A61F 9/02; A61F 9/07

See application file for complete search history.

(56) References Cited

U.S. PATENT DOCUMENTS

| | | | |
|---|---|---|---|
| 4,414,973 | A | 11/1983 | Matheson et al. |
| 4,790,306 | A | 12/1988 | Braun et al. |
| 4,960,121 | A | 10/1990 | Nelson et al. |
| 5,077,839 | A | 1/1992 | Keller |
| 5,653,228 | A | 8/1997 | Byrd |
| 5,724,965 | A | 3/1998 | Handke et al. |
| 6,805,117 | B1* | 10/2004 | Ho .................... A61M 16/0683 128/207.17 |
| 6,892,729 | B2 | 5/2005 | Smith et al. |
| 7,036,508 | B2 | 5/2006 | Kwok |
| 7,877,817 | B1* | 2/2011 | Ho .................... A61M 16/0633 2/452 |
| 8,136,525 | B2 | 3/2012 | Lubke et al. |
| 8,397,727 | B2 | 3/2013 | Ng et al. |
| 8,424,530 | B2 | 4/2013 | Gunaratnam et al. |
| 8,479,736 | B2 | 7/2013 | Ging et al. |
| 8,505,535 | B2 | 8/2013 | Jones et al. |
| 8,757,157 | B2 | 6/2014 | Price et al. |
| 8,905,031 | B2 | 12/2014 | Barlow |
| 8,950,404 | B2 | 2/2015 | Formica et al. |
| 8,967,146 | B2 | 3/2015 | Veliss et al. |
| 9,032,955 | B2 | 5/2015 | Lubke et al. |
| 9,072,855 | B2 | 7/2015 | McAuley et al. |
| 9,095,673 | B2 | 8/2015 | Barlow et al. |
| 9,272,109 | B2 | 3/2016 | Rothermel |
| 9,427,545 | B2 | 8/2016 | Eves et al. |
| 9,480,809 | B2 | 11/2016 | Guney et al. |
| 9,517,320 | B2 | 12/2016 | Barlow et al. |
| 9,526,857 | B2 | 12/2016 | Rummerty et al. |
| 9,717,870 | B2 | 8/2017 | Kwok et al. |
| 9,889,267 | B2 | 2/2018 | Wells et al. |
| 9,937,312 | B2 | 4/2018 | Kwok et al. |
| 9,943,660 | B2 | 4/2018 | Selvarajan et al. |
| 10,232,137 | B2 | 3/2019 | Romagnoli et al. |
| 10,358,829 | B1* | 7/2019 | Kimmerle ............... E04F 13/10 |
| 10,569,044 | B2 | 2/2020 | Dunn et al. |
| 10,702,024 | B2 | 7/2020 | Moon |
| 10,716,961 | B2 | 7/2020 | Moon |
| 10,821,250 | B2 | 11/2020 | Siew et al. |
| 10,828,449 | B2 | 11/2020 | Higgins et al. |
| 10,898,668 | B2 | 1/2021 | Mah et al. |
| 10,953,179 | B2 | 3/2021 | Siew et al. |
| 2003/0005931 | A1 | 1/2003 | Jaffre et al. |
| 2003/0145859 | A1 | 8/2003 | Bohn et al. |
| 2003/0154984 | A1 | 8/2003 | Fernandes |
| 2003/0172445 | A1 | 9/2003 | Kawashima |
| 2005/0028820 | A1 | 2/2005 | Smith et al. |
| 2005/0056286 | A1 | 3/2005 | Huddart et al. |
| 2007/0144525 | A1 | 6/2007 | Davidson et al. |
| 2009/0044808 | A1 | 2/2009 | Guney et al. |
| 2009/0113608 | A1 | 5/2009 | Chou |
| 2009/0151729 | A1 | 6/2009 | Judson et al. |
| 2009/0194111 | A1 | 8/2009 | Fu et al. |
| 2010/0154798 | A1 | 6/2010 | Crumblin et al. |
| 2011/0000492 | A1 | 1/2011 | Veliss et al. |
| 2011/0088700 | A1* | 4/2011 | Ho ........................ A61M 16/06 128/207.11 |
| 2011/0197341 | A1* | 8/2011 | Formica ................ B32B 27/283 2/209.3 |
| 2011/0214674 | A1 | 9/2011 | Ging et al. |
| 2013/0239971 | A1 | 9/2013 | Dantanarayana et al. |
| 2014/0150798 | A1 | 6/2014 | Fong et al. |
| 2014/0174444 | A1 | 6/2014 | Darkin et al. |
| 2014/0174448 | A1 | 6/2014 | Dravitzki et al. |
| 2014/0261433 | A1 | 9/2014 | Guney |
| 2014/0345618 | A1 | 11/2014 | Kwok et al. |
| 2015/0151071 | A1 | 6/2015 | Eves et al. |
| 2015/0217072 | A1 | 8/2015 | D'Souza et al. |
| 2015/0297853 | A1 | 10/2015 | Ho et al. |
| 2015/0352306 | A1 | 12/2015 | Scheiner et al. |
| 2015/0352308 | A1 | 12/2015 | Cullen et al. |
| 2016/0030687 | A1 | 2/2016 | Engelbreth et al. |
| 2016/0030695 | A1 | 2/2016 | Chang |
| 2016/0045700 | A1* | 2/2016 | Amarasinghe .... A61M 16/0683 128/205.25 |
| 2016/0067441 | A1 | 3/2016 | Bearne et al. |
| 2016/0074611 | A1 | 3/2016 | Higgins et al. |
| 2016/0082214 | A1 | 3/2016 | Barlow et al. |
| 2016/0296720 | A1 | 10/2016 | Henry et al. |
| 2017/0028153 | A1 | 2/2017 | Judson et al. |
| 2017/0065787 | A1 | 3/2017 | Rummerty et al. |
| 2017/0087329 | A1 | 3/2017 | Huddart et al. |
| 2017/0232219 | A1 | 8/2017 | Dravitzki et al. |
| 2017/0281894 | A1 | 10/2017 | Walls et al. |
| 2017/0326320 | A1 | 11/2017 | Baigent et al. |
| 2018/0015243 | A1 | 1/2018 | Lee et al. |
| 2018/0064897 | A1 | 3/2018 | Kwok et al. |
| 2018/0104430 | A1 | 4/2018 | Ng et al. |
| 2018/0140791 | A1 | 5/2018 | Jones et al. |
| 2018/0207385 | A1 | 7/2018 | Freestone et al. |
| 2018/0214655 | A1 | 8/2018 | Kooij et al. |
| 2018/0250488 | A1 | 9/2018 | Haskard et al. |
| 2019/0125996 | A1 | 5/2019 | Bentley et al. |
| 2019/0151592 | A1 | 5/2019 | Bornholdt et al. |
| 2019/0160249 | A1 | 5/2019 | Rose et al. |
| 2019/0351172 | A1 | 11/2019 | Formica et al. |
| 2020/0016356 | A1 | 1/2020 | Patel et al. |
| 2020/0121881 | A1 | 4/2020 | Scheiner et al. |
| 2020/0306481 | A1 | 10/2020 | Kooij et al. |

FOREIGN PATENT DOCUMENTS

| | | |
|---|---|---|
| GB | 684788 | 12/1952 |
| WO | WO 2010/131189 | 11/2010 |
| WO | WO 2010/135785 | 12/2010 |
| WO | WO 2015/079396 | 6/2015 |
| WO | WO 2020/170100 | 8/2020 |
| WO | WO 2020/208523 | 10/2020 |

* cited by examiner

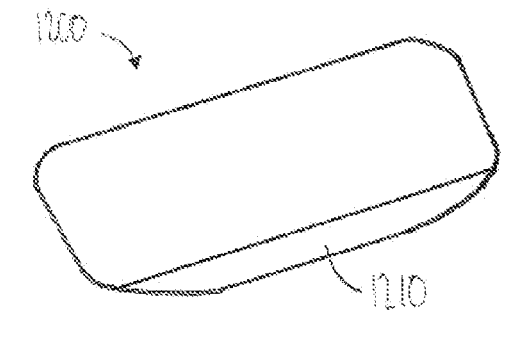
a)
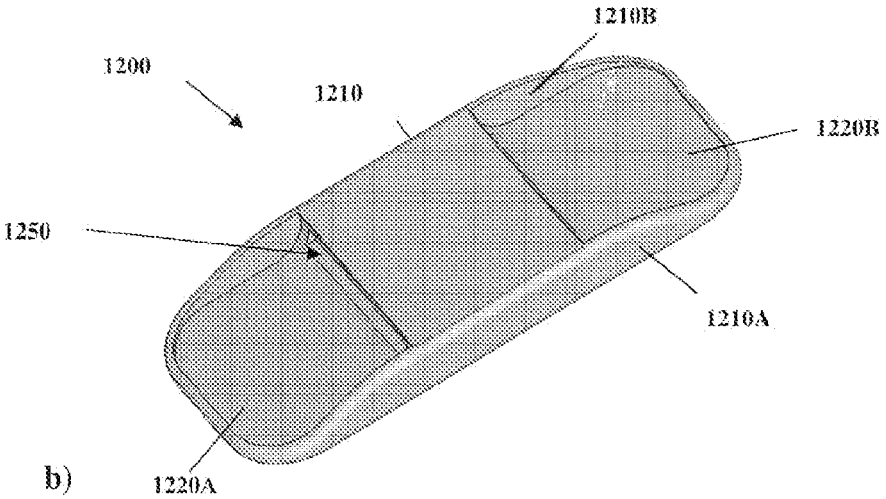
b)
Figure 45 a)                                    b)

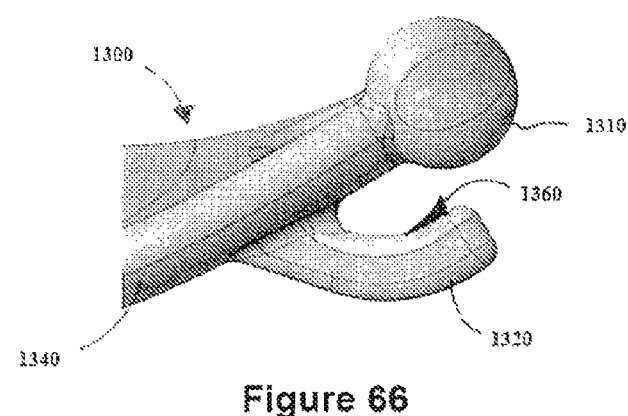
Figure 66
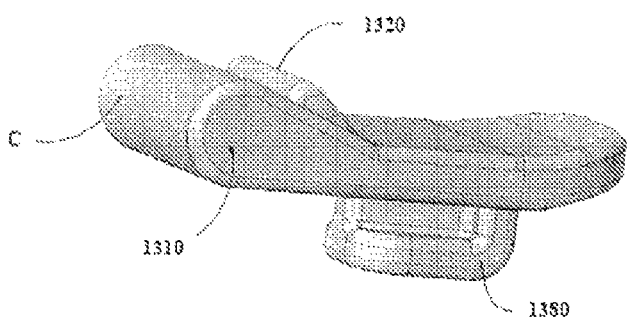
Figure 67
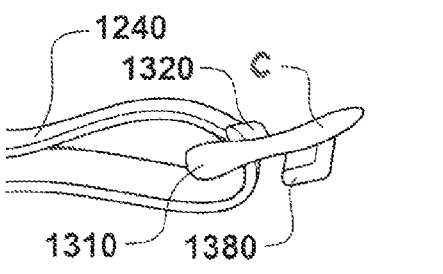
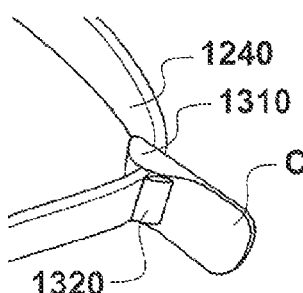
Figure 68A             Figure 68B a)                    b)                    c)

2005B

2005C

2006G

2009

2005B

2006G

2009

HEADGEAR CONNECTORS AND HEADGEAR FOR USE WITH OR COMPRISING PART OF A USER INTERFACE ASSEMBLY

BACKGROUND OF THE DISCLOSURE

Field of the Disclosure

The present disclosure generally relates to headgear connectors and headgear for use with, or comprising part of, a user interface comprising part of a user interface assembly of a respiratory therapy system. In particular, the present disclosure relates to headgear connectors for connecting headgear to a user interface for respiratory therapy. In some embodiments the headgear connectors are integral with a part of the user interface, and in other embodiments the headgear connectors are separate components or assemblies, configured to be connected to the user interface.

Description of the Related Art

Treatment of respiratory conditions with respiratory therapy can involve the delivery of air to the airways of a human via a conduit and a user interface assembly. User interface assemblies are used to provide respiratory therapy to the airway of a person suffering from any of a number of respiratory illnesses or conditions via a user interface. Respiratory therapies can involve the delivery of pressurised air to a respiratory therapy user's airway. Such therapies may include, but are not limited to continuous positive airway pressure (CPAP), bi-level positive airway pressure or non-invasive ventilation (NIV).

Some respiratory therapies, for example nasal high flow (NHF) therapy can include the delivery of air at a flow rate sufficient to flush out residual air within at least part of the user's airway during and/or following exhalation ("dead space") to improve symptoms of some respiratory conditions, for example chronic obstructive pulmonary disease (COPD).

CPAP therapy can be used, amongst other things, to treat obstructive sleep apnea (OSA), a condition in which an OSA patient's airway intermittently collapses, during sleep, preventing the patient from breathing for a period of time. The cessation of breathing, or apnea, can result in the patient awakening. Repetitive and frequent apneas may result in the patient rarely or at least irregularly, achieving a full and restorative night's sleep.

CPAP therapy involves the delivery of a supply of continuous positive air pressure to the airway of a user of the therapy (for example the OSA patient) via the user interface assembly. The continuous positive pressure acts as a splint within the user's airway, which secures the airway in an open position such that the user's breathing and sleep are not interrupted.

User interface assemblies can typically comprise a user interface and a headgear. The user interface can be in the form of a respiratory mask such as a nasal, oral or full face mask, where:

a nasal interface is configured to seal around the nares or nose of the patient;

an oral mask is configured to seal around the mouth of the patient; or a full-face mask is configured to seal around both the mouth and nose of the patient.

The user interface is configured to deliver the supply of continuous positive air pressure to the user's airway via a seal or cushion that forms an airtight seal in or around or within the user's nose and/or mouth. In other examples, the user interface can comprise a nasal cannula comprising prongs that extend into the user's nares, or nasal pillows configured to seal against the user's nares. Most user interfaces, of any of the above types, require headgear to retain and position the user interface on the user's head.

The headgear typically comprises one or more headgear straps and/or panels that connect to the user interface, and pass around the back and/or top of the user's head. The headgear can be used to retain the user interface in place on the user's head, or to position the user interface on the user's head. Once the user interface and headgear are on the user's head, the headgear can assist in generating a seal, if required, between the user interface and the user's face.

The headgear is typically configured to provide one or more of following functions:

a) to locate the patient interface in the desired position on the user's face.

b) to maintain the seal between the patient interface and the user's face by application of compression forces between the seal of the patient interface and the user's face.

c) to distribute the required forces between the patient interface and the user.

d) to improve the comfort of the patient during therapy.

e) to be easy and reliable to use, either by the user, or by a medical professional. One example of this is in a hospital setting where a medical professional may be dealing with multiple patients of different sizes and requirements and where it is nonetheless important that the correct headgear can be quickly selected, and quickly and easily adjusted to fit the user correctly.

Such headgear can be supplied in a variety of sizes, and typically in small, medium and large sizes. Such headgear typically further comprises length adjustable straps, configured such that the user can loosen or tighten the headgear to improve fit, comfort and/or the seal between the patient interface and their face, and to facilitate removal of the headgear. The length adjustment is typically provided by a first end of each headgear strap comprising a region of hook and loop fastener material. The first strap end passes through a headgear connector, which is attached to the patient interface, and which is looped back on itself to form an overlapped headgear strap portion in which the region of hook and loop fastener material is secured to the remainder of the headgear strap. This type of length adjustment can be seen with reference to FIG. 83.

It can be desirable to be able to provide a single size of headgear, or at least a smaller variety of sizes. However, a problem with for example only providing a single size is that that size must be adjustable to fit all, or at least a majority of users. Using such a length adjustment as described above, this can mean that the straps can be relatively long, to allow sufficient adjustment over the range of size of users required, meaning that for smaller users, the straps have to be significantly overlapped. This can lead to the ends of the straps projecting beyond the margins of the rest of the headgear, leaving the ends of the straps exposed such that they have a tendency to flap, impede the user's peripheral vision, or catch on the user's hair, clothing, bedding or other objects. Such an undesirable arrangement can be seen with reference to FIG. 84.

An example of known headgear is that provided with the Simplus® or Nivairo® product of Fisher & Paykel Healthcare Limited. Those particular products use headgear comprising a pair of upper and lower side straps which are configured to be removably secured to respective parts of the patient interface. The upper and lower side straps extend along the sides of the user's head and terminate at a rear panel that engages the rear of the patient's head. A crown strap is further provided, which extends over the crown of the user's head from the upper side straps.

It can be desirable for one or more headgear strap to require some form of adjustment to account for variation in head size, user preference as to the force with which the headgear secures the user interface to the user's face, user preference as to the specific location with which the user interface is secured to the user's face, or a combination thereof. Adjustment mechanisms have been implemented via an adjustment loop between the user interface and the headgear strap. The headgear strap can have hook connectors at an end of the headgear strap, and loop connectors on a body portion of the headgear strap, which together form a hook-and-loop or similar connection system that permits the end of the headgear strap to be passed through a mounting location on the user interface and then connected to the body portion. Such an arrangement can permit some adjustment of the headgear by connecting the end of the headgear strap at a desired location on the body portion of the headgear strap to vary a size of the adjustment loop.

Such existing headgear can require additional material to be provided to allow sufficient adjustment, and can also require a reasonable level of user interaction and, as a result, are prone to misuse or mis-adjustment (e.g. over-tightening). Fine adjustment of such headgear can be relatively difficult and time-consuming to accomplish.

SUMMARY OF THE DISCLOSURE

In a first aspect of the disclosure, there is provided a headgear connector for connecting a headgear strap to a user interface, the headgear connector comprising; a headgear connecting portion comprising a passage configured to receive the headgear strap from a first direction and to enable the headgear strap to loop back on itself in a second direction substantially opposed to the first direction, and a headgear gripping portion configured to grip a portion of the headgear strap to secure the headgear strap with respect to the user interface.

The headgear gripping portion may comprise a gripping element configured to grip the headgear strap.

The headgear connecting portion and the headgear gripping portion may be integrated.

The headgear connecting portion and the headgear gripping portion may be separable.

The headgear gripping portion may be configured to grip the headgear strap when the headgear strap is elastically unloaded.

The headgear connecting portion may be integrally formed with the user interface.

The headgear connecting portion may be configured to be removably connected to the user interface.

The headgear connector may comprise an inner surface and an outer surface, and may be configured such that the headgear strap is adjacent both surfaces when looped back on itself and gripped by the headgear gripping portion.

The headgear gripping portion may be provided on the outer surface so as to grip a looped back portion of the headgear strap.

The gripping portion may be provided on the inner surface so as to grip a non-looped back portion of the headgear strap.

The headgear gripping portion may be configured to grip a portion of the headgear strap that has passed through the passage.

The headgear gripping portion may be configured to grip a portion of the headgear strap that has not passed through the passage.

The headgear gripping portion may comprise hook connectors configured to grip material of the headgear strap.

The headgear connector may connect to the headgear strap with a combination of a frictional force between the headgear strap and a wall of the passage, and a gripping force between the headgear gripping portion and the headgear strap.

The frictional force may be caused by an interference fit between the headgear and the wall of the passage.

The passage may be adjacent to the headgear gripping portion along a longitudinal axis of the headgear connector.

The passage may be spaced apart from the headgear gripping portion by a distance along a longitudinal axis of the headgear connector.

The distance between the passage and the headgear gripping portion may be less than a length of the headgear gripping portion along the longitudinal axis.

The gripping portion may be pivoted about the wall of the passage to bring the headgear strap into connection with the headgear gripping portion.

The headgear gripping portion may be rotatably connected to the headgear connecting portion.

The headgear connector may comprise a post on one of the headgear connecting portion or the headgear gripping portion, and a clip on the other of the headgear connecting portion or the headgear gripping portion, the clip rotatably engaging the post.

A user interface assembly may comprise a user interface, a headgear strap, and a headgear connector as previously described, wherein the post may be provided on the headgear connecting portion, and a wall of the passage may be defined by the post, and the headgear strap may be configured to extend through the passage, to loop around the wall of the passage, and around an outer surface of the clip.

The post may be provided on the headgear connecting portion, and a wall of the passage may be defined by the post, and wherein the headgear strap may be configured to extend through the passage, to loop around the wall of the passage, and around an inner surface of the clip.

Rotation of the headgear gripping portion may bring the gripping element into contact with the headgear strap, thereby connecting the headgear connector to the headgear strap.

The headgear connector may further comprise one or more collars configured to receive the headgear strap after the headgear strap has passed through the passage.

The headgear gripping portion may comprise an inner surface and an outer surface, the one or more collars being disposed on an opposite surface of the headgear gripping portion to the gripping element.

The headgear connector may be rotatably connected to the user interface.

The headgear connector may comprise a post on one of the connector and the user interface, and a clip on the other of the headgear connector and the user interface, the clip being configured to rotatably engage the post.

The headgear connector may comprise one or more collars configured to receive the headgear strap after the headgear strap has passed through the passage.

The headgear connector may comprise an inner surface and an outer surface, the one or more collars being disposed on an opposite surface of the headgear connector to the gripping element.

Rotation of the headgear connector may bring the gripping element into contact with the headgear strap, thereby connecting the headgear connector to the headgear strap.

In a second aspect of the disclosure, there is provided a headgear connector for connecting a headgear strap to a user interface, the headgear connector comprising; a base portion, a movable portion movably mounted on the base portion, and a passage defined at least in part by a space between the base portion and the movable portion, wherein the passage is configured to receive the headgear strap from a first direction, and to enable the headgear strap to loop back on itself in a second direction substantially opposed to the first direction, and wherein the movable portion is movable toward the base portion from an open position to a closed position in which the headgear strap is gripped between the base portion and the movable portion.

The passage may comprise an aperture in the base portion configured to receive the headgear strap from the first direction.

A post may be provided on one of the movable portion or the base portion, the post comprising a post axis, wherein the headgear strap passes through the hole of the passage and around the post axis to a position between the base portion and the movable portion.

The movable portion may be a rotatable portion that is rotatable with respect to the base portion.

The movable portion may comprise a rotatable portion rotatably mounted on the base portion via a hinge defined by a post, the passage being defined by both the base portion and the rotatable portion such that the headgear strap passes through the passage around the post axis to a position between the base portion and the rotatable portion, the rotatable portion being rotatable toward the base portion to a closed position in which the headgear strap is gripped between the base portion and the rotatable portion.

The headgear connector may grip the headgear strap when in the closed position by a frictional connection between the headgear, the movable portion and the base portion.

The headgear connector may grip the headgear strap when in the closed position by compression of the headgear strap by the base portion and the movable portion.

The movable portion may be biased towards the closed position by a spring.

One or both of the base portion and movable portion may comprise gripping formations.

The gripping formations may project from respective surfaces of the base and/or movable portions.

The rotatable portion may comprise a gripping formation which is moved into gripping engagement with the headgear strap by rotating the rotatable portion with respect to the base portion.

The rotatable portion may be configured to vary a width of the passage when rotated.

The rotatable portion and at least one projecting formation may together define a cam structure.

The rotatable portion and projecting formation may together define an over centre mechanism configured to remain in the closed position once rotated into the closed position.

The headgear strap may be secured between the base portion and at least one gripping formation when the rotatable portion is in the closed position.

The base portion may comprise a channel, and the movable portion may comprise a post that is substantially longitudinally movable with respect to the base portion within the channel between an open position in which the post is nearer one end of the channel, and a closed position in which the post is further from the one end of the channel, the space between the base portion and the post defining the passage, and the channel and post being configured such that the headgear strap is gripped between the post and the base portion in the closed configuration.

Movement of the movable portion between the open position and the closed position may be in a direction perpendicular to the axis of the post, and generally parallel with a longitudinal axis of the headgear strap.

The base portion may comprise an inner wall and an outer wall, the inner and outer walls at least partially defining the channel, and the movable portion may be configured to release the headgear from between the inner wall and the outer wall when moved from the closed position to the open position.

The inner wall and/or the outer wall may comprise an elastomeric material.

In a third aspect of the disclosure, there is provided a user interface assembly comprising a user interface, a headgear strap, and a headgear connector for connecting the headgear strap to the user interface, the headgear connector being configured to connect to the user interface, the headgear connector comprising; an elongate connector body having a first end, a second end and a longitudinal axis configured to be substantially aligned with a longitudinal axis of the headgear strap, a first post, and a second post, wherein the first post and the second post extend across the connector body in a direction substantially perpendicular to the longitudinal axis of the connector body; wherein the first post and the second post are spaced apart along the longitudinal axis of the connector body between the first end and the second end to at least partially define a passage, wherein the passage is configured to receive the headgear strap from a first direction and to enable the headgear strap to loop back on itself in a second direction opposed to the first direction, the headgear strap looping back on itself around the first post, wherein the first post is disposed between the first end and the second post, and wherein the second post is disposed between the first post and the second end, and wherein the first post is offset from the second post such that relative rotation between the headgear strap and the headgear connector when the headgear connector is connected to the user interface causes the second post to engage the headgear strap when the headgear strap is under tension, thereby connecting the headgear strap to the user interface.

Rotation of the headgear connector with respect to the user interface may cause the second post to grip the headgear strap when said headgear strap is under tension.

The first post may comprise a first post sectional dimension, the first post sectional dimension being a longitudinal distance of a cross sectional profile of the first post, and the second post may comprise a second post sectional dimension, the second post sectional dimension being a longitudinal distance of a cross sectional profile of the second post, and the second post sectional dimension may be greater than the first post sectional dimension.

The headgear connector may be removably connected to the user interface.

The first post may comprise a first post inner end, and the second post may comprise a second post inner end, and the second post inner end may be configured to engage the headgear strap that has passed through the passage.

The first post inner end may be offset from the second post inner end.

The headgear connector may comprise a user interface coupling configured to rotatably couple to a user interface post to form a hinged connection, thereby allowing rotation of the headgear connector with respect to the user interface.

When the headgear connector is connected to the user interface, a line between the user interface post and the second post inner end may define an inner axis, and the first post inner end may be spaced apart from the inner axis, thereby providing the offset between the first post and the second post.

A portion of the headgear strap that has passed through the passage may be gripped between the second post inner end and a portion of the headgear strap that has not passed through the passage when the headgear connector is in the closed position.

In a fourth aspect of the disclosure, there is provided a user interface assembly comprising; a user interface comprising a user interface body, a headgear strap and a headgear connector for connecting the headgear strap to the user interface body, wherein the headgear connector is connected to the user interface body at a hinge, wherein the headgear connector comprises a passage configured to receive the headgear strap from a first direction and to enable the headgear strap to loop back on itself in a second direction opposed to the first direction, and wherein rotation of headgear connector about the hinge in a first direction secures the headgear strap when the headgear strap is under tension, and rotation of the headgear connector about the hinge in a second direction reduces the tension such that the headgear strap can be released.

The user interface body, hinge and headgear connector may be integrally formed.

The hinge may be defined by a thinned portion of the user interface.

A thickness of the hinge may be less than a thickness of the headgear connector adjacent the hinge, and may be less than a thickness of the user interface body adjacent the hinge.

The hinge may be a living hinge.

The hinge may define a hinge axis about which the headgear connector rotates.

The headgear connector may comprise; a first opening extending from a headgear connector interior surface, through the headgear connector, to a headgear connector exterior surface, and a second opening extending from the headgear connector interior surface, through the headgear connector, to the headgear connector exterior surface, and the first opening and the second opening may together at least partially define the passage.

The second opening may be longitudinally displaced with respect to the first opening on the headgear connector.

The first opening may be configured to receive the headgear strap from the first direction, and the second opening may be configured to receive the headgear strap from the second direction, thereby enabling the headgear strap to loop back on itself.

In a fifth aspect of the disclosure, there is provided a user interface comprising; a first headgear connector, a second headgear connector, and a passage configured to receive a headgear strap from a first direction and to enable the headgear strap to loop back on itself in a second direction opposed to the first direction, wherein the passage comprises a first connector opening in the first headgear connector, and a second connector opening in the second headgear connector, wherein the first headgear connector is connected to the user interface with a first connection, wherein the second headgear connector is connected to the user interface with a second connection, and wherein relative movement between the first headgear connector and the second headgear connector such that they are brought toward one another causes the first headgear connector and the second headgear connector to grip the headgear strap.

The passage may be defined by the first connector opening and second connector opening such that the first connector opening and the second connector opening are configured to receive the headgear strap from the first direction, and the second connector opening is configured to subsequently receive the headgear strap from the second direction after the headgear strap has been looped back on itself around the first headgear connector.

The first headgear connector and the second headgear connector may be configured to grip the headgear strap as the headgear strap is elastically loaded.

The first headgear connector may comprise a first connector outer wall, the second connector opening may comprise a second connector opening outer wall, and the headgear strap may be gripped between the first connector outer wall and the second connector opening outer wall when the first headgear connector and second headgear connector are brought together.

A vertical dimension of the first headgear connector may be greater than a corresponding vertical dimension of the second headgear connector.

The first connection may comprise a strap looped through the first connector opening, and the strap connected at each end to the user interface.

The second connection may comprise a strap looped through the second connector opening, and the strap may be connected at each end to the user interface.

In accordance with an aspect of this disclosure, there may be provided a headgear connector for connecting a headgear strap to a user interface, the headgear connector comprising a sliding sleeve comprising a sleeve body, and a sleeve passage on the body, wherein a free end of the headgear strap is configured to be mounted on the sleeve body, and wherein the headgear strap is configured to extend away from the free end, loop around a post or hook or other locating or guiding feature provided on a user interface, the headgear strap comprising a return portion which extends back through the passage, substantially parallel to the free end of the headgear strap, the passage being configured to frictionally engage the return portion of the headgear strap, the length of the strap being adjustable by sliding the sleeve along the return portion of the strap.

The sleeve may be resiliently deformable such that deformation of the sleeve deforms the passage to reduce the frictional engagement with the strap to facilitate sliding of the sleeve along the strap. The deformation may alter a dimension of the passage, and/or the shape of the passage. The strap, in transverse cross section, may be configured to have substantially the same shape as the passage in the sleeve. The strap may be configured to have at least one dimension which is greater than the corresponding dimension of the passage, when the passage is in a non-deformed state.

The free end of the headgear strap may be permanently mounted on the sleeve body, for example by overmoulding or welding The sleeve may comprise one or more projections configured to engage the return portion of the strap. The sleeve may alternatively or additionally comprise one or more projections configured to engage the free end of the strap.

The free end of the strap may comprise one or more apertures configured to receive the one or more projections, such that when received, the free end of the strap is aligned with and retained on the sleeve. The passage of the sleeve may comprise opposed walls against which the strap rests, the projections may be provided on either or both opposed wall. The sleeve may be resiliently deformable such that deformation of the sleeve disengages, or at least reduces the engagement between, the one or more projections with the return portion of the strap. In an embodiment the one or more projections are configured to abut the return portion of the strap, to exert a clamping force on the return portion of the strap. In another embodiment the one or more projections comprise piercing projections configured to pierce the return portion of the strap to engage the strap. The sleeve may comprise a gripping portion configured to be gripped by a user to move the sleeve. The gripping portion may comprise gripping formations. The gripping portion may comprise a tab or flap, spaced from the headgear strap in use.

In accordance with an aspect of this disclosure, there may be provided a headgear connector for connecting a headgear strap to a user interface, comprising a sliding sleeve comprising a sleeve body, and a sleeve passage on the body, wherein a free end of a headgear strap is configured to be mounted on the sleeve body, and wherein the headgear strap is configured to extend away from the free end, loop around a post or hook provided on a user interface, the headgear strap comprising a return portion of the headgear strap that extends back through the passage, the passage being configured to frictionally engage the return portion of the headgear strap, the length of the headgear strap being adjustable by sliding the sleeve along the return portion of the headgear strap, the passage comprising a tab portion provided with one or more projections configured to engage the strap, the tab portion being movable between an engagement position in which the projection engages the headgear strap, and a release position in which the one or more projections do not engage, or at least have reduced engagement with, the strap.

In one embodiment the tab portion is biased to the engagement position. The tab portion may be pivotally mounted on the sleeve. The tab portion may comprise a living hinge, integral with the sleeve and configured to allow pivotal movement between the tab portion and the sleeve. The sleeve may comprise an aperture adjacent the projection on the tab portion, wherein engagement of the projection with the headgear strap forces the strap into the aperture such that the headgear strap follows a tortuous path through the passage. The tortuous path may assist in increasing the frictional engagement between the headgear strap and the sleeve.

In these embodiments comprising a sleeve, the free end of the strap may be permanently mounted on the sleeve, for example by overmoulding. The free end of the strap may project to some degree from the sleeve so as to provide a user grip portion. The user grip portion can be configured to move the tab portion of the sleeve between the engaged and release positions.

In some embodiments the projection comprises a plurality of projections. The or each projection may comprise a flat or rounded distal end configured to abut the headgear strap to frictionally engage the headgear strap. The or each projection may comprise a pointed or sharp distal end configured to pierce the headgear strap to engage the headgear strap. The or each projection may be configured to pierce the headgear strap sufficiently to project at least partially into the material of the headgear strap.

In accordance with an aspect of this disclosure, there may be provided a headgear connector for connecting a headgear strap to a user interface, comprising a body, and a post and a friction arm on the body, the post being spaced from the friction arm to define a slot through which a headgear strap can extend when looped around the post, the post, friction arm and slot being configured to frictionally engage the part of the headgear strap in the slot, to resist movement of the headgear strap through the slot.

The headgear connector may comprise an integral part of a user interface, or may comprise part of a headgear connector clip configured to connect to a user interface. For example, the headgear connector could comprise a connecting formation such as a hook or post configured to engage with a connecting formation such as a post or hook on the user interface. The connecting formation could be provided on a yoke or frame of the user interface, or directly on a body of the user interface.

The friction arm may be movably mounted on the body such that movement of the friction arm adjusts the dimensions and/or shape of the slot. The friction arm may be resiliently deformable. The friction arm may be pivotally mounted on the body. The friction arm may be integral with the body so as to comprise a living hinge. The friction arm may comprise one or more projections configured to frictionally engage the headgear strap.

The slot comprises a slot inlet configured to receive the headgear strap, and a slot outlet from which a free end of the headgear strap can project, wherein the slot outlet may have at least one dimension and/or be of a shape, which is different from that of the slot inlet. In one example, the slot outlet is smaller than the slot inlet in at least one dimension, such that the movement of the strap through the slot in the direction of the slot inlet to the slot outlet is subject to greater frictional resistance than movement of the strap through the slot in the direction of the slot outlet to the slot inlet. The slot outlet is preferably on an exterior side of the connector in use, facing away from the user's face, whilst the slot inlet is preferably on an interior side of the connector in use, adjacent the user's face.

In accordance with an aspect of this disclosure, there may be provided a headgear connector for connecting a headgear strap to a user interface, comprising a body, and a pair of opposed, spaced apart slots on the body, a post being defined between the pair of slots, and configured such that a headgear strap can pass through one slot, loop around the post and return back through the other slot, wherein at least one of the slots is configured to deform the headgear strap such that the headgear comprises a deformed portion, wherein the deformed portion engages the slot to resist movement of the headgear strap through the slot.

In this embodiment the so configured slot may comprises a slot inlet and a slot outlet, the slot inlet being configured to deform the strap. The slot may be configured to deform the slot by having at least one dimension and/or shape that is smaller, or different, to the corresponding dimension and/or shape of the headgear strap. The slot inlet may be configured to deform the strap by comprising one or more corners or edges or formations which engage the strap to deform the strap. The slots may be substantially oblong having a pair of opposed side margins and a pair of opposed end margins, wherein the side margins are longer than the end margins, and wherein the side margins comprises the corners or edges or formations which deform the headgear strap. The slots may be further arranged to have relatively smooth strap engaging surfaces to provide relatively low resistance between those surfaces and the strap. In some embodiments the outlet of the slot, and the inlet and outlet of the other slot, have relatively smooth strap engaging surfaces, such that the connector provides increased resistance to movement of the strap through the connector in one direction, and reduced resistance to movement of the strap through the connector in an opposite direction.

In accordance with another aspect of this disclosure, there may be provided a headgear connector for connecting a headgear strap to a user interface, comprising a body, a post on the body, and a slot defined between the post and an adjacent part of the body configured to receive a headgear strap such that the headgear strap is in contact with the post, wherein the post comprises a rotatable element configured to rotate about a longitudinal axis of the post, relative to the body, wherein movement of the headgear strap through the slot rotates the roller.

The rotatable element may comprise a sleeve rotatably mounted on the post, such that the post and sleeve are concentric. The rotatable element may be configured to be able to rotate through 360° relative to the post. In other embodiments, the degree of rotation of the rotatable element relative to the post may be limited.

The rotatable element may comprise one or more friction increasing portions configured to frictionally engage the headgear strap such that movement of the strap through the slot, rotates the rotatable element. The or each friction increasing portion may comprise one or more strap engaging formations, such as one or more protrusions. The rotatable element may be resiliently deformable. The rotatable element may comprise a friction roller. The rotatable element may be made from silicone or have a silicone coating.

The headgear connector of any one of the above aspects may comprise an integral part of a user interface, or may comprise part of a headgear connector clip configured to be mounted on the user interface.

A user interface may be provided comprising, a headgear connector according to at least one of the previous aspects of the disclosure, and a cushion module comprising; a seal configured to provide a seal against a user's face so that respiratory therapy can be delivered to the user via the seal, and a housing connected to the seal, wherein the headgear connector may be configured to connect the user interface to a headgear strap.

The user interface may comprise a frame, wherein the housing of the cushion module may be configured to connect to the frame, and wherein the headgear connector may be configured to connect to the frame.

A user interface assembly may be provided, comprising; the user interface of any one of the aforementioned user interfaces, and a headgear for positioning and securing the user interface to the face of the user, the headgear comprising the headgear strap.

The present disclosure also stems from work undertaken towards providing improved headgear to better fulfil any one or more of the above functions, or to at least partially address any one or more of the above problems.

Accordingly in one aspect the disclosure may broadly be said to consist in headgear configured to be secured to a patient interface of a respiratory therapy system, to mount the patient interface on a user's head, the headgear comprising;

at least one strap having first and second ends opposed along a longitudinal axis of the strap; wherein:

a first end of the strap being configured such that the first end of the strap can be looped back to form an overlapped strap portion;

a second end of each strap, opposed to the first end extending from a strap connecting region of the headgear;

the strap having an effective strap length being the distance extending between an apex of the overlapped portion and the strap connecting region of the headgear;

the strap comprising a first strap length adjustment mechanism comprising a first hook and loop fastener configured to releasably engage a portion of the strap to form the overlapped strap portion; wherein the size of the overlapped strap portion can be adjusted to adjust the effective strap length by engaging the first hook and loop fastener with a different portion of the headgear;

the headgear further comprising a second strap length adjustment mechanism, configured to adjust the effective strap length.

The second length adjustment mechanism may comprise a second hook and loop fastener.

The strap may comprise a planar portion extending along the longitudinal axis, the planar portion comprising a first planar face arranged to contact the user's head in use, and a second planar face opposed to the first planar face and configured to face away from the user's head in use, the first hook and loop fastener being provided on the first planar face, and the second hook and loop fastener being provided on the second planar face.

The first hook and loop fastener may be substantially longitudinally aligned with the second hook and loop fastener along the longitudinal axis of the strap.

The first hook and loop fastener may be not longitudinally aligned, or at least not fully longitudinally aligned, with the second hook and loop fastener along the longitudinal axis of the strap.

The second hook and loop fastener may be positioned adjacent the first end of the strap.

The first hook and loop fastener may be spaced apart from the second hook and loop fastener along the longitudinal axis.

The second hook and loop fastener may be positioned adjacent the second end of the strap.

The strap may comprise a planar portion extending along the longitudinal axis, the planar portion comprising a first planar face arranged to contact the user's head in use, and a second planar face opposed to the first planar face and configured to face away from the user's head in use, the first hook and loop fastener and the second hook and loop fastener both being provided on the first planar face.

The first hook and loop fastener may be positioned adjacent a first end of the strap.

The or each hook and loop fastener may comprise an elongate tab or strip of hook and loop fastener material which is secured to the strap.

The or each hook and loop fastener may be secured to the strap using any one or more of.

a. adhesive;

b. stitching;

c. ultrasonic welding;

d. radio-frequency welding.

Each hook and loop fastener may be substantially the same size.

The headgear may comprise a cover configured to removably cover the hook and loop fastener, to prevent that hook and loop fastener from engaging the strap.

The second length adjustment mechanism may comprise a releasable strap retention arrangement, wherein the strap comprises a second overlapped portion comprising two portions of the strap that are overlapped, the two strap portions being retained together with the releasable strap retention arrangement, wherein the effective length of the strap can be adjusted by releasing the strap retention arrangement such that the two strap portions are no longer overlapped.

The releasable strap retention arrangement may comprise stitching configured to stitch the two portions of the strap together. The stitching may comprise frangible stitching, or at least a frangible stitching portion, configured to enable the user to pull apart the two strap portions to release the strap retention arrangement.

The or each strap may have a width measured in a direction perpendicular to the longitudinal axis, the or one of the, hook and loop fastener(s) comprising a strip also having a longitudinal axis and a width measured in a direction perpendicular to the longitudinal axis, wherein the hook and loop fastener is arranged on the strap such that the longitudinal axis of the strip of hook and loop fastener material is inclined so as not to be aligned with the longitudinal axis of the strap.

The width of the strip may be less than 50% of the width of the strap. The width of the strip may be less than 30% of the width of the strap.

The strip may be inclined relative to the longitudinal axis of the strap at an angle between 5° and 85°, preferably between 20° and 70°, more preferably between 30° and 60° and most preferably between 30° and 45°.

The strip of hook and loop fastener may be sufficiently flexible to fold along its length to form an overlapped portion of the hook and loop fastener.

The headgear may comprise a plurality of discrete hook and loop fastener regions that are spaced apart along the longitudinal axis of the strap such that there is a gap of exposed strap between adjacent hook and loop fastener regions. The plurality of discrete hook and loop fastener regions may be equispaced along the longitudinal axis of the strap. At least one of the discrete hook and loop fastener regions may be a different size from another discrete hook and loop fastener region. At least one gap may be a different size from at least one other gap. The plurality of discrete hook and loop fastener regions may extend along at least 30% of the length of the strap, preferably at least 50%, and more preferably at least 75%.

The headgear may further comprise the headgear connector, the headgear connector comprising the slot through which the first end of the strap is received.

The strap may comprise:
a) a side strap configured to extend along the side of the user's head.
b) a crown strap configured to extend over the crown of the user's head.
c) a rear strap configured to extend around the rear of the user's head.

The headgear may comprise a plurality of straps, each of which, or at least two of which comprise first and second strap length adjustment mechanisms.

The headgear may comprise a rear panel configured to engage the rear of the user's head, the second end of the or each strap being joined to the rear panel at the strap connecting region such that the or each strap extends from the rear panel.

The at least one strap may comprise a pair of side straps, each extending from a respective side of the rear panel so as to extend along a side of the user's head in use.

The at least one strap may comprise two pairs of side straps, one pair comprising upper side straps, the other pair comprising lower side straps.

The rear panel may comprise a main body and a pair of laterally extending arms, the second end of each side strap being joined to a respective arm, the main body comprising:
opposed top and base margins which are spaced apart by a distance,
opposed side margins extending between the top and base margins, and
a central longitudinal axis bisecting the top and base margins; wherein each laterally extending arm is inclined relative to the central longitudinal axis, and extends away from a respective side margin of the main body and comprises a distal arm end, each distal arm end having a width measured in a direction substantially parallel with the central longitudinal axis; wherein the width of each distal arm end is between 30% to 60% of the distance between the opposed top and base margins of the main body.

The second end of each strap may be integrally connected to the headgear at the strap connecting region of the headgear.

According to another aspect of this disclosure there is provided headgear configured to be secured to a patient interface of a respiratory therapy system, to mount the patient interface on a user's head, the headgear comprising;
at least one strap having first and second ends opposed along a longitudinal axis of the strap; wherein:
a first end of the strap being configured such that the first end of the strap can be looped back to form an overlapped strap portion;
a second end of each strap, opposed to the first end extending from a strap connecting region of the headgear;
the strap having an effective strap length being the distance extending between an apex of the overlapped portion and the strap connecting region of the headgear;
the strap comprising a first strap length adjustment mechanism comprising a first hook and loop fastener configured to releasably engage a portion of the strap to form the overlapped strap portion; wherein the size of the overlapped strap portion can be adjusted to adjust the effective strap length by engaging the first hook and loop fastener with a different portion of the headgear;
the strap further comprising a secondary strap length adjustment mechanism comprising a second hook and loop fastener configured to engage a portion of the strap to form a second overlapped strap portion.

According to a further aspect of this disclosure there is provided headgear configured to be secured to a patient interface of a respiratory therapy system, to mount the patient interface on a user's head, the headgear comprising;
at least one strap having first and second ends opposed along a longitudinal axis of the strap;
a first end of the strap being configured such that the first end of the strap can be looped back to form an overlapped strap portion;
a second end of each strap, opposed to the first end extending from a strap connecting region of the headgear;
the strap having an effective strap length being the distance extending between an apex of the overlapped portion and the strap connecting region of the headgear;
the strap comprising a first hook and loop fastener configured to releasably engage a portion of the strap to form the overlapped strap portion; wherein the size of the overlapped strap portion can be adjusted to adjust the effective strap length by engaging the first hook and loop fastener with a different portion of the headgear;

the side strap further comprising a second overlapped portion comprising two portions of the strap that are overlapped, the two portions being retained together with a releasable strap retention arrangement, wherein the effective strap length of the strap can be adjusted by releasing the strap retention arrangement such that the two portions are no longer overlapped.

The releasable strap retention arrangement may comprise stitching configured to stitch the two portions of the strap together. The stitching may comprise frangible stitching, or at least a frangible stitching portion, configured to enable the user to pull apart the two strap portions to release the strap retention arrangement.

The releasable strap retention arrangement may comprise a clip comprising a retaining portion configured to retain the two strap portions together to form the second overlapped portion.

The clip may comprise a resiliently movable clamping arm configured to clamp the two strap portions together.

According to another aspect of this disclosure there is provided headgear configured to be secured to a patient interface of a respiratory therapy system, to mount the patient interface on a user's head, the headgear comprising;

at least one strap having first and second ends opposed along a longitudinal axis of the strap; wherein:

a first end of the strap being configured such that the first end of the strap can be looped back to form an overlapped strap portion;

a second end of each strap, opposed to the first end extending from a strap connecting region of the headgear;

the strap having an effective strap length being the distance extending between an apex of the overlapped portion and the strap connecting region of the headgear;

the strap comprising a first strap length adjustment mechanism comprising a first hook and loop fastener configured to releasably engage a portion of the strap to form the overlapped strap portion; wherein the size of the overlapped strap portion can be adjusted to adjust the effective strap length by engaging the first hook and loop fastener with a different portion of the headgear;

wherein each strap has a width measured in a direction perpendicular to the longitudinal axis, the hook and loop fastener comprising a strip also having a longitudinal axis and a width measured in a direction perpendicular to the longitudinal axis of the strip, wherein the hook and loop fastener is arranged on the strap such that the longitudinal axis of the strip or tab of hook and loop fastener material is inclined so as not to be aligned with the longitudinal axis of the strap.

The width of the strip or tab may be less than 50% of the width of the strap.

The width of the strip or tab may be less than 30% of the width of the strap.

The strip or tab may be inclined relative to the longitudinal axis of the strap at an angle between 5° and 85°, preferably between 20° and 70°, more preferably between 30° and 60° and most preferably between 30° and 45°.

The strip or tab of hook and loop fastener may be sufficiently flexible to fold along its length to form an overlapped portion of the hook and loop fastener.

According to a further aspect of this disclosure there is provided headgear configured to be secured to a patient interface of a respiratory therapy system, to mount the patient interface on a user's head, the headgear comprising;

at least one strap having first and second ends opposed along a longitudinal axis of the strap; wherein:

a first end of the strap being configured such that the first end of the strap can be looped back to form an overlapped strap portion;

a second end of each strap, opposed to the first end extending from a strap connecting region of the headgear;

the strap having an effective strap length being the distance extending between an apex of the overlapped portion and the strap connecting region of the headgear;

the strap comprising a first strap length adjustment mechanism comprising a first hook and loop fastener configured to releasably engage a portion of the strap to form the overlapped strap portion; wherein the size of the overlapped strap portion can be adjusted to adjust the effective strap length by engaging the first hook and loop fastener with a different portion of the headgear;

the hook and loop fastener arrangement comprising a plurality of discrete hook and loop fastener regions that are spaced apart along the longitudinal axis of the strap such that there is a gap of exposed strap between the or each pair of hook and loop fastener regions.

The plurality of discrete hook and loop fastener regions may be equispaced along the longitudinal axis of the strap.

At least one of the discrete hook and loop fastener regions may be a different size from another discrete hook and loop fastener region.

At least one gap may be a different size from at least one other gap.

The plurality of discrete hook and loop fastener regions may extend along at least 30% of the length of the strap, preferably at least 50%, and more preferably at least 75%.

According to another aspect of this disclosure there is provided headgear configured to be secured to a patient interface of a respiratory therapy system, to mount the patient interface on a user's head, the headgear comprising;

at least one strap having first and second ends opposed along a longitudinal axis of the strap;

a headgear connector comprising part of, or being configured to be connected to, the patient interface; the headgear connector being arranged such that the first end of the strap can be looped back around part of the connector to form an overlapped strap portion;

a second end of each strap, opposed to the first end, extending from a strap connecting region of the headgear;

the strap having an effective strap length being the distance extending between an apex of the overlapped portion and the strap connecting region of the headgear;

each headgear connector comprising a strap retention arrangement configured to releasably retain the overlapped strap portion in a desired position on the connector, such that the effective strap length can be adjusted when the overlapped strap portion is released from the strap retention arrangement, and such that the effective strap length is prevented or resisted from being adjusted when the overlapped strap portion is retained by the strap retention arrangement.

The clip may comprise a clip body and an arm movably mounted on the clip body, a slot being defined between the clip body and the arm the size of which can be varied by moving the arm relative to the clip body, the slot being configured to receive and retain a portion of the strap when the arm is in a strap retention configuration.

The arm may be resiliently movably mounted on the clip body, and is biased towards to the strap retention configuration.

The arm may comprise a cantilevered arm.

The arm may be tapered when viewed from above.

The arm may comprise a longitudinal axis which is transverse to the longitudinal axis of the strap such that the arm extends transversely across the longitudinal axis of the strap, when the strap is retained on the clip.

The arm may comprise a strap engaging surface, wherein the strap engaging surface is not planar.

The strap engaging surface may comprise a protruding region configured to protrude further from the arm than a remainder of the strap engaging surface.

At least part of the arm is chamfered or tapered to facilitate insertion of the strap into the slot.

The connector may comprise one of a hook or post configured to connect the connector to a patient interface comprising the other of a hook or post.

According to another aspect of this disclosure there is provided a patient interface assembly comprising;

a patient interface, and the headgear of any one of the above statements.

The patient interface assembly may further comprise the headgear connector of any one of the above statements.

According to another aspect of this disclosure there is provided a respiratory therapy system comprising the headgear of any one of the above statements and any one or more of:

a. a breathing gas flow generator;

b. a breathing gas humidifier;

c. a heated gas delivery conduit;

d. a non-heated gas delivery conduit; and/or e. a patient interface.

The respiratory therapy system may further comprise the headgear connector of any one of the above statements.

Further aspects of the disclosure, which should be considered in all its novel aspects, will become apparent from the following description.

DESCRIPTION OF THE DRAWINGS

A number of embodiments of the disclosure will now be described by way of example with reference to the drawings in which:

FIG. 24*b*(*ii*) shows the rotatable portion in an intermediate position.

FIG. 24*b*(*iii*) shows the rotatable portion in the open position.

FIGS. 45*a* and *b* are perspective side views of the headgear connector of FIGS. 43 and 44 showing exterior and interior sides respectively.

FIG. 66 is an enlarged view of a headgear connector portion of the frame of FIG. 65.

FIG. 67 is an enlarged perspective view of a headgear connector for use with the frame of FIG. 63.

FIGS. 68*a* and 68*b* are perspective views of the headgear connector of FIGS. 66 and 67 in use with a headgear strap, in engaged and released conditions respectively.

Figure 96A:
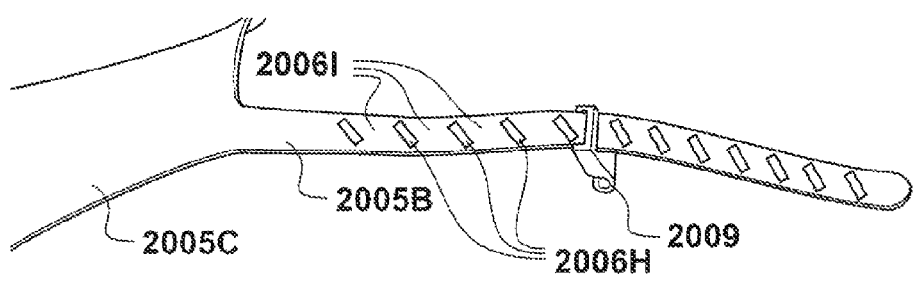
Figure 96B:
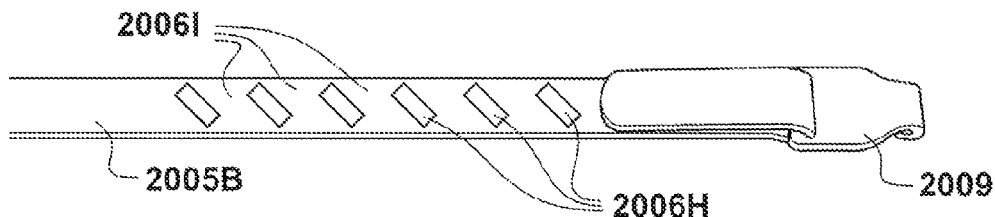
Figure 96C:
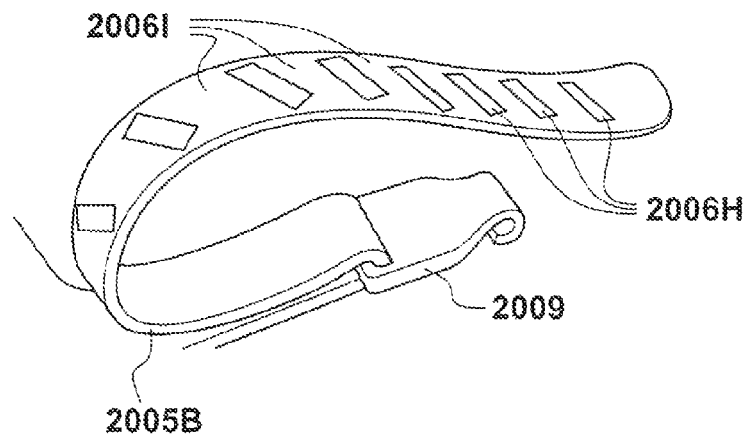

FIGS. 96*a* to 96*c* are views of a fifth embodiment of headgear in accordance with this disclosure, with the straps in different conditions of length adjustment.

Figure 97A:
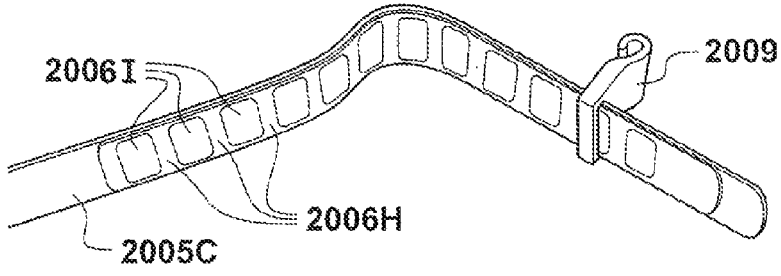
Figure 97B:
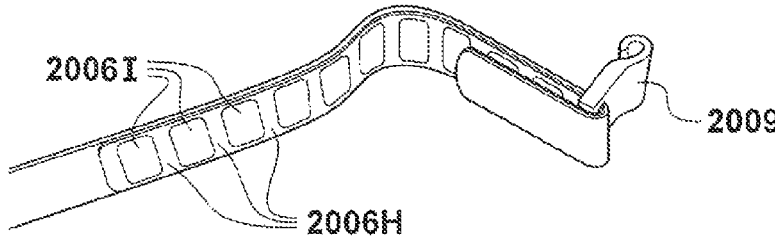

FIGS. 97*a* to 97*b* are views of a modified version of the fifth embodiment of the headgear of FIG. 96.

Figure 98:
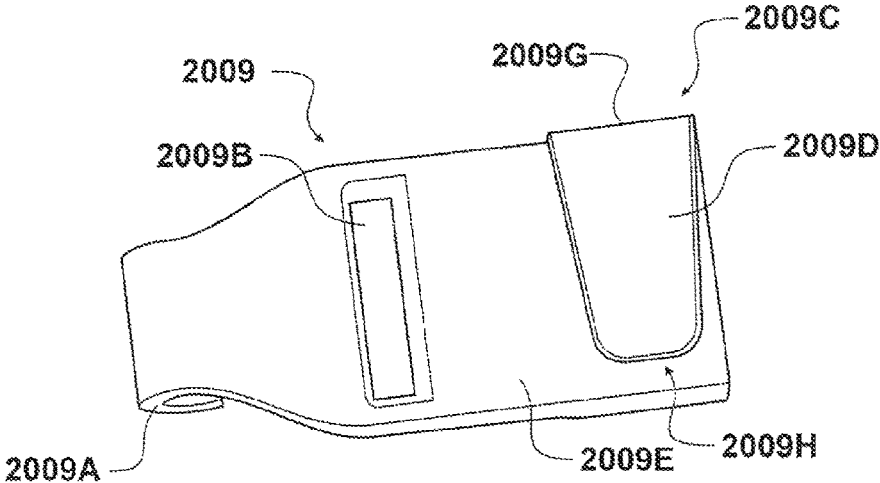
Figure 99:
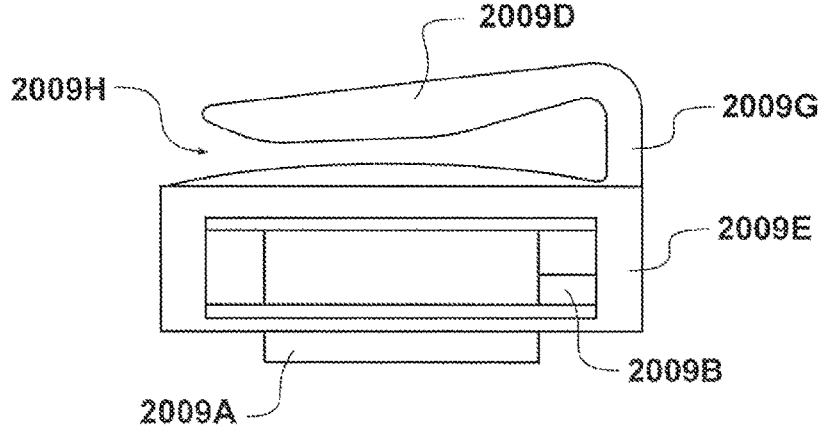
Figure 100:
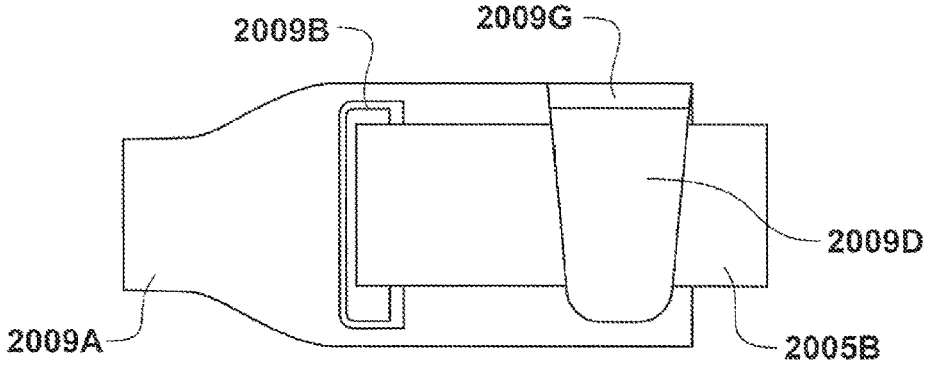

FIGS. 98 to 100 are views of a headgear connector comprising a clip for strap length adjustment, in accordance with an embodiment of this disclosure.

Figure 101A:
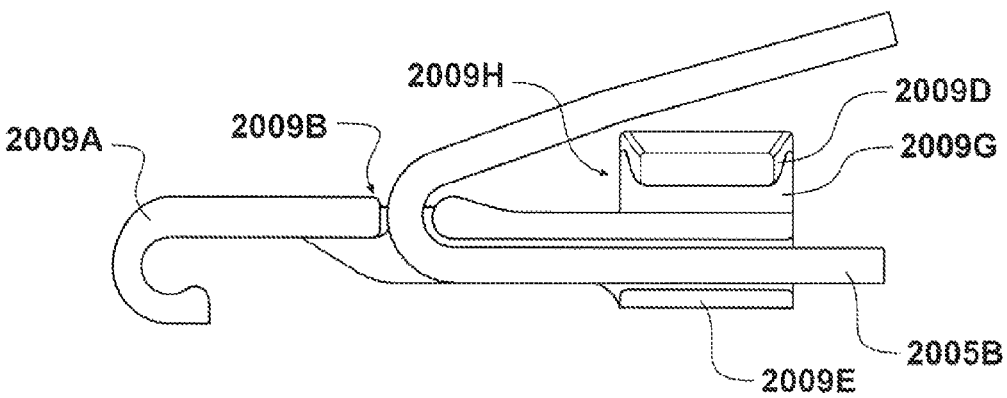
Figure 101B:
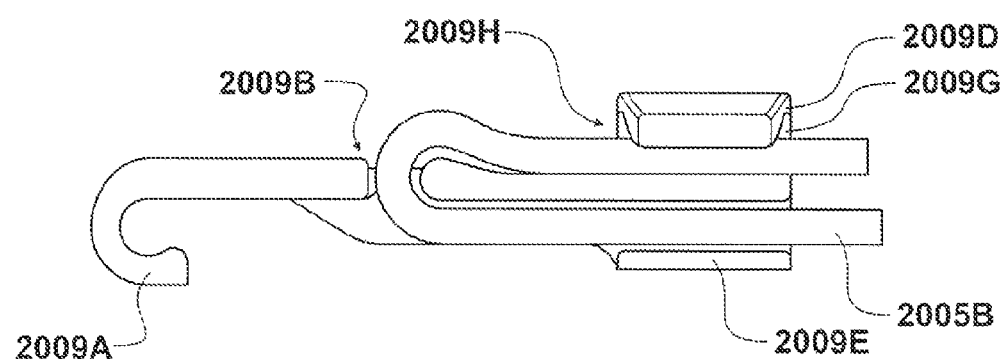

FIG. 101 is a schematic side view of the connector FIGS. 98 to 100, in an adjustment mode and a strap retention mode.

DETAILED DESCRIPTION OF SPECIFIC EMBODIMENTS

Figure 1:
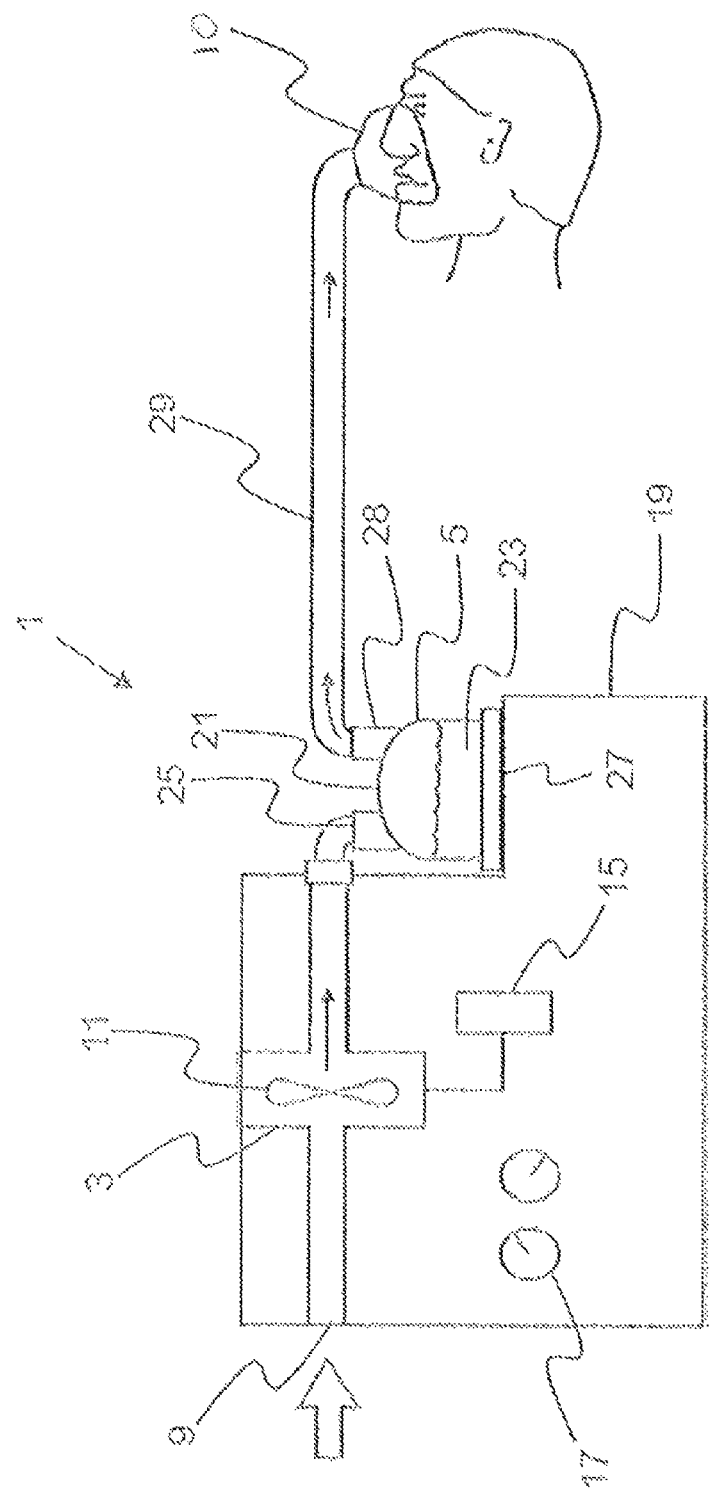
FIG. 1 is a schematic representation of a respiratory therapy system configured to supply pressurized and humidified breathing gases to a user through a user interface assembly.

An example respiratory therapy system suitable for supplying breathing gases to a user for positive airway pressure (PAP) therapy (e.g., continuous positive airway pressure (CPAP) therapy) or non-invasive ventilation (NIV) therapy is illustrated in FIG. 1. The example respiratory therapy system 1 may include a gas source 3, an optional humidifier 5, a user interface assembly 10 and a breathing gas circuit 29 that connects the humidifier (or gas source) to the user interface assembly 10. The gas source 3 can provide a supply of breathing gas to the humidifier 5. The gas source 3 may comprise a blower in which breathing gas, e.g., ambient air and/or oxygen, is drawn into the gas source 3 through a gas source inlet 9 in the gas source casing by an impeller 11. The rotational speed of the impeller 11 may be modulated to regulate the quantity of air drawn into the gas source 3 and/or the supply of breathing gas delivered to the respiratory therapy system 1. In other examples, the impeller 11 is driven at a constant speed with the flow rate of breathable gas delivered to the user being controlled by other means, such as a valve or valves. Breathing gas may include any single gas or multiple gases that are breathable by the user of the respiratory therapy system 1, and can include ambient air, oxygen, or any combination of breathable gases.

The pressure and/or flow rate of breathing gas exiting the gas source 3 may be regulated by a controller 15. The controller 15 may modulate the rotational speed of the impeller 11 according to one or more predetermined algorithms and in accordance with one or more user inputs that may be provided via a user input 17.

The gas source 3 represents an actively controlled flow generator. Other gas sources, such as a compressed air cylinder with suitable pressure or flow regulation, may also be used to supply breathing gas. In at least one configuration, the gas source 3 may be in the form of a blower. The blower may be a centrifugal blower. In at least one configuration, the gas source 3 may be in the form of a fan. The outlet of the gas source 3 may be coupled to a separate humidifier 5. The humidifier 5 may be configured to heat and/or humidify the breathing gas prior to delivery, e.g., delivery to the user. In some embodiments, the humidifier 5 is integrated with the gas source 3. The humidifier 5 may include a base 19 and a humidifier chamber 21. The chamber 21 may be configured to hold humidification fluid 23, such as water, and may be disengaged, e.g., temporarily disengaged or permanently disengaged, from the humidifier base 19 to allow it to be filled or replaced. The humidifier chamber 21 may include a heat conductive base 31. The heat conductive base 31 may be in the form of a heater plate 31. The heat conductive base 31 may form a bottom surface of the humidifier chamber 21. The conductive base 31 may comprise a metal and/or an electrically conductive plastic material. The humidifier 5 receives gases from the gas source 3 through chamber inlet 25. The humidifier base 19 can include a heater such as a heating element 27. The humidifier chamber 21 rests on the heating element 27 when engaged with the humidifier base 19. The heating element 27 dissipates heat, e.g., heat generated by electrical resistance, to the chamber 21. The heating element may dissipate heat to the humidification fluid 23 via the heat conductive base 31 to pass the heat efficiently to the humidification fluid 23. Controller 15 can also control the humidifier 5, and in particular the supply of electrical energy to the heating element 21, to regulate any function of the humidifier 5, e.g., the temperature and/or humidity of the breathing gas supplied to the user.

The breathing gas can be supplied to the user via a chamber outlet 28 and the breathing gas circuit 29. The breathing gas circuit 29 may be in the form of one or more gas delivery conduits and one or more conduit connectors. The breathing gas circuit 29, part or all of which may incorporate a heating or warming element, e.g., a heater wire, to heat or warm the breathing gases during delivery to the user interface assembly 10. The electrical energy supplied to the heater wire may be controlled by the controller 15. The controller 15 may receive feedback from one or more sensors throughout the respiratory therapy system 1 to monitor properties of the breathing gas, such as, but not limited to, any one or more of pressure, flow rate, temperature, and/or humidity.

The user interface assembly 10 couples the user with the respiratory therapy system 1, such that breathable gas, e.g., heated and humidified gases from the humidifier 5, may be delivered to the user's airway. Breathing gas can be delivered to the user at, or near, optimal temperature and humidity (e.g., warmed and fully saturated with water vapor at temperatures of between 27 and 37° C.) as the gas are delivered to the user's nares and/or mouth. Emulating the conditions within healthy adult lungs (37° C., 44 mg/L humidity) can help maintain healthy mucociliary function in users with respiratory disorders affecting secretion. Humidifying the gas can help maintain user comfort and compliance. A number of different styles of user interface assembly 10, such as those disclosed herein, may be used in the example system 1 or a similar system. The user interface assembly 10 can comprise a user interface 50 and a headgear 70. In this example a full face mask 50 is shown, but any other type of user interface, whether or not comprising a seal to seal against the user's face, can be used. Likewise, the examples below refer, for ease, to a particular type of user interface shown in the figures, but the headgear disclosed in each example can be used with any type of user interface. For example, the user interface 50 can be in the form of a full face mask, a nasal mask, an oral mask or a nasal cannula.

Figure 2:
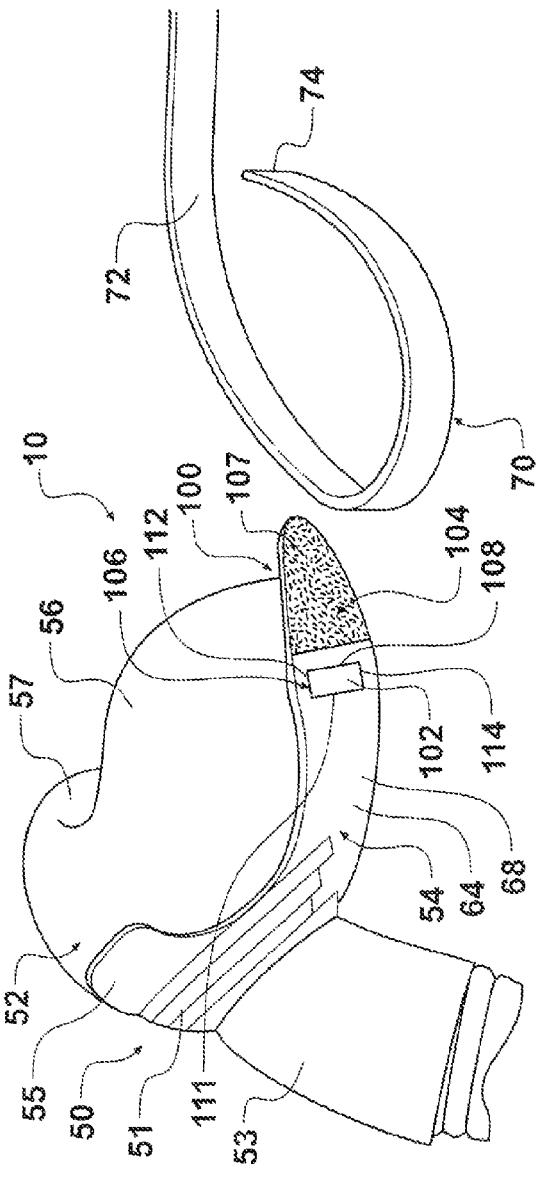
FIG. 2 is a perspective view of a user interface assembly comprising a user interface comprising a cushion module and a frame comprising a headgear connector, and headgear (partially shown), with a headgear strap in a disconnected configuration.
Figure 3:
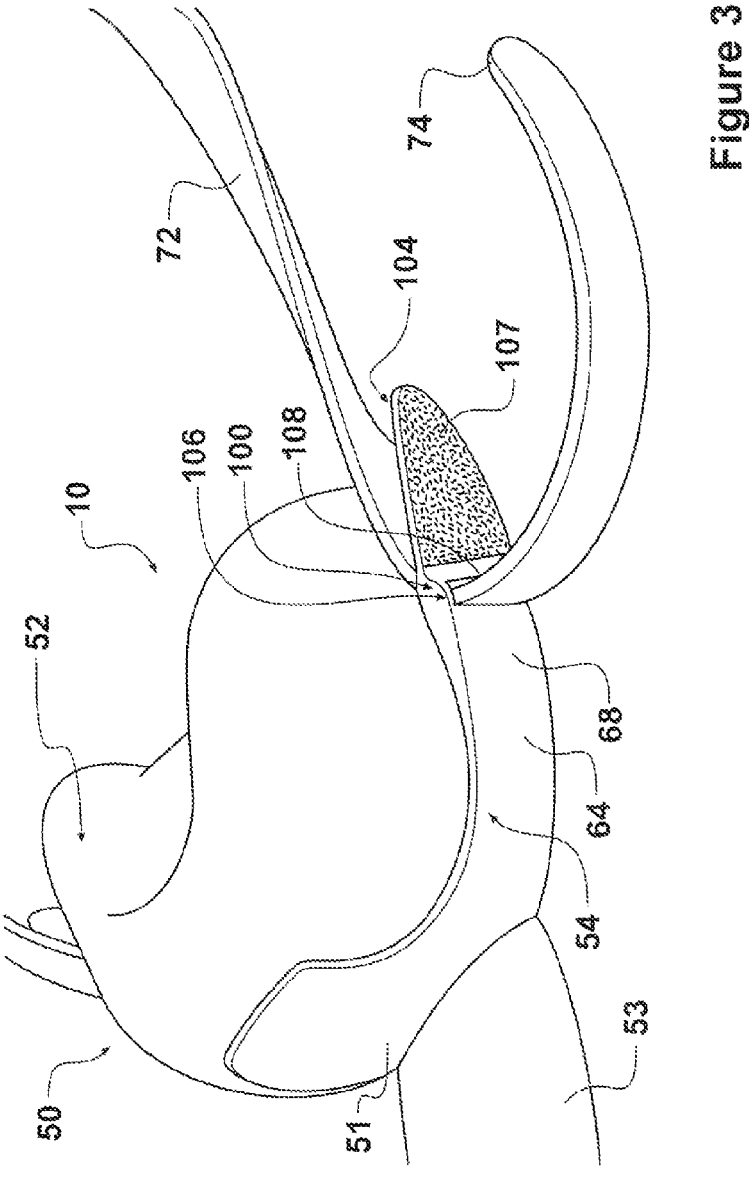
FIG. 3 is a perspective view of the user interface assembly of FIG. 2, with the headgear strap in a partially connected configuration.
Figure 4:
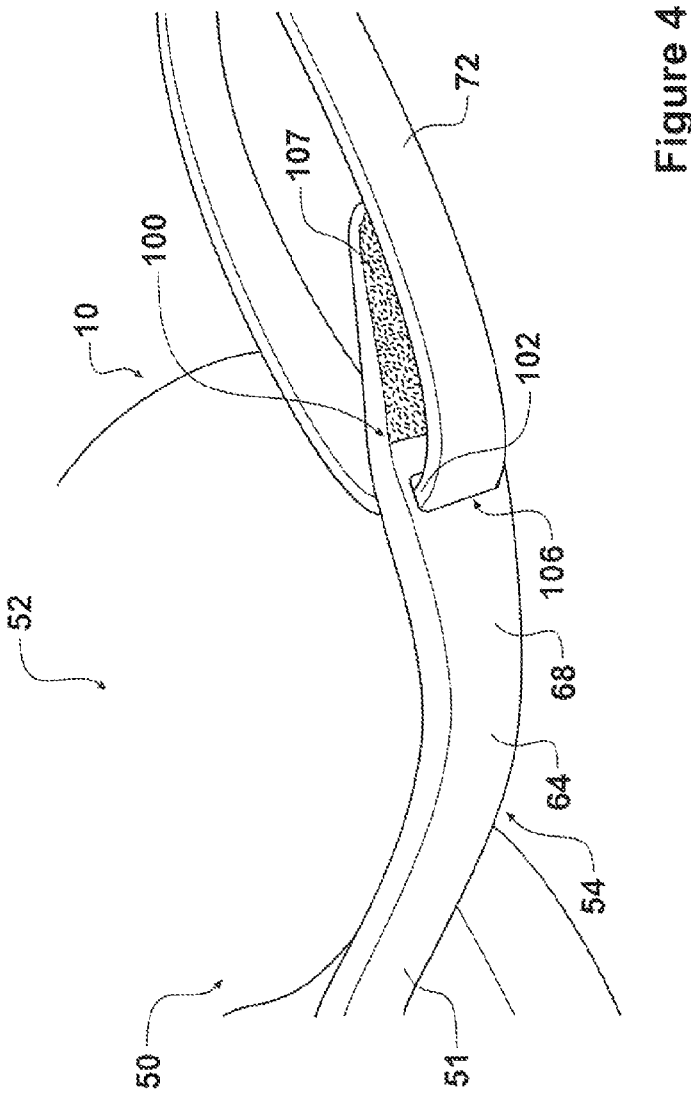
FIG. 4 is a perspective view of the user interface assembly of FIG. 2, with the headgear strap in a connected configuration.

FIGS. 2-4 show a user interface assembly 10 configured for the delivery of respiratory therapy to a user. The user interface assembly 10 comprises a user interface 50, which is configured to secure against the face of the user to define a substantially sealed breathing chamber, and headgear 70 which is configured to connect to the user interface 50 and retain the user interface 50 in place on the user's face. The headgear 70 positions and secures the user interface 50 to the user's face in an operating position enabling the delivery of the respiratory therapy. The user interface assembly 10 delivers respiratory therapy in the form of a flow of pressurized breathing gas (e.g., humidified air) to the breathing chamber of the user interface 50 and, eventually, to the user's airway.

The user interface 50 comprises a frame 54, a cushion module 52, and a breathing gas circuit connector 53. The cushion module 52 is removably connectable to the frame 54. The cushion module 52 comprises a seal 56. The cushion module 52 comprises a housing 55. The illustrated housing 55 is in the form of a seal clip that clips to the seal 56. The housing 55 is harder or more rigid than the seal 56. The seal 56 defines a face-contacting surface 57 configured to contact the face of the user, a seal inlet opening 58 and a seal outlet opening 60. The seal inlet opening 58 is fluidly connected with the breathing gas circuit connector 53. The seal outlet opening 60 is fluidly connected with the breathing gas circuit connector 53 via the seal inlet opening 58. The breathing gas circuit connector 53 connects to the breathing gas circuit 29, and comprises a fluid passage. The breathing gas is therefore delivered to the user from the breathing gas circuit 29 through breathing gas circuit connector 53 via the fluid passage, and the seal 56.

The user interface 50 is configured to be removably connected to headgear 70. The headgear 70 comprises at least one headgear strap 72. The headgear strap 72 is configured to connect with the user interface 50. The headgear strap 72 comprises an elongated portion of the headgear 70. The headgear strap 72 is bendable. In at least one configuration, the headgear strap 72 is flexible, resilient, bendable and/or stretchable.

The frame 54 comprises a frame central portion 51 that defines a central opening 62 configured to cooperate with the breathing gas circuit connector 53 such that breathing gas can be delivered to the user. The breathing gas circuit connector 53 connects to the frame central portion 51 at or near the central opening 62. Breathing gas is therefore directed from the breathing gas circuit connector 53, through the central opening 62, housing opening 59 and seal inlet opening 58 into the seal 56.

The frame 54 also comprises at least one frame lateral portion 64 extending from the frame central portion 51. The illustrated frame 54 comprises a pair of frame lateral portions 64. Each frame lateral portion 64 extends laterally or transversely outwardly from the frame central portion 51, away from central portion 51. One or more or the frame lateral portion(s) 64 can be in the form of a frame elongate member 64. In at least one configuration, the frame 54 is formed from, or comprises a polymer.

The illustrated frame 54 comprises a frame interior surface 66 and a frame exterior surface 68. The frame interior surface 66 is inward-facing with respect to the user when the user interface assembly 10 is in use. The frame exterior surface 68 is outward-facing with respect to the user when the user interface assembly 10 is in use.

Each frame lateral portion 64 comprises a headgear connector 100. The headgear connector 100 facilitates the connection of the frame 54 to the headgear 70. The headgear connector 100 is configured to cooperate with the headgear strap 72 to connect the headgear strap 72 to the frame 54, and therefore connect the user interface 50 to the headgear 70. The headgear connector 100 of the configuration shown in FIGS. 2-4 is disposed outwardly from the frame central portion 51, at or near an end of the frame lateral portion 64.

The headgear connector 100 comprises a headgear connecting portion 106. The headgear connecting portion 106 of the illustrated headgear connector 100 comprises a headgear receiving passage 102. The passage 102 is configured to receive headgear strap 72 so that the headgear strap 72 can pass through the passage 102. The passage 102 is defined by an aperture or hole or slot in the frame 54. The passage 102 is substantially oblong, and comprises a passage outer wall 108, a passage inner wall 111, a passage upper wall 112 and a passage lower wall 114. The walls 108, 110, 112 and 114 defining the passage 102 are integrally formed with the frame 54. The hole defining the passage 102 extends through the frame lateral portion 64 from the frame interior surface 66 to the frame exterior surface 68. The passage 102 in this example is substantially rectangular, corresponding to, but slightly larger than, the rectangular cross section of the headgear strap 72. In at least one configuration, the passage 102 can be circular, oval, trapezoidal, another polygon, or have one or more curved corners or walls.

The headgear connector 100 comprises a headgear gripping portion 104. The headgear gripping portion 104 is configured to grip a portion of the headgear 70 to secure the headgear 70 with respect to the frame 54. The headgear gripping portion 104 is configured to grip a portion of the headgear strap 72 that has been received by and has passed through the passage 102. The headgear gripping portion 104 comprises a gripping element 107 that is configured to grip the headgear strap 72. The gripping element 107 grips the headgear strap 72 when the headgear strap 72 is brought into contact with the gripping element 107. In other words, the gripping element 107 can maintain a physical connection between the headgear gripping portion 104 and the headgear strap 72. The headgear gripping portion 104 therefore grips the headgear strap 72 via the gripping element 107.

In this example, the gripping element 107 is disposed on the frame exterior surface 68. This configuration advantageously improves the ease of use of the user interface assembly 10 as the frame exterior surface 68 can be more easily accessible by the user than other surfaces of the frame 54, for example the frame interior surface 66. Including the headgear connector 100 on the frame 54 also reduces the complexity and cost of manufacturing the headgear 70. The headgear 70 can be cheaper to replace, can be washed more regularly, and more often, and maintain its performance.

The gripping element 107 is secured to the frame exterior surface 68 at the headgear gripping portion 104 of the headgear connector 100. In this example, the gripping element 107 is adhesively bonded to the frame exterior surface 68. Alternatively, the gripping element can be secured to the frame exterior surface 68 by another method, for example high frequency welding (RF welding), chemical bonding etc.

The passage 102 is spaced apart from the headgear gripping portion 104 and the gripping element 107. The passage 102 is disposed between the headgear gripping portion 104 and the frame central portion 51. In other words, the headgear gripping portion 104 is displaced laterally from the passage 102 with respect to the frame central portion 51. In this example, the passage 102 is disposed between the headgear gripping portion 104 and the breathing gas circuit connector 53. In at least one configuration, the passage 102 can be adjacent the headgear gripping portion 104.

As shown in FIGS. 2-4, a distance between the passage 102 and the headgear gripping portion 104 is less than a length of the headgear gripping portion 104. This configuration advantageously improves the ease of use of the headgear connector 100. A relatively large distance between the passage 102 and the headgear gripping portion 104 (for example, a distance greater than a maximum dimension of the headgear gripping portion 104) can bring the passage so close to the central portion of the frame 54 that it is difficult for the user to easily be able to pass the headgear strap 72 through the passage 102 during assembly.

To secure the headgear 70 to the user interface 10, a headgear strap end 74 is passed through the passage 102 in a direction from the frame interior surface 66 towards the frame exterior surface 68, as shown in FIG. 3. The headgear strap end 74 is looped outwards from the passage 102 and towards the headgear gripping portion 104. In other words, the passage 102 receives the headgear strap 72 from a first direction, after which, the headgear strap 72 is looped back on itself in a second direction substantially opposed to the first direction. The user can tighten the headgear 70 by pulling the headgear strap end 74 further away from the passage 102 in the direction of the headgear gripping portion 104.

The headgear strap 72 can be connected to the headgear gripping portion 104. The headgear strap 72 is pivoted or rotated about the passage outer wall 108 and brought towards the gripping element 107. The headgear strap 72 is brought into contact with the gripping element 107, which connects the headgear strap 72 to the headgear connector 100, as shown in FIG. 4. Rotating the headgear strap 72 about the passage outer wall 108 and away from the user disconnects the headgear strap 72 from the headgear connector 100.

In at least one configuration, the headgear strap 72 can pass and/or slide through the passage 102 while a portion of the headgear strap 72 is connected to the headgear gripping portion 104. The headgear gripping portion 104 is therefore configured to grip the headgear strap 72 when the headgear strap 72 is elastically unloaded.

The headgear gripping portion 104 is configured to grip a portion of the headgear 70. In particular, the gripping element 107 grips a portion of the headgear strap 72. The gripping element 107 comprises hook connectors of a hook and loop connection system. The headgear strap 72 (and additionally, where preferable, the remainder of the headgear 70) comprises loop connectors of the hook and loop connection system. These loop connectors can be inherent in the material from which the headgear 70 is fabricated. A hook and loop connection is therefore formed when the headgear strap 72 contacts the gripping element 107, with the hook connectors of the gripping element 107 gripping the loop connectors of the headgear strap 72. The hook and loop connection retains the headgear strap 72 in place during the user's respiratory therapy session. The user can adjust the effective length of the headgear strap 72, thereby providing adjustable headgear 70, by adjusting the length of headgear strap 72 extending through the passage 102, and reconnecting the headgear strap 72 with the gripping element 107.

In at least one configuration, the gripping element 107 is configured to grip a portion of the headgear 70 using another type of connection system (e.g., not a hook and loop connection system). For example, the gripping element 107 can comprise a magnet (e.g., a permanent magnet or an electromagnet), and the headgear strap 72 can comprise a ferromagnetic material. When the headgear strap 72 is brought towards the gripping element 107, the magnet of the gripping element 107 can attract and grip the ferromagnetic material in the headgear strap 72 to secure the headgear strap 72. The ferromagnetic material can be an iron block. In an alternate example, the headgear strap 72 can comprise a ferromagnetic textile, or lengths of ferromagnetic material.

In at least one configuration, the passage 102 can be dimensioned so that it provides a resistive force against movement of the headgear strap 72 through the passage 102. For example, the length of the passage outer wall 108 and/or passage inner wall 111 can be smaller than a corresponding elongate dimension of the headgear strap 72. In such a configuration, as the headgear strap 72 passes and/or slides through the passage 102, the passage upper wall 112 and the passage lower wall 114 press inwards on the headgear strap 72, to resist its movement by frictional engagement with the strap 72. The resistive force is caused by an interference between the headgear strap 72 and one or more walls of the passage 102. Consequently, when the headgear strap 72 is connected to the gripping element 107, the headgear 70 is connected to the user interface 50 by a combination of a resistive force between the headgear 70 and at least one (in this case, two) passage 102 wall, and a gripping force between the gripping element 107 and the headgear 70. Providing friction between the headgear strap 72 and the passage 102, in addition to the connection between the headgear gripping portion 104 and the headgear strap 72 can improve the strength of the connection between the headgear 70 and the user interface 50. Additionally, the friction can provide a form of tactile feedback to the user as they adjust their headgear 70, improving the precision of their adjustment.

In at least one configuration, the dimension of the passage outer wall 108 and/or the passage inner wall 111 can be less than a corresponding headgear strap major dimension. Said passage 102 can also be sized such that the length of the passage upper wall 112 and/or passage lower wall 114 is less than a corresponding headgear minor dimension being the thickness of the headgear strap 72. As the headgear strap 72 passes and/or slides through the passage 102, the passage upper wall 112, passage lower wall 114, passage outer wall 108 and passage inner wall 111 press inwards on the headgear strap 72 to resist its movement. The resistive force of this configuration is caused by an interference between the headgear strap 72 and more than two walls of the passage 102.

In at least one configuration, the frame lateral portions 64 terminate at or adjacent to the headgear connector 100. In at least one configuration, one or more of the frame lateral portions include the headgear connector 100. The gripping element 107 can be an integrally formed part of the frame 54 and/or the frame exterior surface 68. For example, the gripping element 107 can comprise a magnet. The frame 54 can be overmoulded onto the magnet, thereby having a gripping element 107 that is integrally formed with the frame. Alternatively, the frame 54 can be overmoulded onto a portion of hook connectors of a hook and loop connection system, again thereby integrating the gripping element 107 with the frame 54.

In at least one configuration, the distance between the passage 102 and the headgear gripping portion 104 is:
- less than a lateral length of the headgear gripping portion 104,
- less than a maximum length of the headgear gripping portion 104.
- greater than a length of the headgear gripping portion 104, or
- greater than the maximum dimension of the headgear gripping portion 104. This configuration can be beneficial in providing the user additional leverage when tensioning the headgear 70 for connection after passing it through the passage 102.

The distance can be the distance between the centre of the passage 102, passage outer wall 108 or passage inner wall 111 and the closest portion of the headgear gripping portion 104.

The illustrated user interface 50 comprises two frame lateral portions 64. At least one embodiment of the user interface 50 may comprise more than two frame lateral portions 64. For example, a full-face user interface may comprise four frame lateral portions 64.

In at least one configuration, the headgear connector 100 can be used with a user interface 50 configured to deliver breathing gas to one or more of the user's mouth and nose without a sealed connection. For example, the headgear connector 100 can be used with a nasal cannula 50.

Figures 5A, 5B:
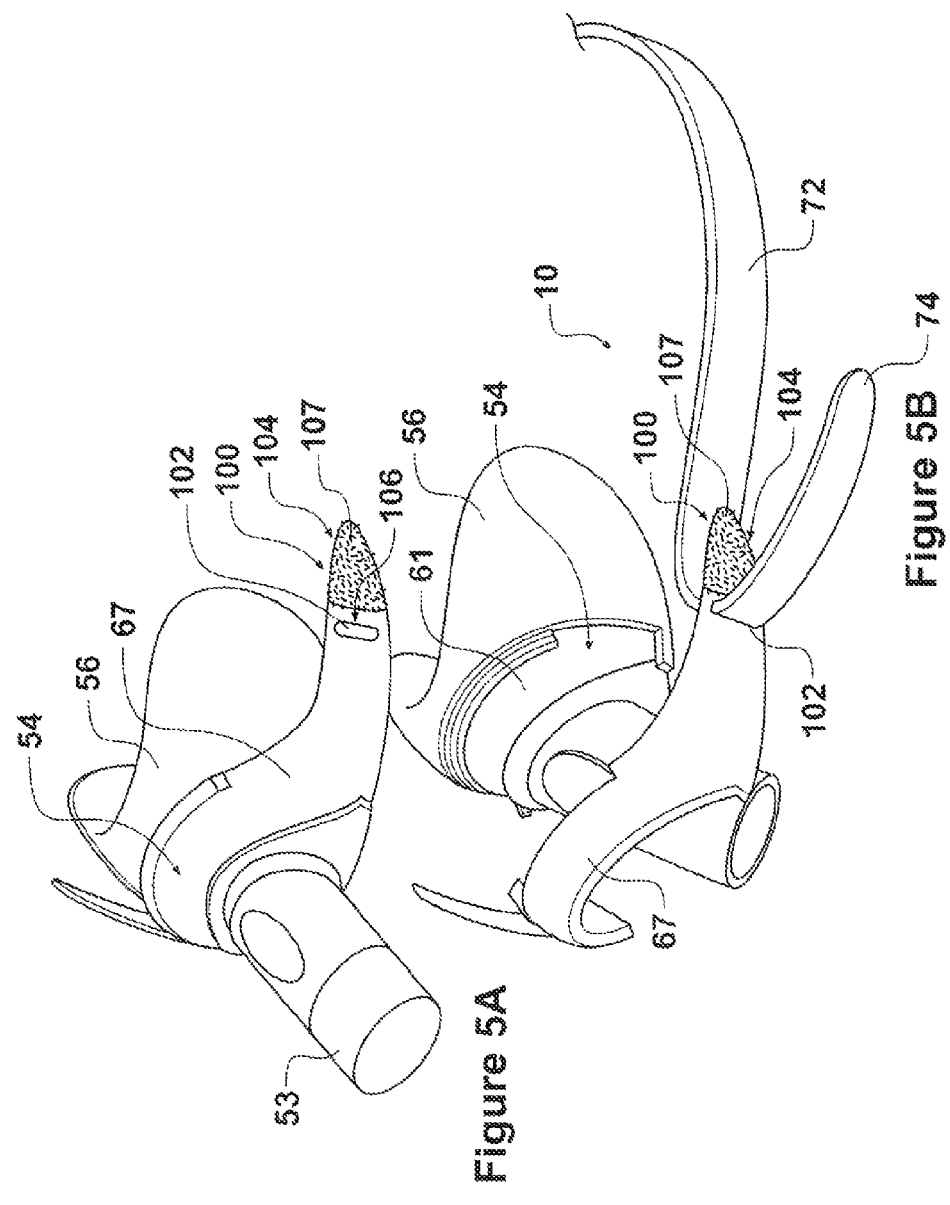
FIG. 5*a* is a perspective view of another embodiment of the user interface assembly of FIG. 2, with the headgear hidden, and where the frame comprises a frame body and a yoke, and the yoke comprises the headgear connector.
FIG. 5*b* is a perspective view of the user interface assembly of FIG. 5*a*, with the yoke disconnected from a frame body, and the headgear strap in a partially connected configuration.
Figure 6:
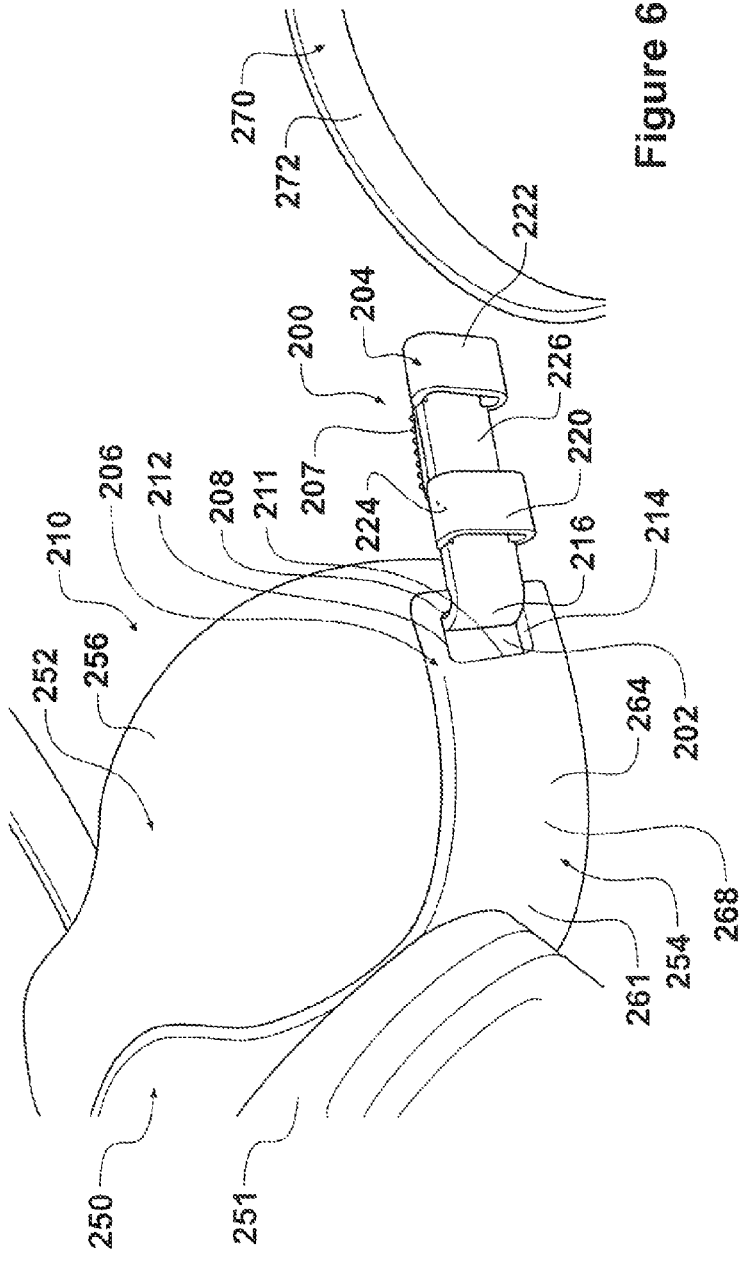
FIG. 6 is a perspective view of a user interface assembly comprising user interface comprising a cushion module and a frame comprising a headgear connector, and headgear (partially shown), with a headgear strap in a disconnected configuration.
Figure 7:
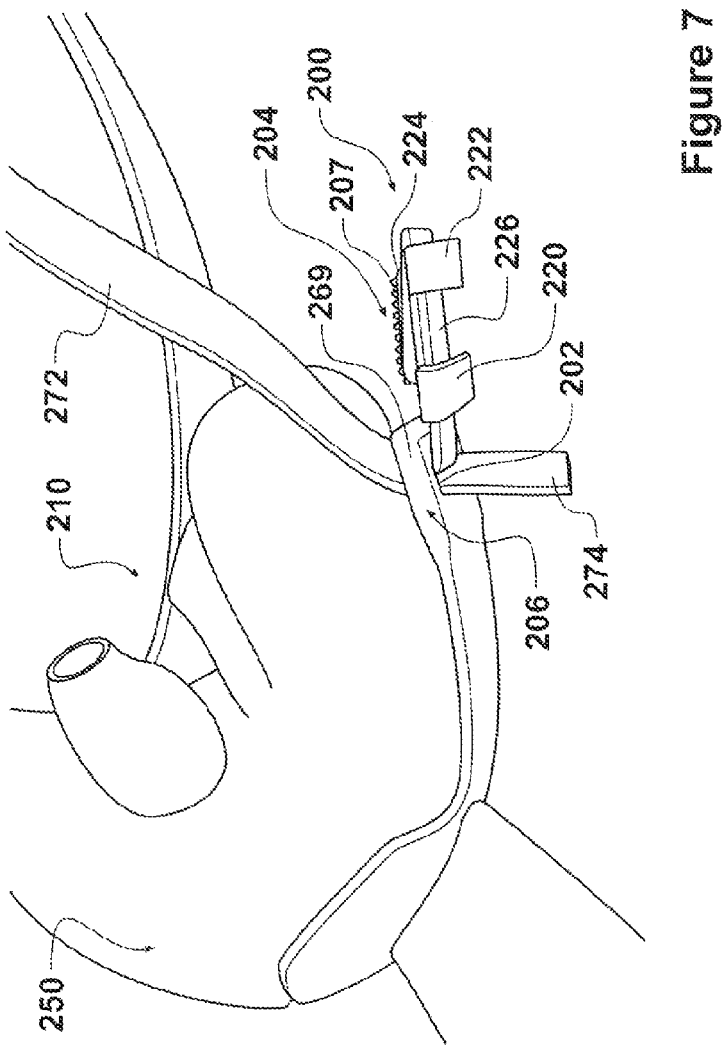
FIG. 7 is a perspective view of the user interface assembly of FIG. 6, with the headgear strap in a partially connected configuration.
Figure 8:
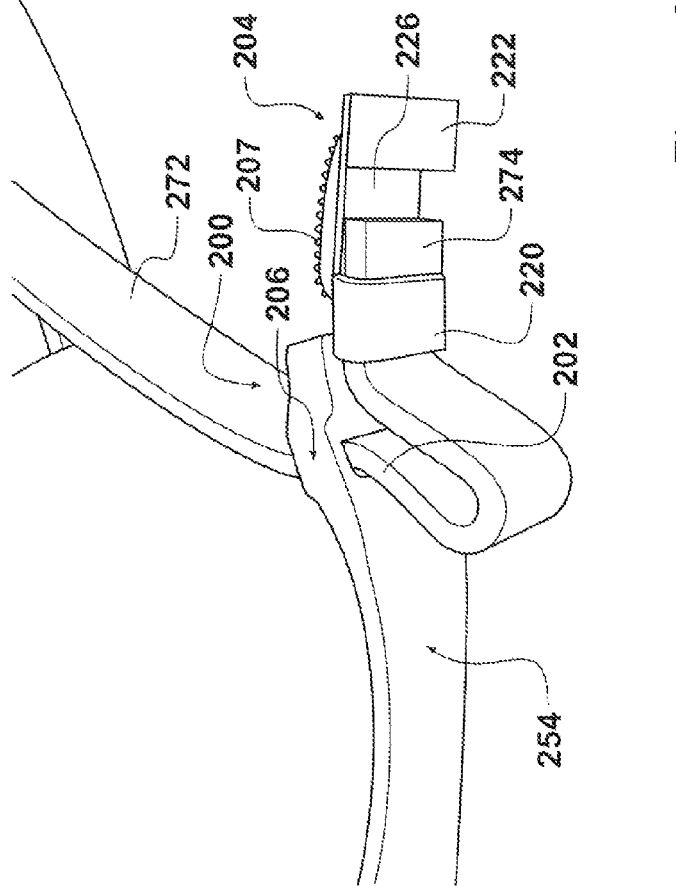
FIG. 8 is a perspective view of the user interface assembly of FIG. 6, with the headgear strap in another partially connected configuration.
Figure 9:
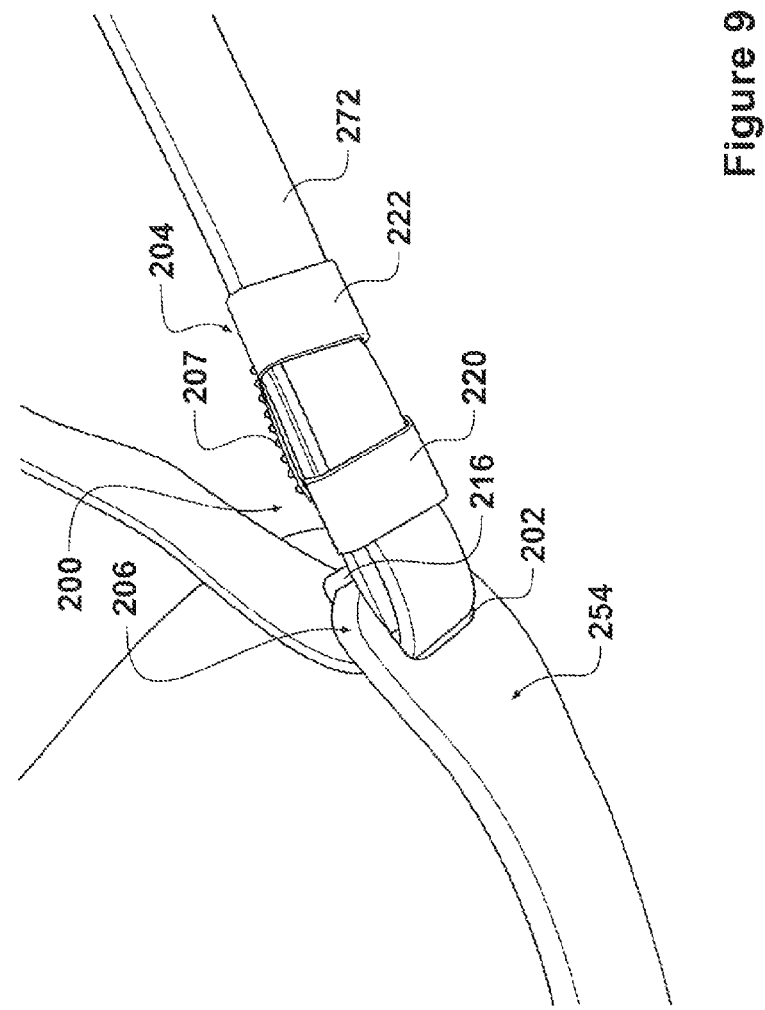
FIG. 9 is a perspective view of the user interface assembly of FIG. 6, with the headgear strap in a third partially connected configuration.
Figure 10:
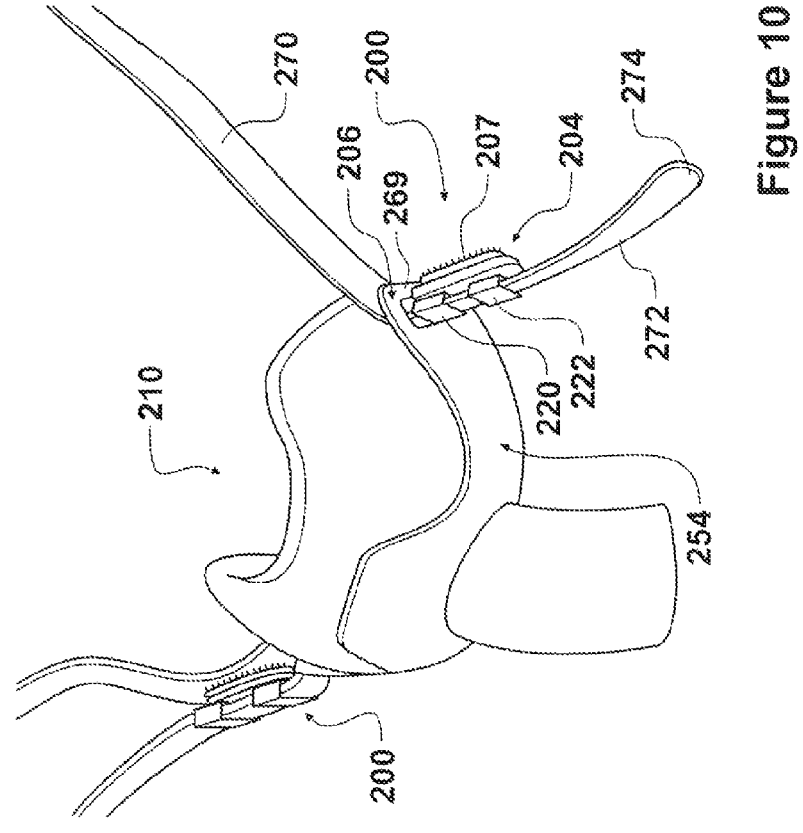
FIG. 10 is a perspective view of the user interface assembly of FIG. 6, with the headgear strap in a fourth partially connected configuration.

FIG. 5*a* and FIG. 5*b* show another embodiment of the user interface assembly 10 of FIGS. 2-4. The user interface assembly 10 shown in FIG. 5*a* and FIG. 5*b* is similar to the user interface assembly 10 of FIGS. 2-4 with the notable exception that the frame 54 comprises a yoke 67 that comprises the headgear connector/s 100.

The user interface assembly 10 again comprises a user interface 50 and headgear 70. The user interface 50 comprises a frame 54, a cushion module 52 and a breathing gas circuit connector 53. The frame 54 comprises a frame body 61 which is configured to connect to the yoke 67. The yoke 67 is removably connected to the frame body 61. The yoke 67 spans laterally across a length of the frame body 61. The yoke 67 comprises a pair of headgear connectors 100 substantially similar to that of FIGS. 2-4, which facilitate the connection of the frame 54 to the headgear 70 via the yoke 67. The yoke 67 can make the frame 54 easier to clean. Gaps or crevices in the frame 54 of FIGS. 2-4 between the seal 56 and the frame interior surface 66 can be difficult to clean due to the small clearances between the parts. The removable yoke 67 can reduce issues related to reaching clearances between the seal 56 and the frame lateral portion(s) 64. This configuration can allow the user to effectively clean more of the user interface 50. Additionally, the user can disconnect the frame body 61 and cushion module 52 from the yoke 67 to clean these parts without having to disconnect the headgear 70 from the yoke 67. This allows the user to clean the cushion module 52, frame body 61 and/or the headgear 70 without having to disconnect, then reconnect and readjust the headgear 70.

FIGS. 6-11*b*, FIG. 12*a* and FIG. 13*a* show another embodiment of a user interface assembly 210 according to the present disclosure. The user interface assembly 210 comprises a user interface 250 which is configured to secure against the face of a user to define a substantially sealed breathing chamber, and headgear 270 which is configured to connect to the user interface 250 and position and secure the user interface 250 in place on the user's face.

The user interface 250 comprises a frame 254, a cushion module 252, and a breathing gas circuit connector 253. In the illustrated configuration, the cushion module 252 is removably connected to the frame 254. The cushion module 252 comprises a seal 256 and a housing 255, and is substantially similar to the cushion module 52 described with reference to FIGS. 2-4.

The user interface 250 is configured to be removably connected to headgear 270. The headgear 270 comprises at least one headgear strap 272. The headgear strap 272 is configured to connect with the user interface 250. The headgear strap 272 comprises an elongated portion of the headgear 270. The headgear 270 and headgear strap 272 are substantially similar to, or the same as the headgear 70 and headgear strap 72 described with reference to FIGS. 2-4.

The frame 254 comprises a frame body 261 and a headgear connector 200. The frame body 261 comprises a frame central portion 251 that defines a central opening 262 configured to cooperate with the breathing gas circuit connector 253 such that breathing gas can be delivered to the user. The breathing gas circuit connector 253 connects to the frame central portion 251 at or near the central opening 262. Breathing gas is therefore directed from the breathing gas circuit connector 253, through the central opening 262, housing opening 259 and seal inlet opening 258 into the seal 56.

The frame body 261 also comprises at least one frame body lateral portion 264 extending from the frame central portion 251. The illustrated frame body 261 comprises a pair of frame body lateral portions 264. Each frame body lateral portion 264 extends laterally or transversely outwardly from the frame central portion 251, away from central portion 251.

The frame body 261 comprises a frame body interior surface 266 and a frame body exterior surface 268. The frame body interior surface 266 is inward-facing with respect to the user when the user interface assembly 210 is in-use. The frame body exterior surface 268 is outward-facing with respect to the user when the user interface assembly 210 is in use.

The headgear connector 200 in this example comprises a headgear connecting portion 206. The headgear connecting portion 206 is integrally formed with the relevant frame body lateral portion 264. The headgear connecting portion 206 comprises a headgear receiving passage 202. The passage 202 is configured to receive the headgear strap 272 so that the headgear strap 272 can pass through the passage 202. The passage 202 is defined by an aperture or hole or slot in the frame body 261. The passage 202 is substantially oblong, and comprises a passage outer wall 208, a passage inner wall 211, a passage upper wall 212 and a passage lower wall 214. The walls 208, 211, 212 and 214 defining the passage are integrally formed with the frame body 261. The hole defining the passage 202 extends through the frame body lateral portion 264 from the frame body interior surface 266, through the frame body 261 to the frame body exterior surface 268. The passage 202 in this example is substantially rectangular, corresponding to, but slightly larger than, the rectangular cross section of the headgear strap 272. In at least one configuration, the passage 202 can be circular, oval, trapezoidal, another polygon, or have one or more curved corners or walls.

The headgear connector 200 comprises a headgear gripping portion 204. The headgear gripping portion 204 connects to the headgear connecting portion 206. The headgear gripping portion 204 is configured to cooperate with the headgear strap 272 to connect the strap 272 to the frame 254, and therefore to connect the user interface 250 to the headgear 270.

The headgear gripping portion 204 is configured to grip a portion of the headgear strap 272 via a gripping element 207. When the headgear strap 272 is brought into contact with the gripping element 207, the gripping element 207 grips the headgear strap 272, thereby connecting the headgear 270 to the frame 254. In other words, the gripping element 207 can maintain a physical connection between the headgear gripping portion 204 and the headgear strap 272. The headgear gripping portion 204 therefore grips the headgear strap 272 via the gripping element 207. The gripping element 207 can grip the headgear strap 272 as described with reference to gripping element 107 and FIGS. 2-4. The headgear gripping portion comprises a gripping portion exterior surface 226 and a gripping portion interior surface 224.

In the illustrated configuration, the gripping portion interior surface 224 comprises the gripping element 207. The gripping element 207 is secured to the gripping portion interior surface 224. The gripping element 207 is adhesively bonded to the headgear connector interior surface 224. Alternatively, the gripping element 207 can be bonded or connected to the headgear connector interior surface 224 by another method, for example high frequency welding, chemical bonding etc.

The headgear gripping portion 204 comprises a frame body coupling 216. The frame body coupling 216 is configured to couple the headgear gripping portion 204 to a frame body post 269 of the headgear connecting portion 206, comprising the passage outer wall 208. The frame body coupling 216 is curved to form a channel which clips onto and receives the post 269 such that the headgear gripping portion 204 is rotatable about the frame body post 269, and therefore, the headgear connecting portion 206. The frame body coupling 216 and frame body post 269, when coupled, provide a hinge. The gripping element 207, being laterally displaced on the headgear gripping portion 204 with respect to the hinge is therefore rotatable with respect to the headgear connecting portion 206, and also therefore the frame body 261 about the hinge.

Figures 11A, 11B, 11C, 11D:
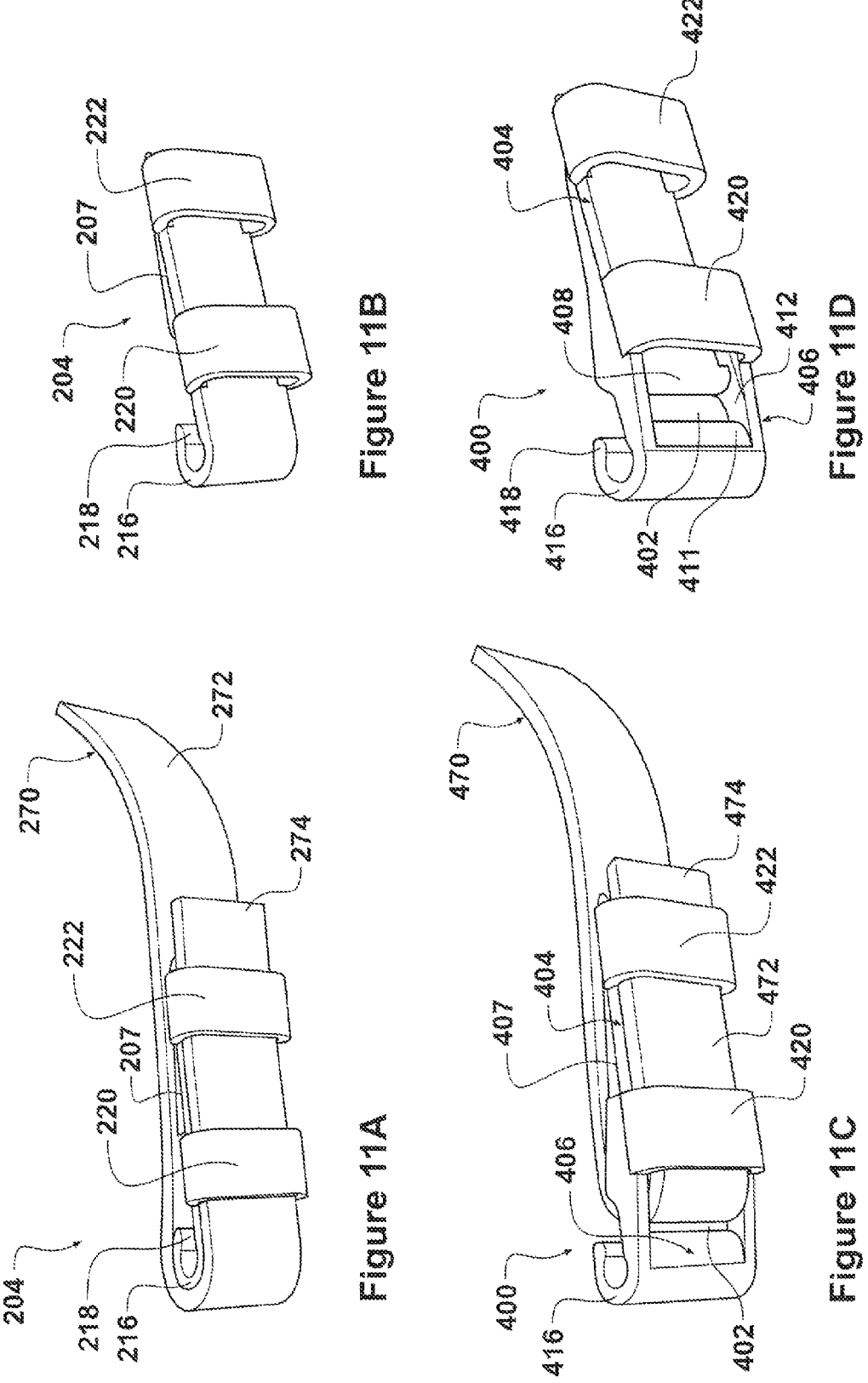
FIG. 11*a* is a perspective view of the headgear gripping portion of the user interface assembly of FIG. 6 connected to the headgear strap.
FIG. 11*b* is a perspective view of the headgear gripping portion of the user interface assembly of FIG. 6.
FIG. 11*c* is a perspective view of a headgear connector connected to a headgear strap.
FIG. 11*d* is a perspective view of the headgear connector of FIG. 11*c*.

The frame body coupling 216 further comprises a frame body coupling projection 218 towards an end of the frame body coupling 216 (FIG. 11c). The frame body coupling projection 218 can be in the form of a lip. The frame body coupling projection 218 functions to retain the frame body coupling 216 to the frame body post 269 after the two components are coupled. The frame body coupling projection 218 provides a physical impediment to the removal of the headgear gripping portion 204 from the headgear connecting portion 206, and therefore the frame body 261. The headgear gripping portion 204 is therefore coupled to the headgear connecting portion 206 with a snap-fit, clip fit, or interference fit between the frame body coupling 216 and the frame body post 269. The headgear connector 200 is removed from the frame body 261 by applying a force that overcomes the snap-fit, clip fit or interference fit.

It will be appreciated that an opposite configuration could be provided in which the frame body coupling 216 can be in the form of a post, and the frame body 261 can comprise a curved elongate member configured to couple to the post.

The headgear gripping portion 204 also comprises a first headgear connector collar 220 and a second headgear connector collar 222, through each of which the looped back part of the headgear strap 272 can pass, to help retain the strap 272 on the headgear gripping portion 204. The first headgear connector collar 220 is spaced apart on the headgear gripping portion 204 from the second headgear connector collar 222. In at least one configuration, the headgear gripping portion 204 comprises only the first headgear connector collar 220.

To connect the headgear 270 to the frame 254, the headgear strap end 274 is passed through the passage 202 from a first direction, with the strap 272 parallel with and adjacent the interior surface of headgear gripping portion 204, and pulled through the passage 202 until the desired fit of the patient interface is achieved. The strap end 274 is then looped back on itself in a second direction and pulled back towards the remainder of strap 272, parallel to and adjacent the exterior surface of connector 200. The headgear strap end 274 is fed through collars 220, 222. Once so adjusted, rotation of the headgear gripping portion 204 towards the patient interface brings strap 272 into contact with the gripping element 207, which grips the headgear strap 272 and retains the strap 272 on the headgear connector 200.

Rotating the headgear gripping portion 204 with respect to the frame body 261 brings the gripping element 207 into contact with the headgear strap 272, thereby connecting the headgear connector 200 to the headgear strap 272. The gripping element 207 grips the headgear strap 272 when they are brought into contact. The headgear connector 200 is disconnected from the headgear strap 272 by rotating the headgear gripping portion 204 about the frame body post 269 away from the user.

In at least one configuration, the passage 202 can be dimensioned to provide a resistive force on the headgear strap 272 passing through the passage 202 as described with reference the headgear connector 100 of FIGS. 2-4.

At least one embodiment of the user interface 250 may comprise more than two frame body lateral portions 264. For example, a full-face user interface may comprise four frame body lateral portions 264.

Figure 42:
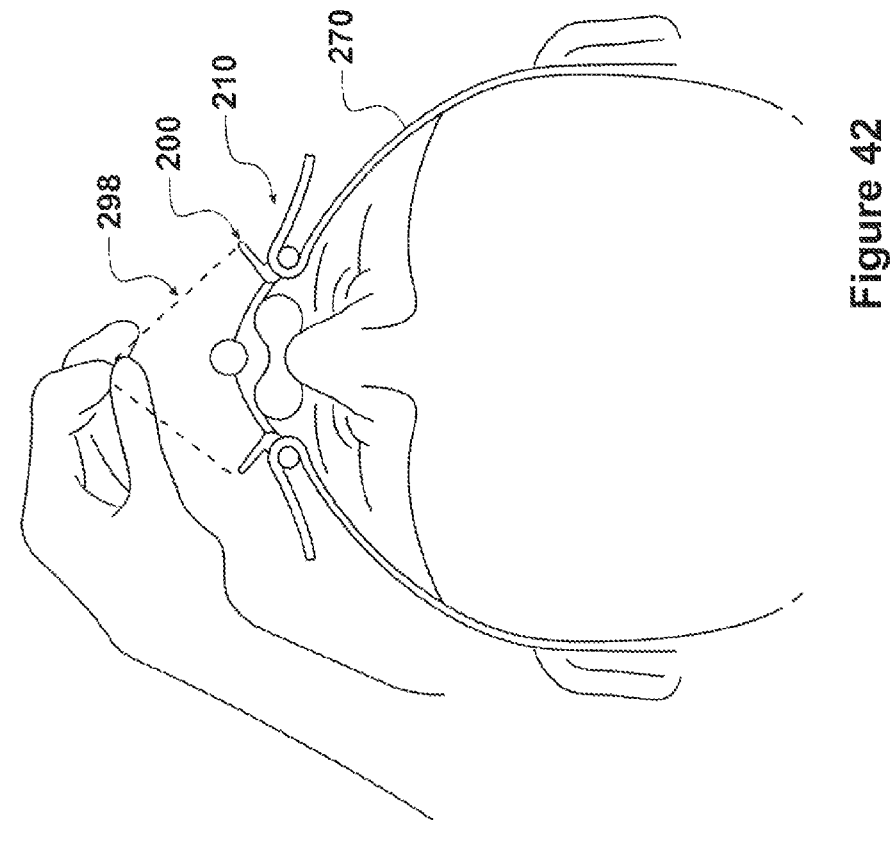
FIG. 42 is a top view of a user using a release member of a user interface assembly to release the connection between the user interface and a headgear.
Figure 43:
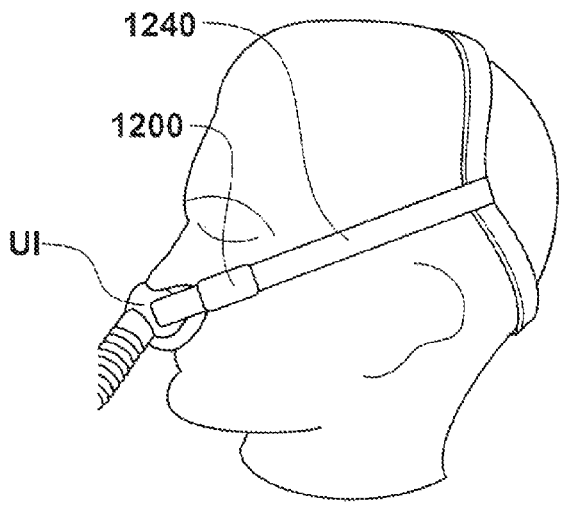
FIG. 43 is a side view of a user interface assembly comprising a frame with a yoke, and a headgear comprising a headgear connector in accordance with another aspect of this disclosure.
Figure 44:
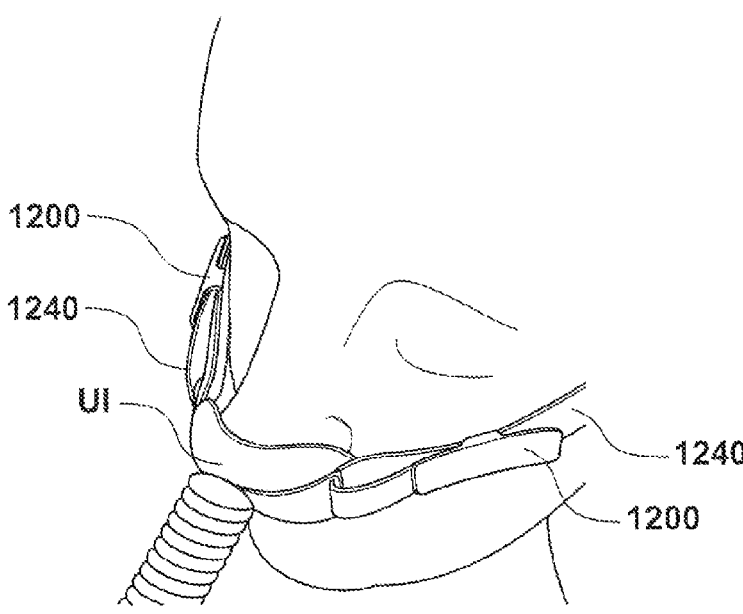
FIG. 44 is a perspective view of the user interface assembly of FIG. 43.
Figure 46:
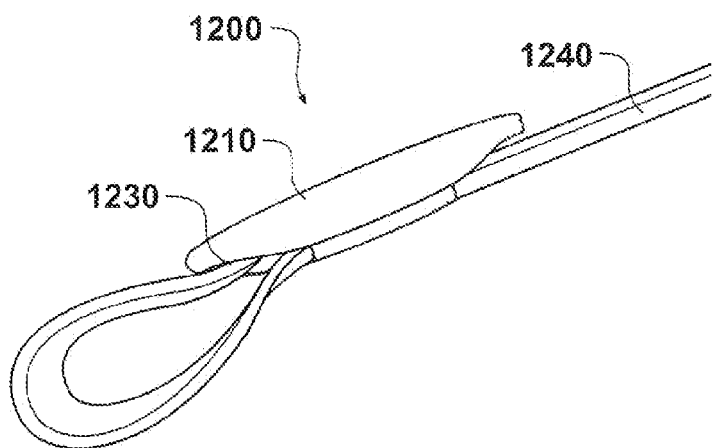
FIG. 46 is an enlarged side view of the headgear strap and the headgear connector of FIGS. 43 to 45.

At least one configuration of the user interface 250 can comprise a release member 298 as shown in FIG. 42. The release member 298 can be in the form of an elongated release member. The release member 298 can be in the form of a release cord. The release member 298 is actuated to release the connection between the headgear 270 and the user interface 250. In particular, the release member 298 can be actuated to release the connection between the headgear strap 272 and the headgear gripping portion 204.

The release member 298 is connected to the headgear connector 200. In particular, the release member 298 is connected to the headgear gripping portion 204. For example, the release member 298 may be connected to the second collar 222 of the headgear gripping portion 204. Actuating the release member 298 rotates the headgear gripping portion 204 about the frame body post 269 and therefore the headgear connecting portion 206, away from the face of the user. Actuating the release member 298 therefore disconnects the headgear connector 200 from the headgear strap 272. The release member 298 can connect more than one headgear gripping portion 204 on the user interface 250. For example, the release member 298 can connect to two opposing headgear gripping portions 204 as shown in FIG. 42. Actuation of the release member 298 can simultaneously disconnect the multiple headgear gripping portions 204 from the headgear 270. The release member 298 can make it easier for the user to disconnect the headgear 270 from the user interface 250 by providing a member that is easier for the user to grip than the headgear gripping portion 204. As such, the release member 298 can be a quick-release.

In at least one configuration, the frame body 261 is formed from, or comprises a polymer. The polymer can be polycarbonate that rigidly defines a 3-dimensional profile of the frame body 261. In at least one configuration, the headgear gripping portion 204 comprises a polymer. The polymer can be a polycarbonate that rigidly defines a 3-dimensional profile of the headgear gripping portion 204.

In at least one configuration, the headgear gripping portion 204 is fixedly connected to the frame body 261, whilst remaining rotatable with respect to the headgear connecting portion 206. That is, the headgear gripping portion 204 is not removably connected to the frame body 261. In said configuration, once the headgear gripping portion 204 is connected to the frame body 261 (for example, during manufacture), it is not removable without the destruction of at least a part of the headgear gripping portion 204, headgear connecting portion 206 and/or the frame body 261. For example, the frame body coupling 216 can comprise a large majority (e.g., 85%) of a hollow cylinder, or the entirety of a hollow cylinder, surrounding a large majority (e.g., 85%), or entirety of the frame body post 269. The fixedly connected headgear gripping portion 204 can therefore still be rotatably connected to the frame body 261, however, because of the extent to which the frame body coupling 216 surrounds the frame body post 269, the parts cannot be separated.

In at least one configuration, the headgear connector 200 can be used with a user interface 250 configured to deliver breathing gas to one or more of the user's mouth and nose without a sealed connection. For example, the headgear connector 200 can be used with a nasal cannula 250.

FIGS. 11c, 11d, 12b and 13b show an embodiment of a headgear connector 400. A user interface assembly 410 comprises a user interface 450 which is configured to secure against the face of a user to define a substantially sealed breathing chamber, and headgear 470 which is configured to connect to the user interface 450 and position and secure the user interface 450 in place on the user's face.

The user interface 450 comprises a frame 454, a cushion module 452, and a breathing gas circuit connector 453. The user interface 450 may comprise the headgear connector 400. In the illustrated configuration, the cushion module 452 is removably connected to the frame 454. The headgear connector 400 is configured to connect to the frame 454. The headgear connector 400 facilitates connection of the frame 454 to the headgear 470.

The user interface 450 is configured to be removably connected to headgear 470 via the headgear connector 400. The headgear connector 400 is an intermediate component through which the headgear 470 is connected to the frame 454. The headgear 470 comprises at least one headgear strap 472. The headgear strap 472 is configured to connect with the user interface 450. The headgear strap 472 comprises an elongated portion of the headgear 470. The headgear 470 and headgear strap 472 can be substantially similar to the headgear 70 and headgear strap 72 described with reference to FIGS. 2-4, and/or the headgear 270 and headgear strap 272 described with reference to FIGS. 6-11c. The headgear connector 400 connects to the headgear strap 472.

The headgear connector 400 facilitates the connection of the frame 454 to the headgear 470. The headgear connector 400 is configured to connect or couple to the frame 454. The headgear connector 400 cooperates with the headgear strap 472 to connect the frame 454 to the headgear strap 472, and therefore to connect the user interface 450 to the headgear 470.

The headgear connector 400 is configured to grip a portion of the headgear 470. The headgear connector 400 comprises a headgear connecting portion 406 and a headgear gripping portion 404. In this example, the headgear connecting portion 406 and the headgear gripping portion 404 are integrated into a single component forming the headgear connector 400. The headgear gripping portion 404 is configured to grip the headgear strap 472. The headgear gripping portion 404 comprises a gripping element 407 that is configured to grip the headgear strap 472. The gripping element 407 can grip the headgear strap 472 as described with reference to gripping element 107 and/or gripping element 207. This secures the headgear 470 with respect to the frame 454. The headgear connector 400 in this example comprises a headgear connector exterior surface 426 and a headgear connector interior surface 424.

In the illustrated configuration, the headgear connector interior surface 424 comprises the gripping element 407. The gripping element 407 is secured to the headgear connector interior surface 424. The illustrated gripping element 407 is adhesively bonded to the headgear connector interior surface 424.

The headgear connector 400 comprises a frame coupling 416. The frame coupling 416 is configured to couple the headgear connector 400 to a frame post 469. The frame coupling 416 couples to the frame post 469. The frame coupling 416 is curved to form a channel which clips onto and receives the frame post 469 such that the headgear connector 400 is rotatable about the frame post 469. The frame coupling 416 and frame post 469, when coupled, provide a hinge. The gripping element 407, being laterally displaced on the headgear connector 400 with respect to the hinge is therefore rotatable with respect to the frame 454 about the hinge.

Figures 13A, 13B:
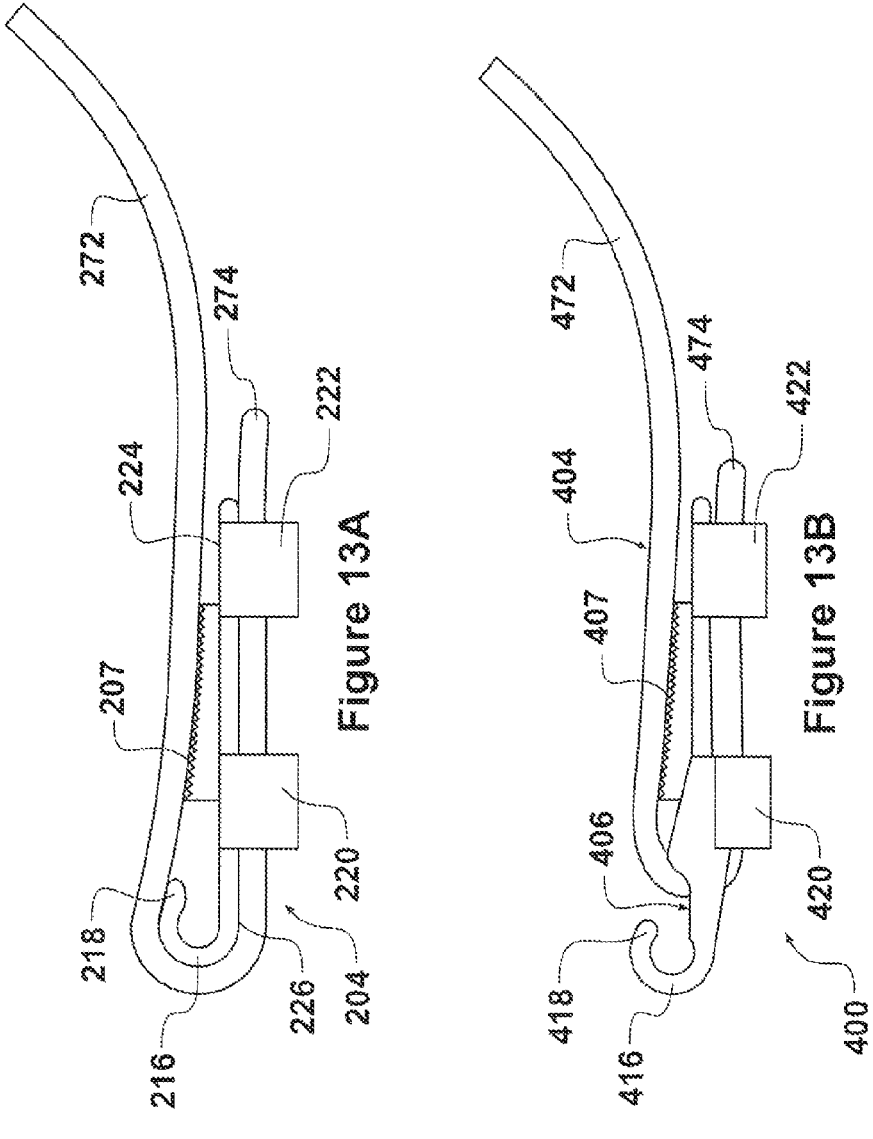
FIG. 13*a* is a top view of the headgear gripping portion of the user interface of FIG. 6 connected to the headgear strap.
FIG. 13*b* is a top view of the headgear connector of FIG. 11*c* connected to the headgear strap.

The frame coupling 416 further comprises a frame coupling projection 418 towards the end of the frame coupling 416 (FIG. 13b). The frame coupling projection 418 can be in the form of a lip. The frame coupling projection 418 functions to retain the frame coupling 416 to the frame post 469 after the two components are coupled. The frame coupling 416 and/or frame coupling projection 418 can be substantially similar to frame body coupling 216 and frame body coupling 218 previously described. The headgear connector 400 is therefore removably coupled to the frame 454.

It will be appreciated that an opposite configuration could be provided in which the frame coupling 416 can be in the form of a post, and the frame 454 can comprise a curved elongate member configured to couple to the post.

The headgear connector 400 also comprises a first headgear connector collar 420 and a second headgear connector collar 422, through each of which the looped back part of the headgear strap 472 can pass, to help retain the strap 472 on the headgear connector 400. The first headgear connector collar 420 is spaced apart on the headgear connector 400 from the second headgear connector collar 422. In at least one configuration, the headgear connector 400 comprises only the first headgear connector collar 420.

The headgear connecting portion 406 in this example comprises a headgear receiving passage 402. The passage 402 is configured to receive the headgear strap 472. The passage 402 is defined by an aperture or hole or slot in the headgear connector 400. The passage 402 is substantially oblong, and comprises a passage outer wall 408, a passage inner wall 411, a passage upper wall 412 and a passage lower wall 414. The walls 408, 411, 412 and 414 defining the passage are integrally formed with the headgear connector 400. The passage outer wall 408 is rounded as shown in FIG. 11d. The passage inner wall 411 is rounded, also as shown in FIG. 11d. Rounding the passage outer wall 408 and/or the passage inner wall 411 can improve the motion of the headgear strap 472 as it is directed through the passage 402 by reducing friction, or the likelihood that the headgear strap will get caught on an edge or corner of the passage 402.

The hole defining the passage 402 extends from the headgear connector interior surface 424, through the headgear connector 400, to the headgear connector exterior surface 426. The passage 402 in this example is substantially rectangular, corresponding to, but slightly larger than, the rectangular cross section of the headgear strap 472. In at least one configuration, the passage 402 can be generally circular, oval, trapezoidal, another polygon, or have one or more curved corners or walls. The passage 402 is disposed on the headgear connector 400, between the headgear gripping portion 404 and the frame coupling 416. The passage 402 is disposed on the headgear connector 400, between the first collar 420 and the frame coupling 416.

Figures 12A, 12B:
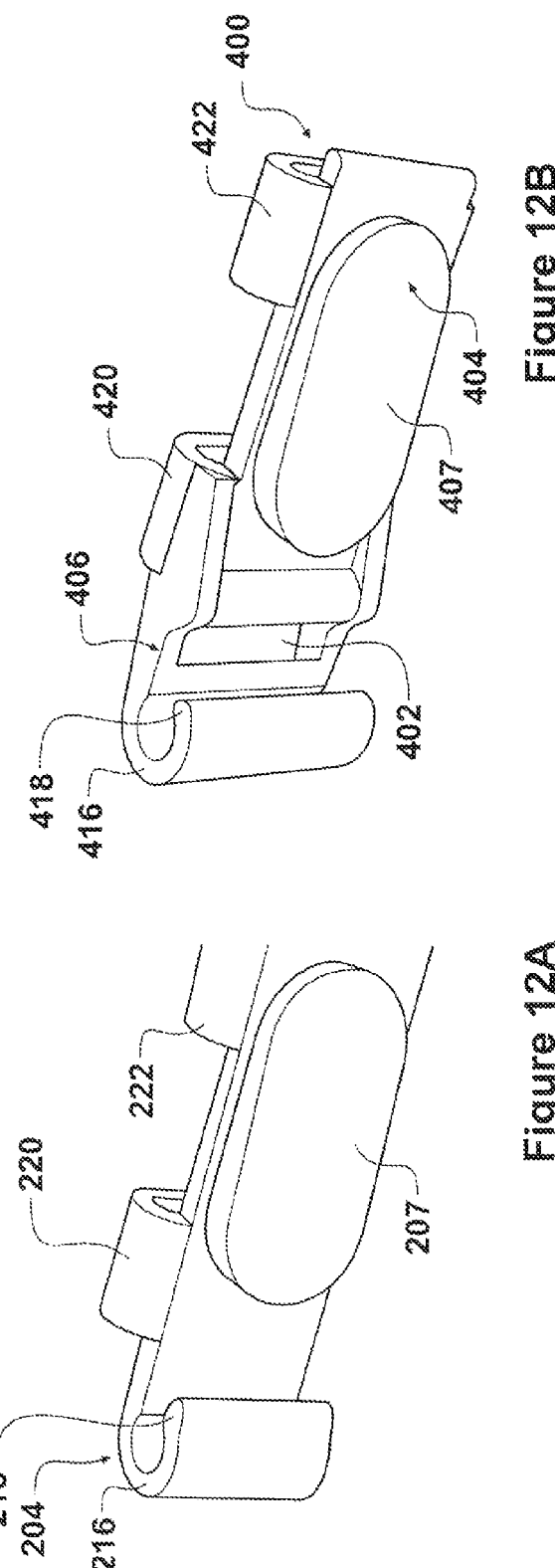
FIG. 12*a* is another perspective view of the headgear gripping portion of the user interface assembly of FIG. 6.
FIG. 12*b* is another perspective view of the headgear connector of FIG. 11*c*.

To secure the headgear 470 to the headgear connector 400, a headgear strap end 474 is passed through the passage 402 in a direction from the headgear connector interior surface 424 towards the headgear connector exterior surface 426 as shown in FIG. 11e and FIG. 12a. The headgear strap end 474 is looped outwards from the passage 402 and towards the first headgear connector collar 420. The headgear strap end 474 is passed through an opening of the first headgear connector collar 420 and an opening of the second headgear connector collar 422. The collars 420, 422 align and/or retain the headgear strap 472 close to the headgear connector 400. This can assist in increasing the ease of use of the adjustment mechanism, by increasing the accuracy with which the user may adjust the length of the headgear strap 472 to be secured. When the headgear strap 472 has been passed through the first headgear connector collar 420 and the second headgear connector collar 422, the portion of the headgear strap 472 that has been passed through the passage 402 will rotate with the headgear connector 400 about the frame post 469 in unison as the headgear connector 400 is rotated about the frame post 469. The user can tighten the headgear 470 by pulling the headgear strap end 474 further away from the passage 402 in the direction of the first headgear connector collar 420. When the headgear 470 is positioning the user interface 450 to the user's face sufficiently, it can be connected to the headgear gripping portion 404 to secure the user interface 450 in place.

Rotating the headgear connector 400 about the frame post 469 towards the user brings the headgear gripping portion 404 into contact with the headgear strap 472, thereby connecting the headgear connector 400 to the headgear strap 472. The headgear connector 400 is disconnected from the headgear strap 472 by rotating the headgear connector 400 about the frame body post 469 away from the user. The gripping portion 407 will release its grip on the headgear strap 472 when the headgear connector 400 is rotated in this way.

In at least one configuration, the passage 402 can be dimensioned to provide a resistive force on the headgear strap 472 passing through the passage 402 as described with reference the headgear connectors previously disclosed.

At least one configuration of the user interface 450 can comprise a release member 498. The release member can be similar to that described with reference to FIG. 42. The release member 498 can be in the form of an elongated release member. The release member 498 can be in the form of a release cord. The release member 498 is actuated to release the connection between the headgear 470 and the user interface 450. In particular, the release member 498 can be actuated to release the connection between the headgear strap 472 and the gripping element 407.

The release member 498 is connected to the headgear connector 400. For example, the release member 498 may be connected to the second collar 422 of the headgear gripping portion 404. Actuating the release member 498 rotates the headgear connector 400 about the frame body post 469, away from the face of the user as described with reference to release member 298. Actuating the release member 498 therefore disconnects the headgear connector 400 from the headgear strap 472.

In at least one configuration, the frame 454 is formed from, or comprises a polymer. The polymer can be polycarbonate that rigidly defines a 3-dimensional profile of the frame 454. In at least one configuration, the headgear connector 400 comprises a polymer. The polymer can be a polycarbonate that rigidly defines a 3-dimensional profile of the headgear connector 400.

The illustrated headgear gripping portion 404 is adhesively bonded to the headgear connector interior surface 424. Alternatively, the headgear gripping portion 404 can be secured to the headgear connector interior surface 424 by another method, for example high frequency welding, chemical bonding etc. In at least one configuration, the headgear gripping portion 404 can be an integrally formed part of the headgear connector 400 and/or the headgear connector interior surface 424 as described with reference to previous embodiments.

In at least one configuration, the headgear connector 400 is fixedly connected to the frame 454. That is, the headgear connector 400 is not removably connected to the frame 454. In said configuration, once the headgear connector 400 is connected to the frame 454, it is not removable without the destruction of at least a part of the headgear connection 400 and/or the frame 454. For example, the frame coupling 416 can comprise a large majority (e.g., 85%) of a hollow cylinder, or the entirety of a hollow cylinder, surrounding a large majority (e.g., 85%), or entirety of the frame post 469 as described with reference to previous embodiments.

In at least one configuration, the headgear connector 400 can be used with a user interface 450 configured to deliver breathing gas to one or more of the user's mouth and nose without a sealed connection. For example, the headgear connector 400 can be used with a nasal cannula 450.

FIGS. 14-16 show an embodiment of a headgear connector 300. A user interface assembly 310 comprises a user interface 350 which is configured to secure against the face of the user to define a substantially sealed breathing chamber, and headgear 370 which is configured to connect to the user interface 350 and position and secure the user interface 350 in place on the user's face.

The user interface 350 comprises a frame 354, a cushion module 352, and a breathing gas circuit connector 353. The user interface 350 may comprise the headgear connector 300. In the illustrated configuration, the cushion module 352 is removably connected to the frame 354. The headgear connector 300 is configured to connect to the frame 354. The headgear connector 300 facilitates connection of the user interface 350 to the headgear 370.

The user interface 350 is configured to be removably connected to headgear 370 via the headgear connector 300.

As such, the headgear connector 300 is removably connectable to the headgear 370. The headgear connector 300 is an intermediate component through which the headgear 370 is connected to the user interface 350. The headgear 370 comprises at least one headgear strap 372. The headgear strap 372 is configured to connect with the user interface 350. The headgear strap 372 comprises an elongated portion of the headgear 370. The headgear 370 and headgear strap 372 are substantially similar to the headgear 70, 270, 470 and headgear strap 72, 272, 472 described with reference to previous figures. The headgear connector 300 is configured to connect to the headgear strap 372.

The headgear connector 300 facilitates the connection of the frame 354 to the headgear 370. The headgear connector 300 is configured to connect or couple to the frame 354. The headgear connector 300 cooperates with the headgear strap 372 to connect the frame 354, and therefore to connect the user interface 350 to the headgear 370.

The headgear connector 300 is configured to grip the headgear strap 372. The headgear connector 300 comprises a base portion 303 and a moveable portion 305. The base portion 303 and the moveable portion 305 together are configured to grip the headgear strap 372. The moveable portion 305 can move with respect to the base portion 303. In the illustrated configuration, the moveable portion 305 is in the form of a rotatable portion 305. The rotatable portion 305 can rotate with respect to the base portion 303. The base portion 303 comprises a base portion interior surface 324. The base portion 303 comprises a base portion exterior surface 326. The rotatable portion 305 comprises a rotatable portion interior surface 328. The rotatable portion 305 comprises a rotatable portion exterior surface 330.

Figures 16A, 16B:
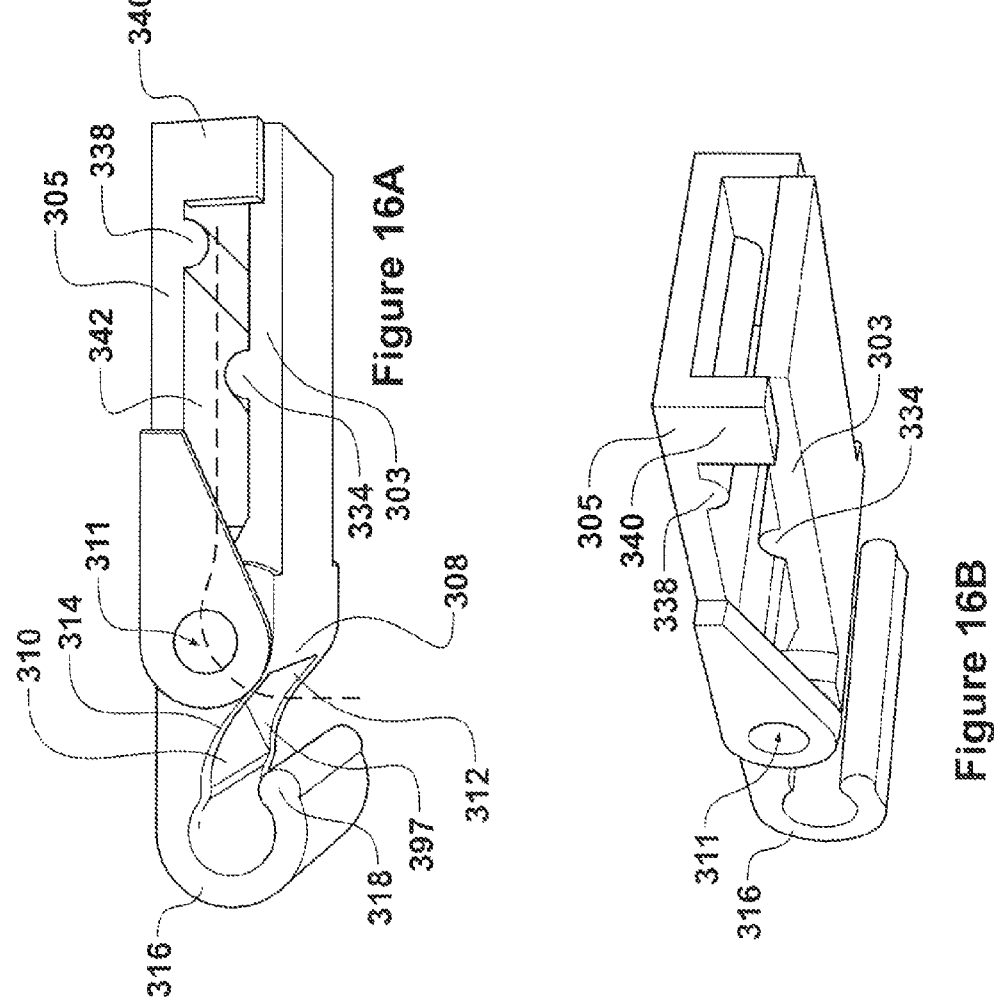
FIG. 16*a* is a perspective view of the headgear connector of FIG. 14*a* in the closed position.
FIG. 16*b* is a perspective view of the headgear connector of FIG. 14*a* in the closed position.

The headgear connector 300 comprises a frame coupling 316. The frame coupling 316 is configured to couple the headgear connector 300 to the frame 354. The frame 354 comprises a frame post 369. The frame coupling 316 connects to the frame post 369. The frame coupling 316 is curved to form a channel which clips onto and receives the frame post 369 such that the headgear connector 300 is rotatable about the frame post 369. The frame coupling 316 and frame post 369, when coupled, provide a hinge. The frame coupling 316 further comprises a frame coupling projection 318 towards the end of the frame coupling 316 (FIG. 16a). The frame coupling 316 and frame post 369 can be substantially similar to previously described frame couplings and/or frame posts. In the illustrated configuration, the frame coupling 316 is integrally formed with the base portion 303.

The headgear connector 300 comprises a headgear receiving passage 302. The passage 302 is configured to receive the headgear strap 372. The passage 302 is defined by a passage opening 397 in the headgear connector 300, and a headgear connecting channel 342 being defined by the space between the base portion 303 and the rotatable portion 305. The passage opening 397 can be in the form of a hole, aperture or slot. The passage opening 397 is substantially oblong, and comprises a passage outer wall 308, a passage inner wall 311, a passage upper wall 312 and a passage lower wall 314. The walls 308, 311, 312 and 314 defining the passage opening 397 are integrally formed with the base portion 303. The passage outer wall 308 is rounded as shown in FIG. 16d. The passage inner wall 311 is rounded. Rounding the passage outer wall 308 and/or the passage inner wall 311 can improve the motion of the headgear strap 372 as it is directed through the passage opening 397 by reducing friction, or the likelihood that the headgear strap will get caught on an edge or corner of the passage opening 397. The passage opening 397 is disposed on the base portion 303 between the connection 311 and the frame coupling 316.

The passage opening 397 extends from the base portion interior surface 324, through the base portion 303, to the base portion exterior surface 326. The passage opening 397 in this example is substantially rectangular, corresponding to, but slightly larger than the rectangular cross section of the headgear strap 372. In at least one configuration, the passage opening 397 can be generally circular, oval, trapezoidal, another polygon, or have one or more curved corners or walls.

The headgear connector 300 comprises at least one headgear connector post 307. The headgear connector post 307 extends outwards from a side of the headgear connector 300. The headgear connector post 307 can extend outwards from a side of the base portion 303. The illustrated headgear connector post 307 is cylindrical. The rotatable portion 305 comprises a connector opening 309. The connector opening 309 is sized and shaped to correspond to the headgear connector post 307. In other words, the connector opening 309 forms a female component of a connection 311 between the rotatable portion 305 and the base portion 303. The headgear connector post 307 forms a male component of the connection 311. The headgear connector post 307 is received by the connector opening 309 such that the rotatable portion 305 and the base portion 303 are rotatably connected at the connection 311. In other words, the connection 311 allows the rotatable portion 305 to rotate with respect to the base portion 303 such that the connection 311 is a hinge. In the illustrated configuration, a headgear connector post 307 extends from each side of the base portion 303. The headgear connector post 307 may also extend through the base portion 303. The rotatable portion 305 comprises a pair of connector openings 309 configured to cooperate with the pair of headgear connecting posts 307.

The rotatable portion 305 can be disconnected or removed from the base portion 303. The rotatable portion 305 can be deformed so that the connector opening 309 disconnects from the headgear connector post 307. This can beneficially allow replacement of the rotatable portion 305, and/or the base portion 303, in the event that either component is damaged. Either component can be replaced individually, without the need to replace the entire headgear connector 300.

Figures 14A, 14B:
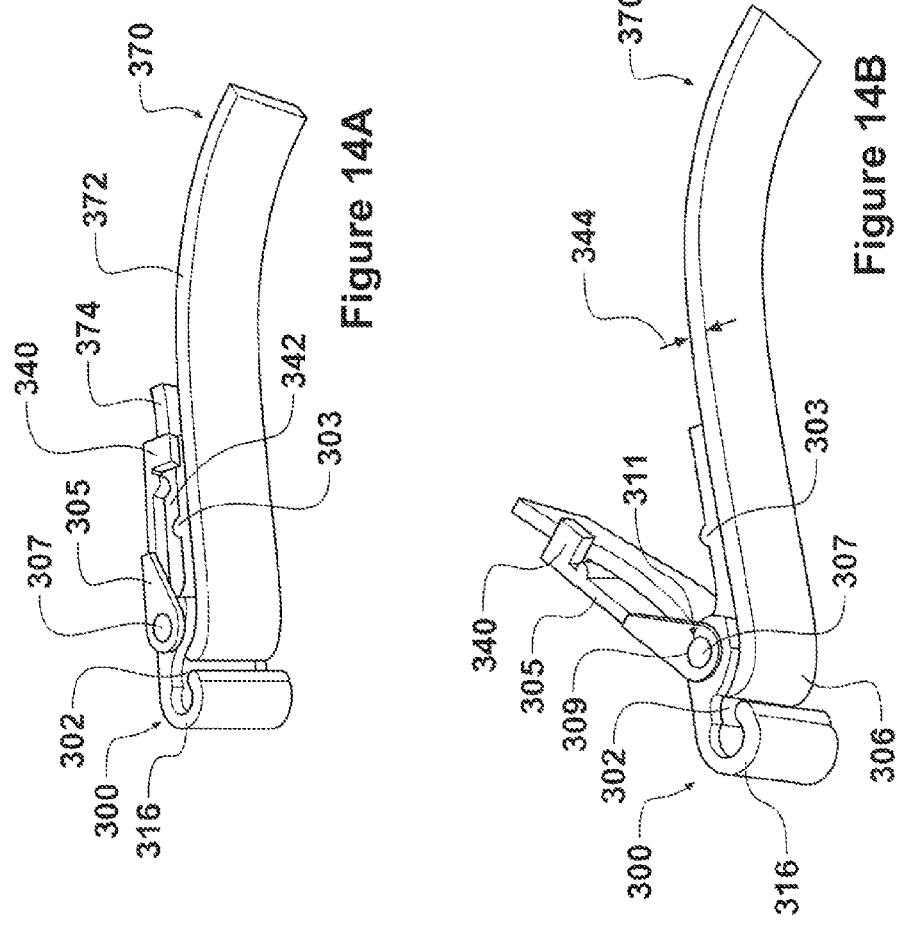
FIG. 14*a* is a perspective view of a headgear connector with a base portion and a rotatable portion, where the headgear connector is connected to a headgear strap in a closed position.
FIG. 14*b* is a perspective view of the headgear connector of FIG. 14*a* in an open position, with the headgear strap passed through a passage of the headgear connector.
Figure 15B:
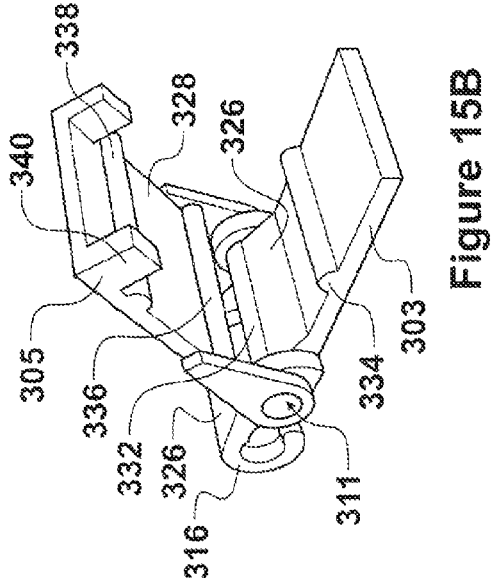
FIG. 15*b* is a perspective view of the headgear connector of FIG. 14*a* in the open position.
Figure 15A:
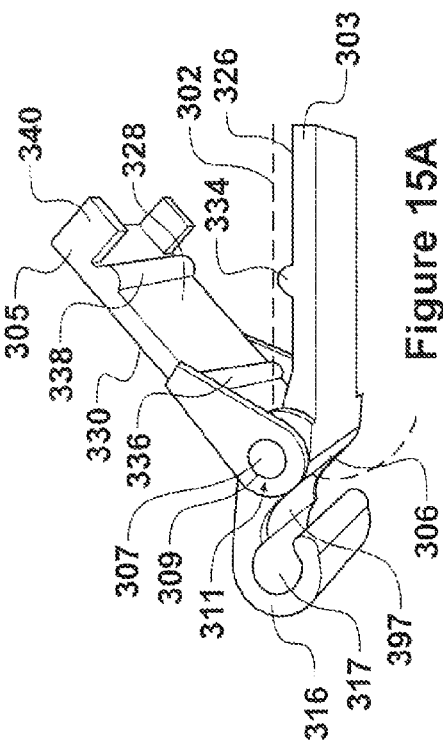
FIG. 15*a* is a perspective view of the headgear connector of FIG. 14*a* in the open position.

The rotatable portion 305 can rotate with respect to the base portion 303 between a closed position (shown in FIG. 14a, FIG. 16a and FIG. 16b), and an open position (shown in FIG. 14b, FIG. 15a and FIG. 15b). The headgear connecting channel 342 is defined by the space between the base portion exterior surface 326 and the rotatable portion interior surface 328. The headgear connecting channel 342 is configured to receive the headgear strap 372. When in the closed position, the headgear connector 300 grips the headgear strap 372.

The base portion 303 comprises a first gripping formation 332. The base portion 303 also comprises a second gripping formation 334. The rotatable portion 305 comprises a first rotatable gripping formation 336. The rotatable portion 305 also comprises a second rotatable gripping formation 338. The first gripping formation 332 is adjacent to the passage opening 397. The first gripping formation 332 can form at least part of the passage outer wall 308. The first gripping formation 332 is closer to the connection 311 than the second gripping formation 334. The first rotatable gripping formation 336 is closer to the connection 311 than the second rotatable gripping formation 338. The gripping formations 332, 334, 336, 338 grip the headgear strap 372 when the headgear connector 300 is in the closed position.

The first gripping formation 332 is rounded. The second gripping formation 334 is rounded. The first rotatable gripping formation 336 is rounded. The second rotatable gripping formation 338 is rounded. Alternatively, one or more of the formations 332, 334, 336 and/or 338 can be rectangular, chamfered, or another shape.

The rotatable portion 305 comprises a retaining structure 340. The retaining structure 340 is configured to retain the headgear connector 300 in the closed position when the rotatable portion 305 is brought towards the base portion 303. The retaining structure 340 can form a snap-fit connection, for example, with the base portion 303. Alternately, the retention can be magnetic, or of another form. The illustrated rotatable portion 305 comprises a pair of retaining structures 340.

To secure the headgear 370 to the headgear connector 300, the rotatable portion 305 is rotated such that the headgear connector 300 is in the open position shown in FIGS. 15a and 15b. The headgear strap end 374 is passed through the passage opening 397 in a direction from the base portion interior surface 324 towards the base portion exterior surface 326 as shown in FIG. 14b. The headgear strap end 374 is looped outwards from the passage opening 397 and between the rotatable portion 305 and the base portion 303. In other words, the headgear strap 372 is passed through the headgear connecting channel 342. The headgear connecting channel 342 helps align and/or retain the headgear strap 372 close to the headgear connector 300. This can assist in increasing the ease of use of the adjustment mechanism, by increasing the accuracy with which the user may adjust the length of the headgear strap 372 to be secured. When the headgear strap 372 has been passed through the passage 302, the portion of the headgear strap 372 that has been passed through the headgear connecting channel 342 will rotate with the headgear connector 300 about the frame post 369 in unison as the headgear connector 300 is rotated about the frame post 369. The user can tighten the headgear 370 by pulling the headgear strap end 374 further away from the passage opening 397 in the direction of the headgear connecting channel 342. When the headgear 370 is positioning the user interface 350 to the user's face sufficiently, it can be secured in place with the headgear connector 300 to secure the user interface 350 in place.

Rotating the rotatable portion 305 towards the base portion 303 brings each of the rotatable portion 305 and the base portion 303 into contact with the headgear strap 372. Rotating the rotatable portion 305 towards the base portion 303 such that the headgear connector 300 is in the closed position therefore causes the headgear connector 300 to grip the headgear strap 372. Securing the headgear connector 300 in the closed position using the retaining structure 340 connects the headgear connector 300 to the headgear strap 372. A frictional connection is formed between the rotatable portion 305, the base portion 303 and the headgear strap 372.

The frictional connection is formed because a thickness of the headgear connecting channel 342 is less than a transverse headgear strap thickness 344 of the headgear strap 372 passing through the headgear connecting channel 342 of the passage 302. The thickness of the headgear connecting channel 342 at the gripping formations 332, 334, 336, 338 is less than an uncompressed transverse headgear strap thickness 344. In other words, a distance between at least a portion of the base portion exterior surface 326 and the rotatable portion interior surface 328 is less than the uncompressed transverse headgear strap thickness 344 of the headgear strap 372 passing through the headgear connecting channel 342. Rotating the rotatable portion 305 towards the base portion 303 can therefore be said to reduce a thickness of the headgear connecting channel 342.

The first gripping formation 332, second gripping formation 334, first rotatable gripping formation 336 and/or second rotatable gripping formation 338 provide regions of reduced thickness within the headgear connecting channel 342. Friction between one or more of the first gripping formation 332, second gripping formation 334, first rotatable gripping formation 336 and second rotatable gripping formation 338, and the headgear strap 372 can provide or enhance the frictional connection between the headgear strap 372 and the headgear connector 300 when the headgear connector 300 is in the closed position. The gripping formations 332, 334, 336 and 338 project into the headgear connecting channel 342 to produce regions of reduced channel thickness. The thickness of the headgear connecting channel 342 therefore changes along the length of the headgear connecting channel 342 with the headgear connector in the closed position. The headgear connecting channel 342 can therefore be considered a semi-tortuous channel.

Rotating the rotatable portion 305 away from the base portion 303, such that the headgear connector 300 is moved into the open position releases the connection between the headgear connector 300 and the headgear strap 372.

In at least one configuration, the passage opening 397 can be dimensioned to provide a resistive force on the headgear strap 372 passing through the passage opening 397 as described with reference to headgear connectors previously disclosed.

At least one configuration of the user interface 350 can comprise a release member 398. The release member can be similar to that described with reference to FIG. 42. The release member 398 can be in the form of an elongated release member. The release member 398 can be in the form of a release cord. The release member 398 is actuated to release the connection between the headgear 370 and the user interface 350. In particular, the release member 398 can be actuated to release the connection between the headgear strap 372 and one or more headgear connector 300.

The release member 398 is connected to the headgear connector 300. For example, the release member 398 may be connected to the rotatable portion 305. Actuating the release member 398 rotates the rotatable portion 305 about the about the base portion 303, away from the face of the user. Actuating the release member 398 therefore disconnects the headgear connector 300 from the headgear strap 372 by moving the headgear connector 300 into the open position. The release member 398 can connect to more than one headgear connector 300 on the user interface 350. For example, the release member 398 can connect to two opposing headgear connectors 300. Actuation of the release member 398 can simultaneously disconnect the multiple headgear connectors 300 from the headgear 370. The release member 398 can make it easier for the user to disconnect the headgear 370 from the user interface 350 by providing a member that is easier for the user to grip than the headgear connector 300. As such, the release member 398 can be a quick-release.

In at least one configuration, the frame 354 is formed from, or comprises a polymer. The polymer can be polycarbonate that rigidly defines a 3-dimensional profile of the frame 354. In at least one configuration, the headgear connector 300 comprises a polymer. The polymer can be a polycarbonate that rigidly defines a 3-dimensional profile of the headgear connector 300. In at least one form, the base portion 303 comprises the polymer. In at least one form, the rotatable portion 305 comprises the polymer. In at least one form, both the base portion 303 and the rotatable portion 305 comprise the polymer.

In at least one configuration, the headgear connector 300 is fixedly connected to the frame 354. That is, the headgear connector 300 is not removably connected to the frame 354. In said configuration, once the headgear connector 300 is connected to the frame 354, it is not removable without the destruction of at least a part of the headgear connection 300 and/or the frame 354.

In at least one configuration, at least a portion of the headgear connector 300 is integrally formed with the frame 354. For example, the base portion 303 can be integrally formed with the frame 354. In at least one configuration, the frame 354 comprises a frame body 361 and a yoke 367 (as described in previous embodiments), and the headgear connector 300 is at least partially integrally formed with the yoke 367. For example, the base portion 303 can be integrally formed with the yoke 367.

The illustrated base portion 303 comprises the headgear connector post 307, and the illustrated rotatable portion 305 comprises the pair of connector openings 309. In an alternative configuration, the base portion 303 may comprise one or more connector opening/s 309, and the rotatable portion 305 may comprise the headgear connector post 307.

The illustrated rotatable portion 305 can be removed from the base portion 303. In at least one configuration, the rotatable portion 305 is permanently connected to the base portion 303. This can reduce the likelihood that the user will disconnect the rotatable portion 305 and lose the component.

In at least one configuration, the headgear connector 300 can be used with a user interface 350 configured to deliver breathing gas to one or more of the user's mouth and nose without a sealed connection. For example, the headgear connector 300 can be used with a nasal cannula 350.

Figure 17A:
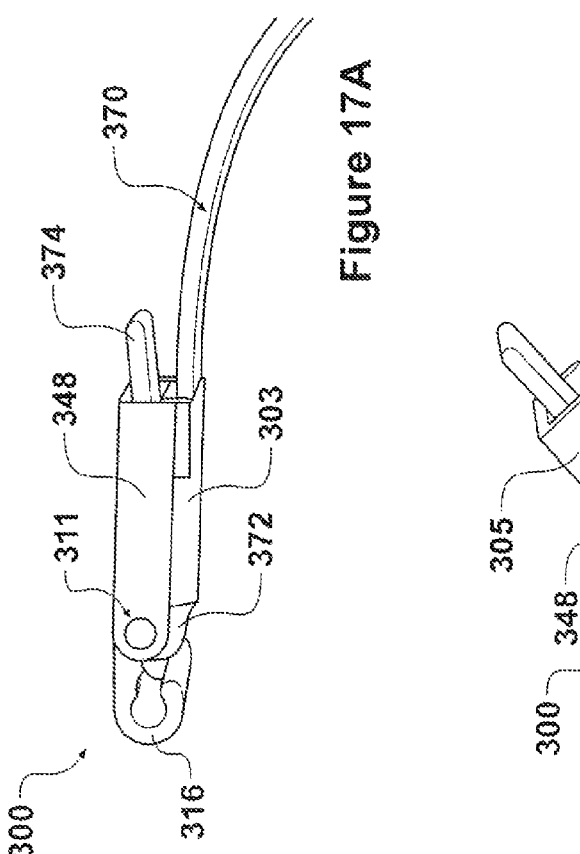
FIG. 17*a* is perspective view of a headgear connector with a base portion and a rotatable portion, where the headgear connector is connected to a headgear strap in a closed position.
Figure 17B:
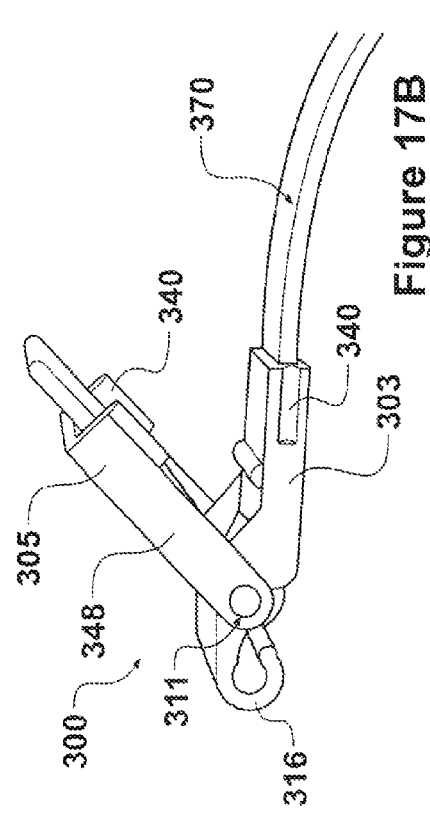
FIG. 17*b* is a perspective view of the headgear connector of FIG. 17*a* in an open position with the headgear strap passed through the headgear connector.
Figures 18A, 18B:
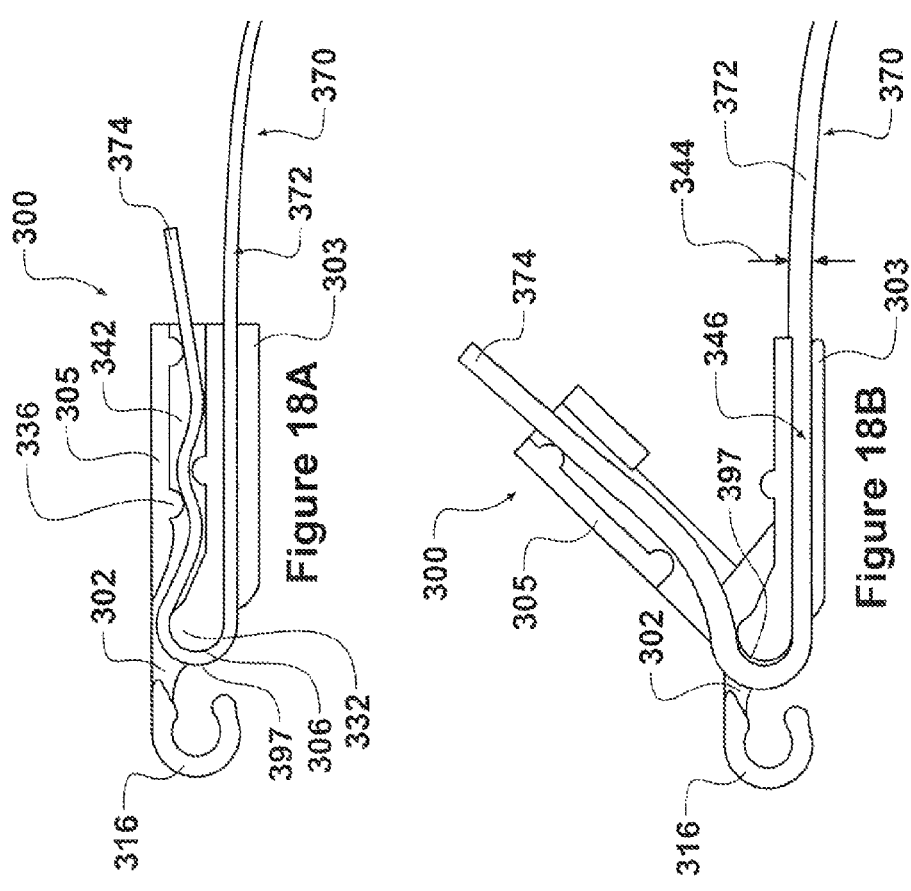
FIG. 18*a* is a cross sectional view of the headgear connector and headgear strap shown in FIG. 17*a* in the closed position.
FIG. 18*b* is a cross sectional view of the headgear connector and headgear strap shown in FIG. 17*b* in the open position.
Figure 19B:
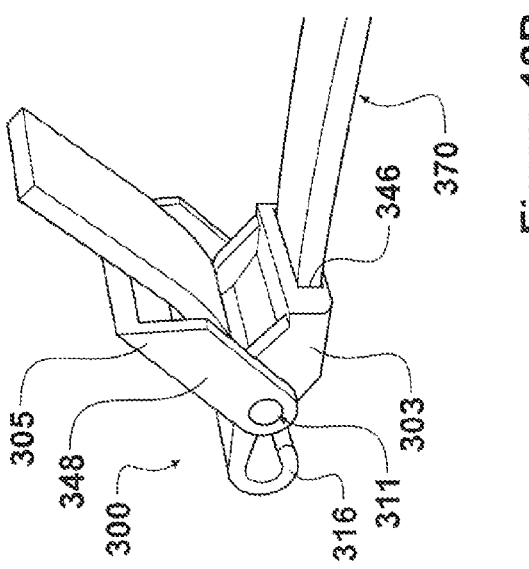
FIG. 19*b* is a perspective view of another transverse cross section of the headgear connector of FIG. 17*a* in the open position.
Figure 19A:
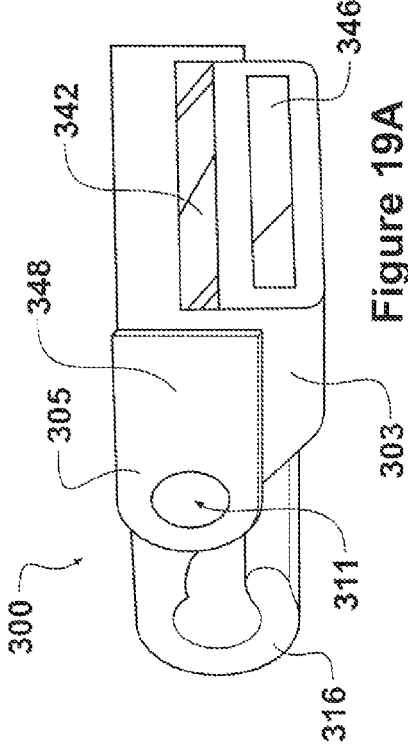
FIG. 19*a* is a perspective view of a transverse cross section of the headgear connector of FIG. 17*a* in the closed position.

FIGS. 17-19 show an alternative embodiment of the headgear connector 300 of FIGS. 14-16. The headgear connector 300 shown in FIGS. 17-19 is similar to the headgear connector 300 of FIGS. 14-16 with the notable exceptions that the base portion 305 comprises a base portion channel 346, and the rotatable portion 305 comprises a pair of enclosing side walls 348.

The base portion channel 346 is configured to receive the headgear strap 372 prior to the headgear strap 372 passing through the passage 302. The base portion channel 346 spans a length of the base portion 305. In the illustrated configuration, the base portion channel 346 spans a majority of the base portion 303. The base portion channel 346 is substantially aligned with the headgear connecting channel 342. As such, the portion of the headgear strap 372 received within the base portion channel 346 is generally parallel to the portion of the headgear strap 372 within the headgear connecting channel 342.

Inclusion of the base portion channel 346 can improve the usability and/or comfort of the headgear connector 300. For example, the base portion 303 can comprise a soft surface configured to contact the side of the face of the user, rather than the headgear strap 372 adjacent to, but not having passed through the channel 302 contacting the face of the user.

As previously mentioned, the rotatable portion 305 illustrated in FIGS. 17-19 comprises a pair of enclosing side walls 348. Each of the enclosing side walls 348 extends from the rotatable portion 305 towards the base portion 303. As such, the enclosing side walls 348 enclose at least a portion, and preferably an entirety of the sides of the headgear connecting channel 342 of the passage 302. The enclosing side walls 348 assist in maintaining alignment of the headgear strap 372 within the headgear connector 300 after it has been passed through the channel 302. The enclosing side walls 348 can also be advantageous by reducing dirt ingress into the headgear connector 300.

In at least one configuration, instead of the rotatable portion 305 comprising the pair of enclosing side walls 348, the base portion 303 can comprise the enclosing sidewalls 348. The enclosing side walls 348 of the base portion 303 can extend towards the rotatable portion 305 to enclose the sides of the headgear connecting channel 342.

Figure 20:
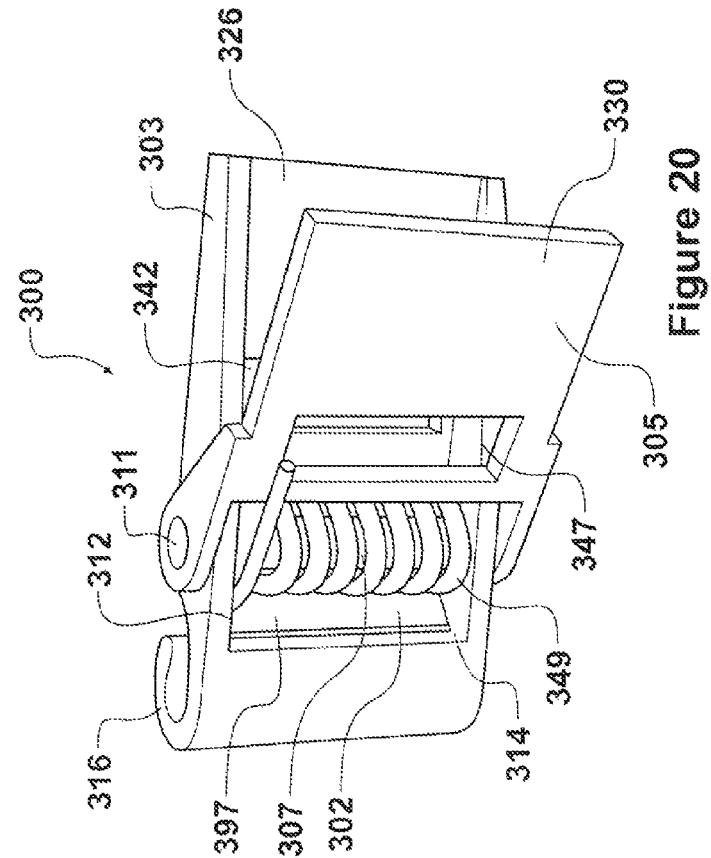
FIG. 20 is a perspective view of a headgear connector comprising a base portion and a rotatable portion connected to a headgear strap and biased towards a closed position by a spring.
Figure 21:
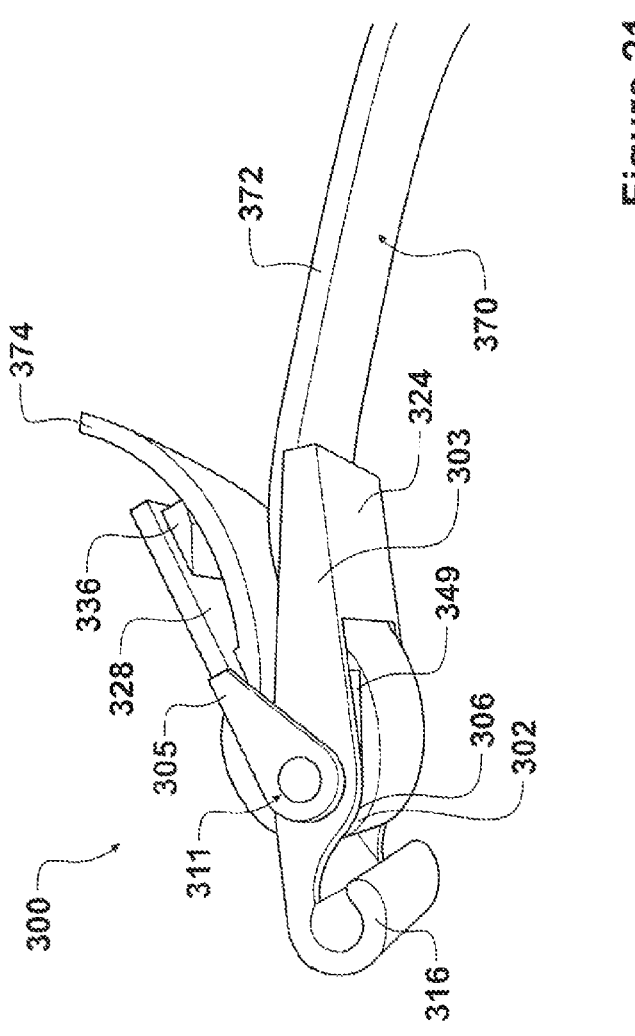
FIG. 21 is a perspective view the headgear connector of FIG. 20.

FIG. 20 and FIG. 21 show another embodiment of the headgear connector 300 of FIGS. 14-16. The headgear connector 300 shown in FIG. 20 and FIG. 21 is similar to the headgear connector 300 of FIGS. 14-16 with the notable exceptions that the headgear connector 300 comprises a connector spring 349 configured to bias the headgear connector 300 in the closed position, the rotatable portion 305 comprises a rotatable portion opening 347, and the headgear connecting channel 342 is of modified construction.

The headgear connector 300 comprises a connector spring 349 configured to bias the headgear connector 300 in the closed position. Preferably, the connection 311 comprises the connector spring 349. The connector spring 349 comprises a first spring arm that contacts the base portion 303, and a second spring arm that contacts rotatable portion 305. The connector spring 349 is tensioned so that the spring arms bias the rotatable portion 305 towards the base portion 303. This therefore biases the headgear connector 300 towards the closed position. The headgear connector 300 can be secured in the closed position similarly to as previously disclosed using the retaining structure/s 340. In an alternative configuration however, the retaining structure 340 may not be included, and the connector spring 349 may bias the headgear connector 300 closed with sufficient force to secure the headgear connector 300 in the closed position within the functional range of forces exerted on the headgear strap 372 during use.

The rotatable portion 305 comprises a rotatable portion opening 347. The rotatable portion opening 347 is configured to receive the headgear strap 372. The rotatable portion opening 347 is defined by an aperture or hole or slot in the rotatable portion 305. The rotatable portion opening 347 corresponds to, but is slightly larger than the rectangular cross section of the headgear strap 372. In at least one configuration, the rotatable portion opening 347 can be circular, oval, trapezoidal, another polygon, or have one or more curved corners or walls.

The headgear connector 300 again comprises a headgear connecting channel 342. This configuration of the headgear connecting channel 342 however, is modified to be configured to grip two portions of the headgear strap 372. The portions of the headgear strap 372 are gripped simultaneously, with one being gripped by the base portion 303 and another being gripped by the rotatable portion 305 within the headgear connecting channel 342 when assembled.

To secure the headgear 370 to the headgear connector 300, the headgear strap end 374 is passed through the headgear connecting channel 374 and the passage opening 397 in a direction from the base portion interior surface 324 towards the base portion exterior surface 326. The headgear strap end 374 is then passed through the passage opening 397 in a direction from the base portion exterior surface 326 towards the base portion interior surface 324. The headgear strap end 374 is looped outwards from the base portion 303 and passed through the rotatable portion opening 347 in a direction from the rotatable portion exterior surface 330 towards the rotatable portion interior surface 328. The headgear strap 372 is therefore passed through the headgear connecting channel 342 a second time. The user can tighten the headgear 370 by pulling the headgear strap end 374 further away from the headgear connector 300.

Rotating the rotatable portion 305 towards the base portion 303 brings each of the rotatable portion 305 and the base portion 303 into contact with the headgear strap 372. Rotating the rotatable portion 305 towards the base portion 303 such that the headgear connector 300 is in the closed position causes the headgear connector 300 to grip the headgear strap 372. The connector spring 349 biases the headgear connector 300 towards the closed position. A frictional connection is formed between the rotatable portion 305, the base portion 303 and the headgear strap.

The frictional connection is formed because a thickness of the headgear connecting channel 342 is generally less than a transverse headgear strap thickness 344 of the headgear strap 372 passing through the headgear connecting channel 342. In other words, a distance between at least a portion of the base portion exterior surface 326 and the rotatable portion interior surface 328 is less than the uncompressed transverse headgear strap thickness 344 of the headgear strap 372 passing through the headgear connecting channel 342. Rotating the rotatable portion 305 towards the base portion 303 can therefore be said to reduce a thickness of the headgear connecting channel 342.

The rotatable portion 305 comprises a first rotatable gripping formation 336. The first rotatable gripping formation 336 is chamfered. In at least one alternative configuration, the first rotatable gripping formation 336 can be rounded, rectangular, or another shape. The first rotatable gripping formation 336 provides a region of reduced thickness within the headgear connecting channel 342 as previously described.

Rotating the rotatable portion 305 away from the base portion 303, such that the headgear connector 300 is moved into the open position releases the connection between the headgear connector 300 and the headgear strap 372.

Figure 22:
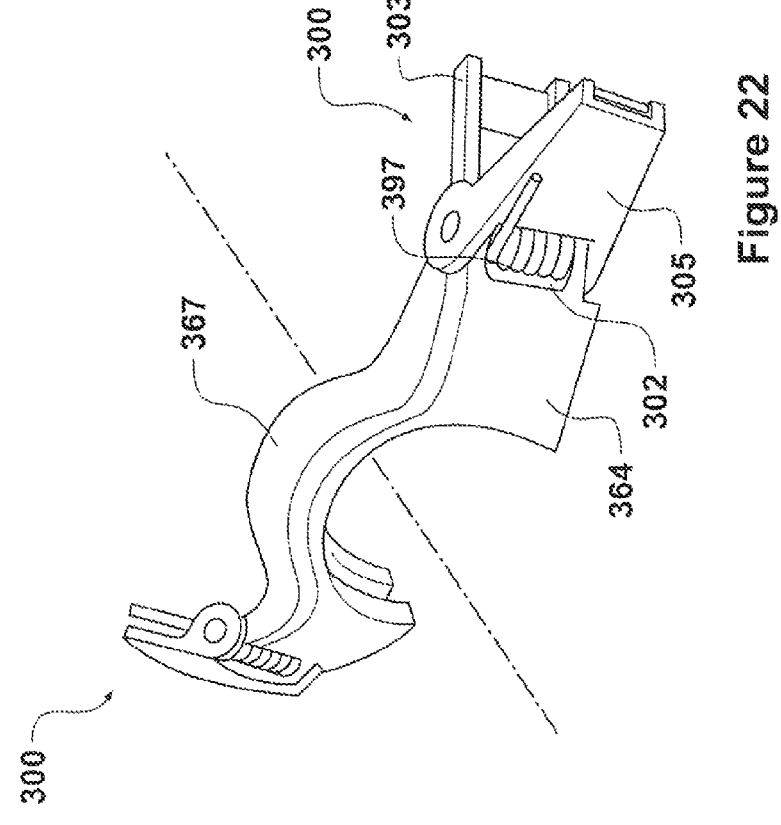
FIG. 22 is a perspective view of another embodiment of the headgear connector of FIG. 20, where the headgear connector is integrated with a yoke of a user interface.

FIG. 22 shows a yoke 367 of a user interface assembly 310. The user interface assembly 310 shown in FIG. 22 is similar to the user interface assembly 310 described with reference to FIGS. 14-21 with the notable exception that the frame 354 comprises the a 367 that comprises the headgear connector/s 300. The yoke 367 may comprise the headgear connector 300 described with reference to FIGS. 14-16, the headgear connector 300 described with reference to FIGS. 17-19, or the headgear connector 300 described with reference to FIGS. 20-21.

The user interface assembly 310 again comprises a user interface 350 and headgear 370. The user interface 350 comprises a frame 354, a cushion module 352 and a breathing gas circuit connector 353. The frame 354 comprises a frame body 361 which is configured to connect to the yoke 367. The yoke 367 is removably connected to the frame body 361. The yoke 367 is configured to span laterally across a length of the frame body 361. The headgear connector 300 facilitates the connection of the frame 352 to the headgear 370 via the yoke 367. The yoke 367 can make the frame easier to clean. The yoke 367 can be of similar construction to the yoke 67 described with reference to FIGS. 5a and 5b. In the configuration illustrated in FIG. 22, the base portion 303 is integrated with the yoke 367.

FIG. 23 and FIG. 24 shows an embodiment of a headgear connector 500. A user interface assembly 510 comprises a user interface 550 which is configured to secure against the face of the user to define a substantially sealed breathing chamber, and headgear 570 which is configured to connect to the user interface 550 and position and secure the user interface 550 in place on the user's face.

The user interface 550 comprises a frame 554, a cushion module 552, and a breathing gas circuit connector 553. The user interface 550 may comprise the headgear connector 500. The cushion module 552 is removably connected to the frame 554. The headgear connector 500 facilitates connection of the frame 554 to a headgear 570.

The user interface 550 is configured to be removably connected to headgear 570 via the headgear connector 500. As such, the headgear connector 500 is removably connectable to the headgear 570. The headgear connector 500 is an intermediate component through which the headgear 570 is connected to the user interface 550. The headgear 570 comprises at least one headgear strap 572. The headgear strap 572 comprises an elongated portion of the headgear 570. The headgear 570 and headgear strap 572 can be substantially similar to the previously described headgear and/or headgear straps.

The headgear connector 500 facilitates the connection of the frame 554 to the headgear strap 572. The headgear connector 500 is also configured to connect to the frame 554. The headgear connector 500 cooperates with the headgear strap 572 to connect the frame 554 to the headgear strap 572.

The headgear connector 500 is configured to grip the headgear strap 572. The headgear connector 500 comprises a moveable portion 505 and a base portion 503. The base portion 503 and the moveable portion 505 together are configured to grip the headgear strap 572. The moveable portion 505 can move with respect to the base portion 503. In the illustrated configuration, the moveable portion 505 is in the form of a rotatable portion 505. The rotatable portion 505 can rotate with respect to the base portion 503. The base portion 503 comprises a base portion interior surface 524. The base portion 503 comprises a base portion exterior surface 526.

The headgear connector 500 comprises a frame coupling 516. The frame coupling 516 is configured to couple the headgear connector 500 to the frame 554. The frame 554 comprises a frame post 569. The frame coupling 516 couples to the frame post 569. The frame coupling 516 and/or the frame post 569 can be substantially similar or the same as the frame coupling 316 and/or the frame post 369 described with reference to FIGS. 14-21.

The headgear connector 500 comprises a headgear connector post 507. The headgear connector post 507 extends from a passage upper wall 512 of the base portion 503 to a passage lower wall 514 (not shown in the figures) of the base portion 503. The illustrated headgear connector post 507 is cylindrical. The rotatable portion 505 comprises a connector opening 509. The connector opening 509 is sized and shaped to correspond to the headgear connector post 507. In other words, the connector opening 509 forms a female component of a connection 511 between the rotatable portion 505 and the base portion 503. The headgear connector post 507 forms a male component of the connection 511. The headgear connector post 507 is received by the connector opening 509 such that the rotatable portion 505 and the base portion 503 are rotatably connected at the connection 511. In other words, the connection 511 allows the rotatable portion 505 to rotate with respect to the base portion 503.

The headgear connector post 507 can be removably connected to the base portion 503. For example, the headgear connector post 507 can form an interference fit with a cooperating structure/s of the base portion 503, for example holes. The base portion 503 can be deformed to release the interference fit, and the headgear connector post 507 can be removed.

The rotatable portion 505 can be disconnected or removed from the base portion 503. Facilitating removal of the rotatable portion 505 from the base portion 503 can beneficially allow replacement of the rotatable portion 505, and/or the base portion 503, in the event that either component is damaged. Either component can be replaced individually, without the need to replace the entire headgear connector 500.

Figure 23B:
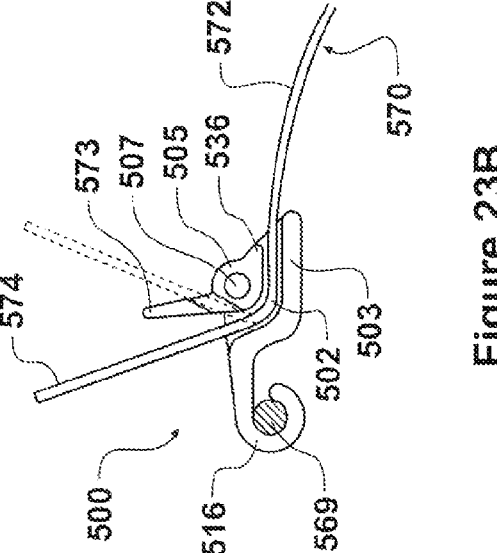
FIG. 23*b* is a cross section of the headgear connector of FIG. 23*a* in an open position.
Figure 23A:
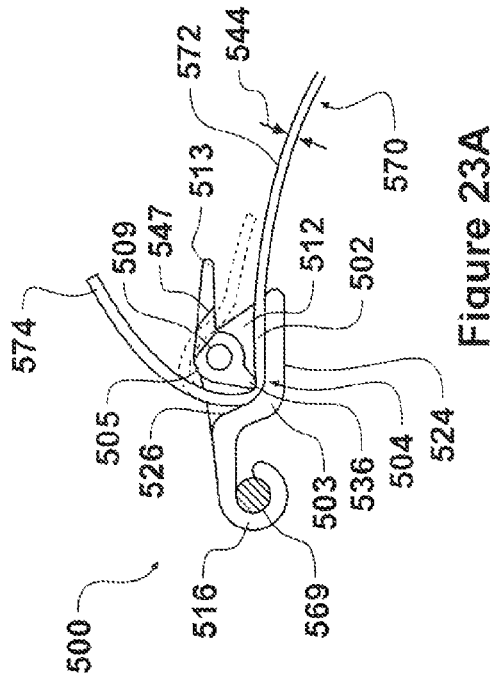
FIG. 23*a* is a cross section of a headgear connector with a base portion and a rotatable portion, where the headgear connector is connected to a headgear strap in a closed position.
Figures 24A, 24B:
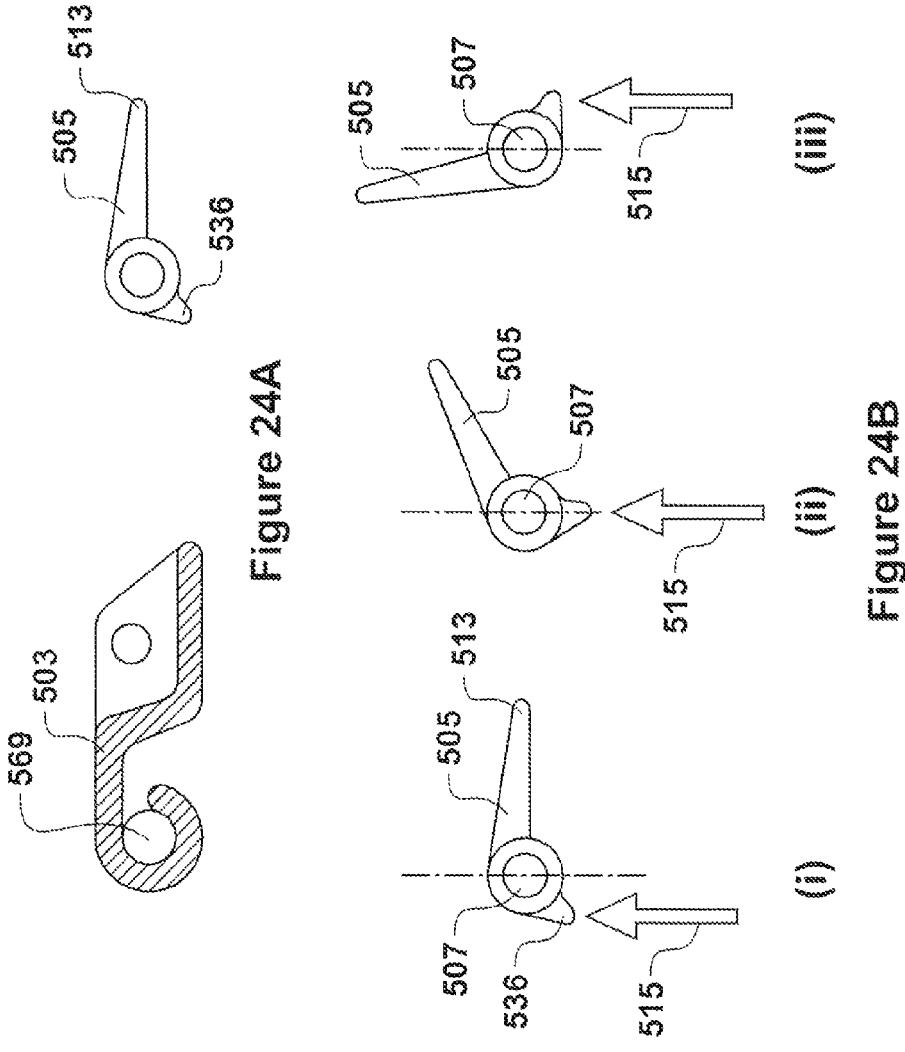
FIG. 24*a* is a cross section of the base portion and the rotatable portion of the headgear connector of FIG. 23*a*.
FIG. 24*b*(*i*) shows the rotatable portion in the closed position.

The rotatable portion 505 can rotate with respect to the base portion 503 between a closed position (shown in FIG. 23a), and an open position (shown in FIG. 23b). The rotatable portion 505 can rotate through an intermediate position as shown in FIG. 24b(i). The rotatable portion 505 and the base portion 503 define a headgear receiving passage 502. In other words, the passage 502 is the space between the rotatable portion 505 and the base portion 503. The passage 502 is defined by the space between the base portion exterior surface 526 and the rotatable portion 505. The passage 502 is configured to receive the headgear strap 572. The passage 602 receives the headgear strap 572 from a first direction and enables the headgear strap 572 to loop back onto itself in a second direction substantially opposed to the first direction. When in the closed position, the headgear connector 500 is configured to grip the headgear strap 572. The passage 502 can comprise the base portion exterior surface 526, the passage upper wall 512 and the passage lower wall 514.

The rotatable portion 505 comprises a rotatable gripping formation 536. The rotatable portion 505 comprises a tail 513. The tail 513 extends away from the connector opening 509. The rotatable gripping formation 536 can form at least a part of a passage outer wall 508. The rotatable portion 505 can comprise a cam structure. The cam structure can comprise the rotatable gripping formation 536. The rotatable gripping formation 536 is rounded. Alternatively, the rotatable gripping formation 536 can be rectangular, chamfered, triangular, or another shape.

To secure the headgear 570 to the headgear connector 500, the rotatable portion 505 is rotated such that the headgear connector 500 is in the open position. A longitudinal direction can be defined as the direction from where the headgear connector 500 connects to the frame towards the free end of the headgear connector 500. The headgear strap end 574 is passed through the passage 502 in a direction from the longitudinal side of the headgear connector 500 towards the frame coupling 516, as shown in FIG. 23b. The headgear strap end 574 is looped outwards and away from the passage 502. In other words, the headgear strap 572 is passed through the passage 502. The rotatable portion 505 comprises a rotatable portion opening 547. The rotatable portion opening 547 is configured to receive the headgear strap 572. The headgear strap 572 is passed through the rotatable portion opening 547. The rotatable portion opening 547 helps align and/or retain the headgear strap 572 close to the headgear connector 500. This can assist in increasing the ease of use of the adjustment mechanism, by increasing the accuracy with which the user may adjust the length of the headgear strap 572 to be secured. When the headgear strap 572 has been passed through the passage 502 and the rotatable portion opening 547, the portion of the headgear strap 572 that has been passed through the passage 502 will rotate with the headgear connector 500 about the frame post 569 in unison as the headgear connector 500 is rotated about the frame post 569. The user can tighten the headgear 570 by pulling the headgear strap end 574 further away from the headgear connector 500.

Rotating the rotatable portion 505 can adjust the headgear connector 500 from the open position to the closed position. Rotating the rotatable portion 505 such that the rotatable gripping formation 536 is rotated towards the frame coupling 516, and the tail 513 is rotated away from the frame coupling 516 brings the rotating projection 536 into contact with the headgear strap 572. Further rotation of the rotatable portion 505 secures the headgear strap 572 within the headgear connector 500. The rotatable gripping formation 536 urges the headgear strap 572 onto the base portion exterior surface 526. This compresses the headgear strap 572 in the region of the rotatable gripping formation 536. Rotating the rotatable portion 505 therefore causes the headgear connector 500 to grip the headgear strap 572. In particular, the headgear strap 572 is gripped between the rotatable portion 505 and the base portion 503. A frictional connection is formed between the rotatable portion 505, the base portion 503 and the headgear strap 572.

The frictional connection is formed because a thickness of the passage 502 is less than a transverse headgear strap thickness 544 of the headgear strap 572 passing through the passage 502. In other words, a distance between at least a portion of the base portion exterior surface 526 and the rotatable portion 505 is less than the uncompressed transverse headgear strap thickness 544 of the headgear strap 572 passing through the passage 502. Rotating the rotatable portion 505 can therefore be said to reduce a thickness of the passage 502.

Rotating the rotatable portion 505 such that the rotatable gripping formation 536 is rotated away from the frame coupling 516, and the tail 513 is rotated towards the frame coupling 516, such that the headgear connector 500 is moved into the open position, releases the connection between the headgear connector 500 and the headgear strap 572. In other words, rotating the rotatable portion 505 in an opposite direction to the direction it was rotated to secure the headgear strap 572 releases the connection between the headgear connector 500 and the headgear strap 572.

At least one configuration of the user interface 550 can comprise a release member 598. The release member 598 can be similar to that described with reference to FIG. 42. The release member 598 can be similar to release member 398 previously described. The release member 598 is actuated to release the connection between the headgear 570 and the user interface 550. In particular, the release member 598 can be actuated to release the connection between the headgear strap 572 and the headgear connector 500.

In at least one configuration, the frame 554 is formed from, or comprises a polymer. The polymer can be polycarbonate that rigidly defines a 3-dimensional profile of the frame 554. In at least one configuration, the headgear connector 500 comprises a polymer. The polymer can be a polycarbonate that rigidly defines a 3-dimensional profile of the headgear connector 500. In at least one form, the base portion 503 comprises the polymer. In at least one form, the rotatable portion 505 comprises the polymer. In at least one form, both the base portion 503 and the rotatable portion 505 comprise the polymer.

In at least one configuration, the headgear connector 500 is fixedly connected to the frame 554. That is, the headgear connector 500 is not removably connected to the frame 554. In said configuration, once the headgear connector 500 is connected to the frame 554, it is not removable without the destruction of at least a part of the headgear connection 500 and/or the frame 554. In at least one configuration, at least a portion of the headgear connector 500 is integrally formed with the frame 554. For example, the base portion 503 can be integrally formed with the frame 554.

The illustrated base portion 303 comprises the connector post 507, and the illustrated rotatable portion 305 comprises the connector opening 509. In an alternative configuration, the base portion 503 may comprise one or more connector opening/s 509, and the rotatable portion 505 may comprise the headgear connector post 507.

The illustrated rotatable portion 505 is removable from the base portion 503. In at least one configuration, the rotatable portion 505 is permanently connected to the base portion 503. This can reduce the likelihood that the user will disconnect the rotatable portion 505 and lose the component.

In at least one configuration, the headgear connector 500 can be used with a user interface 550 configured to deliver breathing gas to one or more of the user's mouth and nose without a sealed connection. For example, the headgear connector 500 can be used with a nasal cannula 550.

Figure 25:
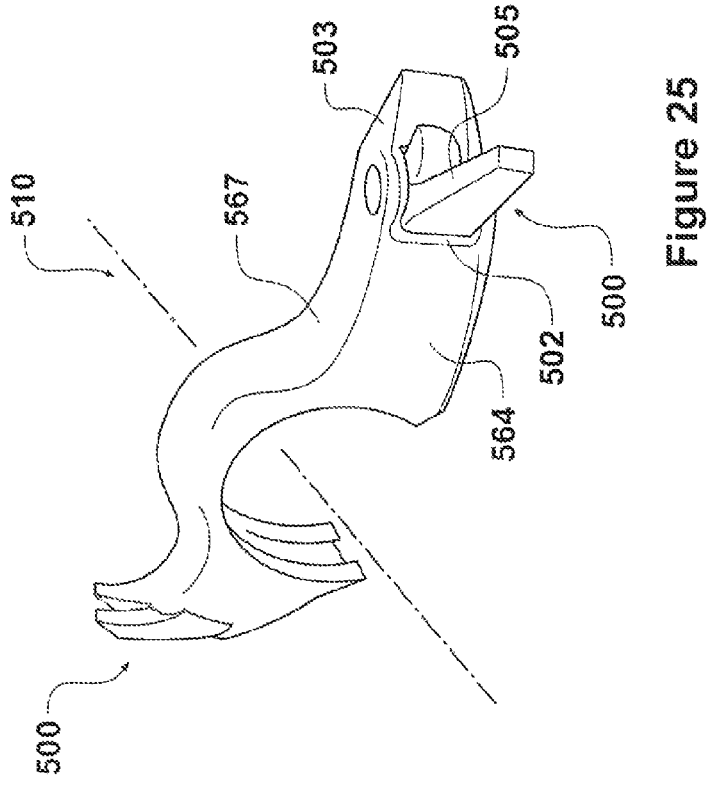
FIG. 25 is a perspective view of another embodiment of the headgear connector of FIG. 23*a*, where the fixed headgear connector is integrated with a yoke of a user interface assembly.

FIG. 25 shows a yoke 567 of a user interface assembly 510. The user interface assembly 510 of which the yoke 567 is shown in FIG. 25 is similar to the user interface assembly 510 described with reference to FIG. 23 and FIG. 24 with the notable exception that the frame 554 comprises a frame body 561 and the yoke 567. The yoke 567 comprises the headgear connector/s 500. The yoke 576 is integrally formed with the base portion 503. The rotatable portion 505 can rotate with respect to the base portion 503 to grip the headgear strap 572 as described with reference to FIGS. 23 and 24.

FIG. 26 and FIG. 27 show an embodiment of a headgear connector 600. A user interface assembly 610 comprises a user interface 650 which is configured to secure against the face of the user to define a substantially sealed breathing chamber, and headgear 670 which is configured to connect to the user interface 650 and position and secure the user interface 650 in place on the user's face.

The user interface 650 comprises a frame 654, a cushion module 652, and a breathing gas circuit connector 653. In the illustrated configuration, the cushion module 652 is removably connected to the frame 654. The user interface 650 may comprise the headgear connector 600. The headgear connector 600 facilitates connection of the user interface 650 to the headgear 670.

The user interface 650 is configured to be removably connected to headgear 670 via the headgear connector 600. The headgear connector 600 is an intermediate component through which the headgear 670 is connected to the frame 654. The headgear 670 comprises at least one headgear strap 672. The headgear strap 672 is configured to connect with the user interface 650. The headgear strap 672 comprises an elongated portion of the headgear 670. The headgear 670 and headgear strap 672 are substantially similar to previously described headgear and/or headgear straps. The headgear connector 600 facilitates the connection of the frame 654 to the headgear strap 672. The headgear connector 600 is also configured to connect to the frame 654.

The headgear connector 600 is configured to grip a portion of the headgear strap 672. The headgear connector 600 comprises a moveable portion 605 and a base portion 603. The base portion 503 and the moveable portion 605 together are configured to grip the headgear strap 672. The moveable portion 605 can move with respect to the base portion 603. In the illustrated configuration, the moveable portion 605 is in the form of a rotatable portion 605. The rotatable portion 605 can rotate with respect to the base portion 603.

The headgear connector 600 comprises a frame coupling 616. The frame coupling 616 is configured to couple the headgear connector 600 to the frame 654. The frame 654 comprises a frame post 669. The frame coupling 616 couples to the frame post 669. In at least one configuration, the frame coupling 616 and/or frame post 669 can be substantially similar or the same as any of the frame couplings previously described.

The headgear connector 600 comprises a first headgear connector post 607. The first headgear connector post 607 extends from a passage upper wall 612 of the base portion 603 to a passage lower wall 614 of the base portion 603. The illustrated first headgear connector post 607 is cylindrical. The headgear connector 600 comprises a second headgear connector post 601. The second headgear connector post 601 extends from the passage upper wall 612 to the passage lower wall 614. The illustrated second headgear connector post 601 is cylindrical. The first headgear connector post 607 and the second headgear connector post 601 are generally parallel. A longitudinal direction can be defined as the direction from where the headgear connector 600 connects to the frame towards the free end of the headgear connector 600. The second headgear connector post 601 is displaced longitudinally from the first headgear connector post 607 along the length of the base portion 603. The first headgear connector post 607 and the second headgear connector post 601 are of similar or the same diameter. The first headgear connector post 607 and the second headgear connector post 601 are separated by a space.

The rotatable portion 605 comprises a connector opening 609. The connector opening 609 is sized and shaped to correspond to the first headgear connector post 607. In other words, the connector opening 609 forms a female component of a connection 611 between the rotatable portion 605 and the base portion 603. The connection 611 is a removable connection. The first headgear connector post 607 forms a male component of the connection 611. The first headgear connector post 607 is received by the connector opening 609 such that the rotatable portion 605 and the base portion 603 are rotatably connected at the connection 611. In other words, the connection 611 allows the rotatable portion 605 to rotate with respect to the base portion 603.

The first headgear connector post 607 can be removably connected to the base portion 603. For example, the first headgear connector post 607 can form an interference fit with a cooperating structure/s of the base portion 603, for example holes, as described with reference to previous embodiments. The second headgear connector post 601 can be removably connected to the base portion 603 in a similar way.

The rotatable portion 605 can be disconnected or removed from the base portion 603. For example, the illustrated connector opening 609 is tapered towards one end such that the rotatable portion 605 is connected to the first headgear connector post 607 by a snap-fit, clip fit and/or interference fit. The rotatable portion 605 can be disconnected or removed from the base portion 603 by pulling the rotatable portion 605 away from the base portion 603 with sufficient force to overcome the connection 611. Facilitating removal and re-connection of the rotatable portion 605 from the base portion 603 can assist in improving the ease with which the headgear connector 600 can be manufactured, by improving the ease of assembly of the headgear connector 600. Additionally, facilitating removal of the rotatable portion 605 from the base portion 603 can beneficially allow replacement of the rotatable portion 605, and/or the base portion 603, in the event that either component is damaged. Either component can be replaced individually, without the need to replace the entire headgear connector 600.

Figure 26A:
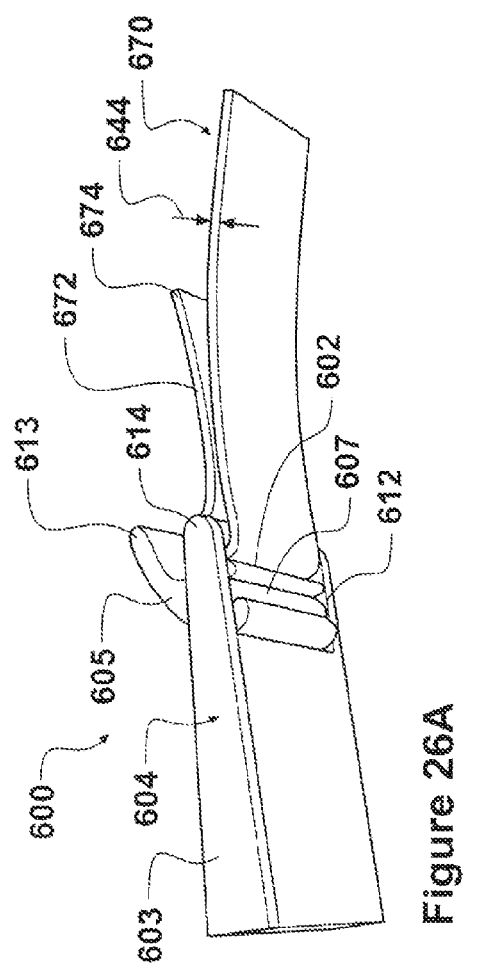
FIG. 26*a* is a perspective view of a headgear connector with a base portion and a rotatable portion, where the headgear connector is in an open position.
Figure 26B:
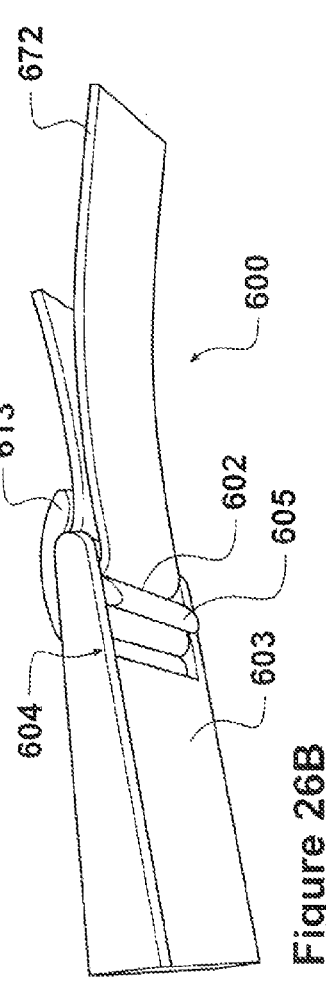
FIG. 26*b* is a perspective view of the headgear connector of FIG. 26*a* in a closed position.
Figures 27A, 27B:
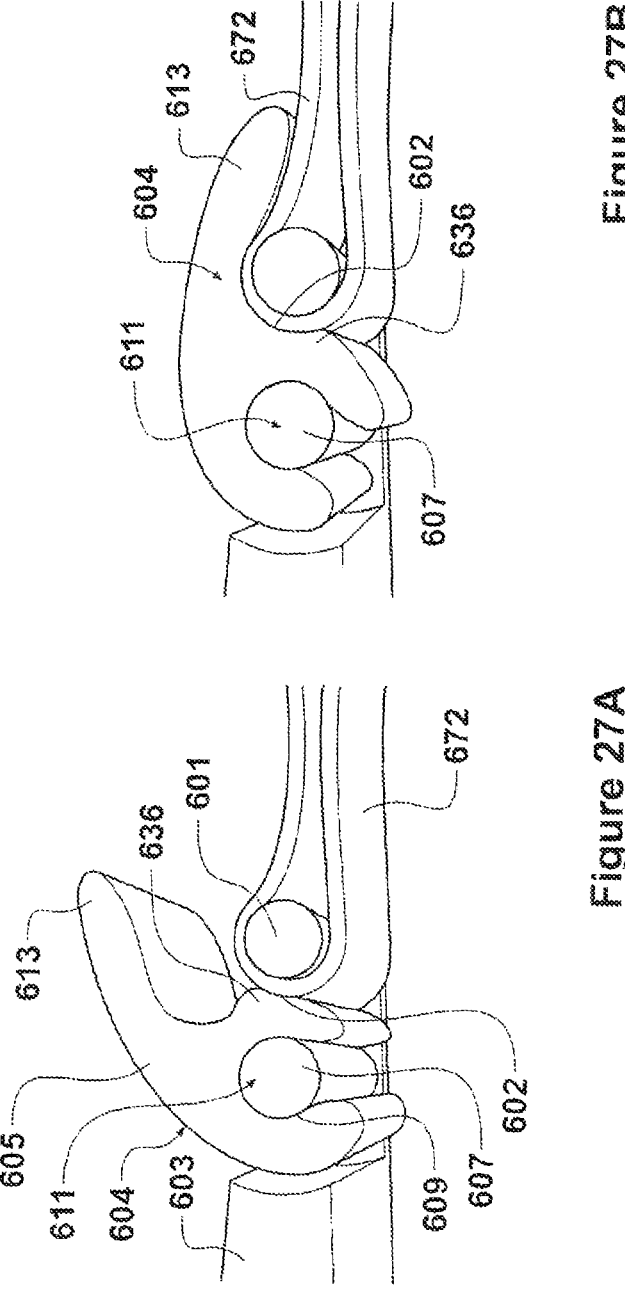
FIG. 27*a* is a cross section of the headgear connector of FIG. 26*a* in the open position.
FIG. 27*b* is a cross section of the headgear connector of FIG. 26*a* in the closed position.

The rotatable portion 605 can rotate with respect to the base portion 603 between a closed position (shown in FIG. 26*b* and FIG. 27*b*), and an open position (shown in FIG. 26*a* and FIG. 27*a*). The rotatable portion 605 and the base portion 603 together define a headgear receiving passage 602. In other words, the passage 602 is the space between the rotatable portion 605 and the base portion 603. In the illustrated configuration, the passage 602 is a space between the rotatable portion 605 and the second headgear connector post 601. The passage 602 is configured to receive the headgear strap 672. The passage 602 receives the headgear strap 672 from a first direction and enables the headgear strap 672 to loop back onto itself in a second direction substantially opposed to the first direction. When in the closed position, the headgear connector 600 is configured to grip the headgear strap 672. The passage 602 can be at least partially defined by a rotatable portion interior surface 628, the passage upper wall 612 and the passage lower wall 614.

The rotatable portion 605 comprises a rotatable gripping formation 636. The rotatable portion 605 comprises a tail 613. The tail 613 extends away from the connector opening 609. The rotatable gripping formation 636 can form at least a part of the rotatable portion interior surface 628. The rotatable portion 605 can comprise a cam structure. The cam structure can comprise the rotatable gripping formation 636. The illustrated rotatable gripping formation 636 is rounded. Alternatively, the rotatable gripping formation 636 can be rectangular, chamfered, triangular, or another shape.

To secure the headgear 670 to the headgear connector 600, the rotatable portion 605 is rotated such that the headgear connector 600 is in the open position, and the headgear strap end 674 is passed through the passage 602 in a direction from the base portion 603 towards the tail 613 of the rotatable portion 605, as shown in FIG. 26*a*. The headgear strap end 674 is looped outwards and away from the passage 602. The headgear strap end 674 is looped around the second fixed headgear connecting post 601. In other words, the headgear strap 672 is passed through the passage 602. The user can tighten the headgear 670 by pulling the headgear strap end 674 away from the headgear connector 600 after passing it through the passage 602.

Rotating the rotatable portion 605 can adjust the headgear connector 500 from the open position to the closed position. Rotating the rotatable portion 605 such that the tail 613 is rotated towards the second headgear connector post 601, and the rotatable gripping formation 636 is rotated towards the second headgear connector post 601 brings the rotating projection 636 into contact with the headgear strap 672. Further rotation of the rotatable portion 605 secures the headgear strap 672 within the headgear connector 600. The headgear strap 672 is gripped by the headgear connector 600. In particular, the headgear strap 672 is gripped by the rotatable portion 605 and the base portion 603. A frictional connection is formed between the rotatable portion 605, the base portion 603 and the headgear strap 672.

The frictional connection is formed because a thickness of the passage 602 is less than a transverse headgear strap thickness 644 of the headgear strap 672 passing through the passage 602. In other words, a distance between at least a portion of the second fixed headgear connector post 601 and the rotatable portion 605 is less than the uncompressed transverse headgear strap thickness 644 of the headgear strap 672 passing through the passage 602. Rotating the rotatable portion 605 can therefore be said to reduce a thickness of the passage 602.

Rotating the rotatable portion 605 such that the rotatable gripping formation 636 is rotated away from the second fixed headgear connector post 601, and the tail 613 is rotated away from the second fixed headgear connector post 601, such that the headgear connector 600 is moved into the open position, releases the connection between the headgear connector 600 and the headgear strap 672. In other words, rotating the rotatable portion 605 in an opposite direction to the direction it was rotated to secure the headgear strap 672 releases the connection between the headgear connector 600 and the headgear strap 672. The headgear strap 672 can slide or pass through the passage 602 in the open position.

In at least one configuration, the passage 602 can be dimensioned to provide a resistive force on the headgear strap passing through the passage 602 as described with reference to headgear connectors previously disclosed.

At least one configuration of the user interface 650 can comprise a release member 698. The release member can be similar to that described with reference to FIG. 42. The release member can be similar to release member 398 and/or release member 498 previously described. The release member 698 is actuated to release the connection between the headgear 670 and the user interface 650. In particular, the release member 698 can be actuated to release the connection between the headgear strap 672 and the headgear connector 600.

In at least one configuration, the frame 654 is formed from, or comprises a polymer. The polymer can be polycarbonate that rigidly defines a 3-dimensional profile of the frame 654. In at least one configuration, the headgear connector 600 comprises a polymer. The polymer can be a polycarbonate that rigidly defines a 3-dimensional profile of the headgear connector 600. In at least one form, the base portion 603 comprises the polymer. In at least one form, the rotatable portion 605 comprises the polymer. In at least one form, both the base portion 603 and the rotatable portion 605 comprise the polymer.

In at least one configuration, the headgear connector 600 is fixedly connected to the frame 654. That is, the headgear connector 600 is not removably connected to the frame 654. In said configuration, once the headgear connector 600 is connected to the frame 654, it is not removable without the destruction of at least a part of the headgear connection 600 and/or the frame 654. In at least one configuration, at least a portion of the headgear connector 600 is integrally formed with the frame 654. For example, the base portion 603 can be integrally formed with the frame 654. In at least one configuration, the frame 654 comprises a frame body 661 and a yoke 667 (as described in previous embodiments), and the headgear connector 600 is integrally formed with the yoke 667. For example, the base portion 603 can be integrally formed with the yoke 667.

The illustrated base portion 603 comprises the first headgear connector post 607, and the illustrated rotatable portion 605 comprises the connector opening 609. In an alternative configuration, the base portion 603 may comprise one or more connector opening/s 609, and the rotatable portion 605 may comprise the first headgear connector post 607.

The illustrated rotatable portion 605 is removable from the base portion 603. In at least one configuration, the rotatable portion 605 is permanently connected to the base portion 603. This can reduce the likelihood that the user will disconnect the rotatable portion 605 and lose the component.

In at least one configuration, the headgear connector 600 can be used with a user interface 650 configured to deliver breathing gas to one or more of the user's mouth and nose without a sealed connection. For example, the headgear connector 600 can be used with a nasal cannula 650.

FIGS. 28-31 show an embodiment of a headgear connector 700. A user interface assembly 710 comprises a user interface 750 which is configured to secure against the face of the user to define a substantially sealed breathing chamber, and headgear 770 which is configured to connect to the user interface 750 and position and secure the user interface 750 in place on the user's face.

The user interface 750 comprises a frame 754, a cushion module 752, and a breathing gas circuit connector 753. The user interface 750 may comprise the headgear connector 700. In the illustrated configuration, the cushion module 752 is removably connected to the frame 754. The headgear connector 700 is configured to connect to the frame 754. The headgear connector 700 facilitates connection of the frame 754 to the headgear 770.

The user interface 750 is configured to be removably connected to headgear 770 via the headgear connector 700. The headgear connector 700 is an intermediate component through which the headgear 770 is connected to the frame 754. The headgear 770 comprises at least one headgear strap 772. The headgear strap 772 is configured to connect with the user interface 750. The headgear strap 772 comprises an elongated portion of the headgear 770. The headgear 770 and headgear strap 772 are substantially similar to previously described headgear and/or headgear straps. The headgear connector 700 facilitates the connection of the frame 754 to the headgear strap 772. The headgear connector 700 is also configured to connect to the frame 754. The headgear connector 700 cooperates with the headgear strap 772 to connect the frame 754 to the headgear strap 772.

The headgear connector 700 is configured to grip the headgear strap 772. The headgear connector 700 comprises a moveable portion 705 and a base portion 703. The base portion 703 and the moveable portion 705 together are configured to grip the headgear strap 772. The moveable portion 705 can move with respect to the base portion 703. In the illustrated configuration, the moveable portion 705 is in the form of a rotatable portion 705. The rotatable portion 705 can rotate with respect to the base portion 703.

The headgear connector 700 comprises a frame coupling 716. The frame coupling 716 is configured to couple the headgear connector 700 to the frame 754. The frame 754 comprises a frame post 769. The frame coupling 716 couples to the frame post 769. The frame coupling 716 and/or frame post 769 can be substantially similar or the same as any of the frame couplings and/or frame posts previously described.

The headgear connector 700 comprises a first headgear connector post 707. The first headgear connector post 707 extends from an upper side wall 727 of the base portion 703 to a lower side wall 729 of the base portion 703. The illustrated first headgear connector post 707 is cylindrical. The headgear connector 700 comprises a second headgear connector post 701. The second headgear connector post 701 extends from the upper side wall 727 to the lower side wall 729. The illustrated second headgear connector post 701 is cylindrical. The first headgear connector post 707 and the second headgear connector post 701 are generally parallel. A longitudinal direction can be defined as the direction from where the headgear connector 600 connects to the frame towards the free end of the headgear connector 600. The second headgear connector post 701 is displaced longitudinally from the first headgear connector post 707 along the length of the base portion 703. The first headgear connector post 707 and the second headgear connector post 701 are of similar or the same diameter.

The rotatable portion 705 comprises a connector opening 709. The connector opening 709 is sized and shaped to correspond to the first headgear connector post 707. In other words, the connector opening 709 forms a female component of a connection 711 between the rotatable portion 705 and the base portion 703. The first headgear connector post 707 forms a male component of the connection 711. The first headgear connector post 707 is received by the connector opening 709 such that the rotatable portion 705 and the base portion 703 are rotatably connected at the connection 711. In other words, the connection 711 allows the rotatable portion 705 to rotate with respect to the base portion 703.

The rotatable portion 705 also comprises a rotatable post 725. The rotatable post 725 extends from a passage upper wall 712 of the rotatable portion 705 to a passage lower wall 714 of the rotatable portion 705. The rotatable post 725 is cylindrical. The rotatable post 725 is integrally formed with the rotatable portion 705. The rotatable post 725 and the first headgear connector post 707 are generally parallel. The rotatable post 725 and the second headgear connector post 701 are generally parallel.

The first headgear connector post 707 can be removably connected to the base portion 703. For example, the first headgear connector post 707 can form an interference fit with a cooperating structure/s of the base portion 703, for example holes as described with reference to previous embodiments. Similarly, the second headgear connector post 701 can be removably connected to the base portion 703. Again similarly, the rotatable post 725 can be removably connected to the rotatable portion 705.

The rotatable portion 705 can be disconnected or removed from the base portion 703, and/or the first headgear connector post 707. For example, the illustrated connector opening 709 is tapered towards one end such that the rotatable portion 705 is connected to the first headgear connector post 707 by a snap-fit, clip fit and/or interference fit. The rotatable portion 705 can be disconnected or removed from the base portion 703 by pulling the rotatable portion 705 away from the base portion 703 with sufficient force to overcome the connection 711.

Figure 28:
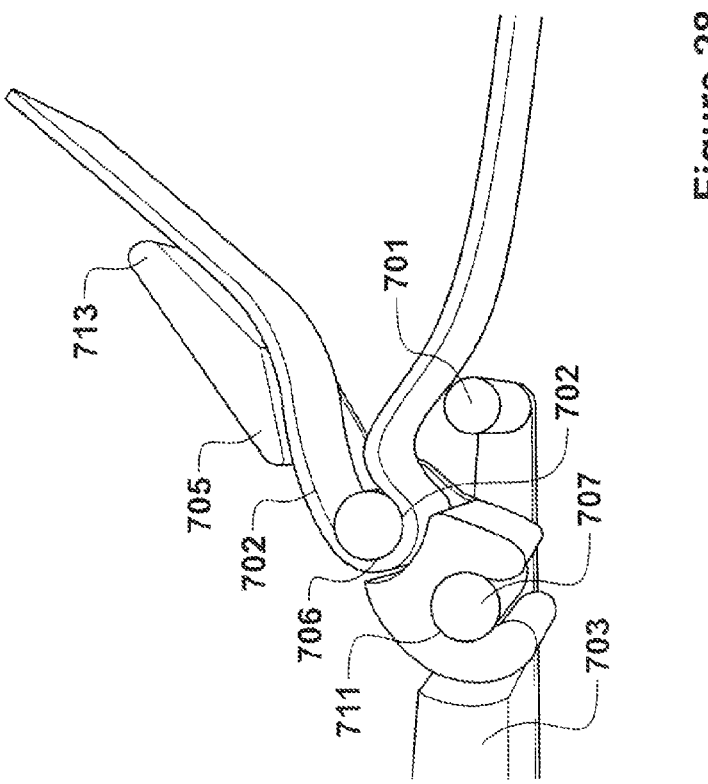
FIG. 28 is a cross section of a headgear connector in an open position, with a headgear strap passed through a passage of the headgear connector.
Figure 29:
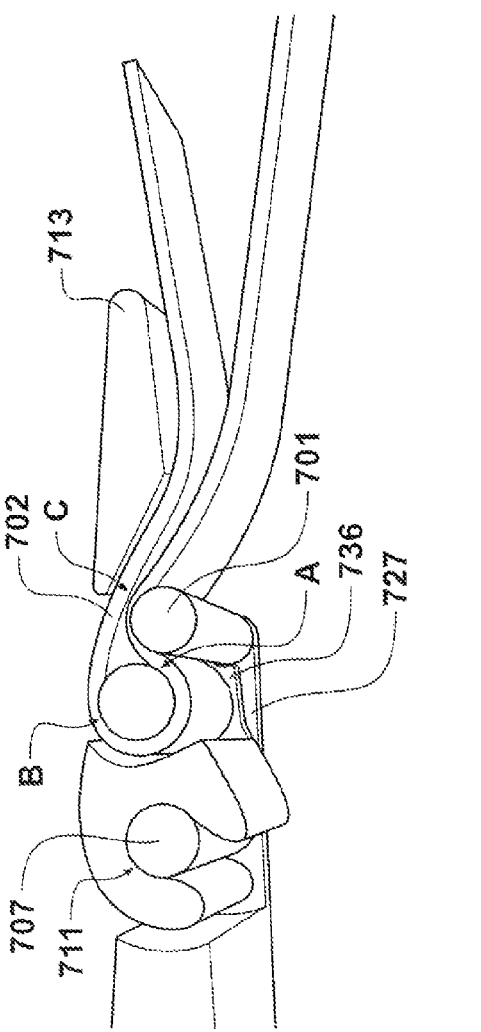
FIG. 29 is a cross section of the headgear connector of FIG. 28 connected to the headgear strap in a closed position.
Figure 30:
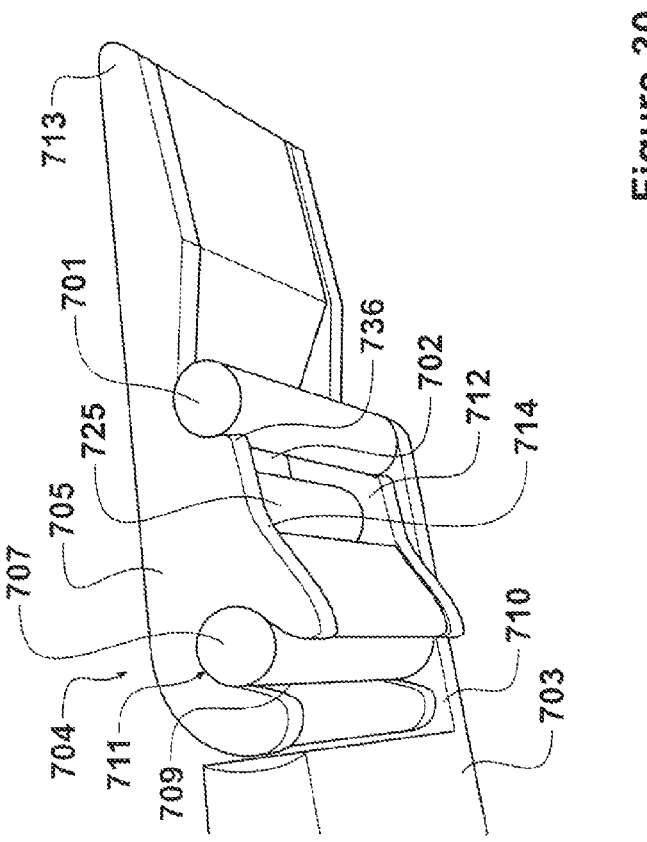
FIG. 30 is a cross section of the headgear connector of FIG. 28, in the closed position.
Figures 31A, 31B, 31C, 31D:
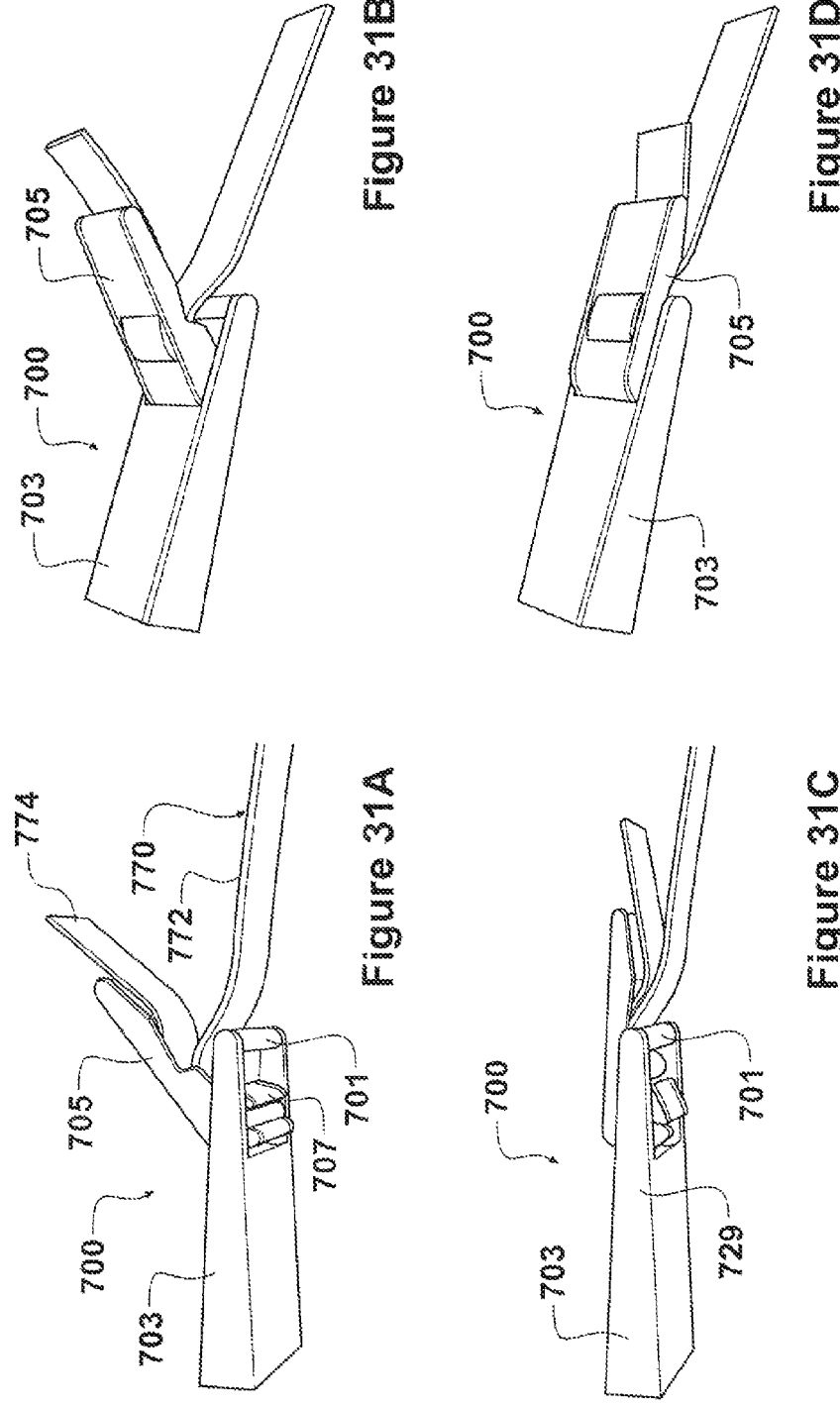
FIG. 31*a* is a perspective view of the headgear connector of FIG. 28 in the open position with the headgear strap passed through the passage.
FIG. 31*b* is a perspective view of the headgear connector of FIG. 28 in the open position with the headgear strap passed through the passage.
FIG. 31*c* is a perspective view of the headgear connector of FIG. 28 in the closed position connecting to the headgear strap.
FIG. 31*d* is a perspective view of the headgear connector of FIG. 28 in the closed position connecting to the headgear strap.

The rotatable portion 705 can rotate with respect to the base portion 703 between a closed position (shown in FIG. 29, FIG. 30, FIG. 31c and FIG. 31d), and an open position (shown in FIG. 28, FIG. 31a and FIG. 31b). The rotatable portion 705 and the base portion 703 define a headgear receiving passage 702. The passage 702 comprises a space between the rotatable portion 705 and the base portion 703. The passage 702 comprises a first space A between the second headgear connector post 701 and the rotatable post 725 (shown in FIG. 31). The passage 702 also comprises a second space B between a perimeter of the rotatable post 725 and a portion of the rotatable portion 705 (shown in FIG. 31). The passage 702 also comprises a third space C between the second headgear connector post 701 and the rotatable portion 705 (shown in FIG. 31). The passage 702 can be generally 'U' shaped. The passage 702 is configured to receive the headgear strap 772. The passage 702 receives the headgear strap 772 from a first direction and enables the headgear strap 772 to loop back onto itself in a second direction substantially opposed to the first direction. When in the closed position, the headgear connector 700 is configured to connect to the headgear strap 772. The passage

702 can be at least partially defined by the passage upper wall 712 and the passage lower wall 714.

The rotatable portion 705 comprises pair of rotatable gripping formations 736. The rotatable portion 705 comprises a tail 713. The tail 713 extends away from the connector opening 709. The rotatable gripping formations 736 can form at least a part of the upper side wall 727 and/or the lower side wall 729. The rotatable portion 705 can comprise and/or be in the form of a cam structure. Each rotatable gripping formation 736 is rounded. Alternatively, the rotatable gripping formation 736 can be rectangular, chamfered, triangular, or another shape.

To secure the headgear 770 to the headgear connector 700, the rotatable portion 705 is rotated such that the headgear connector 700 is in the open position, and the headgear strap end 774 is passed through the passage 702. The headgear strap end 774 is passed through the passage 702 first through the space A between the second headgear connector post 701 and the rotatable post 725. The headgear strap end 774 is then passed through the space B between the rotatable post 725 and the portion of the rotatable portion 705 on an opposing side of the passage 702 as the rotatable post 725. The headgear strap end 774 is then passed through the space C between the rotatable post 725 and the second headgear connector post 701. As such, two portions of the headgear strap 774 are adjacent each other within the passage 702. In other words, two portions of the headgear strap 774 are adjacent to each other within the space C between the rotatable post 725 and the second headgear connector post 701. The two portions of the headgear strap 774 can directly contact each other within the passage 702.

The user can tighten the headgear 770 by pulling the headgear strap end 774 away from the headgear connector 700. When the headgear 770 is positioning the user interface 750 to the user's face sufficiently, it can be secured in place with the headgear connector 700 to secure the user interface 750 in place.

Rotating the rotatable portion 705 can adjust the headgear connector 700 from the open position to the closed position. The headgear connector 700 grips the headgear strap 772 in the closed position. Rotating the rotatable portion 705 such that the tail 713 is rotated towards the second headgear connector post 701, and the rotatable gripping formations 736 is rotated towards the second headgear connector post 701 brings the rotating projections 736 into contact with the second headgear connector post 701 at the periphery of the headgear strap 772. Further rotation of the rotatable portion 705 secures the headgear strap 772 within the headgear connector 700. The rotatable portion 705 urges the headgear strap 772 onto the second headgear connector post 701. This can compress the headgear strap 772 in the region of the second headgear connector post 701. Rotating the rotatable portion 705 therefore causes the headgear connector 700 to grip the headgear strap 772. The same rotation causes the rotatable portion 705 to connect with the second headgear connector post 701. The rotatable gripping formations 736 form a snap-fit, clip fit and/or interference fit against or with the second headgear connector post 701. The illustrated rotatable portion 705 comprises a pair of rotatable gripping formations 736, however in an alternative configuration, the rotatable portion 705 can comprise only a single rotatable gripping formation 736 on one side wall of the rotatable portion 705.

A frictional connection is formed between the rotatable portion 705, the base portion 703 and the headgear strap 772. The frictional connection is formed because a thickness of the passage 702 is less than twice a transverse headgear strap thickness 744 of the headgear strap 772 passing through the passage 702. The thickness of the passage 702 in the closed position at one or more points along the passage 702 is less than twice an uncompressed transverse headgear strap thickness 744. In other words, a distance between at least a portion of the second fixed headgear connector post 701 and the rotatable portion 705 is less than twice the uncompressed transverse headgear strap thickness 744 of the headgear strap 772 passing through the passage 702. Rotating the rotatable portion 705 can therefore be said to reduce a thickness of the passage 702. Preferably, rotating the rotatable portion 705 such that the rotatable gripping formation 736 is rotated towards the second fixed headgear connector post 701, and the tail 713 is rotated towards the second fixed headgear connector post 701 reduces the thickness of the passage 702.

Rotating the rotatable portion 705 such that the rotatable gripping formation 736 is rotated away from the second fixed headgear connector post 701, and the tail 713 is rotated away from the second fixed headgear connector post 701, moves the headgear connector 700 into the open position. This releases the connection between the headgear connector 700 and the headgear strap 772. In other words, rotating the rotatable portion 705 in an opposite direction to the direction it was rotated to secure the headgear strap 772 releases the connection between the headgear connector 700 and the headgear strap 772. The headgear strap 772 can slide or pass through the passage 702 in the open position.

In at least one configuration, the passage 702 can be dimensioned to provide a resistive force on the headgear strap 772 passing through the passage 702 as described with reference to headgear connectors previously disclosed.

At least one configuration of the user interface 750 can comprise a release member 798. The release member can be similar to that described with reference to FIG. 42. The release member can be similar to any of release members 398, 598, 698 previously described. The release member 798 is actuated to release the connection between the headgear 770 and the user interface 750. In particular, the release member 798 can be actuated to release the connection between the headgear strap 772 and the headgear connector 700.

In at least one configuration, the frame 754 is formed from, or comprises a polymer. The polymer can be polycarbonate that rigidly defines a 3-dimensional profile of the frame 754. In at least one configuration, the headgear connector 700 comprises a polymer. The polymer can be a polycarbonate that rigidly defines a 3-dimensional profile of the headgear connector 700. In at least one form, the base portion 703 comprises the polymer. In at least one form, the rotatable portion 705 comprises the polymer. In at least one form, both the base portion 703 and the rotatable portion 705 comprise the polymer.

In at least one configuration, the headgear connector 700 is fixedly connected to the frame 754. The headgear connector 700 can be fixedly connected with the frame 754 as described with reference to headgear connector 600. In at least one configuration, at least a portion of the headgear connector 700 is integrally formed with the frame 754. For example, the base portion 703 can be integrally formed with the frame 754. In at least one configuration, the frame 754 comprises a frame body 761 and a yoke 767 (as described in previous embodiments), and the headgear connector 700 is at least partially integrally formed with the yoke 767. For example, the base portion 703 can be integrally formed with the yoke 767.

The illustrated base portion 703 comprises the first headgear connector post 707, and the illustrated rotatable portion 705 comprises the connector opening 709. In an alternative configuration, the base portion 703 may comprise one or more connector opening/s 709, and the rotatable portion 705 may comprise the first headgear connector post 707.

The illustrated rotatable portion 505 is removable from the base portion 503. In at least one configuration, the rotatable portion 505 is permanently connected to the base portion 503. This can reduce the likelihood that the user will disconnect the rotatable portion 505 and lose the component.

In at least one configuration, the headgear connector 700 can be used with a user interface 750 configured to deliver breathing gas to one or more of the user's mouth and nose without a sealed connection. For example, the headgear connector 700 can be used with a nasal cannula 750.

Figure 32:
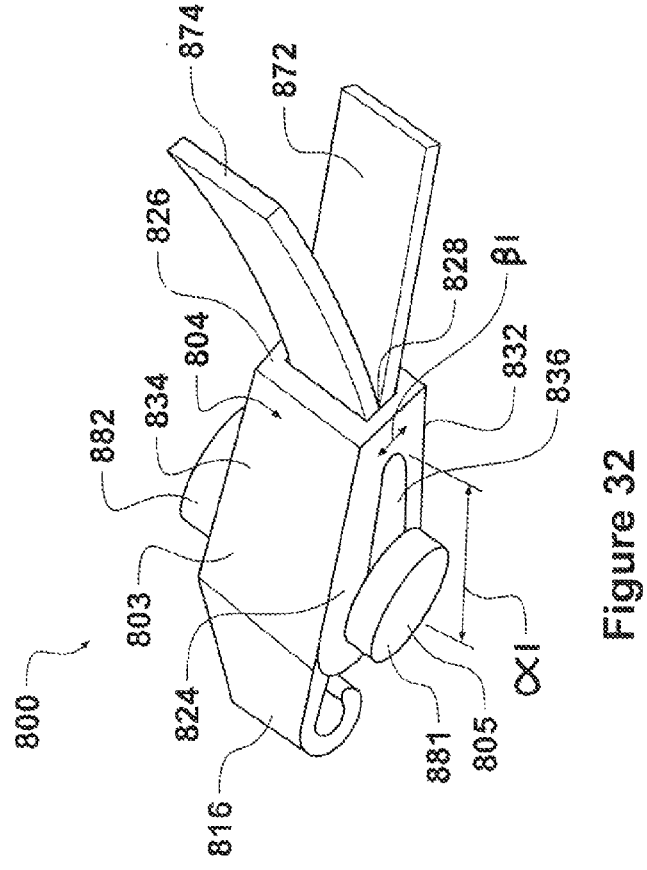
FIG. 32 is a perspective view of a configuration of a headgear connector with a base portion and a longitudinally translatable member.

FIG. 32 an embodiment of a headgear connector 800. FIGS. 33a-33d show cross sectional views of the headgear connector 800 of FIG. 32. A user interface assembly 810 comprises a user interface 850 (not shown) which is configured to secure against the face of the user to define a substantially sealed breathing chamber, and headgear 870 which is configured to connect to the user interface 850 and position and secure the user interface 850 in place on the user's face.

The user interface 850 comprises a frame 854, a cushion module 852, and a breathing gas circuit connector 853. The user interface 850 may comprise the headgear connector 800. The cushion module 852 is removably connected to the frame 854. The headgear connector 800 is configured to connect to the frame 854. The headgear connector 800 facilitates connection of the frame 854 to the headgear 870.

The user interface 850 is configured to be removably connected to headgear 870 via the headgear connector 800. As such, the headgear connector 800 is removably connectable to the headgear 870. The headgear connector 800 is an intermediate component through which the headgear 870 is connected to the frame 854. The headgear 870 comprises at least one headgear strap 872. The headgear strap 872 comprises an elongated portion of the headgear 870. The headgear 870 and headgear strap 872 can be substantially similar to previously described headgear and/or headgear straps.

The headgear connector 800 facilitates the connection of the frame 854 to the headgear 870. The headgear connector 800 is therefore configured to connect to the frame 854. The headgear connector 800 cooperates with the headgear strap 872 to connect the frame 854 to the headgear strap 872, and therefore to connect the user interface 850 to the headgear 870.

The headgear connector 800 is configured to grip a portion of the headgear strap 872. This secures the headgear 870 with respect to the frame 854. The headgear connector 800 comprises a moveable portion 805 and a base portion 803. The illustrated moveable portion 805 is in the form of a moveable post 805. The base portion 803 comprises a channel 825. The base portion 803 comprises an inner wall 832 and an outer wall 834. The inner wall 832 is spaced apart from the outer wall 834. The inner wall 832 is closer to the user's face when the user interface assembly 810 is in use than the outer wall 834. A longitudinal direction can be defined as the direction from where the headgear connector 800 connects to the frame towards the free end of the headgear connector 800. The moveable post 805 is moveable in a longitudinal direction with respect to the base portion 803.

The headgear connector 800 comprises a headgear opening 828. The headgear opening communicates with the channel 825. The channel 825 of the base portion 803 is formed by the space between the inner wall 832 and the outer wall 834. The channel 825 can be in the form of a hollow core. The channel 825 can be in the form of a hollow central portion. The base portion 803 can therefore be at least partially hollow.

The headgear connector 800 comprises a frame coupling 816. The frame coupling 816 is configured to couple the headgear connector 800 to the frame 854. The frame 854 comprises a frame post 869. The frame coupling 816 connects to the frame post 869. The frame coupling 816 and/or frame post 869 can be substantially similar or the same as any of the frame couplings and/or frame posts previously described.

The inner wall 832 comprises an inner wall end 812. The outer wall 834 comprises an outer wall end 814. The inner wall end 812 and the outer wall end 814 can be separated by a space. The space between the inner wall end 812 and the outer wall end 814 defines the headgear opening 828. The illustrated outer wall 834 extends at an angle with respect to the inner wall 832. The angle is such that the distance between the inner wall 832 and the outer wall 834 decreases as one travels along each wall along the channel 825 towards the headgear opening 828. In other words, the distance between the inner wall 832 and the outer wall 834 decreases as the inner wall 832 and the outer wall 834 extend away from the frame coupling 816. In other words, the inner wall 832 and the outer wall 834 are non-parallel.

The inner wall 832 and the outer wall 834 also define a first opening 836 and a second opening 838. The first opening 836, second opening 838 and the channel 825 can define a through-hole between the inner wall 832 and the outer wall 834.

The moveable post 805 can move within the channel 825. A direction from the inner wall 832 towards or away from the outer wall 834 can be a transverse direction. In one form, the movement of the moveable post 805 is longitudinal movement. The moveable post 805 can move longitudinally within the channel 825. The moveable post 805 can span a length of the inner wall 832 and/or the outer wall 834. The moveable post 805 extends through the first opening 836, spans the length of the inner wall 832 and/or the outer wall 834, and extends through the second opening 838. In other words, the moveable post 805 extends through the channel 825. As such, the moveable post 805 is accessible from outside the channel 825 when extending through the channel 825.

The inner wall 832 and the outer wall 834 are configured such that longitudinal movement of the moveable post 805 towards the inner wall end 812 and/or the outer wall end 814 causes the inner wall 834 and the outer wall 834 to grip the moveable post 805. The inner wall 832 and the outer wall 834 are configured such that longitudinal movement of the moveable post 805 away from the inner wall end 812 and/or the outer wall end 814 causes the inner wall 834 and the outer wall 834 to release the moveable post 805.

The base portion 803 and the moveable post 805 together define a headgear receiving passage 802. The passage 802 is a space in the channel 825 between the base portion 803 and the moveable post 805. In the illustrated configuration, the passage 802 comprises a space between the moveable post 805 and the inner wall 832, and a space between moveable post 805 and the outer wall 834. The passage 802 is configured to receive the headgear strap 872.

The first opening 836 comprises a major dimension α1 and a minor dimension β1. The major dimension α1 is larger than the minor dimension β1. That is, the first opening 836 is longer in one direction than another. The first opening 836 is longer in the longitudinal direction than the transverse direction. The illustrated first opening 836 is a rounded rectangle. Alternately, the first opening 836 can be an oval, triangular, ovate, obovate, trapezoidal, or another polygon. The minor dimension β1 of the first opening 836 can vary along the length of the first opening 836. For example, the minor dimension β1 can decrease along the length of the first opening 836 as the first opening 836 spans from near the headgear connector 816 towards the headgear opening 828.

The second opening 838 comprises a major dimension α2 and a minor dimension β2. The major dimension α2 is larger than the minor dimension β2. The second opening can have similar relationships between the major dimension β2 and the minor dimension as those described with reference to the first opening 836. The headgear connector 800 is symmetric about at least one plane. In the illustrated configuration, the headgear connector 800 is symmetric about a central plane such that the first opening 836 and the second opening 838 are substantially the same shape.

The moveable portion 805 comprises a first end portion 881 and a second end portion 882. The first end portion 881 and second end portion 882 are disposed outside the channel 825. The first end portion 881 and second end portion 882 are adjacent the first opening 836 and the second opening 838 respectively. The first end portion 881 and the second end portion 882 are configured to be gripped by the user. The first end portion 881 and the second end portion 882 make it easier for the user to move the moveable portion 805. The first end portion 881 and second end portion 882 can be larger than the part of the moveable portion 805 that extends through the channel 825 so they are easier for the user to grip. The first end portion 881 and the second end portion 882 are circular. Alternatively, the first end portion 881 and/or the second end portion 882 can be oval, triangular, or another polygon. The first end portion 881 and/or the second end portion 882 can comprise a gripping feature to make it easier for the user to grip them. For example, the gripping feature can be a recess or dimple in a surface of the first end portion 881 and/or the second end portion 882.

Figures 33A, 33B, 33C, 33D:
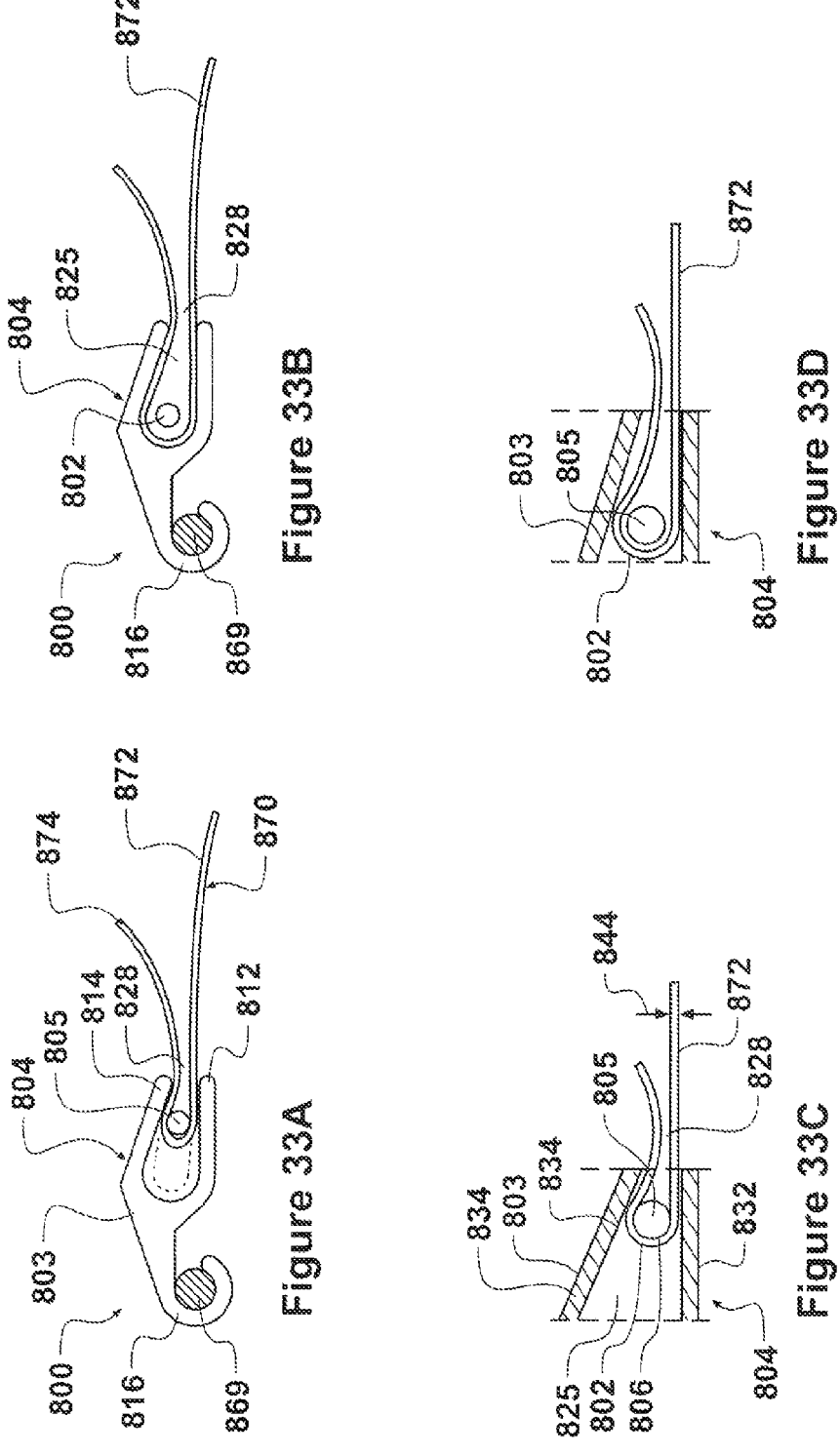
FIG. 33*a* is a cross section of the headgear connector of FIG. 32, with the base portion and the longitudinally translatable member in a closed position, where the headgear connector is gripping a headgear strap.
FIG. 33*b* is a cross section of the headgear connector of FIG. 32 in an open position.
FIG. 33*c* is a cross section of a headgear connecting portion of the headgear connector of FIG. 32, in the closed position.
FIG. 33*d* is a cross section of the headgear connecting portion of FIG. 32, in the open position.

To secure the headgear 870 to the headgear connector 800, the moveable post 805 is moved such that the headgear connector 800 is in the open position (as shown in FIG. 33d). In other words, the moveable post 805 is moved towards the frame coupling 816 within the channel 825. As a result, the moveable post 805 is moved within the channel 825 away from the headgear opening 828. A headgear strap end 874 is passed through the passage 802. The headgear strap end 874 is passed through the headgear opening 828. The headgear strap end 874 is passed through the portion of the passage 802 between the moveable post 805 and the inner wall 832. The headgear strap end 874 is looped around the moveable post 805. The curved surface of the passage 802 can assist the user looping the headgear strap end 874 around the moveable post 805 within the channel 825. The headgear strap end 874 is passed through the portion of the passage 802 between the moveable post 805 and the outer wall 834. The headgear strap end 874 is then passed through headgear opening 828, and extends out from the channel 825. The user can tighten the headgear 870 by pulling the headgear strap end 874 away from the headgear connector 800. When the headgear 870 is positioning the user interface 850 to the user's face sufficiently, it can be secured in place with the headgear connector 800 to secure the user interface 850 in place.

As such, moving the moveable post 805 when the headgear strap 872 has been passed through the passage 802 adjusts the headgear connector 800 from the open position to the closed position. In other words, moving the moveable post 805 away from the frame coupling 816, and/or towards the inner wall end 812 and/or the outer wall end 814, causes the headgear connector 800 to grip the headgear strap 872 between the moveable post 805, the inner wall 832 and the outer wall 834. The headgear strap 872 is therefore wedged between the inner wall 832, outer wall 834 and the moveable post 805 (as shown in FIG. 33c). The inner wall 832 and/or the outer wall 834 may comprise a projecting structure to prevent or minimise the probability that the moveable post 805 can be pulled through the headgear opening 828.

A frictional connection is formed between the inner wall 832, outer wall 834, the headgear strap 872 and the moveable post 805. A frictional connection is therefore formed between the headgear strap 872 and the headgear connector 800. The frictional connection is formed because a thickness of the passage 802 when the moveable post 805 is wedged is less than a transverse headgear strap thickness 844. In other words, a distance between the moveable post 805 and the inner wall 832 and/or the outer wall 834 is less than the uncompressed transverse headgear strap thickness 844, of the headgear strap 872 passing through the passage 802. Moving the moveable post 805 away from the frame coupling 816, and/or towards the inner wall end 812 and/or the outer wall end 814 can therefore be said to reduce a thickness of the passage 802.

Moving the moveable post 805 towards the frame coupling 816, and/or away from the inner wall end 812 and/or the outer wall end 814 moves the headgear connector 800 into the open position. This releases the connection between the headgear connector 800 and the headgear strap 872. In other words, moving the moveable post 805 in an opposite direction to the direction it was moved to secure the headgear strap 872 releases the connection between the headgear connector 800 and the headgear strap 872. The headgear strap 872 can slide or pass through the passage 802 in the open position.

In at least one configuration, the frame 854 is formed from, or comprises a polymer. The polymer can be polycarbonate that rigidly defines a 3-dimensional profile of the frame 854. In at least one configuration, the headgear connector 800 comprises a polymer. The polymer can be a polycarbonate that rigidly defines a 3-dimensional profile of the headgear connector 800. In at least one form, the base portion 803 comprises the polymer. In at least one form, the moveable post 805 comprises the polymer. In at least one form, both the base portion 803 and the moveable post 805 comprise the polymer.

In at least one configuration, the headgear connector 800 is fixedly connected to the frame 854. The headgear connector 800 can be fixedly connected with the frame 854 as described with reference to headgear connector 600, or headgear connector 700. In at least one configuration, at least a portion of the headgear connector 800 is integrally formed with the frame 854. For example, the base portion 803 can be integrally formed with the frame 854. In at least one configuration, the frame 854 comprises a frame body 861 and a yoke 867 (as described in previous embodiments), and the headgear connector 800 is at least partially integrally formed with the yoke 867. For example, the base portion 803 can be integrally formed with the yoke 867.

In at least one configuration, the headgear connector 800 can be used with a user interface 850 configured to deliver breathing gas to one or more of the user's mouth and nose without a sealed connection. For example, the headgear connector 800 can be used with a nasal cannula 850.

Figure 34B:
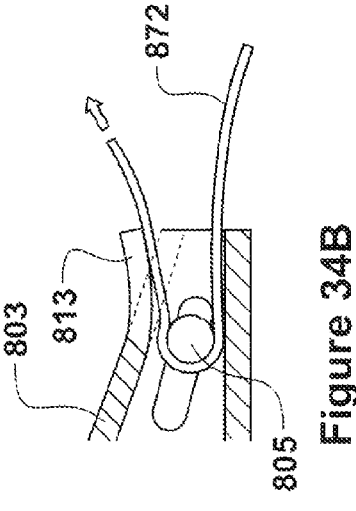
FIG. 34*b* is a cross section of the headgear connector of FIG. 34*a* showing flex of the flexible portion with a headgear strap being adjusted.
Figure 34A:
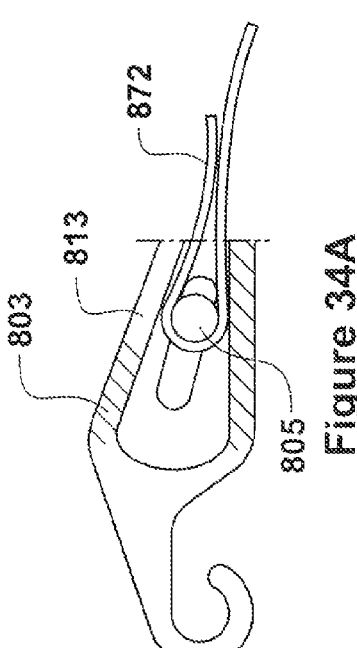
FIG. 34*a* is a cross section of another configuration of the headgear connector of FIG. 32, where the base portion comprises a flexible portion.
Figure 34C:
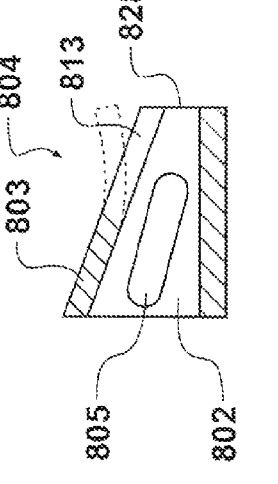
FIG. 34*c* is a cross section of another configuration of the headgear connector of FIG. 34*a*, with an elongate longitudinally translatable member.

FIG. 34a-FIG. 34c shows alternate configurations of the headgear connector 800. The headgear connector 800 of FIGS. 34a and 34b is substantially similar to the headgear connector 800 of FIGS. 23-33d with the notable exception that the headgear connector 800 of FIGS. 34a and 34b comprises a deformable portion 813. The headgear connector 800 of FIG. 34c is similar to the headgear connector 800 of FIGS. 32-33d with the notable exception that the moveable portion 805 is substantially rectangular moveable post 805, and the headgear connector 800 comprises a deformable portion 813. In particular, the moveable post 805 of the headgear connector 800 of FIG. 34c is a rounded rectangle in cross section. A rectangular moveable post 805 can provide an improved connection to the headgear strap 872. For example, a rectangular moveable post 805 can wedge the headgear strap 872 between the inner wall 832 and the outer wall 834 more effectively than a circular moveable post 805.

The outer wall 834 illustrated in the headgear connectors 800 of FIGS. 34a-34c comprises the deformable portion 813. The deformable portion 813 can be deformed by the moveable post 805 when the headgear connector 800 is in the closed position. Longitudinal movement of the moveable post 805 towards the inner wall end 812 and/or the outer wall end 814 causes deformation of the deformable portion 813 as the moveable post 805 contacts the deformable portion 813. The deformable portion 813 deforms to accommodate the movement of the moveable post 805. This can enhance the connection between the headgear strap 872, the moveable post 805 and the outer wall 834. In at least one configuration, the deformable portion 813 can be a flexible portion that flexes outward when the headgear connector 800 is in the closed position. The deformable portion 813 can be an elastomeric portion 813. The deformable portion 813 can comprise silicone.

In at least one configuration, the inner wall 832 can comprise the deformable portion 813. In at least one configuration, both the inner wall 832 and the outer wall 834 can comprise deformable portions.

Figures 35A, 35B:
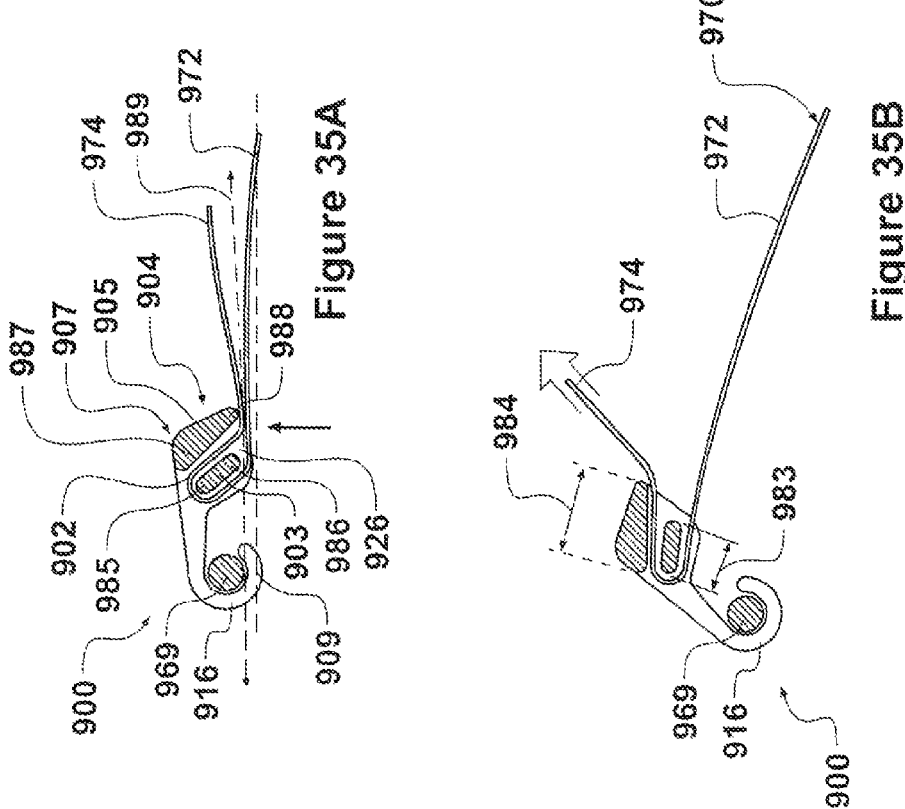
FIG. 35*a* is a cross section of a headgear connector comprising a first elongate member, a second elongate member, and a passage between the first elongate member and the second elongate member, where the headgear connector is in a closed position.
FIG. 35*b* is a cross section of the headgear connector of FIG. 35*a* in an open position.

FIG. 35 and FIG. 36 show an embodiment of a headgear connector 900. A user interface assembly 910 comprises a user interface 950 which is configured to secure against the face of the user to define a substantially sealed breathing chamber, and headgear 970 which is configured to connect to the user interface 950 and position and secure the user interface 950 in place on the user's face.

The user interface 950 comprises a frame 954, a cushion module 952, and a breathing gas circuit connector 953. The user interface 950 may comprise the headgear connector 900. In the illustrated configuration, the cushion module 952 is removably connected to the frame 954. The headgear connector 900 is configured to connect to the frame 954. The headgear connector 900 facilitates connection of the frame 954 to the headgear 970.

The user interface 950 is configured to be removably connected to headgear 970 via the headgear connector 900. The headgear connector 900 is an intermediate component through which the headgear 970 is connected to the frame 954. The headgear 970 comprises at least one headgear strap 972. The headgear strap 972 is configured to connect with the user interface 950. The headgear strap 972 comprises an elongated portion of the headgear 970. The headgear 970 and headgear strap 972 can be substantially similar to previously described headgear and/or headgear straps. The headgear connector 900 facilitates the connection of the frame 954 to the headgear strap 972. The headgear connector 900 is configured to connect to the frame 954. The headgear connector 900 connects to the headgear strap 972, and therefore connects the user interface 950 to the headgear 970.

The headgear connector 900 is configured to grip the headgear strap 972. The headgear connector 900 comprises a connector body 907. The illustrated connector body 907 can be considered an elongate connector body 907. A longitudinal direction can be defined as the direction from where the headgear connector 900 connects to the frame towards the free end of the headgear connector 900. The connector body 907 comprises a longitudinal axis 909 configured to be substantially aligned with a longitudinal axis of the headgear strap 972 in use. The connector body 907 comprises a first side wall 924 (not shown). The connector body 907 comprises a second side wall 926. In one form, for example, in use, the first side wall 924 can be an upper side wall and the second side wall 926 can be a lower side wall. In another form, the first side wall 924 can be the lower side wall and the second side wall 926 can be the upper side wall. The first side wall 924 and the second side wall 926 are separated by a distance. In other words, there is a space between the first side wall 924 and the second side wall 926.

The headgear connector 900 comprises a frame coupling 916. The frame coupling 916 is configured to couple the headgear connector 900 to the frame 954. The frame 954 comprises a frame post 969. The frame coupling 916 couples to the frame post 969. The frame coupling 916 and/or frame post 969 can be substantially similar to any of the frame couplings and/or frame posts previously described.

The headgear connector 900 comprises a first post 903. The first post 903 extends across the connector body 907 in a direction substantially perpendicular to the longitudinal axis of the connector body, spanning the distance separating the first side wall 924 and the second side wall 926. The headgear connector 900 comprises a second post 905. The second post 905 extends across the connector body 907 in a direction substantially perpendicular to the longitudinal axis of the connector body, spanning the distance separating the first side wall 924 and the second side wall 926. The first post 903 and second post 905 are spaced apart along the longitudinal axis 909 of the connector body 907 defining at least part of a headgear receiving passage 902. The first post 903 and second post 905 are substantially parallel. The first post 903 is disposed between the second post 905 and the frame coupling 916.

The first post 903 has a first post outer end 985 and a first post inner end 986. A distance between the first post outer end 985 and the first post inner end 986 defines a first post elongate dimension 983. The second post 905 has a second post outer end 987 and a second post inner end 988. A distance between the second post outer end 987 and the second post inner end 988 defines a second post elongate dimension 984. The first post elongate dimension 983 is greater than the second post elongate dimension 984.

A line between the frame post 969 and the second post inner end 988 (when the headgear connector 900 is connected to the frame 954) can define an inner axis 989 of the headgear connector 900. The first post inner end 986 is spaced apart from the inner axis 989. The first post inner end 986 is displaced outwardly from the inner axis 989. There is therefore a distance between the first post inner end 989 and the nearest portion of the inner axis 989. In other words, the first post inner end 986 is offset from the second post inner end 988. The second post inner end 988 can comprise one or more teeth configured to improve the extent to which second post inner end 988 can grip the headgear strap 972.

To secure the headgear 970 to the headgear connector 900, a headgear strap end 974 is passed between the first post 903 and the frame coupling 916. The headgear strap end 974 is looped around the first post outer end 985 and is passed through the passage 902. The headgear strap end 974 is passed through the passage 902 and around the second post inner end 988.

Figures 36A, 36B:
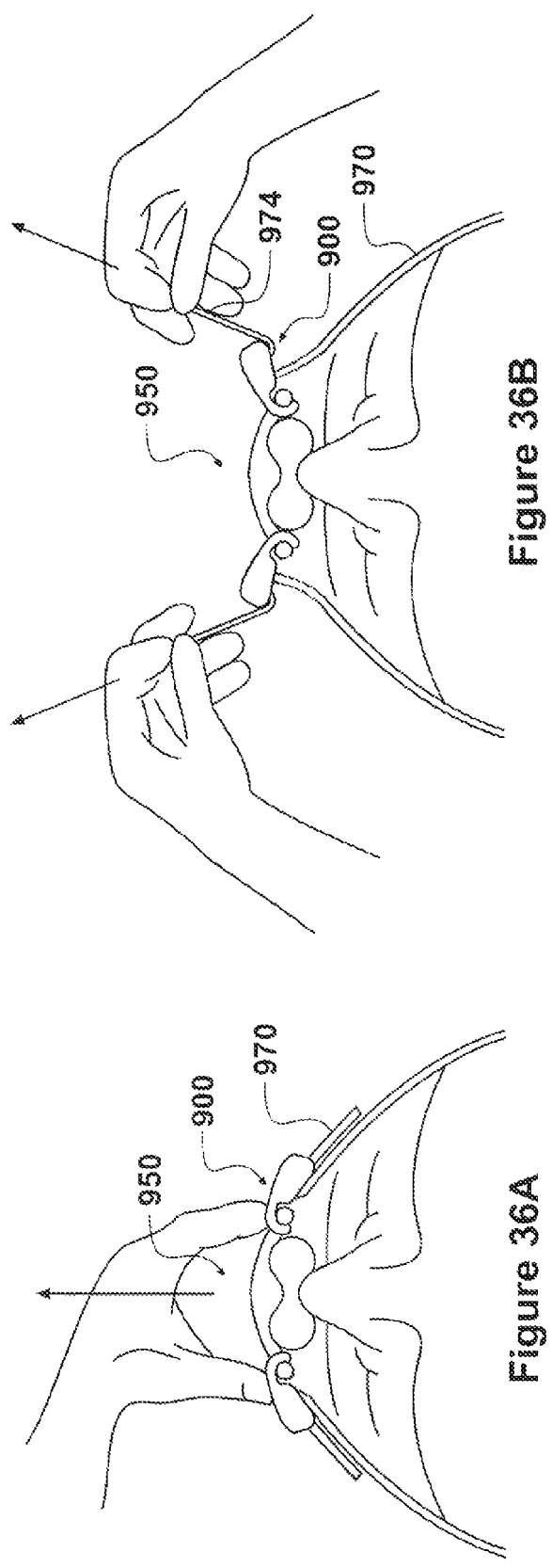
FIG. 36*a* is a top view of a user adjusting a user interface assembly on their head, where the user interface assembly comprises the headgear connector of FIG. 35*a*.
FIG. 36*b* is a top view of the user adjusting headgear tension using the headgear connector of FIG. 35*a*.

The user can tighten the headgear 970 by pulling the headgear strap end 974 away from the headgear connector 900 (as shown in FIG. 36*b*). Pulling the headgear strap end 974 applies a tensile force on the portion of the headgear strap 972 that has passed through the passage 902. With the user interface assembly 910 positioned on the user's head, an opposing tensile force is therefore applied to the portion of the headgear strap 972 that has not passed through the passage 902, due to this portion of the headgear strap 972 compressing the user's head.

The headgear connector 900 is configured such that the application of tension on the portion of the headgear strap 972 that has not been passed through the passage 902 causes the headgear connector 900 to rotate about the frame post 969 securing the headgear 970 with respect to the frame 954. The tensile force on the headgear strap 972 that has not been passed through the passage 902 is present after the user interface assembly 910 has been tightened when the gas source 3 is operating because of a 'blow-off' force exerted on the mask and headgear 970 by the pressurised gas being delivered to the user. That is, when the gas source 3 is delivering pressurised gas, the flow of the pressurised gas into the seal 956, and out of one or more openings of the seal 956 to be delivered to the user produces a force that can be referred to as the aforementioned 'blow-off' force. This force maintains the tension in the headgear strap 972 that has not passed through the passage 902

Rotation of the headgear connector 900 with respect to the frame 954 causes the headgear connector 900 to grip the headgear strap 972 when the headgear strap 972 is under tension. When the portion of the headgear strap 972 that has not passed through the passage 902 is under tension (e.g. when the headgear 970 has been tightened on the user's head), it provides a rigid structure. The force on the headgear strap 972 acts on the headgear connector 900 to bias it in a closed position (as shown in FIG. 34*a*). In other words, the tension biases the headgear connector 900 to be against or parallel to the adjacent surface of the user's face.

A frictional connection is formed between the second post inner end 988, the portion of the headgear strap 972 that has passed through the passage 902, and the tensioned portion of the headgear strap 972 that has not passed through the passage 902. In other words, the second post inner end 988 pinches the portion of the headgear strap 972 that has passed through the passage 902 onto the tensioned portion of the headgear strap 972 that has not passed through the passage 902.

Rotating the headgear connector 900 about the frame post 969 such that the second post inner end 988 is rotated away from the user's face releases the connection between second post inner end 988 and the headgear strap 972. In other words, rotating the headgear connector 900 about the frame post 969 in an opposite direction to the direction it was rotated by the tension in the portion of the headgear strap 972 that had not been passed through the passage 902 releases the connection between the headgear connector 900 and the headgear strap 972.

In at least one configuration, the passage 902 can be dimensioned so that it provides a resistive force against movement of the headgear strap 972 through the passage 902 as described with reference to previous embodiments.

At least one configuration of the user interface 950 can comprise a release member 998. The release member can be similar to that described with reference to FIG. 42. The release member 998 can be similar to any one of the previously described release members. The release member 998 is actuated to release the connection between the headgear strap 972 and the user interface 950.

The illustrated headgear connector 900 is removably connected to the frame 954. In at least one configuration, the headgear connector 900 is fixedly connected to the frame 954. The headgear connector 900 can be fixedly connected with the frame 954 as described with reference to headgear connector 600, or headgear connector 700. In at least one configuration, the frame 954 comprises a frame body 961 and a yoke 967 (as described in previous embodiments), and the headgear connector 900 connects to the yoke 967.

In at least one configuration, the frame 954 is formed from, or comprises a polymer. The polymer can be polycarbonate that rigidly defines a 3-dimensional profile of the frame 954. In at least one configuration, the headgear connector 900 comprises a polymer. The polymer can be a polycarbonate that rigidly defines a 3-dimensional profile of the headgear connector 900.

In at least one configuration, the headgear connector 900 can be used with a user interface 950 configured to deliver breathing gas to one or more of the user's mouth and nose without a sealed connection. For example, the headgear connector 900 can be used with a nasal cannula 950.

Figure 37:
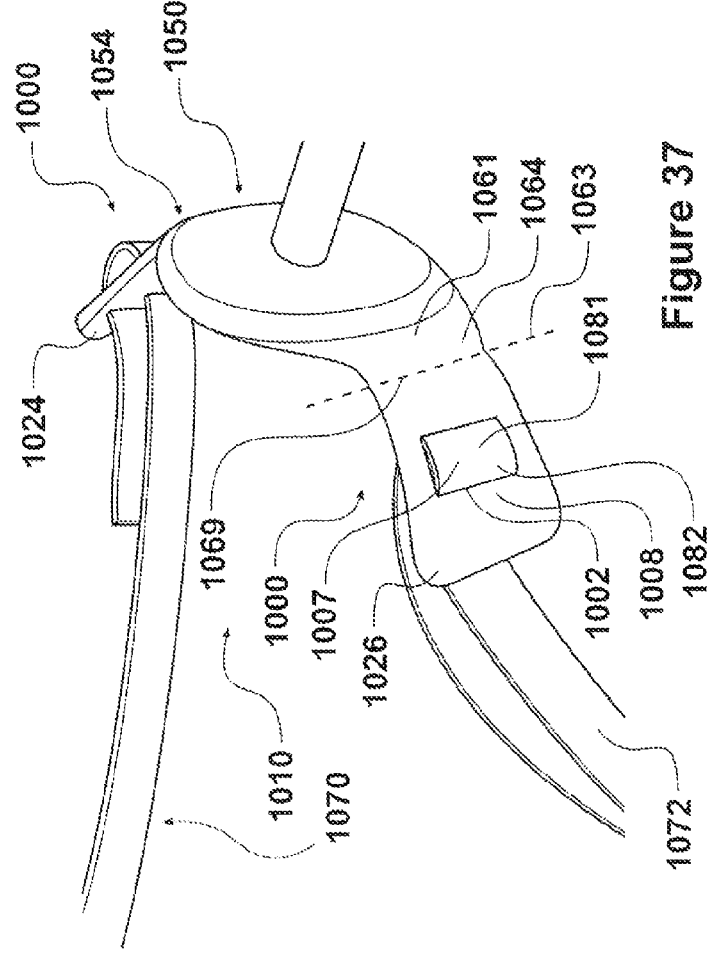
FIG. 37 is perspective view of a user interface comprising a headgear connector connected to a frame body at a hinge.

FIG. 37 shows an embodiment of a user interface assembly 1010. A user interface assembly 1010 comprises a user interface 1050 which is configured to secure against the face of the user to define a substantially sealed breathing chamber, and headgear 1070 which is configured to connect to the user interface 1050 and position and secure the user interface 1050 in place on the user's face.

The user interface 1050 comprises a frame 1054, a cushion module 1052 (not shown), and a breathing gas circuit connector 1053 (not shown). The user interface 1050 may comprise the headgear connector 1000. The cushion module 1052 is removably connected to the frame 1054.

The user interface 1050 is configured to be removably connected to the headgear 1070 via the headgear connector 1000. The headgear 1070 comprises at least one headgear strap 1072. The headgear strap 1072 is configured to connect with the user interface 1050. The headgear strap 1072 comprises an elongated portion of the headgear 1070. The headgear 1070 and headgear strap 1072 are substantially similar to previously described headgear and/or headgear straps.

The frame 1054 comprises a user interface body 1061 and two headgear connectors 1000. Each headgear connector 1000 is disposed at or near a respective frame lateral portion 1064 of the user interface body 1061. The headgear connector 1000 is connected to the user interface body 1061 at a hinge 1069. The hinge 1069 is a living hinge. The headgear connector 1000 is therefore integrally formed with the user interface body 1061. The hinge 1069 is defined by a thin portion of the frame 1054. A thickness of the hinge 1069 is less than a thickness of the headgear connector 1000 adjacent the hinge 1069. A thickness of the hinge 1069 is less than a thickness of the user interface body 1061 adjacent the hinge 1069. The hinge 1069 is configured to flex without breaking. The headgear connector 1000 can therefore rotate with respect to the user interface body 1061 about the hinge 1069. The hinge 1069 defines a hinge axis 1063. The headgear connector 1000 rotates with respect to the user interface body 1061 about the hinge axis 1063.

The headgear connector 1000 comprises a headgear connector interior surface 1024. The headgear connector 1000 comprises a headgear connector exterior surface 1026. The headgear connector interior surface 1024 is inward-facing with respect to the user when the user interface assembly 1010 is in use. The headgear connector exterior surface 1026 is outward-facing with respect to the user when the user interface assembly 1010 is in use. The headgear connector 1000 comprises a first opening 1081. The first opening 1081 extends from the headgear connector interior surface 1024, through the headgear connector 1000, to the headgear connector exterior surface 1026. The headgear connector 1000 comprises a second opening 1082. The second opening 1082 extends from the headgear connector interior surface 1024, through the headgear connector 1000, to the headgear connector exterior surface 1026. The first opening 1081 and the second opening 1082 are separated by a headgear connector post 1007. A longitudinal direction can be defined as the direction from the hinge 1069 towards the free end of the headgear connector 1000. The second opening 1082 is longitudinally displaced along the headgear connector 1000 with respect to the first opening 1081. The first opening 1081 and the second opening 1082 together define a headgear receiving passage 1002. The passage 1002 is configured to receive the headgear strap 1072.

To secure the headgear 1070 to the headgear connector 1000, a headgear strap end 1074 is passed through the first opening 1081 in a first direction from the headgear connector interior surface 1024 towards the headgear connector exterior surface 1026. The headgear strap end 1074 is looped around the headgear connecting post 1007. The headgear strap end 1074 is then passed through the second opening 1082 in a second direction from the headgear connector exterior surface 1026 towards the headgear connector interior surface 1024. The headgear strap 1072 is therefore passed through the passage 1002 as shown in FIG. 37.

The user can tighten the headgear 1070 by pulling the headgear strap end 1074 further away from headgear connector 1000 (as shown in FIG. 36*b* with reference to the previous headgear connector 900). In other words, the user can tighten the headgear 1070 by pulling the headgear strap end 1074 away from the user interface body 1061 after having passed it through the passage 1002. Pulling the headgear strap end 1074 applies a tensile force on the portion of the headgear strap 1072 that has passed through the passage 1002. With the user interface assembly 1010 positioned on the user's head, an opposing tensile force is therefore applied to the portion of the headgear strap 1072 that has not passed through the passage 1002 as a result of the previously described 'blow-off' force as a result of the delivered pressurised gas. This force maintains the tension in the headgear strap 1072 that has not passed through the passage 1002.

The headgear connector 1000 is configured such that the application of tension on the portion of the headgear strap 1072 that has not been passed through the passage 1002 causes the headgear connector 1000 to rotate about hinge 1069, thereby securing the headgear 1070 with respect to the frame 1054. This effect is most pronounced with the user is not applying the tensile force on the portion of the headgear strap 1072 that has passed through the passage 1002. The tensile force on the headgear strap 1072 that has not been passed through the passage 1002 is present after the user interface assembly 1010 has been tightened because the headgear 1070 is effectively pulling the user interface 1050 against the face of the user.

Rotation of the headgear connector 1000 with respect to the frame body 961 causes the headgear connector 1000 to engage the headgear strap 1072 when the headgear strap 1072 that has not been passed through the passage 1002 is under tension. This rotation may be caused by the tension in the headgear strap 1072 that has not passed through the passage 1002. In particular, rotation of the headgear connector 1000 about the hinge 1069 such that the second opening 1082 approaches the user's head causes the headgear connector 1000 to grip the headgear strap 1072. When the portion of the headgear strap 1072 that has not passed through the passage 1002 is under tension (e.g. when the headgear 1070 has been tightened on the user's head), it provides a rigid structure. The force on the headgear strap 1072 acts on the headgear connector 1000 to bias it in a closed position.

A frictional connection is formed between an outer side wall 1008 of the second opening 1082, the portion of the headgear strap 1072 that has passed through the passage 1002, and the tensioned portion of the headgear strap 1072 that has not passed through the passage 1002. In other words, the outer side wall 1008 of the second opening 1082 pinches the portion of the headgear strap 1072 that has passed through the passage 1002 onto the tensioned portion of the headgear strap 1072 that has not passed through the passage 1002.

Rotating the headgear connector 1000 about the frame post 1069 such that the second opening 1082 is rotated away from the user's face releases the connection between the headgear connector 1000 and the headgear strap 1072. In other words, rotating the headgear connector 1000 about the hinge 1069 in an opposite direction to the direction it was rotated by the tension in the portion of the headgear strap 1072 that had not been passed through the passage 1002 releases the connection between the headgear connector 1000 and the headgear strap 1072.

In at least one configuration, the passage 1002 can be dimensioned so that it provides a resistive force against movement of the headgear strap 1072 through the passage 1002 as described with reference to previous embodiments.

At least one configuration of the user interface 1050 can comprise a release member 1098. The release member can be similar to that described with reference to FIG. 42. The release member can be similar to any of the release members previously described. The release member 1098 can be actuated to release the connection between the headgear strap 1072 and the headgear connector 1000.

In at least one configuration, the frame 1054 is formed from, or comprises a polymer. The polymer can be polycarbonate that rigidly defines a 3-dimensional profile of the frame 1054. In at least one configuration, the headgear connector 1000 comprises a polymer. The polymer can be a polycarbonate that rigidly defines a 3-dimensional profile of the headgear connector 1000.

In at least one configuration, the headgear connector 1000 and hinge 1069 can be used with a user interface 1050 configured to deliver breathing gas to one or more of the user's mouth and nose without a sealed connection. For example, the headgear connector 1000 can be used with a nasal cannula 1050.

The illustrated headgear connectors 1000 are integrally formed with the user interface body 1061 such that the hinge 1069 is a living hinge. In at least one configuration, one or more headgear connectors 1000 may be formed separately from the user interface body 1061, and connected to the user interface body 1061 at a connection that forms each hinge 1069. The hinge 1069 can be formed from a material overmoulded onto the user interface body 1061 and each headgear connector 1000. The material can be flexible or bendable to form a hinge. For example, the material can be a silicone that is overmoulded onto surfaces of the headgear connectors 1000 and the user interface body 1061 near the location of the hinge 1069.

In at least another configuration, the hinge 1069 can comprise a detachable post that is received by holes one or more of the headgear connectors 1000 and the user interface body 1061. Alternatively, the post can be integrated with at least one of the headgear connectors 1000 or the user interface body 1061, and received by the respective other of the headgear connectors 1000 or the user interface body 1061.

FIG. 38a-FIG. 40 show a user interface assembly 1110 configured for the delivery of respiratory therapy to a user. The illustrated user interface assembly 1110 comprises a user interface 1150, which is configured to secure against the face of the user to define a substantially sealed breathing chamber, and headgear 1170 which is configured to connect to the user interface 1150 and position and secure the user interface 1150 in place on the user's face. The headgear 1170 secures the user interface 1150 to the user's face in an operating position enabling the delivery of the respiratory therapy. The illustrated user interface assembly 1110 delivers respiratory therapy in the form of a flow of pressurized breathing gas (e.g., humidified air) to the breathing chamber of the user interface 1150 and, eventually, to the user's airway.

The user interface 1150 comprises a frame 1154, a cushion module 1152 (not shown), and a breathing gas circuit connector 1153. The cushion module 1152 is removably connectable to the frame 1154. The cushion module 1152 comprises a seal 1156 and can be substantially similar to the cushion modules previously described.

The user interface 1150 is configured to be removably connected to headgear 1170. The headgear 1170 comprises at least one headgear strap 1172. The headgear strap 1172 is configured to connect with the user interface 1150. The headgear strap 1172 comprises an elongated portion of the headgear 1170. The headgear 1170 and headgear strap 1172 are substantially similar to, or the same as headgear and headgear straps previously described.

The user interface 1150 comprises a first headgear connector 1100 and a second headgear connector 1101. The first headgear connector 1100 is connected to the frame 1154 with a first strap 1103. The first strap 1103 connects to the frame 1154 at a first connection 1105. The first strap 1103 is bendable. The first strap 1103 therefore allows the first headgear connector 1100 to move with respect to the frame 1154. The second headgear connector 1101 is connected to the frame 1154 with a second strap 1104. The second strap 1104 is connected to the frame 1154 at a second connection 1106. The second strap 1104 is bendable. The second strap 1104 therefore allows the second headgear connector 1101 to move with respect to the frame 1154. The first headgear connector 1100, when connected to the first strap 1103 is positioned generally forward (with respect to the user) of the second headgear connector 1101 when connected to the second strap 1104. The first connection 1105 is displaced forward on the frame 1154 with respect to the second connection 1106. In other words, the first connection 1105 is further away from a user of the user interface assembly 1110 than the second connection 1106 when the user interface assembly 1110 is in use.

The first headgear connector 1100 comprises a first connector opening 1107. The first headgear connector 1100 comprises a first connector outer side 1109 and a first connector inner side 1111. The first connector outer side 1109 is outward-facing with respect to the user when the user interface assembly 1110 is in use. That is, the first connector outer side 1109 faces away from the user when the user interface assembly 1110 is in use. The first connector inner side 1111 is inward-facing with respect to the user when the user interface assembly 1110 is in use. That is, the first connector inner side 1111 faces the user when the user interface assembly 1110 is in use. The first connector opening 1107 extends from the first connector outer side 1109, through the first connector 1100, to the first connector inner side 1111. The first connector opening 1107 is substantially rectangular. In at least one configuration, the first connector opening 1107 can be circular, oval, trapezoidal, another polygon, or have curved corners.

The second headgear connector 1101 comprises a second connector opening 1108. The second connector 1101 comprises a second connector outer side 1112 and a second connector inner side 1113. The second connector outer side 1112 is outward-facing with respect to the user when the user interface assembly 1110 is in use. That is, the second connector outer side 1112 faces away from the user when the user interface assembly 1110 is in use. The second connector outer side 1112 faces the first connector inner side 1111. The second connector inner side 1113 is inward-facing with respect to the user when the user interface assembly 1110 is in use. That is, the second connector inner side 1113 faces the user when the user interface assembly 1110 is in use. The second connector opening 1108 extends from the second connector outer side 1112, through the second connector 1101, to the second connector inner side 1113. The second connector opening 1108 is substantially rectangular. In at least one configuration, the second connector opening 1108 can be circular, oval, trapezoidal, another polygon, or have curved corners.

The first strap 1103 loops through the first connector opening 1107 to connect the first headgear connector 1100 to the frame 1154. The second strap 1104 loops through the second connector opening 1108 to connect the second headgear connector 1101 to the frame 1154.

The first headgear connector 1100 and second headgear connector 1101 together define a passage 1102. The passage 1102 is configured to receive headgear 1170. Preferably, the passage 1102 is configured to receive the headgear strap 1172 so that the headgear strap 1172 can pass through the passage 1102. The passage 1102 comprises the first connector opening 1107 and the second connector opening 1108. The first connector opening 1107 and second connector opening 1108 are substantially aligned in at least one plane so that the headgear strap 1172 can pass through the passage 1102 without twisting.

To secure the headgear 1170 to the frame 1154, a headgear strap end 1174 is passed through the second connector opening 1108 in a direction from the second connector inner side 1113 towards the second connector outer side 1112. The headgear strap end 1174 is then passed through the first connector opening 1107 in a direction from the first connector inner side 1111 towards the first connector outer side 1109. The headgear strap end 1174 is then looped around the first headgear connector 1100. The headgear strap end 1174 is passed through the second connector opening 1108 in a direction from the second connector outer side 1112 towards the second connector inner side 1113. The headgear strap 1172 has therefore been passed through the passage 1102, defined by the path that the headgear strap traversed the first connector opening 1107 and the second connector opening 1108.

The user can tighten the headgear 1170 by pulling the headgear strap end 1174 further away from the second headgear connector 1101. Pulling the headgear strap end 1174 applies a tensile force on the portion of the headgear strap 1172 that has passed through the passage 1102. With the user interface assembly 1110 positioned on the user's head, another tensile force is therefore applied to the portion of the headgear strap 1172 that has not passed through the passage 1102, due to this portion of the headgear strap 1172 compressing the user's head.

As the user is tightening the headgear, the tensile force on the portion of the headgear strap 1172 that has passed through the passage 1102, together with the tensile force on the portion of the headgear strap 1172 that has not passed through the passage 1102 act to pull the first headgear connector 1100 towards the second headgear connector 1101.

The tensile force on the portion of the headgear strap 1172 that has not passed through the passage 1102 pulls a first connector outer wall 1114 towards a second connector opening outer wall 1115. This compresses the portion of the headgear strap 1172 that has passed through the first connector opening 1107 but has not yet passed through the second connector opening 1108 between the first headgear connector 1100 and the second headgear connector 1101. The first headgear connector 1100 and the second headgear connector 1101 can be said to pinch the headgear strap 1172. The tension in the portion of the headgear strap that has not passed through the passage 1102 maintains this connection between the first headgear connector 1100, second headgear connector 1101, and the headgear strap 1172.

In other words, relative movement between the first headgear connector and the second headgear connector such that they are bought toward one another causes the first headgear connector 1100 and the second headgear connector 1101 to grip the headgear strap 1172. In such a position, the first headgear connector 1100 and the second headgear connector 1101 can be said to be in a closed position. The first headgear connector 1100 and the second headgear connector 1101 can therefore be said to grip the headgear strap 1172. The first headgear connector 1100 and the second headgear connector 1101 grip the headgear strap 1172 when the first headgear connector 1100 is moved towards the second headgear connector 1101. A frictional connection is formed between the first headgear connector 1100, the headgear strap 1172, and the second headgear connector 1101 when in the closed position.

Figures 38A, 38B:
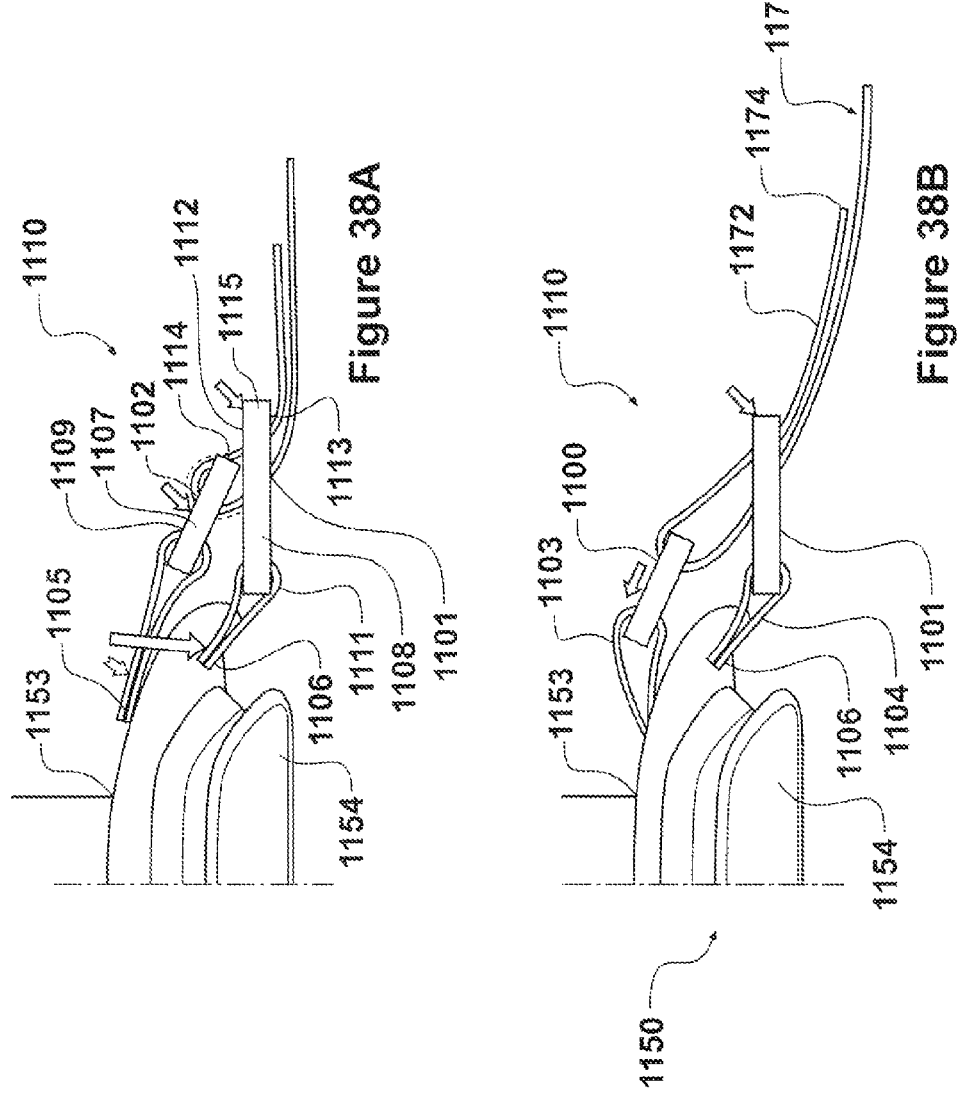
FIG. 38*a* is a top view of a user interface assembly comprising a first headgear connector comprising a first opening, and a second headgear connector comprising a second opening, where the first headgear connector and second headgear connector are in a closed position gripping a headgear strap.
FIG. 38*b* is a top view of the user interface assembly of FIG. 38*a*, where the first headgear connector and the second headgear connector are in an open position.
Figures 39A, 39B:
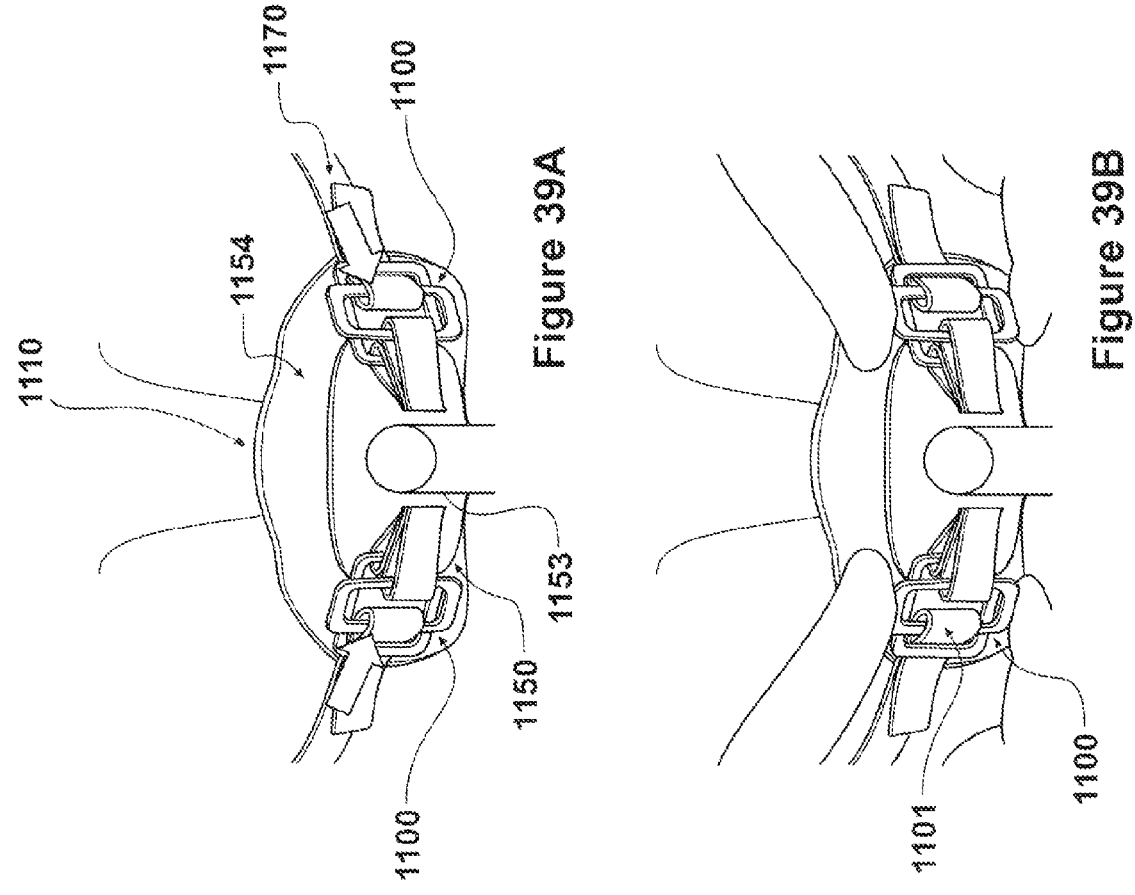
FIG. 39*a* is a perspective view of the user interface assembly of FIG. 38*a* showing a direction that the first headgear connector can be moved with respect to the second headgear connector to release the connection between the first headgear connector, second headgear connector and the headgear strap.
FIG. 39*b* shows a perspective view of a user adjusting the first headgear connector of FIG. 38*a* with respect to the second headgear connector.

The headgear strap 1172 can be released from the first headgear connector 1100 and the second headgear connector 1101 by relative movement of the first headgear connector 1100 in a direction away from the second headgear connector 1101 (as shown in FIG. 38b, FIG. 39a and FIG. 39b). Moving the first headgear connector 1100 towards the frame 1154 releases the headgear strap 1172.

Figure 40:
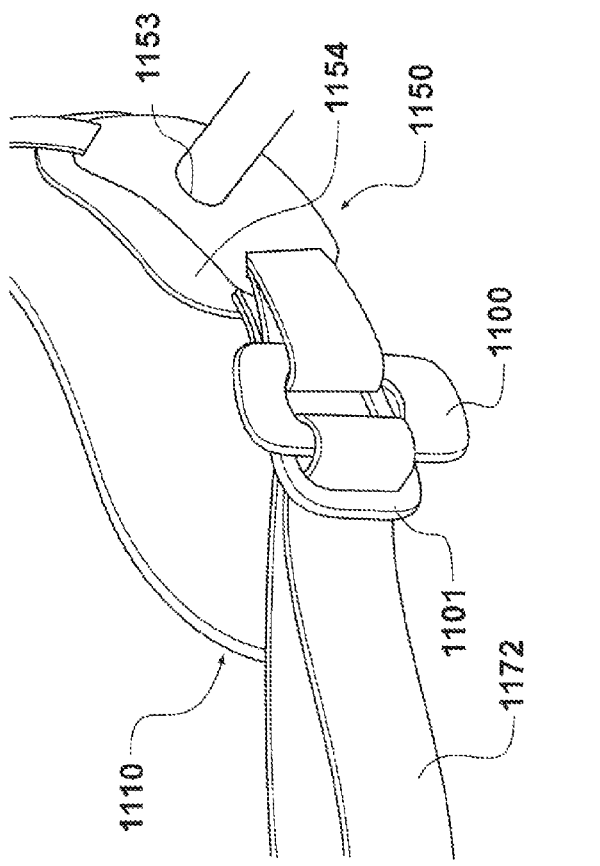
FIG. 40 is a perspective view of the user interface assembly of FIG. 38*a*.

The first headgear connector 1100 can be dimensioned so that it is less likely to be wedged into the second connector opening 1108 when the user tightens the headgear 1170. The first headgear connector 1100 can have a greater vertical dimension than the second headgear connector 1101 (as shown in FIG. 40). This prevents, or minimises the risk that the first headgear connector 1100 will be wedged into the second connector opening 1108. This also improves the ease of use of the mechanism by providing an area for the user to grip the first headgear connector 1100 that is distinguished from the second headgear connector 1101. In other words, the user can more easily grab the first headgear connector 1100 without accidently simultaneously grabbing the second headgear connector.

In at least one configuration, the passage 1102 can be dimensioned so that it provides a resistive force against movement of the headgear strap 1172 through the passage 1102 as described with reference to previous embodiments.

At least one configuration of the user interface 1150 can comprise a release member 1198. The release member can be similar to that described with reference to FIG. 42. The release member 1198 is actuated to release the connection between the headgear strap 1172 and the user interface 1150.

The release member 1198 can be connected to the first headgear connector 1100. For example, the release member 1198 may be connected to the first headgear connector 1100 near the first connector opening 1107. Actuating the release member 1098 moves the first headgear connector 1100 away from the second headgear connector 1101. Actuating the release member 1098 therefore disconnects the first headgear connector 1100 and second headgear connector 1101 from the headgear strap 1072. The release member 1198 can connect more than one opposing first headgear connectors 1100 on the user interface 1050. Actuation of the release member 1198 can simultaneously disconnect the multiple first headgear connectors 1100 from the headgear 1170. The release member 1198 can make it easier for the user to disconnect the headgear 1170 from the user interface 1150 by providing a member that is easier for the user to grip than the first headgear connector 1100. As such, the release member 1198 can be a quick-release.

In at least one configuration, the first headgear connector 1100 comprises a polymer. The polymer can be a polycarbonate that rigidly defines a 3-dimensional profile of the first headgear connector 1100. In at least one configuration, the second headgear connector 1101 comprises a polymer. The polymer can be a polycarbonate that rigidly defines a 3-dimensional profile of the second headgear connector 1101.

In at least one configuration, the first headgear connector 1100 and the second headgear connector 1101 can be used with a user interface 1150 configured to deliver breathing gas to one or more of the user's mouth and nose without a sealed connection. For example, the first headgear connector 1100 and second headgear connector 1101 can be used with a nasal cannula 1150.

Figure 41:
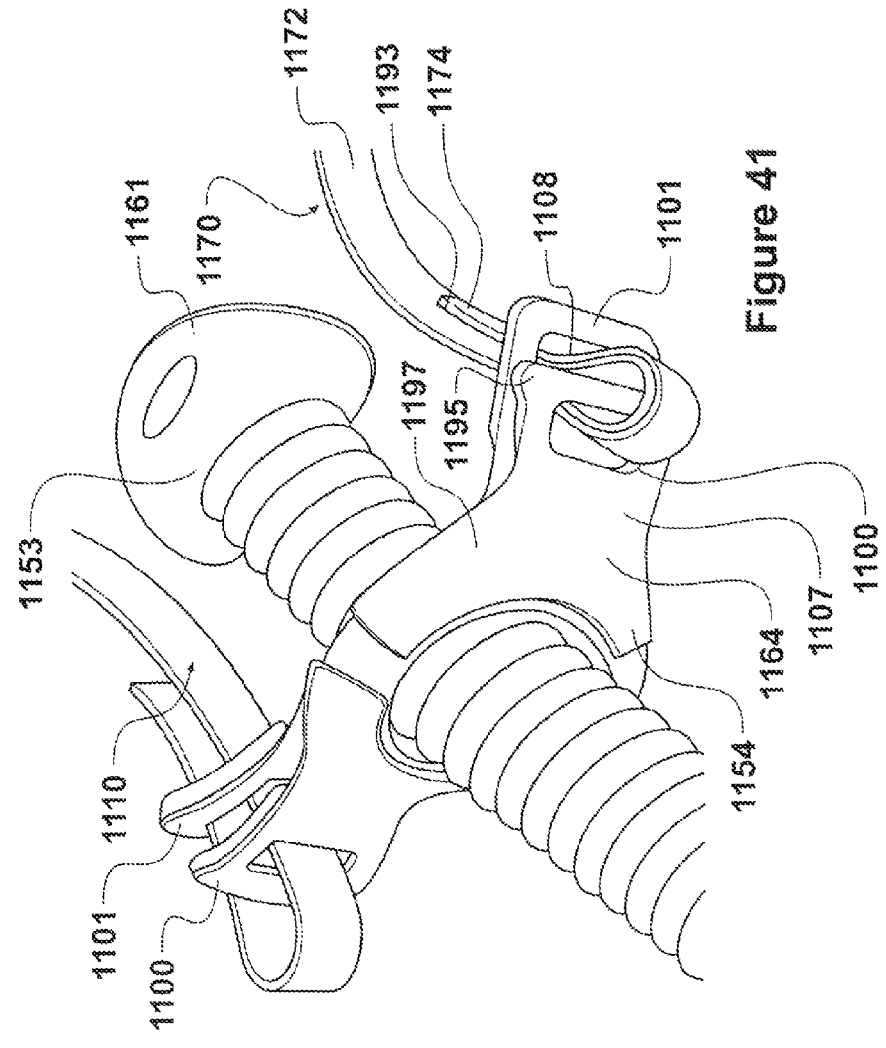
FIG. 41 is a perspective view of a user interface assembly comprising a frame with a yoke, where a first headgear connector and second headgear connector are integrated with the yoke, and where the yoke comprises a textile material.

FIG. 41 shows an alternative configuration of the user interface assembly 1110 described with reference to FIG. 38-FIG. 40. The user interface assembly 1110 of FIG. 41 is similar to the user interface assembly 1110 of FIGS. 38-40 with the notable exception that the frame 1154 comprises a yoke 1167 that comprises the first headgear connector 1100 and the second headgear connector 1101, and the yoke 1167 comprises a textile material.

The user interface assembly 1110 again comprises a user interface 1150 and headgear 1170. The user interface 1150 comprises a frame 1154, a cushion module 1152 (not shown) and a breathing gas circuit connector 1153. The frame 1154 comprises a user interface body 1161 which is configured to connect to the yoke 1167 as described with reference to previous embodiments. The yoke 1167 is removably connected to the user interface body 1161. The yoke 1167 spans laterally across the length of the user interface body 1161. The yoke 1167 comprises the first headgear connector 1100 and the second headgear connector 1101. The first headgear connector 1100 and the second headgear connector 1101 facilitate the connection of the frame 1154 to the headgear 1170 via the yoke 1167.

The first headgear connector 1100 is integrated with the yoke 1167. The yoke 1167 comprises a textile material 1197. The first headgear connector 1100 also comprises the textile material 1197. The illustrated first headgear connector 1100 also comprises a rigid layer 1195. The rigid layer is bonded to the textile material 1197. In one form, the textile material 1197 is a fabric. The second headgear connector 1101 is integrated with the yoke 1167. The illustrated second headgear connector 1101 comprises the textile material 1197 and a second rigid layer 1193. The second rigid layer 1193 is bonded to the textile material 1197.

The first headgear connector 1100 and second headgear connector 1101 together define the headgear receiving passage 1102. The passage 1102 is configured to receive the headgear strap 1172. The passage 1102 comprises the first connector opening 1107 and the second connector opening 1108. The headgear is secured and disconnected similarly to as described with reference to FIG. 38-FIG. 40.

Referring to FIGS. 43 to 61, further headgear connector embodiments are provided. These embodiments comprise adjustment components configured to engage a headgear strap, and having flexible characteristics configured to vary the level of friction between an adjustment component and the headgear strap, and therefore adjustment of the headgear strap length. These headgear connectors provide a minimal headgear strap adjustment mechanism which relatively comfortably and relatively easily allows adjustment of headgear strap lengths to improve user interface stability on the user's face, and/or user comfort, and/or an effective seal on the user's face.

In these examples, the free end of the headgear strap is attached to part of the connector, which when disengaged allows adjustment of the strap length by releasing the strap from the connector. The strap is looped around a post (either on the user interface or on the headgear connector that is itself mounted on the user interface), resulting in a return headgear strap portion looping back towards the free end. Tension load is held by the free end of the strap being fixed to the connector, and by the variable engagement of the connector with the return strap portion. Adjustment occurs when the connector is moved along the longitudinal length of the headgear strap.

All embodiments are applicable to any of the different regions of headgear and are not limited to any one or more of the side straps (such as two-point and four-point headgear), crown strap, rear strap and forehead strap, where present. Examples of two headgear embodiments comprising a pair of upper and a pair of lower side straps are provided in FIGS. 75 and 76. However, these are examples only, and any other configuration of headgear is envisaged.

The embodiments of FIGS. 43 to 53 include a connector comprising an adjustment component in the form of a sliding sleeve comprising a resiliently deformable material such as silicone. Silicone is an example of material that allows the adjustment component to be flexible, elastic and exhibit relatively high friction characteristics. The free end of the headgear strap is attached to the slider and the fixed end passes through a passage formed by the sliding sleeve The fixed end of the strap is able to pass through the passage with variable amounts of friction or resistance. Friction is present between the headgear strap and the interior walls of the passage. The passage may feature additional retaining or friction increasing structures such as teeth or ribs on the interior walls of the passage. Release (i.e. reduction in friction) of the headgear strap is achieved by pinching the top and bottom sides of the sleeve which causes the sleeve walls to bow, deflect outwards and widen the passage. This decreases the contact area between the headgear strap and passage walls, therefore decreases friction and resistance to the strap passing through the passage, allowing adjustment of the headgear strap length.

The embodiments of FIGS. 54 to 61 comprise a connector comprising another adjustment mechanism which includes an adjustment component featuring a passage through which the headgear strap passes. This component is a slider constructed of a rigid or semi-rigid material and features an exterior wall (facing away from the user's face) with a pivot. The wall acts as a tab that can be lifted to release the strap and decrease friction between the wall and the strap. This friction is achieved using inwardly projecting engagement formations such as ribs or teeth that create interference between the strap and the buckle. In one embodiment the interior wall features a window that together with the ribs/teeth forces the strap into a tortuous path through the sleeve, while in a further embodiment the exterior pivoting wall comprises a piercing protrusion in the form of a spike that is embedded in the strap or compresses the strap against the interior wall. The wall behaves like a cantilevered spring and returns to its resting, strap engaging position after it is released from the lifted, strap release position.

Resilient Sliding Sleeve

With reference to FIGS. 43 to 53, this embodiment comprises a connector comprising a single adjustment component constructed of a resilient material such as silicone, herein referred to as the sliding sleeve 1200. The sliding sleeve 1200 features a sleeve body 1210 and one or two tab portions 1220; each tab portion 1220 adjacent each longitudinal end of the sleeve body 1210. The free end 1230 of the headgear strap 1240 is mounted the sliding sleeve 1200 through any one or more of various techniques such as adhesive, overmoulding or welding (such as ultrasonic welding for example).

The relative flexibility and softness of the sliding sleeve 1200 allows it to compress and bend when force is applied, therefore making it comfortable when worn, particularly on the side of the user's face. This material also allows the sliding sleeve 1200 to return to its resting state when released from compressive forces (as may be applied by the user). The relatively small size of the sliding sleeve 1200 makes it less noticeable and intimidating, increasing attractiveness to users. In particular, relative to the strap 1240, the sliding sleeve 1200 is relatively short, and projects only a relatively short distance from the user's face.

The side walls 1210A, 1210B of the sleeve body 1210 extend towards the longitudinal ends of the tab portions 1220 as can best be seen in FIG. 45. This provides a barrier to structures other than the headgear strap 1240 from entering a passage 1250 defined by the sleeve body 1210, and reduces the likelihood of the corner between the tab portions 1220 and sleeve body 1210 tearing from tension and stress. This structure can also be seen in FIG. 45.

Figure 47:
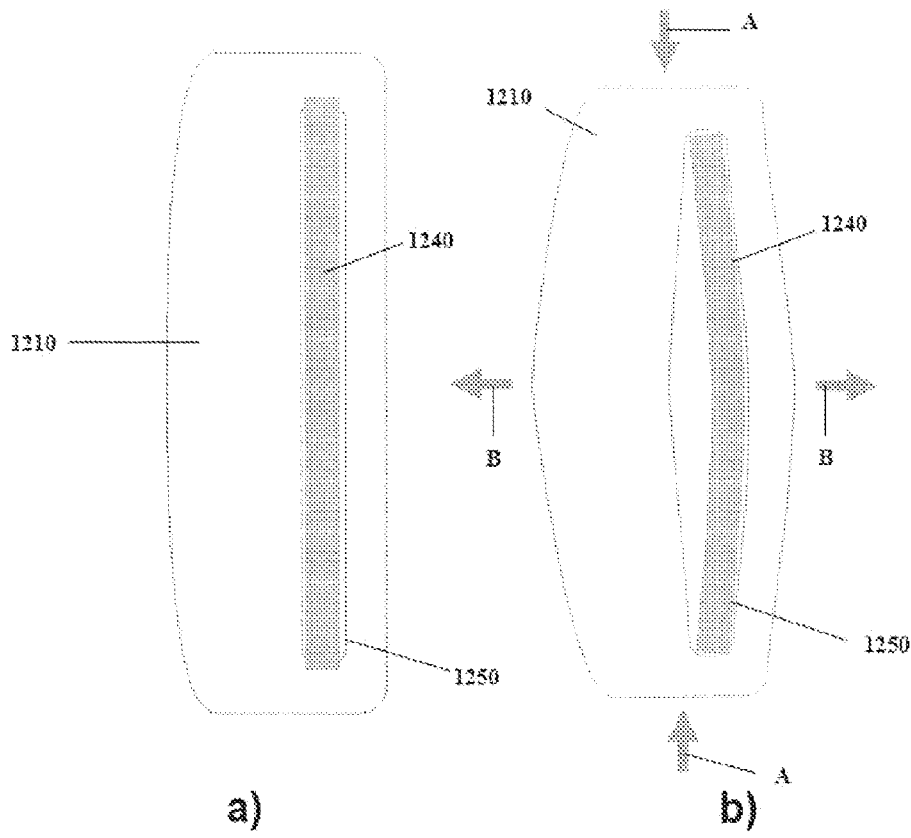
FIGS. 47*a* and 47*b* are cross sectional views taken transversely through the headgear connector of FIGS. 43 to 46, showing the headgear connector in resting and compressed states respectively.

The strap 1240 is fed through undersized passage 1250 formed by the sleeve body 1210 such that friction occurs on the top and bottom of the strap 1240, as can best be seen in FIG. 47. The passage 1250 is undersized, relative to one or more dimensions of the headgear strap 1240, and in this example it is the width of the passage 1250, transverse to the longitudinal axis of the sliding sleeve 1200 and the strap 1240, that is slightly less than the width of the strap 1240, or at least a width of part of the strap 1240. This is shown, in exaggerated form, in FIG. 47a. The soft strap 1240 buckles or curls slightly to fit through the undersized passage 1250, increasing the area of contact between the soft strap 1240 and high-friction interior walls of the passage 1250, thus increasing resistance to pull when tension is applied to the strap 1240.

With reference to FIG. 47b, the vertical arrows A show the direction of compression of the sliding sleeve 1200 and the horizontal arrows B show the direction of the resulting deflection of the passage walls.

The amount of friction can be changed by squeezing the longitudinally opposed ends of the sliding sleeve 1200, which causes the sides of the sliding sleeve 1200 and the passage 1250 to bow out, thus reducing contact area between the interior walls of the passage 1250 and strap 1240, loosening the strap 1240 (allowing increase in strap length). Alternatively, pulling the front tab portion 1220A in a longitudinal forwards direction allows loosening of the user interface (by increasing strap length). Pulling the rear tab portion 1220B in a longitudinal rearwards direction allows tightening of the user interface (by decreasing the strap length) as this motion overcomes the friction between strap 1240 and passage walls.

Figure 48:
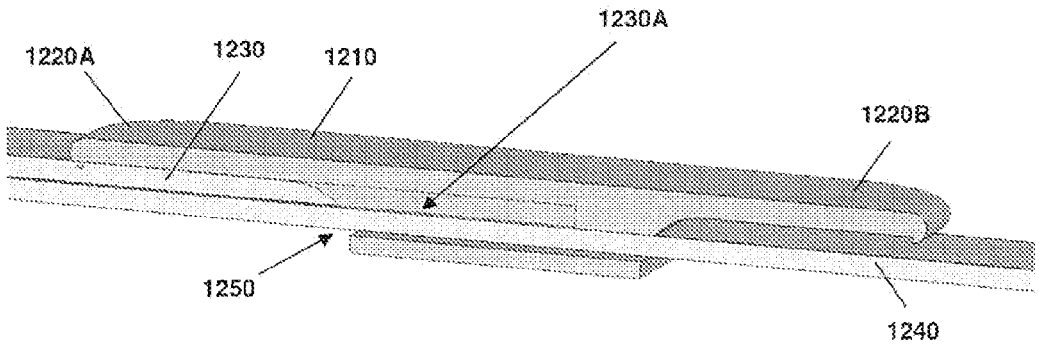
FIG. 48 is an enlarged perspective view of the headgear connector of FIGS. 43 to 47 in use with a headgear strap.
Figure 49:
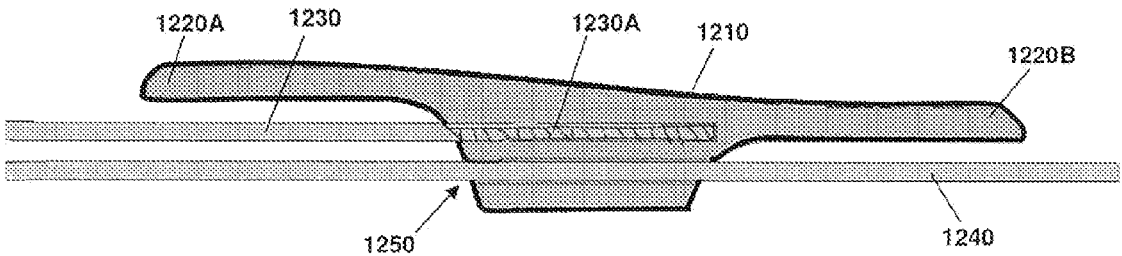
FIG. 49 is a side view corresponding to FIG. 48.

With reference to FIG. 48, the sliding sleeve 1200 may be substantially flat along its length so that there is no gap between the sliding sleeve 1200 and the headgear strap 1240. Portion 1230A of strap free end 1230 may be overmoulded to the sliding sleeve 1200. With reference to FIG. 49, the sliding sleeve 1200 has a gripping portion being a raised medial end portion 1260 which is spaced away from the adjacent part of the headgear strap 1240, to enable the sliding sleeve 1200 to be more easily gripped by a user.

Figure 50:
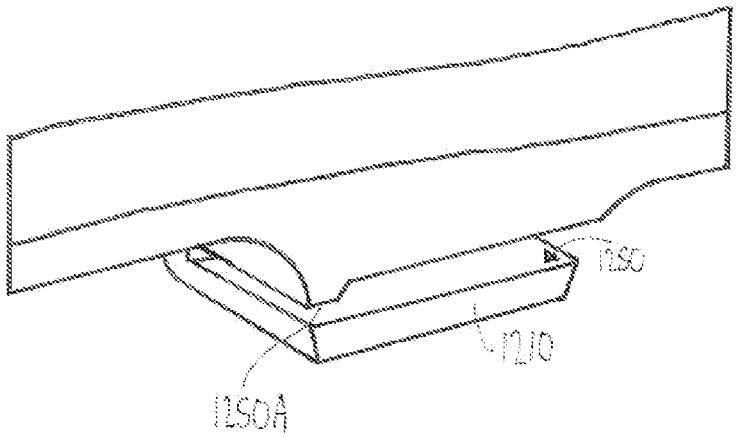
FIG. 50 is an enlarged perspective view corresponding to FIG. 48.
Figure 51:
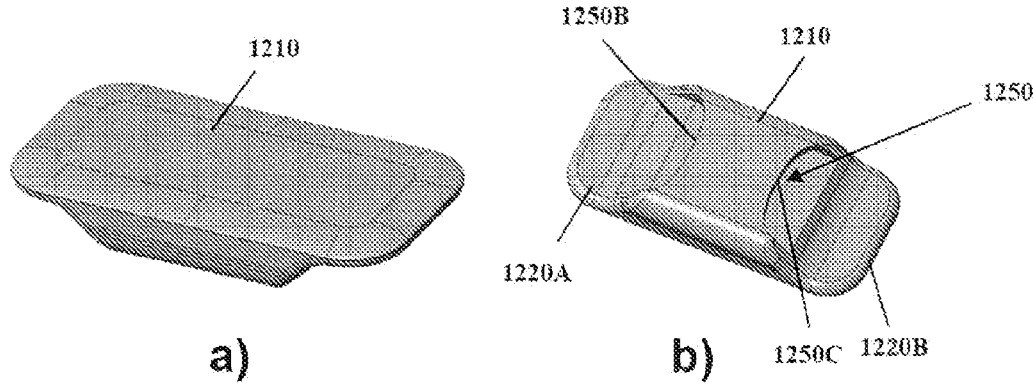
FIGS. 51*a* and 51*b* are perspective side views of the headgear connector of FIGS. 43 to 50 showing exterior and interior sides of the connector, respectively.

With reference to FIG. 50, the forward end 1250A of the passage 1250 may have a reduced height or width to create a stronger hold on the strap 1240 during use of the user interface. This leads to increased grip and friction between the strap 1240 and sleeve 1250 that resists the lengthening of the headgear strap 1250 (i.e. free end 1230 of strap slippage in the longitudinal forwards direction) to secure the patient interface against the face, while allowing the strap 1240 to easily move longitudinally rearwardly therefore allowing the user interface to be easily pulled towards the user's face. The narrowed passage 1250 increases friction and resistance when the user interface is pushed or blown away from the face during CPAP therapy (i.e. when subject to blow-off force).

The longitudinal rear and front openings 1250B, 1250C of the sleeve passage 1250 may have an arcuate shape when viewed from above, perpendicular to the longitudinal axis of the sliding sleeve 1200. In this example, the arcuate shape is a crescent shape as can best be seen in FIG. 51, to prevent the edges of the strap 1240 from folding in on itself and creating more friction in the adjustment. The crescent shape promotes buckling of the strap 1240 near the longitudinal axis of the strap 1240, not at the edges. Buckling at the edges of the strap 1240 can undesirably lead to the edges folding inwards.

Figure 52:
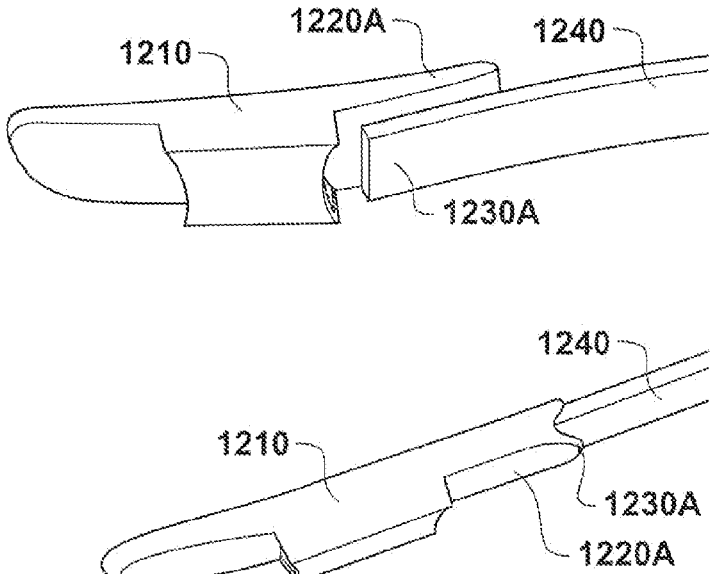
FIGS. 52*a* and 52*b* are perspective and side views of the headgear connector of FIGS. 43 to 51 and a free end of the headgear strap.

With reference to FIG. 52, in this example, the free end 1230 of the strap 1240 is overmoulded 1230A in the sleeve portion 1250 of the sliding sleeve 1200 or on the tab portion 1220A on the longitudinal front end of the sliding sleeve 1200 that is closest to the user interface.

Figure 53:
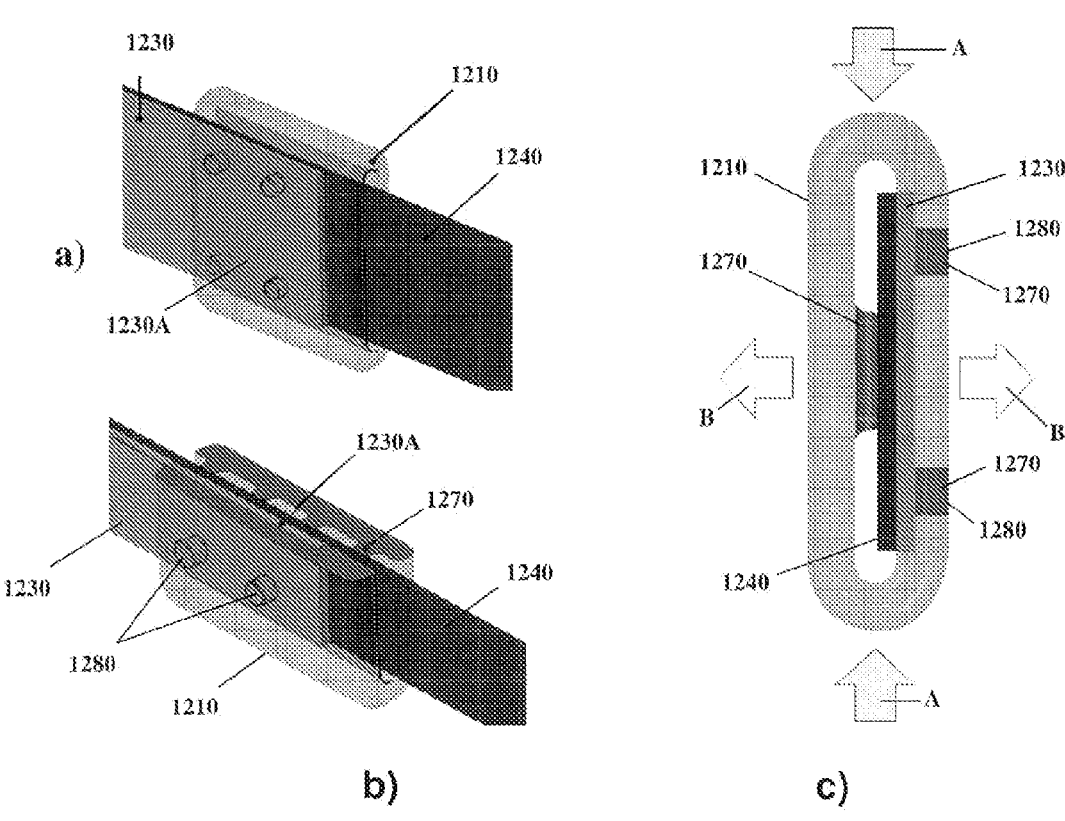
FIGS. 53*a* and 53*b* are perspective and end views of a modification of the headgear connector of FIGS. 43 to 52.
Figure 54:
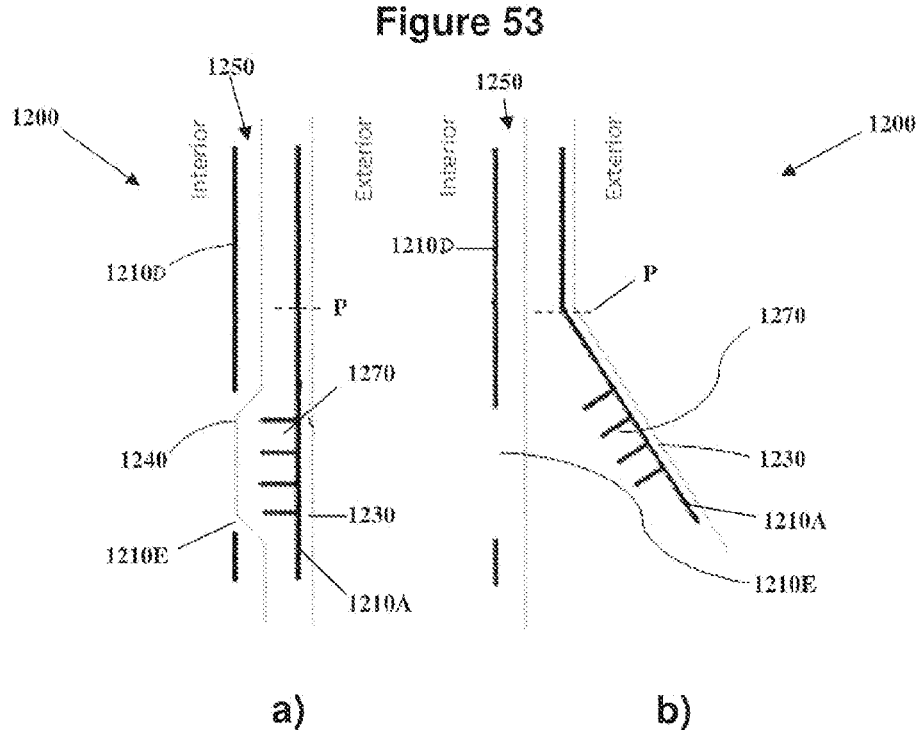
FIGS. 54*a* and 54*b* are schematic side views of another headgear connector in accordance with this disclosure in engaged and released conditions respectively.
Figure 55:
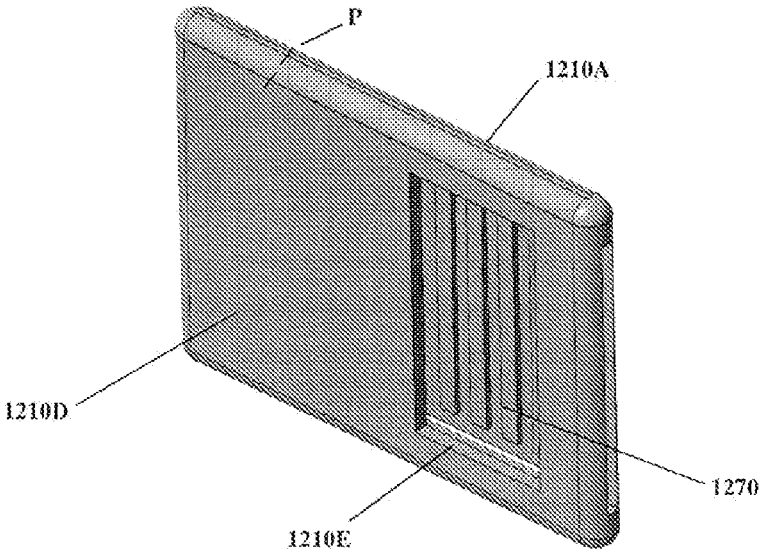
FIG. 55 is a perspective view of the headgear connector of FIG. 54.
Figure 56:
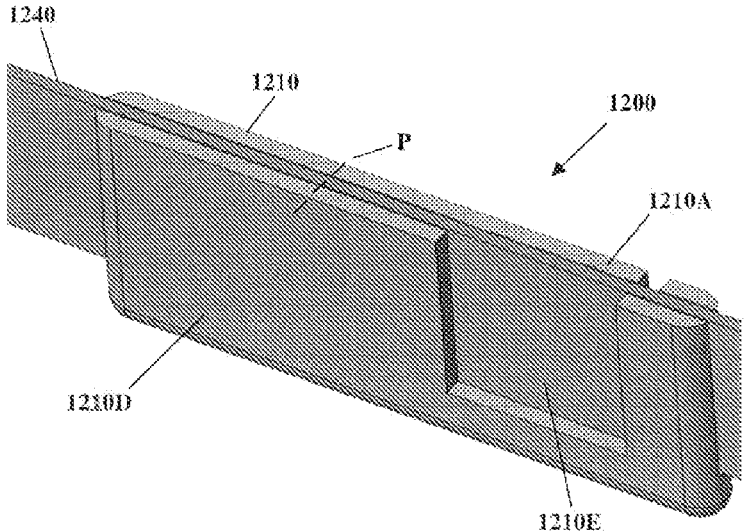
FIG. 56 is a perspective cutaway view of the headgear connector of FIGS. 54 and 55 in use with a headgear strap.

With reference to FIG. 53, this embodiment comprises a resilient sliding sleeve 1200 comprising a sleeve body 1210 that is overmoulded onto the free end 1230 of the headgear strap 1240. The sleeve 1220 interferers with the flat surfaces of the strap 1240 and has clearance from the edges of the strap 1240, allowing compression of the sleeve 1220 without causing the strap 1240 to buckle or fold. The amount of friction can be changed by squeezing the transversely opposed sides of the sleeve 1220, which causes the interior and exterior walls of passage 1250 to bow and deflect outwards thus removing the interference between the strap 1240 and sleeve 1200.

Strap alignment and retention features in the sleeve body 1210 are provided in the form of one or more protrusions 1270 which engage with apertures 1280 in the free end 1230 of the strap 1240. These alignment and retention features 1270 may be formed through the apertures 1280 during the overmoulding process, if overmoulding is used. The alignment and retention features 1270 may be formed separately, with the free end 1230 of the strap 1240 then being welded, for example, to the sleeve body 1210. The free end 1230 of the strap 1240 is located on one wall of the sleeve body 1210 such as the interior wall 1250A as can be seen in FIG. 53*c*. The exterior wall 1250B of the sleeve body 1210 is provided with inwardly projecting protrusions 1270, in the form in this example of ribs or teeth, that create friction between the strap 1240 and sleeve body 1210. Compressing the lateral walls of the sleeve body 1210, that is the walls the extend parallel with the longitudinal axis of the sleeve body 1210, lifts the ribs or teeth 1270 off the strap 1240 and decreases the contact area and friction between the strap 1240 and sleeve body 1210.

With reference to FIG. 53*a*, this perspective view shows the relationship of the components in the headgear adjustment assembly. The free end of the headgear strap 1240 is overmoulded by the sliding sleeve 1200, which comprises the passage 1250 that the fixed end of the headgear strap 1240 passes through. FIG. 53*b* is a perspective view of the same assembly but sectioned longitudinally. The resilient sleeve passage 1250 comprises ribs or teeth 1270 which compress the fixed end 1230 of the strap 1240 towards the opposing interior wall of the passage 1250, increasing friction and resistance. FIG. 53*c* is a transverse cross-section of resilient sliding sleeve 1200 showing the method of releasing headgear strap retention (i.e. resistance) such that the sliding sleeve 1200 can move along the headgear strap 1240.

Hinged Slider

With reference to FIGS. 54 to 59, an embodiment is provided comprising a relatively rigid plastic sliding sleeve 1200 with a minimal thickness. In this example, the sleeve 1200 is plastic, but other materials or combinations of materials can be used to achieve the desired relative rigidity. The strap 1240 is fed through the passage 1250 of the sleeve 1200, the passage comprising a series of projections 1270, such as ribs or teeth, which project into the passage 1250 and create a tortuous path that provides frictional resistance. The free end 1230 of the strap 1240 is tethered to an exterior wall 1210A of the sleeve body 1210 to form a handgrip.

The exterior wall 1210A of the sleeve body 1210 comprises a tab that can be deflected upwards but returns to its resting state due to spring forces generated by the material and construction of the exterior wall 1210A. Tab of exterior wall 1210A is configured to function as a cantilever, pivoting about pivot P. Tab of exterior wall 1210A can be described as a living hinge or flexure joint, where the tab of exterior wall 1210A is integral with the sleeve 1200, but part of the tab of exterior wall 1210A can move relative to the sleeve body 1210. The free end of the tab of exterior wall 1210A is located on a longitudinally rear end of the sleeve body 1210 while the tab of exterior wall 1210A is fixed on the longitudinally front end of the sleeve body 1210. An interior surface of the tab 1220B forming part of the passage 1250 comprises the projections 1270, such as ribs or teeth, that project inwardly, towards the user's face. These projections 1270 contact the strap 1240 when the sleeve body 1210 is in the resting state.

An interior wall 1210D of the sleeve 1210 comprises an aperture 1210E, the shape of which corresponds to that of the projections 1290 on the exterior wall of the sleeve body 1210. This creates a tortuous path for the strap 1240 that is compressed by the inwardly facing projections 1270 on the exterior wall 1210A.

Figure 57:
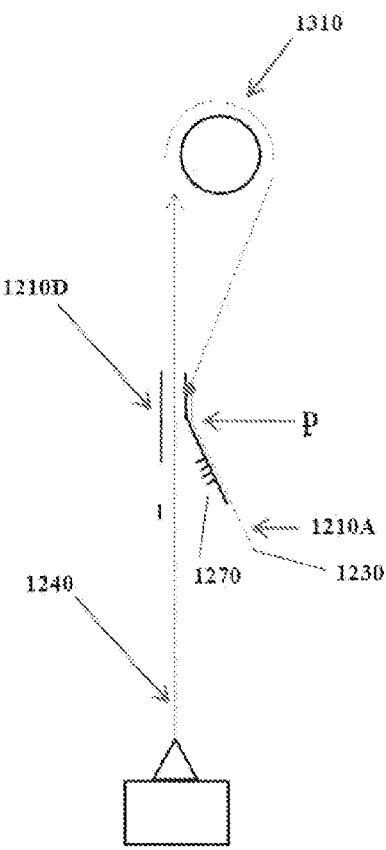
FIG. 57 is a schematic view of headgear adjustment using the headgear connector of FIGS. 54 to 56.
Figure 58:
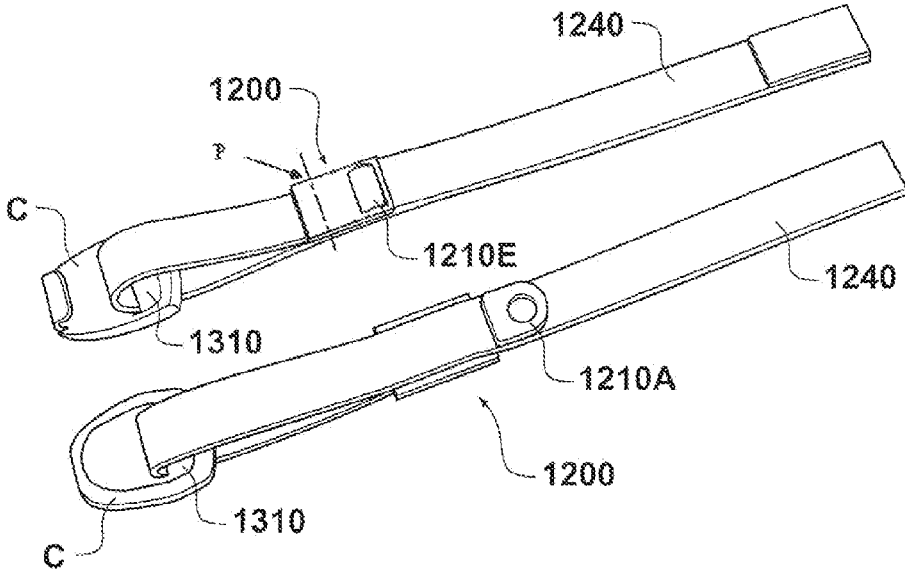
FIG. 58 is a perspective view of the two sides of a headgear strap with the headgear connector of FIGS. 54 to 57.
Figure 59A:
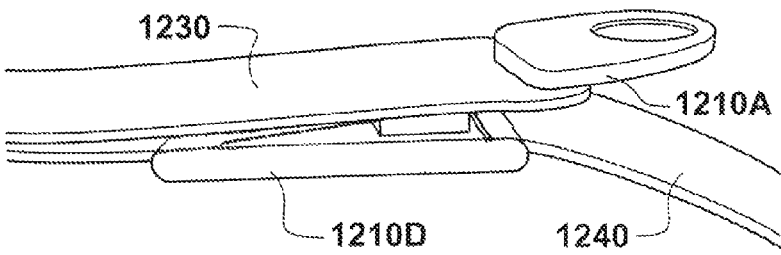
FIGS. 59*a* and 59*b* are perspective views from the side corresponding to FIG. 58, showing the headgear connector in engaged and released conditions respectively.
Figure 59B:
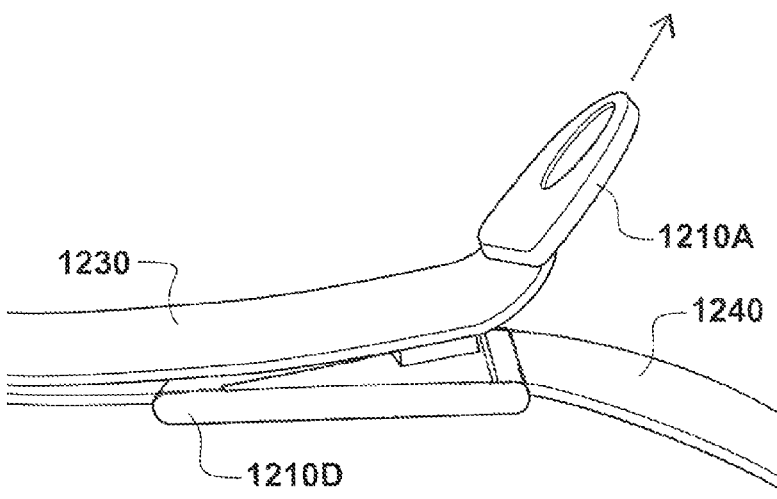

With reference to FIG. 57, this schematic diagram shows the arrangement of the strap 1240, sleeve 1200, and post 1310 that the strap 1240 loops around. Load is carried through the fixed end of the headgear strap 1240. With reference to FIGS. 58 and 59, the post 1310 may be provided on a headgear connector or clip C which is configured to be mounted on the user interface, or may be provided on the user interface itself, for example on a yoke or frame of the user interface.

Figure 60:
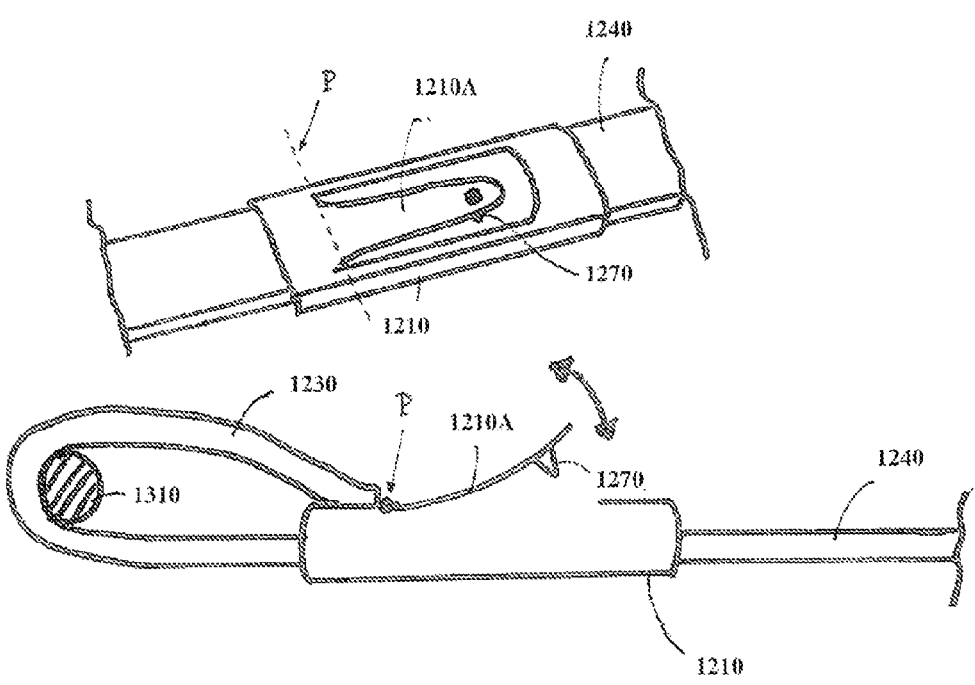
FIG. 60 is a side view of another headgear connector in accordance with this disclosure.
Figure 61:
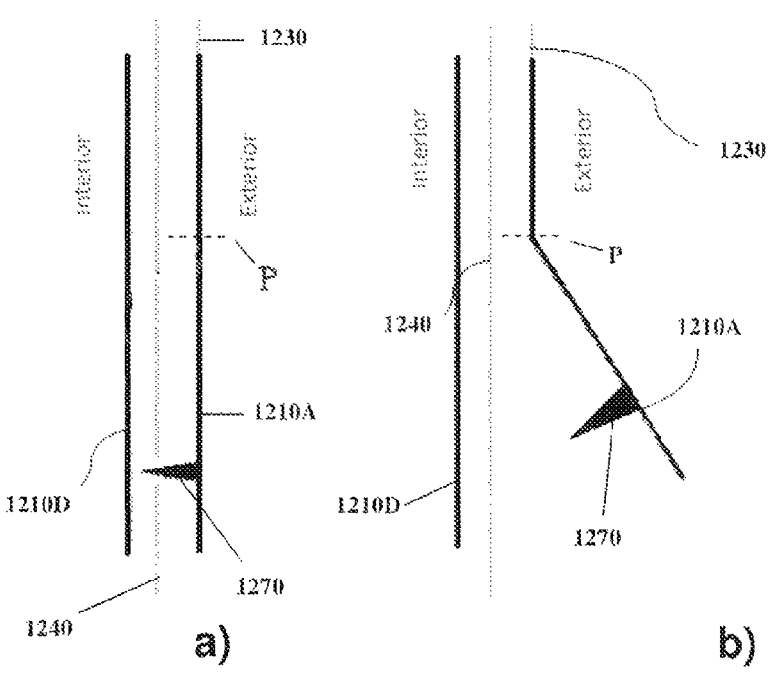
FIGS. 61*a* and 61*b* are schematic side views of the headgear connector of FIG. 60 in engaged and released conditions respectively.
Figure 62:
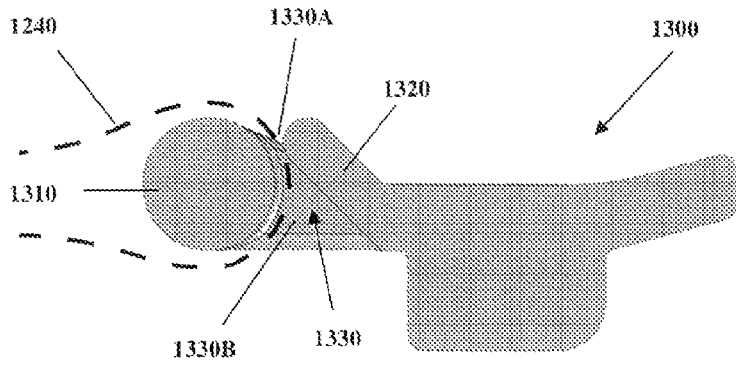
FIG. 62 is a plan view of another headgear connector in accordance with this disclosure, with a headgear strap shown in dashed line.
Figure 63:
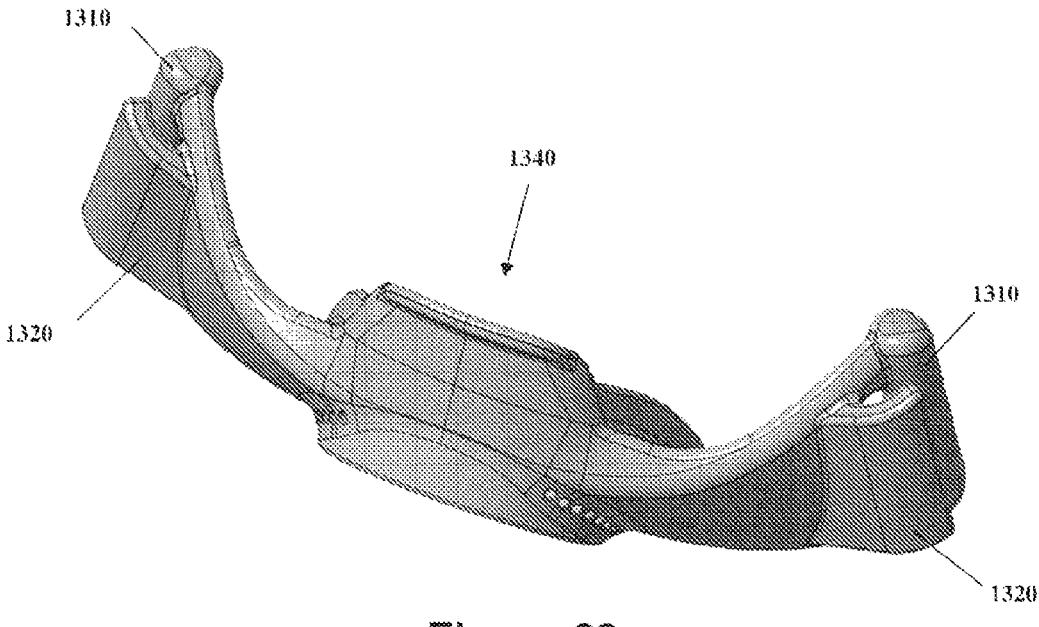
FIG. 63 is a perspective view of a frame of a patient interface comprising the headgear connector of FIG. 62.
Figure 64:
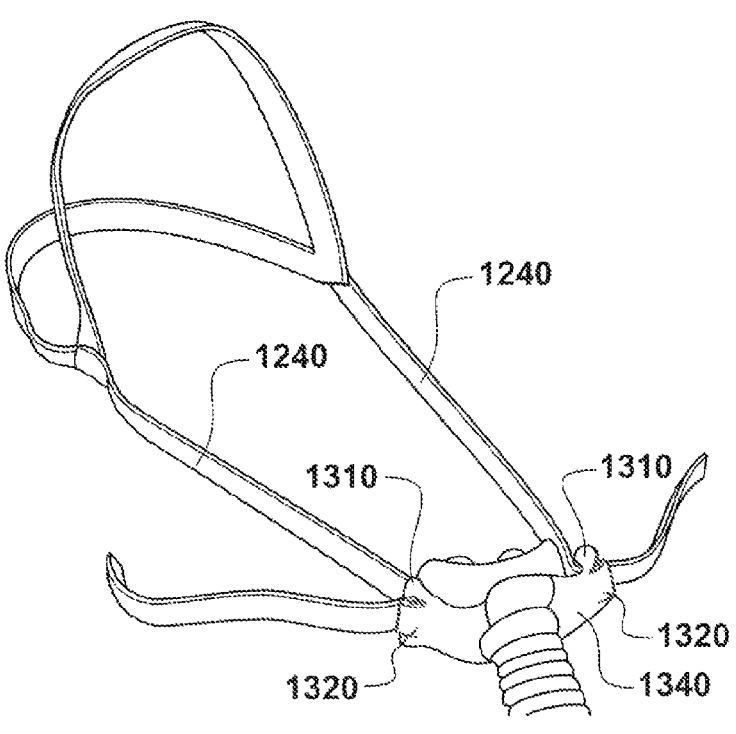
FIG. 64 is a perspective view of a user interface assembly comprising the frame of FIG. 63 with headgear and a user interface.
Figure 65:
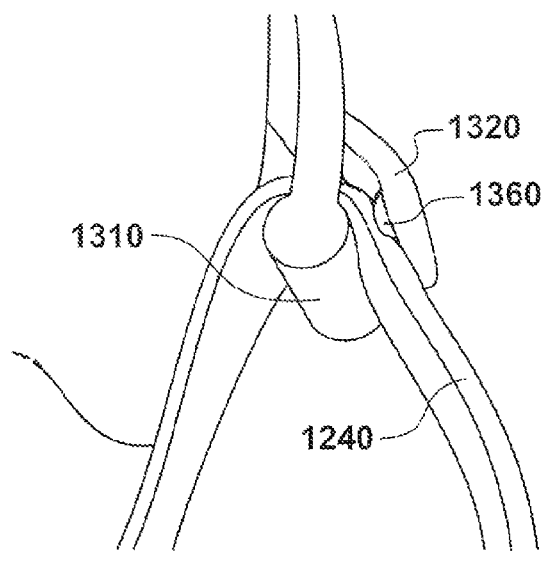
FIG. 65 is an enlarged view of the headgear connector of the user interface assembly of FIG. 63.

With reference to FIGS. 60 and 61, a further embodiment comprises a sliding sleeve 1200 comprising a flexible living hinge P with the inwardly facing surface of the tab 1210A featuring one or more piercing protrusions, in this example a single spike 1270, which are configured to be embedded in the headgear strap 1240 when the tab 1220B is in its resting position, that is the piercing protrusions are configured to pierce into the material of the headgear strap 1240, rather than just engage the surface of the strap 1240. The tab 1220B forms part of the exterior wall of the rigid sliding sleeve 1200 through which the fixed end of the strap 1240 passes. The free end 1230 of the strap 1240 is attached to the top surface of the sleeve 1200.

In this embodiment the sleeve 1200 achieves strap retention using a projection 1320 that pierces or compresses the strap 1240 against the interior or skin-facing side of the sleeve 1200, whereas the previous embodiment creates a tortuous path for the strap 1240 using projections 1290 that fit into an aperture 1220E on the interior wall of the sleeve 1220.

With reference to FIGS. 62 to 74, further headgear connector embodiments are provided in which there is less resistance to the shortening of a headgear strap than to the lengthening of the headgear strap. In other words, the headgear adjusters require less adjustment force to shorten the headgear strap than to lengthen the headgear strap. This allows the user to relatively easily tighten the user interface to achieve a sufficient seal, while reducing the likelihood of one or more of the headgear straps from slipping and inadvertently lengthening during use of the user interface. This configuration of headgear connector therefore reduces the likelihood of the user interface becoming loose due to, for example, blow-off force pushing the user interface away from the user's face during CPAP therapy. The following headgear connectors comprise headgear strap fastening and length adjustment mechanisms which can be implemented using a non-stretch strap such as a woven fabric strap.

Figure 69:
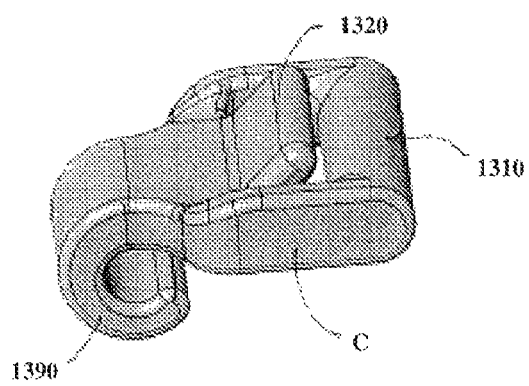
FIG. 69 is an enlarged perspective view of a headgear connector for use with the frame of FIG. 63.

With reference to FIGS. 62 to 69, a headgear connector 1300 is provided comprising a post 1310 with a friction arm 1320 adjacent but spaced from the post 1310 so as to define a passage 1330 therebetween, through which the headgear strap 1240 can pass. Post 1310 may be provided on a distal/lateral part of a user interface frame 1340 or frame arm as per FIGS. 63 to 66, or on a separate clip component, as shown in FIGS. 67 to 69, which is configured to mount on the frame 1340 of the user interface.

In this embodiment, friction arm 1320 is located more medially/close to the vertical centreline of the user interface, when viewed from the front, than the post 1310, and protrudes anteriorly, forming passage 1330 between the post 1310 and friction arm 1320. The strap 1240 passes through this passage 1330 during length adjustment. In this example, when viewed along the longitudinal axis of the post 1310, the friction arm 1320 is inclined relative to the longitudinal axis of the main body of the headgear connector 1300.

If applied to a separate headgear connector clip C, headgear connector 1300 may be connected to the arms of the user interface frame 1340 via slots on the user interface frame 1340 and corresponding slot connectors on the clip C, or a hook on the clip C that clips onto a post on the user interface frame.

The friction arm 1320 may be constructed of a resilient and flexible material, such as silicone for example, that biases the friction arm 1320 towards the user interface frame arm. This provides a constant friction force and resistance in the case that the strap 1240 undergoes changes in properties through continuous use.

The friction arm 1320 provides friction between the arm 1320 and strap 1240 to provide relative resistance against strap slippage in one direction (strap lengthening) but provide relative ease of strap tightening. The friction arm 1320 may have unidirectional teeth or other projections that function as barbs to allow strap movement in one direction but resist strap movement in an opposite direction.

The outlet opening 1330A of the passage 1330 on the exterior side of the mask frame arm or clip component is narrower than the inlet opening 1330B of the passage 1330 on the interior side, the interior side being adjacent a user's face. There is therefore increased resistance to the strap 1240 travelling from the exterior to the interior side than interior side to the exterior side. In other words, there is increased resistance to strap slipping and loosening than to strap tightening.

The free end of the strap 1240 may be free or attached to the fixed end 1230 of the strap 1240, for example, using a collar. The length of the fixed end 1230 of the headgear strap 1240 determines the size of the overall headgear system and the sealing or placement of the user interface frame on the user's face.

The opening 1330A of passage 1330 on the exterior side formed between the friction arm 1320 and the post 1310 is narrower than the opening 1330B at the interior side (skin-facing) of the user interface frame 1340. This leads to less resistance to the strap 1240 passing through the passage 1330 in the rearwards direction, therefore making it easier to tighten the user interface than it is to loosen the user interface. This can best be seen in FIG. 62.

The distance between the post 1310 and friction arm 1320 is about 1 mm in this example, which is thinner than the thickness of the strap 1240. The strap 1240 is of a compressible material and/or structure, allowing it to pass through the passage 1330 between the post 1310 and friction arm 1320.

The friction arm 1320 may feature teeth 1360 or other projections on the interior side, in the passage 1330, to further increase friction between the friction arm 1320 and strap 1240. These teeth 1360 can be seen in FIGS. 65 and 66.

This embodiment can be applied to a headgear connector clip C, see FIGS. 67 to 69, that allows the headgear strap 1240 to be easily removable from the user interface frame 1340 without requiring length adjustment every time the user dons or doffs the user interface 1340. The clip C is connected to the user interface frame 1340 using slot connectors 1380 (FIGS. 67 and 68) that engage with slots on the user interface frame 1340, or via a hook portion 1390 (FIG. 69) that hooks onto a post on the user interface frame 1340.

Figure 70:
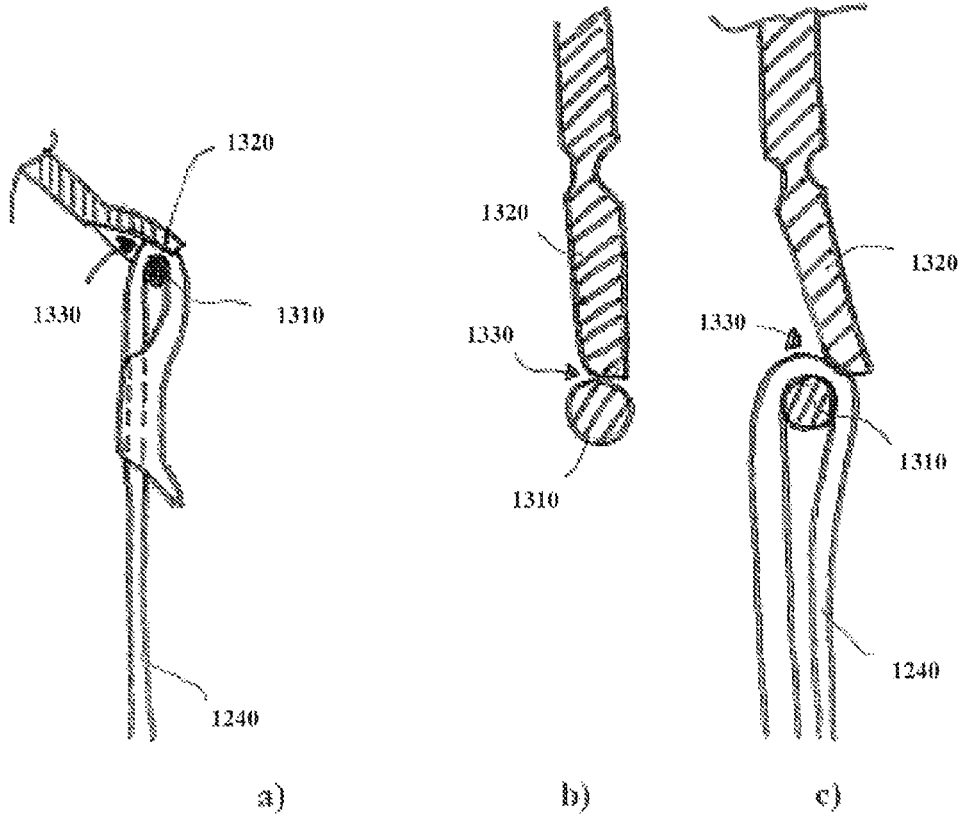
FIGS. 70*a* to 70*c* are side views of another headgear connector in accordance with this disclosure, in use with a headgear strap, enlarged without the headgear strap, and enlarged with the headgear strap, respectively.

Referring to FIG. 70, a modification of the embodiment of FIGS. 62 to 69 is provided in which the friction arm 1320 is a living hinge, integral with the user interface frame 1340 or headgear connector clip C, but also movable relative thereto.

The friction arm 1340 may be constructed of a resilient and flexible material such as silicone which is able to return to its resting state after deflection so as to function as a living hinge or flexure joint. FIGS. 70*a* and *c* show the friction arm 1320 engaging the headgear strap 1240. FIG. 70*b* shows the friction arm 1320 in its resting condition, abutting post 1310. Release of the strap 1240 is achieved by lifting the friction arm 1320 away from the strap 1240 and post 1310 (i.e. in the exterior direction in this example).

The resting state of the friction arm 1320, as can best be seen in FIG. 70*b*, is one that is in line with the post 1310. The presence of a strap loop around the post 1310 leads to slight deflection of the friction arm 1320. The spring return force of the friction arm 1320 is applied to the strap 1240 and post 1310, compressing the strap 1240 against the post 1310. This, together with the relatively tacky, relatively high-friction, surface that may be provided on the friction arm 1320, leads to relatively high friction and strap length retention in the resting configuration.

The resilient friction arm 1320 can also provide constant friction force and resistance in the case that the strap 1240 undergoes changes in properties through continuous use.

Figure 71:
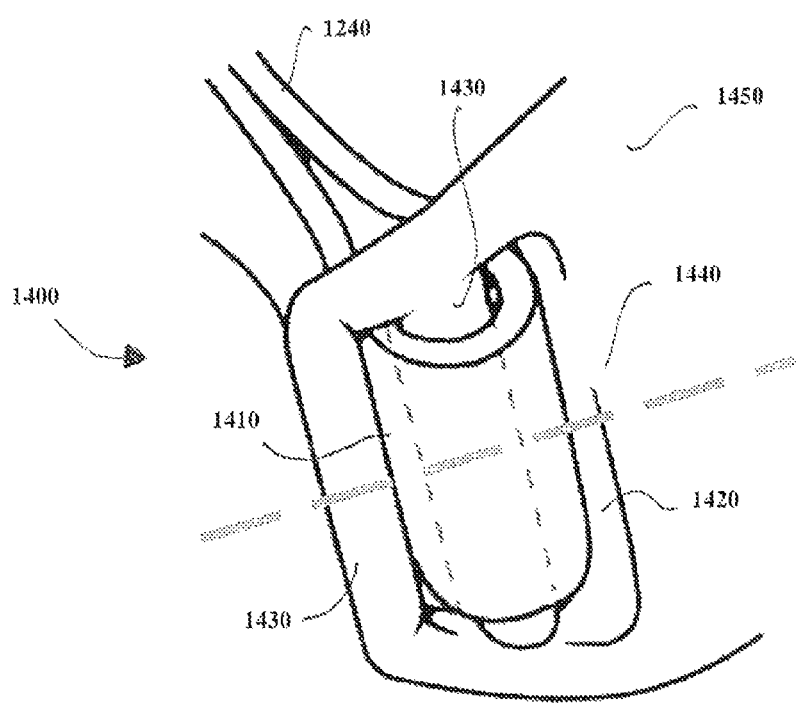
FIG. 71 is an enlarged perspective view of another headgear connector in accordance with this disclosure.
Figure 72:
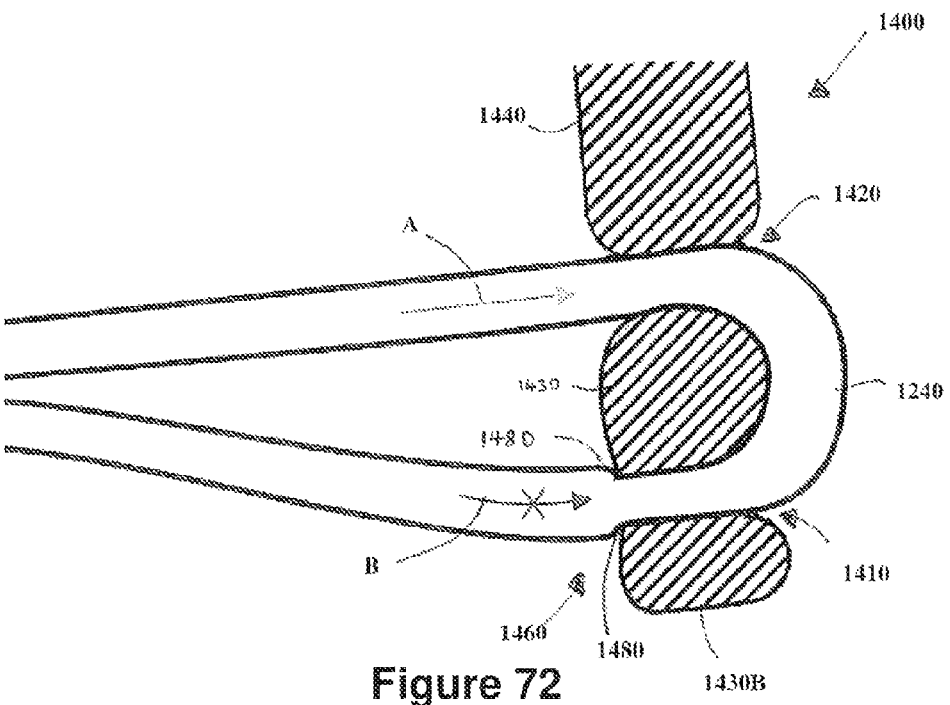
FIG. 72 is an enlarged transverse cross section view through the headgear connector of FIG. 71.

Referring now to FIGS. 71 and 72, a headgear connector 1400 comprises a headgear clip or frame arm of a user interface, comprising two slots 1410, 1420 formed between three posts 1430 or between two posts 1430 (one central and one outer/lateral) and the medial portion 1440 of the mask frame arm 1450. The strap 1240 loops around the central of the posts 1430.

All surfaces that the strap 1240 contacts have a smooth curvature except the rear side of the outer and central posts 1430 that are adjacent the strap 1240 passing through the outer slot 1410 (i.e. the slot through which the free end 1430 of the strap passes). This creates a relatively narrow pinch point increasing resistance to the strap 1240 sliding through towards the front side of the user interface, leading to strap lengthening). Therefore, the strap 1240 is able to be tightened with little friction, while there is greater resistance to strap lengthening.

In this embodiment, there is a relatively narrow pinch point 1460 formed between two edges 1480, namely the edges 1480 of the central post 1430A and outer post 1430B forming the lateral end of the frame arm 1450. The edges 1480 are located on the rear side of the frame arm 1450 and all other surfaces of the posts 1430 are relatively smooth to allow the strap 1240 to slide over those surfaces with less friction. The strap 1240 is able to slide relatively easily over surfaces with smooth curvatures, allowing tightening of the strap 1240 when strap 1240 is pulled in a first direction indicated by arrow A (via reduction in length of fixed end 1230 of strap 1240 under load) with relative ease relative to loosening of the strap 1240 in the opposite direction, indicated by arrow B. The edges 1480 are formed from angular, corner like parts of the posts 1430A, 1430B. These edges 1480 narrow the width of the slot 1410 between posts 1430A, 1430B so as to be narrower than the thickness of the strap 1240. This causes the strap material to pinch 1460, at the edges 1480, as the edges 1480 compress the strap 1240 to create a deformed strap portion. This deformed strap portion engages the posts 1430A, 1430B and increases the friction between the strap 1240 and posts 1430A, 1430B, resisting pulling of the strap 1240 in direction B.

Figure 73:
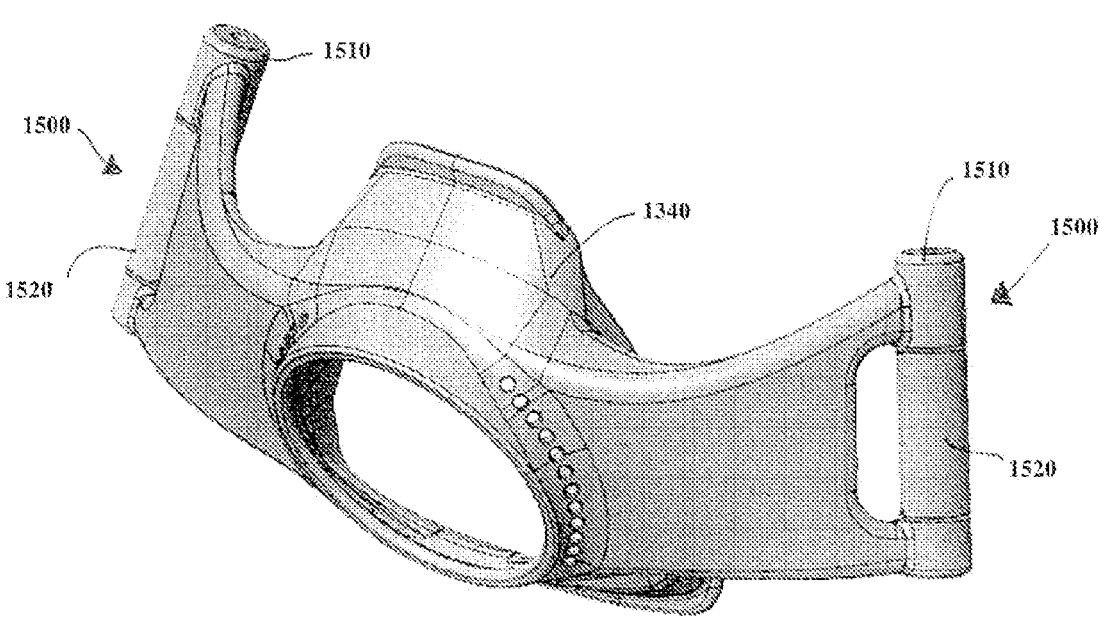
FIG. 73 is a perspective view of a frame of a patient interface comprising headgear connectors in accordance with this disclosure.
Figure 74:
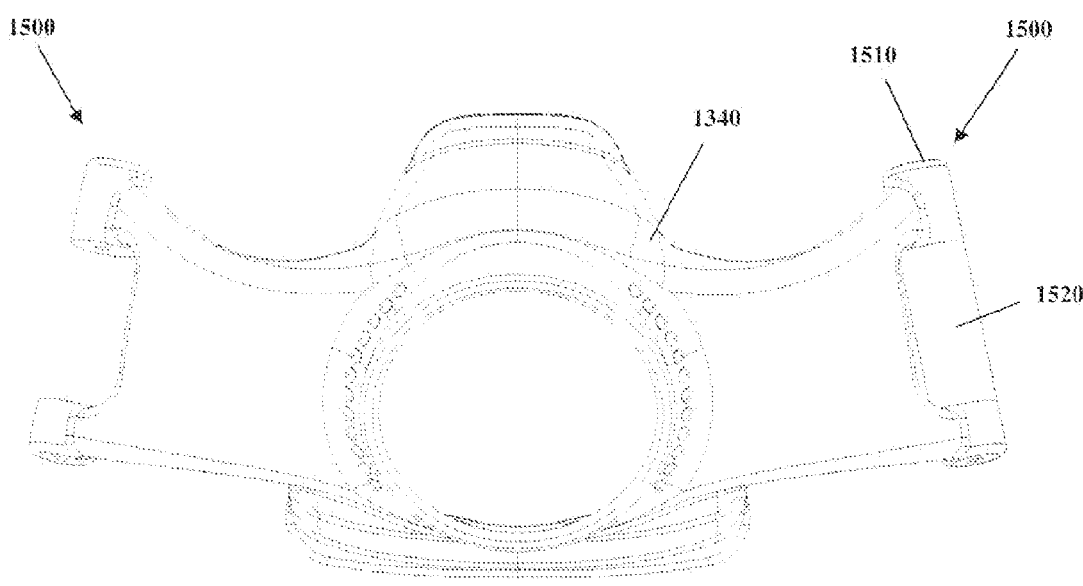
FIG. 74 is a perspective view of the frame of FIG. 73.

Referring now to FIGS. 73 and 74, a headgear connector 1500 provides a strap length adjustment mechanism that uses a headgear strap looping around a post 1510, either on the user interface frame 1530 as shown in FIGS. 73 and 74, or on another component that connects to the user interface, such as a headgear connector clip C.

To facilitate adjustment of the strap length adjustment mechanism (which could include any of the features described in any of the embodiments above), the post 1510 features a cylindrical bearing 1520 that surrounds part of, and is rotatably mounted on, the cylindrical post 1510 so as to function as a roller. The bearing 1520 is concentric and coaxial with the post 1510. The exterior surface of the bearing 1520, or at least a portion of that surface, may have features and/or material selected to provided relatively high friction with the strap 1240 that comes into contact with it, such that movement of the strap 1240 relative to the user interface, also rotates the sleeve 1520 relative to the user interface. When used with a strap length adjustment mechanism, changing the strap length can be achieved with less resistance due to the sleeve 1520 rolling with the strap 1240.

The bearing 1520 is able to rotate about the central axis of the cylindrical post 1510 with low resistance and friction. The strap 1240 passes through the slot 1550 adjacent the post 1510 contacts the bearing 1520, rather than the post 1510 itself. The bearing 1520 acts as a friction roller, decreasing the amount of friction experienced when pulling the strap through the slot 1550. The reduction in friction allows the strap to be tightened and loosened with relative ease.

This concept can be used in conjunction with a headgear strap length adjustment mechanism such as any of those disclosed above, where the strap loops around a post. For example, the roller post 1510 could be used with a headgear connector 1300 such as that shown in FIG. 62, or any other connector that uses a post. Strap length retention is not affected due to the narrowing of the passage but due to this feature, there may be some friction between the strap and the post affecting the ability to loosen the strap. The bearing 1520 acts to reduce this resistance. Another example of such a post can be seen in FIGS. 43 and 44, where the headgear strap 1240 loops around a post on the user interface UL. It is intended that the disclosure relating to the roller post 1510 be used with any other post in a headgear connector arrangement, whether the post be on the user interface, a frame or yoke of the user interface, or on a headgear connector clip that mounts on the user interface.

Figure 75:
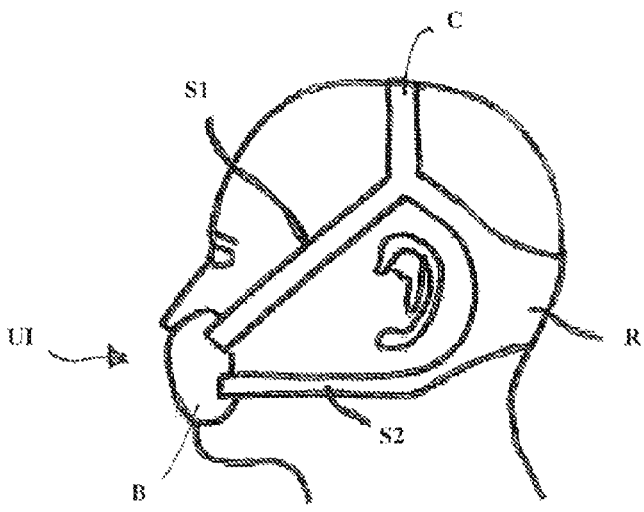
FIG. 75 is a side view of a prior art headgear and user interface with upper and lower side straps.
Figures 77, 78:
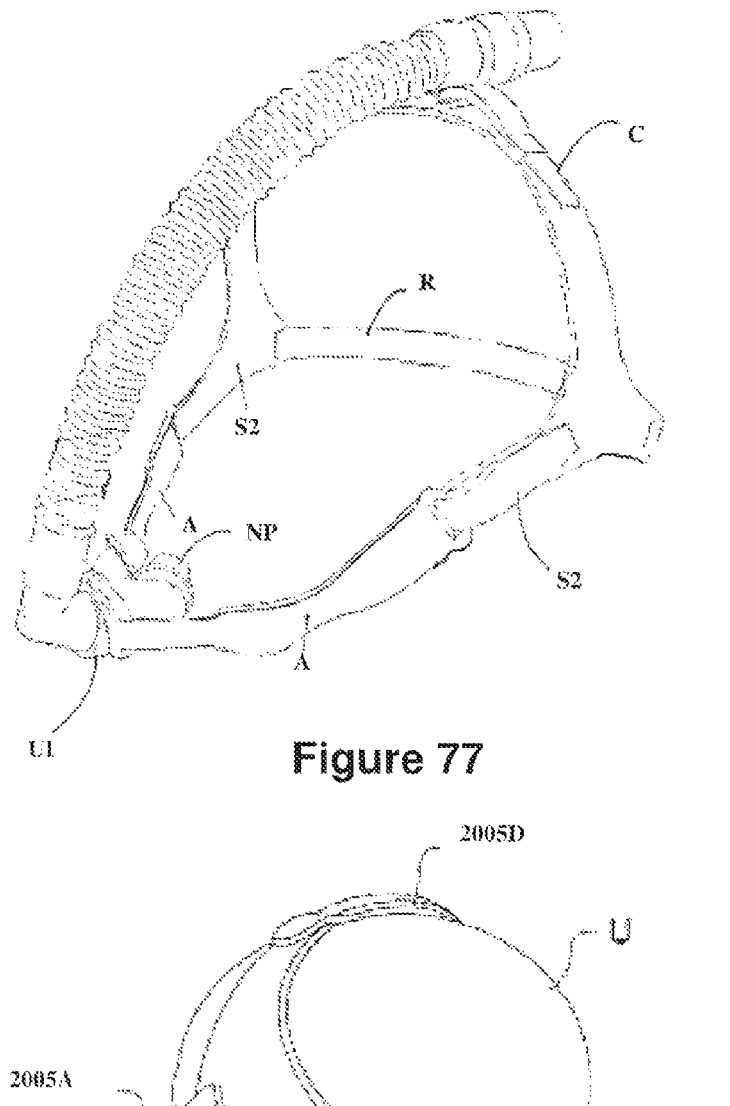
FIG. 77 is a perspective view of another prior art headgear and user interface with side straps.
FIG. 78 is a perspective view from the rear of a headgear in accordance with the present disclosure.

With reference to FIGS. 75 and 78, any of the above described headgear connectors and headgear strap adjusters can be used with any one or more straps of any type of headgear, and with any type of user interface. Such a user interface may comprise a nasal, oral or full face interface, and/or comprise nasal pillows or nasal cannula, and may comprise a cushion mounted on a more rigid body, and/or a frame or yoke removably or integrally provided with a cushion and/or body or shell. The body, and/or the frame or yoke if provided, may comprise lateral portions or arms provided with connectors configured to enable headgear to be connected to the user interface. The body, frame or yoke may comprise a forehead support member or forehead rest configured to be adjacent the user's forehead.

The headgear can comprise any configuration, number, and layout of a strap or straps arranged to connect to the user interface and to mount the user interface on the user's head.

Such headgear can comprise any combination of any one or more of side straps which extend along the sides of the user's face, one or more crown straps extending over the user's crown, and one or more rear straps extending around the rear of the user's head. Any of said straps may comprise elongate straps, or wider panels. A single pair of side straps may be provided, or multiple pairs of side straps may be provided, so as to comprise a pair of upper side straps extending above the user's ears, and a pair of lower side straps extending below the user's ears.

For exemplary reference only, FIG. 75 illustrates headgear comprising a pair of lower and upper side straps S1, S2, a crown strap C, and a rear strap R in the form of a rear panel. The side straps S1, S2, are connected to a body B of a user interface UI, and may comprise any of the connector and adjustment features as described in any of the embodiments above.

Figure 76:
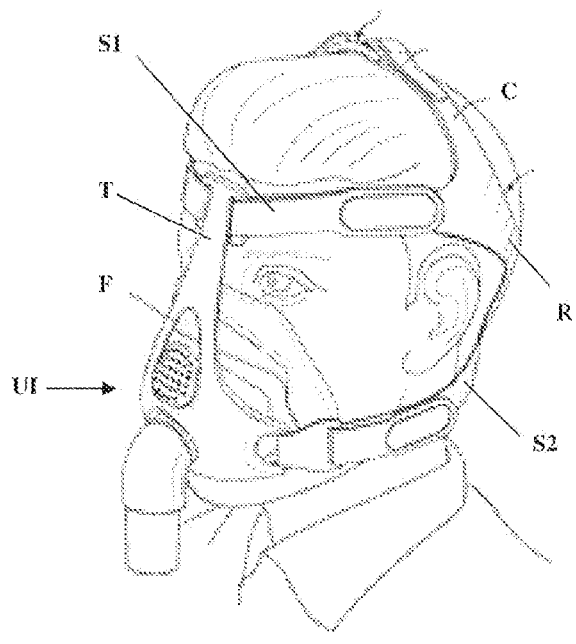
FIG. 76 is a perspective view of another prior art headgear and user interface with upper and lower side straps.

With reference to FIG. 76, a similar headgear arrangement is provided. In this example, the user interface UI comprises a frame F having a T-piece or forehead rest T. The lower side straps S1 are connected to lateral portions of the frame F adjacent the user's nose and mouth, whilst the upper side straps S2 are connected to the T-piece T, at the user's forehead.

For exemplary reference only, FIG. 77 illustrates headgear comprising a single pair of side straps S2, a crown strap C, and a rear strap R. The side straps S1, S2 are connected to a body B of a user interface UI via laterally extending arms A of the user interface UI. The user interface UI in this example comprises nasal pillows NP. In this example side straps S2 extend above the ears of the user. In other embodiments the single pair of side straps could comprise lower side straps S1 that extend below the ears of the user.

The examples of FIGS. 75 to 77 are not intended to limit the scope of this disclosure, but are provided as examples of possible uses of the headgear connectors, headgear length adjusters and headgear connector clips, described in this disclosure.

Figure 79:
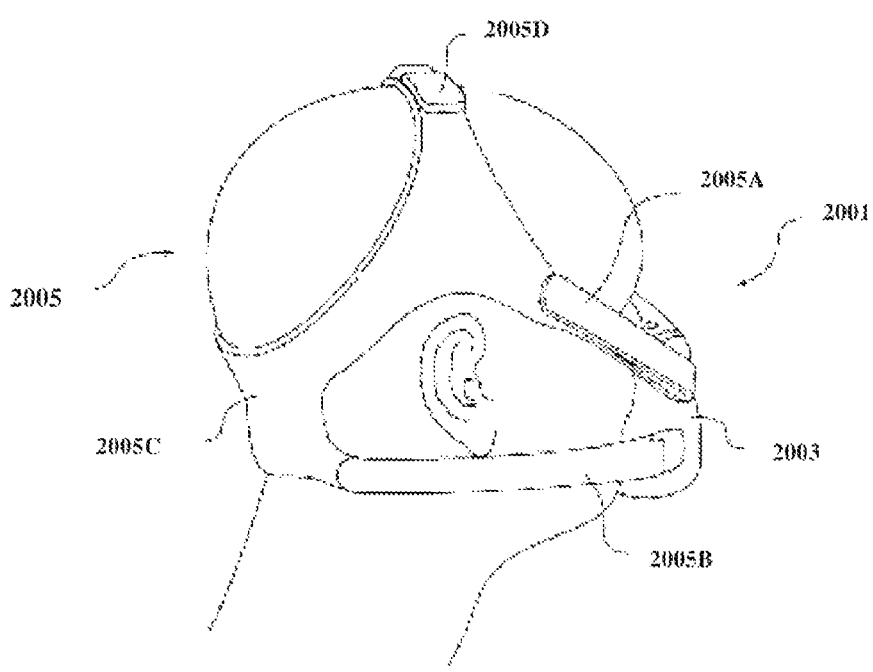
FIG. 79 is a perspective view from the rear and side of the headgear of FIG. 77.
Figure 80:
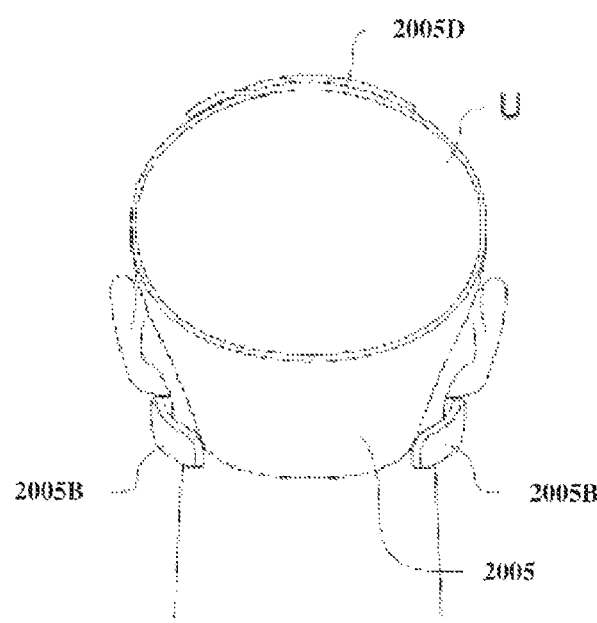
FIG. 80 is a rear view of the headgear of FIGS. 77 and 78.

With reference initially to FIGS. 78 to 80, an embodiment of a patient interface assembly 2001 comprising a user interface, sometimes known as a patient interface 2003 and headgear 2005 is illustrated on a user U, the patient interface in this example being a full face mask covering both the nose and mouth of the user U. The patient interface assembly 2001 can be used in the field of respiratory therapy and therefore in any respiratory treatment, respiratory assistance, resuscitation or ventilation system. In some embodiments, the interface assembly 2001 has particular utility with forms of positive pressure respiratory therapy. For example, the interface assembly 1 can be used for administering continuous positive airway pressure ("CPAP") treatments, variable positive airway pressure ("VPAP") treatments and/or bi-level positive airway pressure ("BiPAP") treatments. The interface assembly 2001 can be compatible with one or more different types of suitable CPAP or non-invasive ventilation (NIV) systems. The patient interface 2003 can comprise any of a plurality of different types of suitable mask configurations. For example, certain features, aspects and advantages of the present disclosure can be utilized with nasal masks, full face masks, oronasal masks, total face, or any other positive pressure mask. Although the illustrated mask is a full face mask, the scope of the present disclosure should not be limited by the particular embodiments described. In the illustrated configuration, the patient interface 2003 comprises a mask body, optionally a mask frame and a connection port assembly. The mask body is configured to cover the user's mouth and/or nose to deliver respiratory gases to the user. The mask body can be secured to the mask frame. The patient interface 2003 is held in place on the user U by the headgear 2005 that wraps around a part or parts of the user's head. The connection port assembly can be connected to the mask body and/or mask frame. In some configurations, the connection port assembly comprises an elbow connector configured to be connected between the mask body and/or mask frame and a gas delivery conduit (not shown). The mask frame can couple to the mask body and help stabilize the interface 2003 on the user's face. The mask frame can be any shape and size to functionally secure the interface 2003 to the user's face. The mask frame can be attached to the mask body with interlocking clips, tabs or other functional couplers or may be permanently attached during the assembly process. In this latter case the mask body and mask frame are integral and configured to form a single component. The mask frame can be rigid, substantially rigid or semi-rigid to provide support for the mask body. For example, the mask frame can be at least partially made of a metal or rigid plastic, such as acrylic, polycarbonate or high-density polyethylene.

The mask frame can extend to the user's forehead and may optionally include a forehead rest. The forehead rest, if provided, can help stabilize the interface 2001 to the user's face by providing a support point for the interface 1 and connection points for the headgear 2005.

If provided, the forehead rest can be a separate flexible piece that is attached or overmoulded onto the mask frame. For example, the forehead rest can be made of a flexible silicone that is overmoulded onto the frame bridge. The flexible material advantageously conforms to the user's forehead anatomy and helps improve comfort to the user with soft material contact. In some configurations, the forehead rest can be attached or integrally formed as part of the mask frame and can be made of the same material as the mask frame and frame bridge.

In this example headgear 2005 comprises a pair of upper side straps 2005A extending from laterally spaced upper connections on the mask body or mask frame, a pair of lower side straps 2005B extending from laterally spaced lower connections on the mask body or mask frame, a rear panel 2005C which joins the upper and lower side straps 2005A, 5B, at the rear of the head of the user U, and a crown strap 2005D which extends over the crown of the head of the user U, from each upper side strap 2005A. Suitable connectors 2009, such as incorporating hook and loop fasteners, may be provided to secure the headgear 5 to the mask body or mask frame. Such connectors 2009 typically comprise a slot through which the free end of headgear strap 2005A, 5B passes and is then looped back on itself, the looped strap portion being secured in place by a hook and loop fastener. The connector may be provided on the mask body or frame as an integral feature. Alternatively, the connector may be a separate connector configured to be releasably clipped or otherwise connected to the mask body or frame. Such a removable connector typically comprises a post or hook, configured to clip onto a hook or post provided on the mask body or frame.

In this example, both pairs of upper and lower straps 2005A, 5B comprise hook and loop fasteners 2006 at their respective strap ends, each strap being looped through the mask frame and/or forehead rest and/or headgear connector, and back on itself. The amount by which each strap 2005A, 5B is looped back on itself can provide some adjustment of the size and fit of the headgear 2005. Both pairs of upper and lower straps 2005A, 5B are further provided with gripping formations 2008 at their distal ends.

Any one or more of the straps 2005A. 5B, 5C and/or rear panel 2005C may be elastic or inelastic or comprise portions that are elastic or inelastic. Any one or more of the straps 2005A. 5B, 5C or rear panel 2005C may comprise more rigid portions, for example, to help maintain a desired shape of the headgear 2005. The materials, construction, and elasticity may vary between straps 2005A. 5B, 5C and/or rear panel 2005C however, the headgear 2005 alternatively may be of uniform construction with the same material and elasticity used throughout the headgear. This may further reduce costs by enabling the entire assembly to be cut from sheets of the same material.

In this example crown strap 2005C comprises two crown strap portions 2005DA, 5DB that are releasably connected together via the end of one crown strap portion 2005DA being received in an aperture 2021 of the other crown strap portion 5DB. The end of first crown strap portion 2005DA is waisted such that there is a narrower width portion 2023 spaced from the end of the first crown strap portion 2005DA. The waisted portion 2023 is substantially the same width as the aperture 2021 and is located in the aperture 2021 when the two crown strap portions 2005DA, 2005DB are connected together, with the wider end 2024 of first crown strap portion 2005DA protruding through the aperture and resisting removal of the first crown strap portion 2005DA through the aperture 2021.

Figure 81:
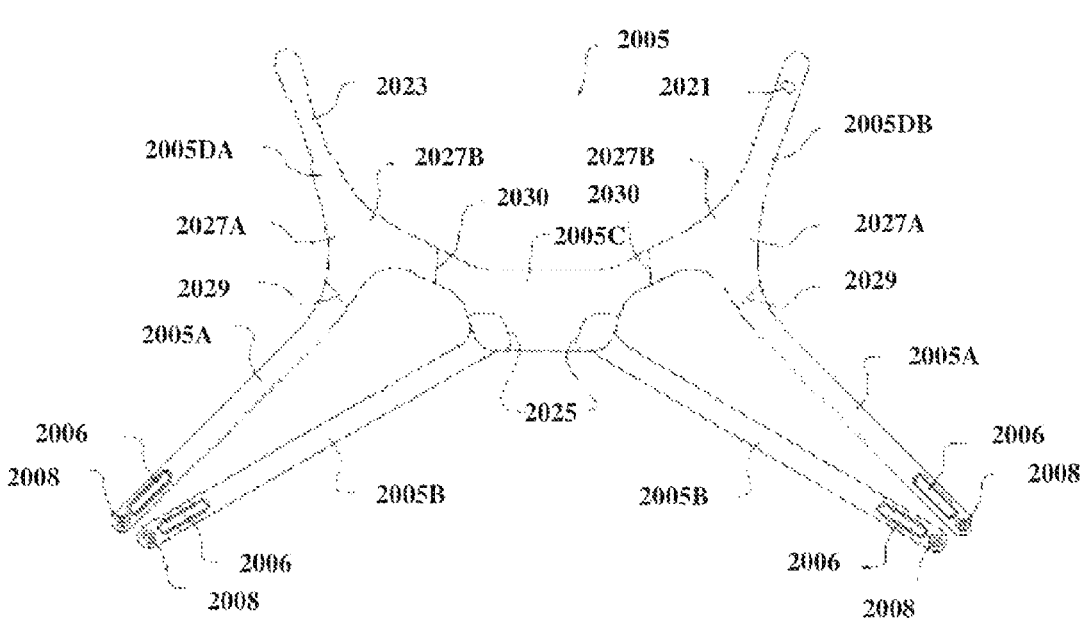
FIG. 81 is a plan view of the exterior of the headgear of FIGS. 77 to 79 when laid flat.
Figure 82:
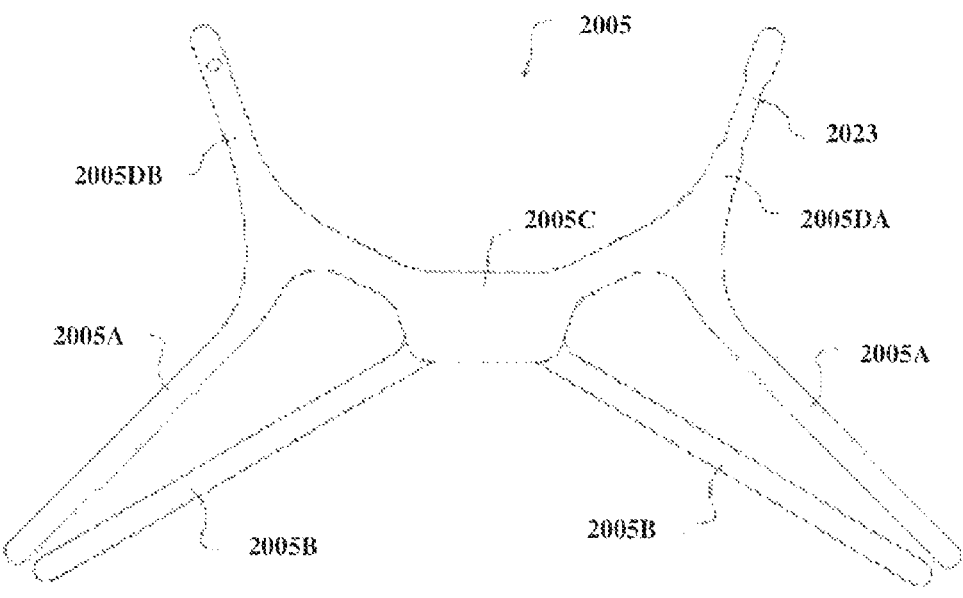
FIG. 82 is a plan view of the interior of the headgear of FIGS. 77 to 80 when laid flat.

With reference additionally to FIGS. 81 and 82, the margins of the rear panel 2005C are shown, with the lower side straps 2005B being joined to the rear panel 2005C at joins 2025. The inner end of each crown strap portion 2005DA, 2005DB comprises a bifurcated region 2027 forming two legs 2027A, 2027B. The upper side straps 2005A are joined to respective legs 2027A at joins 2029 whilst legs 2027B are joined 2030 to respective upper margins 2031 of the rear panel 2005C. The joins may use any suitable joining means which can include any one or more of stitching, gluing, ultra-sonic welding, RF welding or any other form of seam welding.

The upper and lower side straps 2005A, 5B are joined to the rear panel 2005C such that the upper straps 2005A are non-parallel with the lower side straps 2005B such that the distal ends of the upper and lower side straps 2005A, 2005B on each side of the rear panel 2005C are inclined toward one another. The angle between the upper and lower side straps 2005A, 2005B can be varied depending on the connection of the upper and lower side straps 2005A, 2005B to the patient interface.

The rear panel 2005C can be considered to comprise a main portion or body 2033 and two opposed lateral portions or arms 2035, with a notional transition line 2034 between the main and lateral portions 2033, 2035. In this example, the main portion 2033 can be considered to be rectangular. The two lateral portions 2035 each extend outwardly from the central plane or longitudinal axis XX and are inclined upwardly away from the main portion 2033 and away from the longitudinal axis to facilitate connection with the upper straps 2005A and locate those straps 2005A in the correct position on the back of the user's head.

Each upper strap 2005A is connected entirely to a respective one of the lateral portions 2035 of the rear panel 2005C in an upper corner region of the rear panel 2005C. Each lower strap 2005B is connected to a lower corner area of the rear panel 2005C, that includes at least a portion of the lateral portion 2035 and main portion 2033.

The boundaries of the main portion 2033 are defined by a centrally located rectangle with upper and lower limits formed by the substantially straight parallel regions of the upper and lower margins of the rear panel 2005C and lateral limits formed by notional vertical lines 2034 the ends of which are located at points where the upper margin transitions from substantially horizontal by a line of best fit, to a curved line into the lateral portions 2035. By 'substantially horizontal', we include that the upper margin is slightly curved.

Referring to FIG. 78 to 82, example relative dimensions (mm) of the rear panel 2005C are:

The main portion 2033 is defined by a rectangle with dimensions of less than 100 mm by 70 mm, and in one example 77.9 mm by 61.5 mm.

The lateral portions 2035 are constrained within a rectangle of less than 60 mm by 90 mm, and in one example 56.6 mm by 83.5 mm.

The entire rear panel 2005C is constrained within a rectangle R, shown in dashed line, of less than 200 mm by 100 mm, and in one example 191 mm by 83.5 mm.

The ratio of the area of each lateral portion 2035 to the area of the main portion 2033 is between 0.8 and 0.9 and preferably 0.886.

Figure 83A:
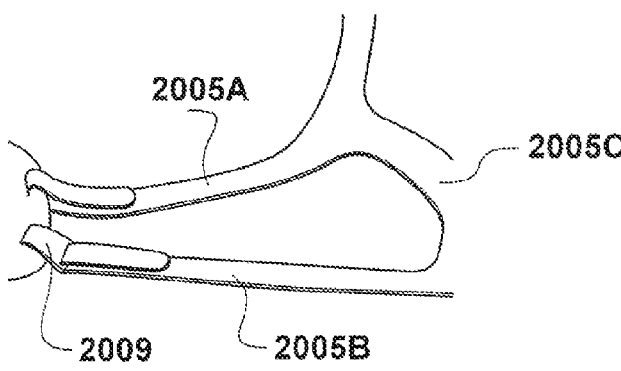
FIGS. 83*a* and 83*b* are perspective views of part of straps of prior art headgear respectively in an extended and a shortened or retracted condition.
Figure 83B:
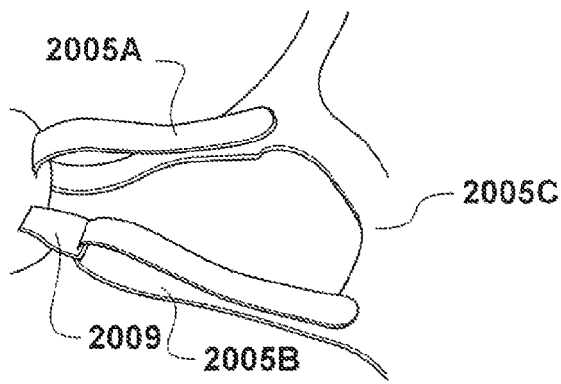
Figure 84:
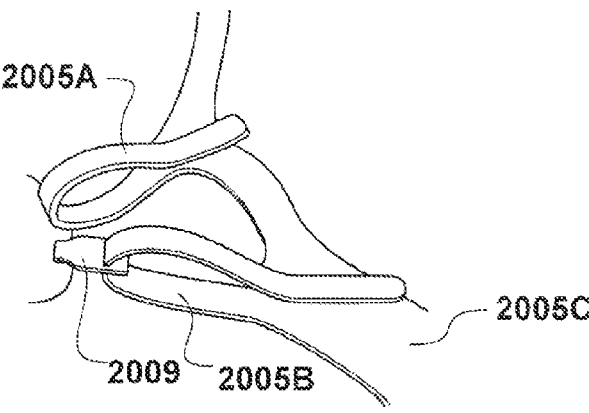
FIG. 84 is a perspective view of straps of the headgear of FIG. 83 in a further shortened or retracted condition.
Figure 85:
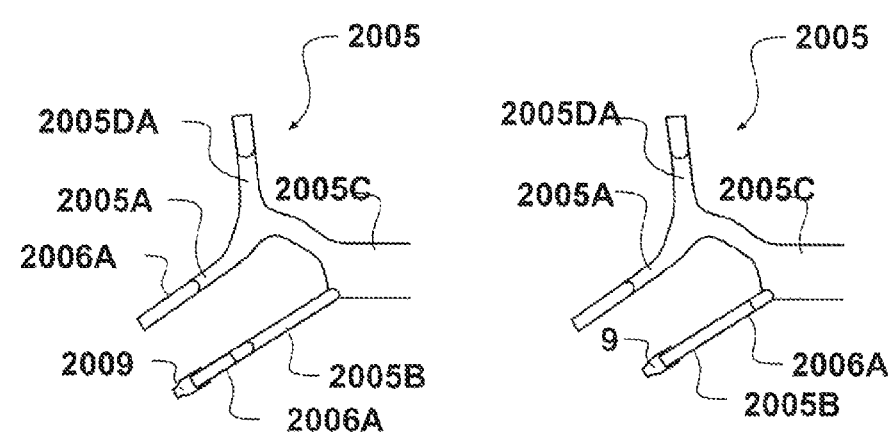
FIGS. 85 to 88 are plan views of a first embodiment of headgear in accordance with this disclosure, with the straps in different conditions of length adjustment.

Such a headgear 2005 is further shown in FIGS. 83 and 84, with the upper and lower headgear straps 2005A, 2005B in different conditions of length adjustment, using the hook and loop fastener 2006. Such different conditions of length adjustment are described above in the background section.

Referring to FIGS. 85 to 88, headgear 2005 in accordance with this disclosure is modified from the above such that any or all of the upper and lower headgear straps 2005A, 2005B are modified such that each strap 2005A, 2005B comprises a pair of hook and loop fasteners 2006A, 2006B, one on each side face of the straps 2005A, 2005B. In other words, each strap 2005A, 2005B comprises a length or strip of substantially planar material, with a first planar face being configured to contact the user's face, and an opposed, second planar face being configured to face outwardly from the user's face. A hook and loop fastener 2006 is provided on both planar faces. Hook and loop fastener 2006A is positioned on the user contacting face of straps 2005A, 2005B as per the prior art headgear described above, and enables length adjustment of each strap 2005A, 2005B as described above, and as also shown in FIG. 85. The length adjustment provided by the second hook and loop fastener 2006B is not used here.

Figure 86:
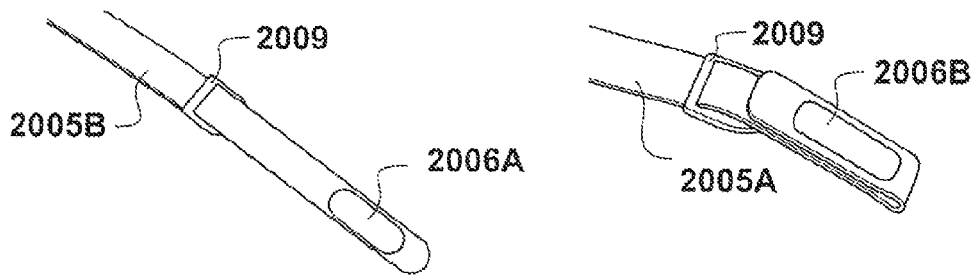
Figure 87:
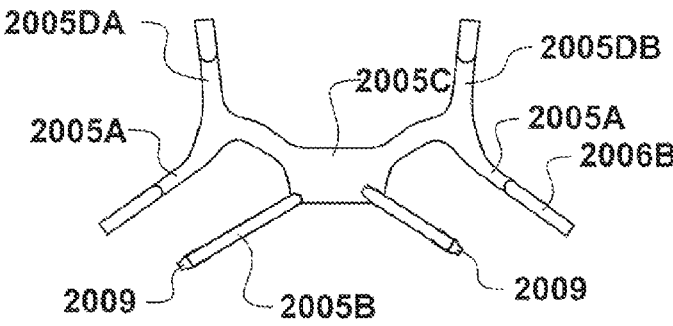

Hook and loop fastener 2006B is positioned on the non-user contacting opposed face of the straps 2005A, 2005B. The length of the shortened straps 2005A, 2005B can be adjusted using the first hook and loop fastener 2006A, as per the prior art arrangement, i.e. by pulling the shortened strap through the connector loop on the patient interface, and then securing the first hook and loop fastener 2006A to the strap 2005A, The second hook and loop fastener 2006B enables the straps 2005A, 2005B to be subject to an subsequent length adjustment step where the ends of straps 2005A, 2005B are looped back on each other such that the second hook and loop fastener 2006B engages the looped back end of the straps 2005A, 2005B so as to, for example further shorten the straps 2005A, 2005B. This shortening step is shown in FIG. 86. The prior art type length adjustment is shown on the left hand straps of the headgear 2005 of FIG. 87, whereas the improved length adjustment is shown on the right hand straps of the headgear 2005 of FIG. 87, noting that the right hand straps can therefore be adjusted so as to be shorter than the left hand straps, and that when so shortened, the straps 2005A, 2005B are nonetheless still contained within the margins of the headgear 5, without any part of straps 5A, 5B projecting beyond those margins.

Figure 88:
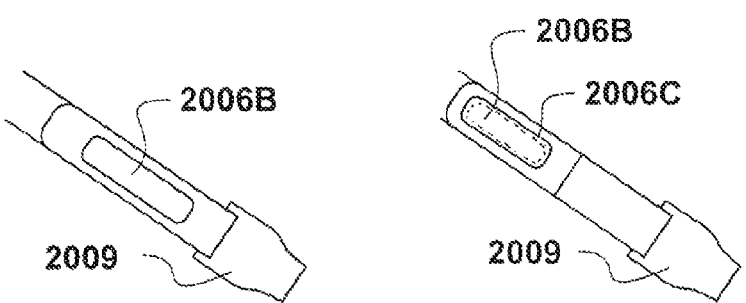

FIG. 88 shows the second hook and loop fastener 2006B being provided with a removable cover 2006C to conceal the second hook and loop fastener 2006B until it is required, to prevent the second hook and loop fastener 2006B inadvertently catching on other objects.

Figure 89A:
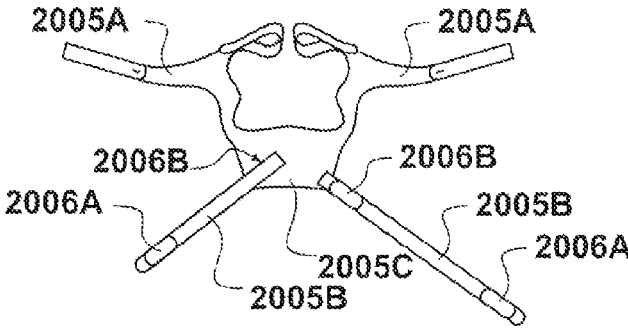
FIGS. 89 to 91 are plan views of a second embodiment of headgear in accordance with this disclosure, with the straps in different conditions of length adjustment.
Figure 89B:
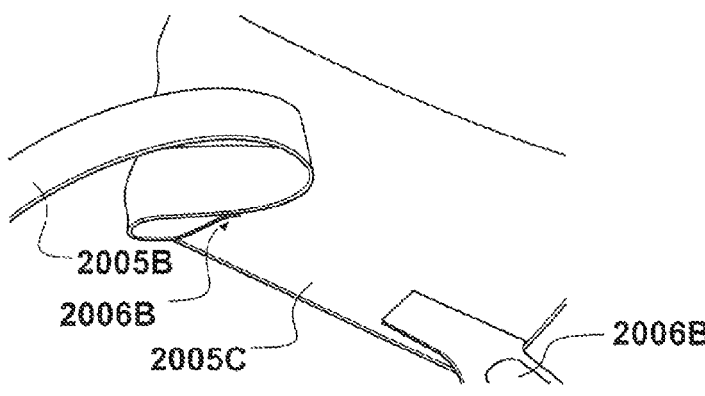
Figure 90A:
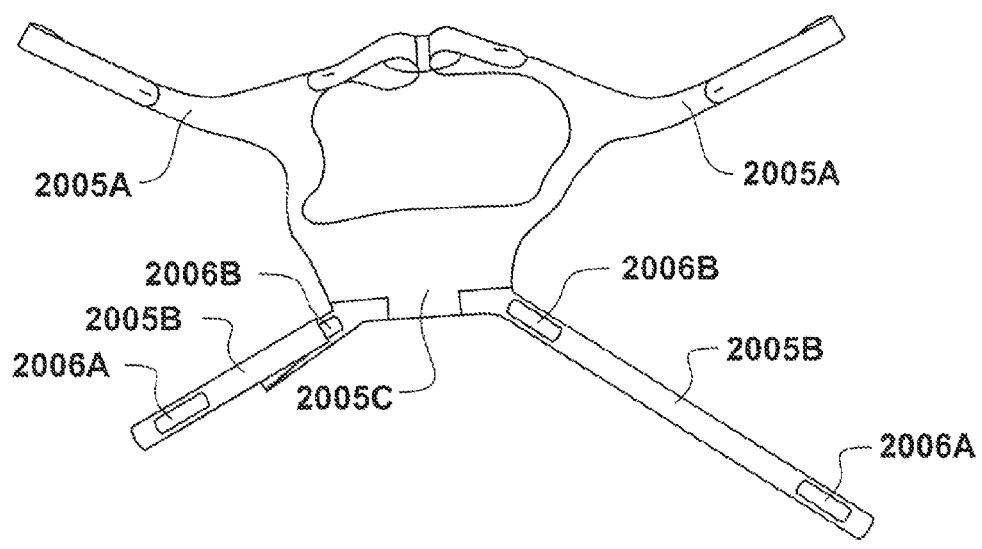
Figure 90B:
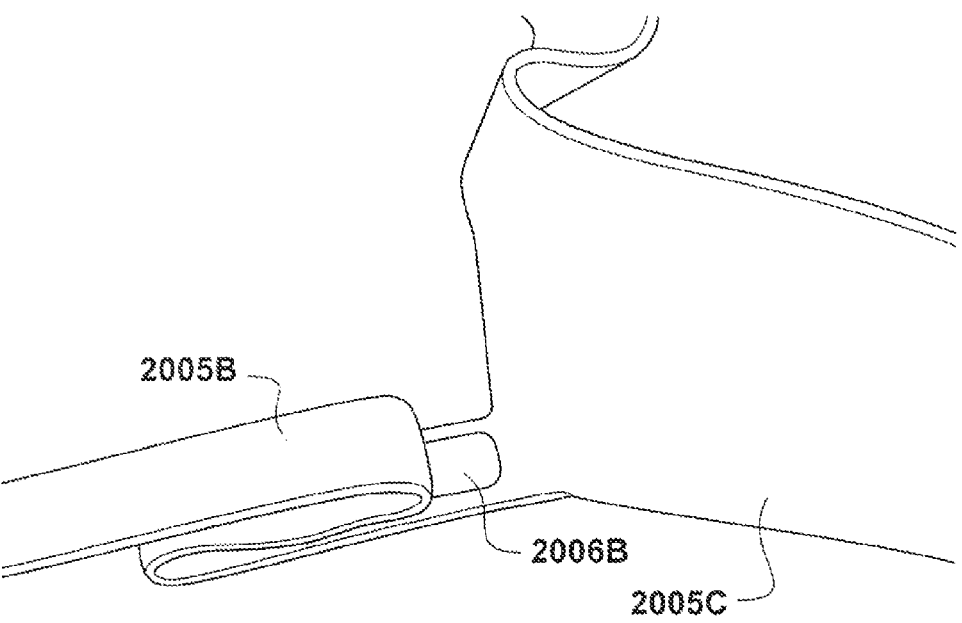

Referring now to FIGS. 89 to 91 a second embodiment of adjustable headgear 2005 is shown in which again two hook and loop fasteners 6A, 6B are provided, but in this embodiment the hook and loop fasteners 2006A, 2006B are spaced apart along the same face of the straps 2005A, 2005B, namely the user non-contacting face of each strap 2005A, 2005B. This enables two types of pre- or first strap adjustment. As can best be seen in FIG. 89, the part of strap 2005A nearest the headgear rear panel can be folded onto the rear panel such that the second hook and loop fastener 2006B engages the rear panel. This shortens the strap 2005A, with further length adjustment being provided via first hook and loop fastener 2006A, if necessary. Alternatively, as can best be seen in FIG. 90, the part of strap 2005A nearest the second hook and loop fastener 2006B can be folded onto itself such that the second hook and loop fastener 2006B engages the strap 2005A itself to provide a pre-shortening of strap 2005A, with further length adjustment being provided via first hook and loop fastener 2006A, if necessary.

Figures 91A, 91B:
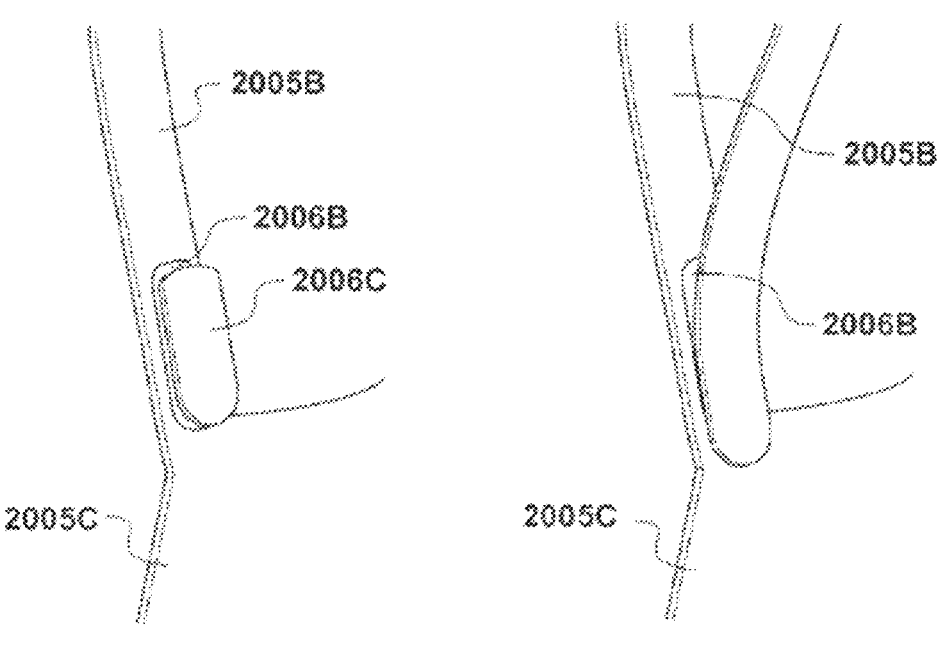
Figures 91C, 91D:
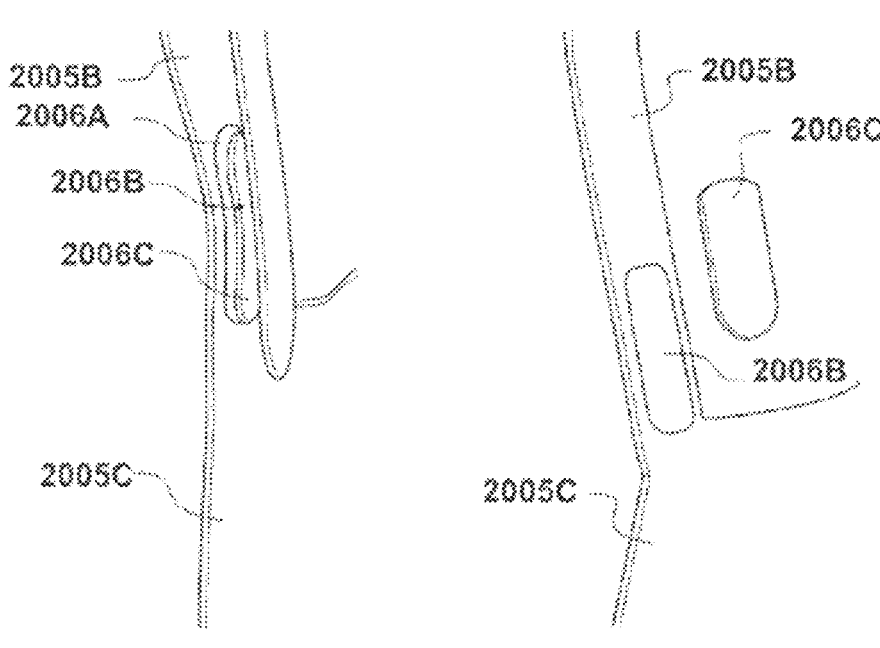

During normal use, straps 2005A, 2005B could be looped back on themselves such that the two hook and loop fasteners 2006A, 2006B were facing and aligned as can be seen in FIG. 91*a*. Whilst this might be convenient, the two fasteners 2006A, 2006B would not stick together. To enable the two fasteners to be conveniently secured together, a double sided tab of unbroken loop material 2006C could be provided for location intermediate the two fasteners 2006A, 2006B. Tab 2006C can be gripped by both fasteners 2006A, 2006B, enabling the fasteners 2006A, 2006B to be retained together to conveniently hold the looped strap 2005A, 2005B in place, as shown in FIG. 91*c*.

Figure 92A:
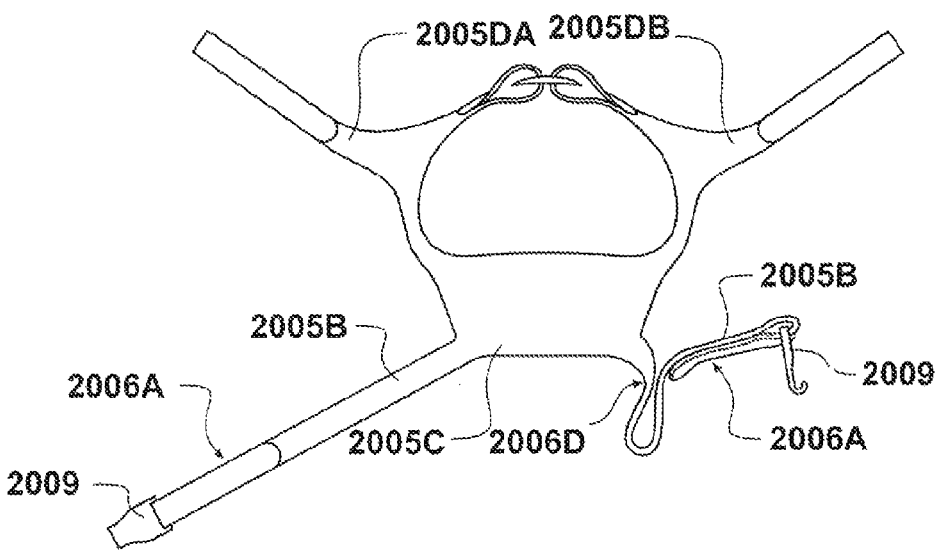
FIGS. 92*a* and 92*b* are plan views of a third embodiment of headgear in accordance with this disclosure, with the straps in different conditions of length adjustment.
Figure 92B:
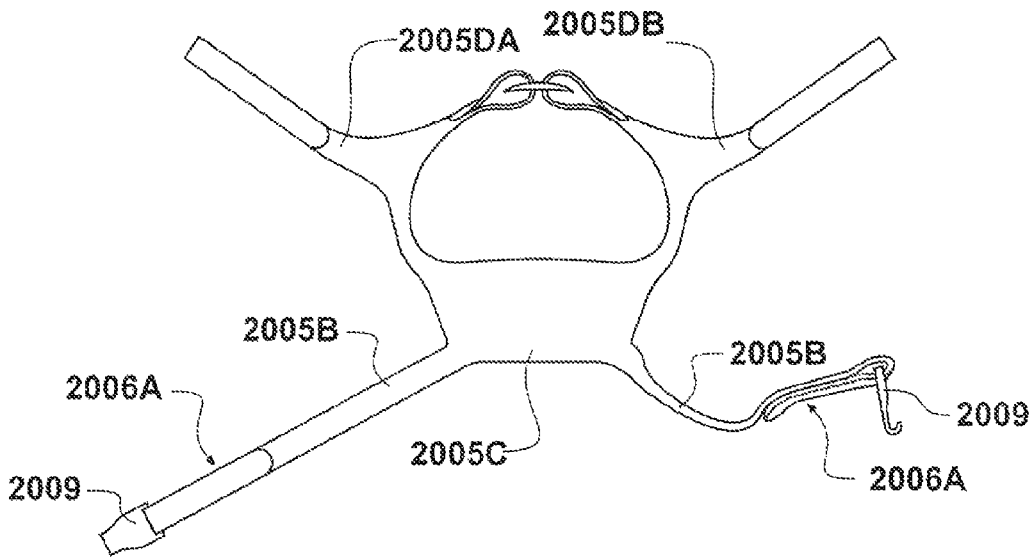

Referring now to FIG. 92, a third embodiment of adjustable headgear 2005 is shown in which a single hook and loop fastener 2006A is provided as per the prior art examples. However, in this example a secondary length adjustment mechanism is provided by way of a strap retention arrangement which in this example comprises stitching 2006D part way along the length of strap 2005A, 2005B, between the headgear rear panel and the hook and loop fastener 2006A. Such stitching can be seen in the bottom right hand lower strap 2005A of FIG. 92*a*, and stiches together a looped or overlapped portion OP of the strap 2005A, 2005B to reduce the effective length of the strap, that is the distance between the rear panel and the headgear connector. The stitching is arranged such that it can be cut or otherwise broken or removed, such that the overlapped strap portion OP is pulled apart so as to no longer be overlapped, for example as can be seen in the bottom right hand lower strap 2005A of FIG. 92*b*, which enables the overall length of the strap to be permanently increased should the additional adjustment be required. The stitching could be configured to be frangible so as to be able to be broken or removed by the user without cutting or requiring tools. A suitable thread material can be selected accordingly, or only such length of stitching provided to enable a user to pull the overlapped strap portion OP apart. The strap retention arrangement could alternatively comprise a retaining feature different to stitching, for example, a clip or the like configured to retain the overlapped strap portions together.

Figure 93A:
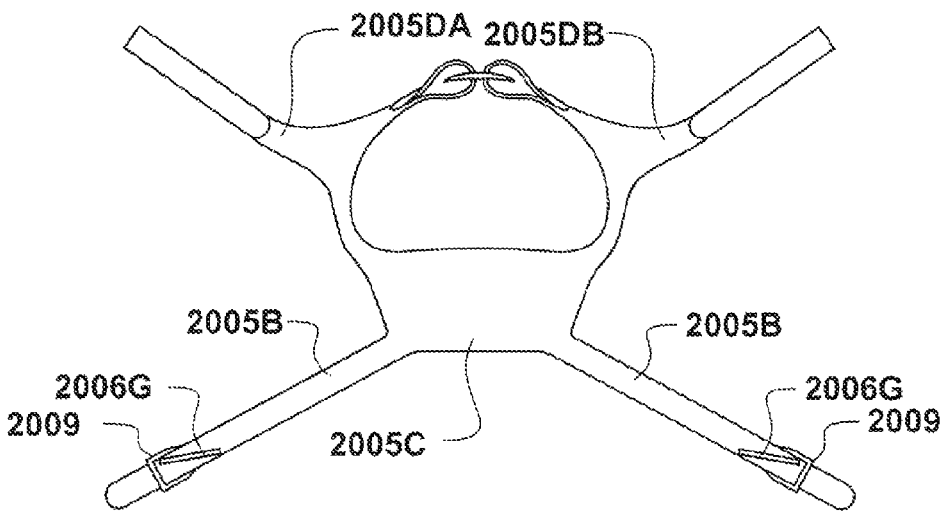
FIGS. 93 to 95 are plan views of a fourth embodiment of headgear in accordance with this disclosure, with the straps in different conditions of length adjustment.
Figure 93B:
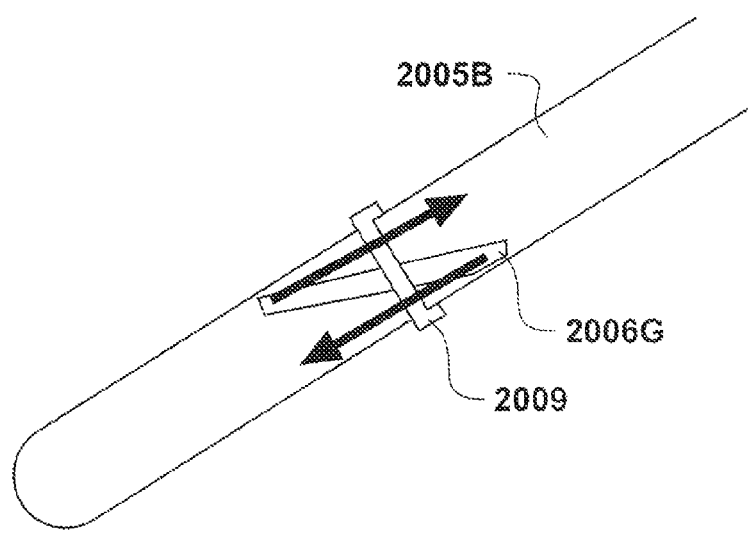
Figure 94A:
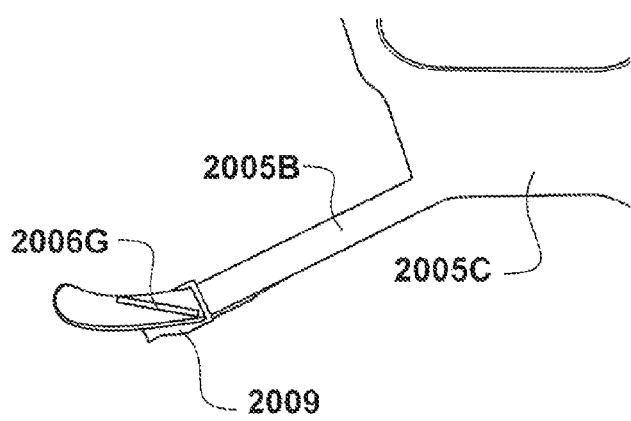
Figure 94B:
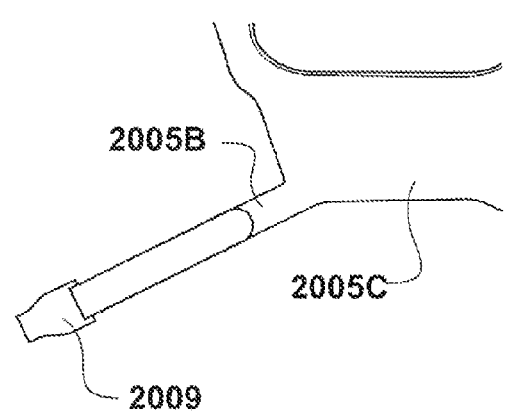
Figure 94C:
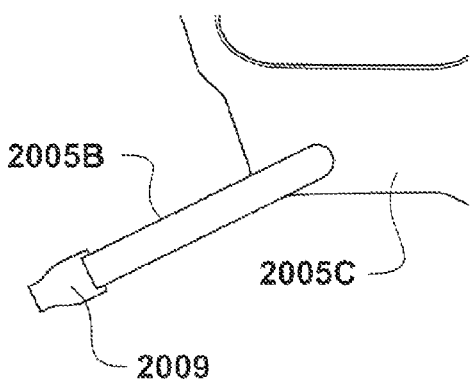
Figure 95A:
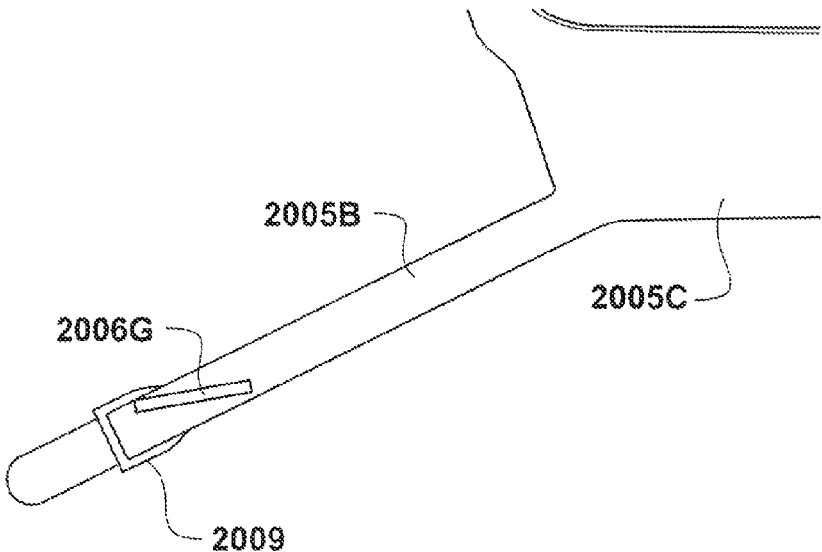
Figure 95B:
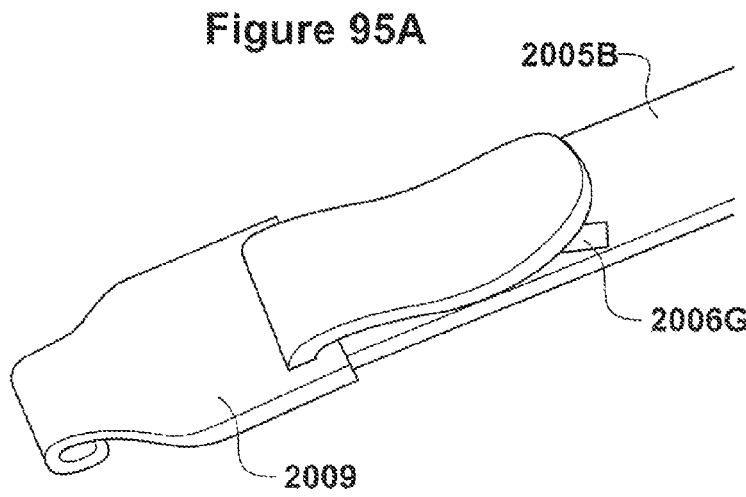

Referring now to FIGS. 93 to 95, a fourth embodiment of adjustable headgear 2005 is shown in which the first hook and loop fastener 2006A is replaced with secondary length adjustment mechanism comprising a flexible strip of hook and loop fastener 2006G. Strip 2006G is of narrower width than the width of strap 2005A, 2005B, and can therefore be positioned on strap 2005A, 2005B at an angle offset from the longitudinal axis of the strap 2005A, 2005B. In the example of FIG. 93, strip 2006G is approximately 20-505 of the width of strap 2005A, 2005B and is offset at an angle of between 1° and 45°. As indicated by the arrows in FIG. 93b, this configuration enables fastener 2006G to be folded around the headgear connector such that the strip of fastener 2006G still has strap 2005A, 2005B to grip with once folded. This enables a greater degree of length adjustment than the prior art arrangements because the fastener 2006G can be folded onto itself and still grip. FIG. 94 shows the length adjustment possible when the strap 2005A is folded with the fastener 2006G projecting initially beyond the headgear connector. FIG. 95 shows the length adjustment possible when the strap 2005A is folded with the fastener 2006G initially no projecting beyond the headgear connector. Fastener 2006G allows any amount of length adjustment between these two extremes.

Referring now to FIG. 96, a fifth embodiment of adjustable headgear 2005 is shown in which the first hook and loop fastener 2006A is replaced with secondary length adjustment mechanism comprising a plurality of hook and loop fasteners 2006H spaced along the longitudinal axis of the strap 2005A, 2005B, such that there is a gap 20061 between each hook and loop fastener 2006H. This provides a significant range of length adjustment of each strap 2005A, 5B. The spacing of the hook and loop fasteners 2006H may be varied along the length of the straps 2005A, 2005B such that the length of gap varies. This provides an increased likelihood of at least one hook and loop fastener 2006H being able to grip strap 2005A, 2005B, regardless of the amount of length adjustment. In other words, even if some of the hook and loop fasteners 2006H are aligned (and therefore do not grip each other), there should be other of the hook and loop fasteners 2006H which are aligned with the straps 2005A, 2005B themselves (and which therefore do grip).

Referring now to FIG. 97, a modification of the fifth embodiment is provided in which the plurality of hook and loop fasteners 2006H are provided in a single strip of hook and loop fastener material in which gaps have been cut so as to define discrete transversely extending strips or tabs of hook and loop fastener material. the headgear connector clip can be slid along the strap 2005A, 2005B and the strap 2005A, 2005B looped back on itself, with the tabs and gaps being such that whatever length is selected, at least one hook and loop fastener tab 2006H grips strap 2005A, 2005B.

With reference to FIGS. 98 to 101 a headgear connector 2009 is provided with a headgear strap length adjustment mechanism comprising a strap retention arrangement. The headgear connector 2009 comprises a hook 2009A for clipping onto a corresponding post on the mask or mask frame, and a slot 2009B for the free end of the headgear strap 2005A, 2005B to pass through.

The strap retention arrangement comprises a strap retention clip 2009C. The clip 2009C is resiliently movably towards and away from the body 2009E of the connector 2009 by way of comprising a cantilevered arm 2009D mounted on the connector body by a short wall portion 2009G. A recess or slot 2009H is defined between the underside of the arm 2009D and the connector body 2009E and is configured to receive and engage the portion of the strap 2005A, 2005B that has passed through slot 2009B and is looped back. The underside of arm 2009D is profiled such that its outer margin is chamfered or rounded, to enable the strap 2005A, 2005B to be more easily inserted into the recess 2009H. The underside of arm 2009D comprises a strap contacting face or surface which is arcuate so as to protrude a portion which protrudes further from the arm 2009D than the remainder of the strap contacting surface.

When the strap 2005A, 2005B is inserted in the slot 2009B, the dimensions of the recess 2009H, and the resiliently movable mounting of the arm 2009D on the connector body, is such that the arm 2009D engages the strap 2005A, 2005B sufficiently to retain the strap 2005A, 2005B in the recess 2009H and to prevent the strap 2005A, 2005B from being further pulled through the slot 2009B. Thus, when the strap 2005A, 2005B is received in the recess 2009H, the length of the strap 2005A, 2005B is fixed by the frictional engagement between the arm 2009D and the strap 2005A, 2005B.

To adjust the effective length of the strap 2005A, 2005B, that is, the distance between the connector 2009 and the headgear rear panel 2005C, the strap 2005A, 2005C is pulled laterally out of the recess 2009H so as to be freely movable through slot 2009B to achieve the desired effective strap length. Once achieved, the strap 2005A, 2005B may be reinserted into recess 2009H to prevent or at least resist any further strap length adjustment. Releasing the strap 2005A, 2005B may be facilitated by the user moving the arm 2009D away from the connector body by applying a force to the free end of the arm 2009D, against the biasing force generated by the resiliently movable nature of the arm 2009D. A gripping feature such as a tab or lip or indent may be provided to assist the user in moving the arm 2009D.

Connector 2009 thus provides strap length adjustment mode in which the arm 2009D does not engage the strap 2005A, 2005B, and a strap retention mode in which the arm 2009D does engage the strap 2005A, 2005B, at least sufficiently to resist any further adjustment of the effective strap length.

This mechanism can also be used to prevent excessive force being applied to the mask, as long as the maximum friction required to hold the strap 2005A, 2005B corresponds to the maximum force a strap 2005A, 2005B is allowed to experience in normal use. This can be tuned by adjusting the headgear strap material (thickness/material properties) and dimensions of the cantilevered arm 2009D and wall 2009G, and/or the material of those components such that the force required to overcome the frictional engagement between the cantilevered arm and the connector body is less than the determined allowable force a strap can exert on a patient.

The arm 2009D of connector 2009 could comprise a region of hook and loop fastener, for example, in recess 2009H, to engage strap 2005B, 2005D when in the strap engaging condition.

It will be appreciated that the above examples describe the straps as being side straps, in an example where there are two pairs of side straps, one upper pair and one lower pair. However, it is envisaged that the strap could comprise any strap of a headgear, including, for example, a top strap, crown strap or rear strap.

Further it is envisaged that the different strap length adjustment arrangements described above could be combined together in any combination required. In one such combination any of the strap length adjustment arrangements of any of FIGS. 85 to 97 could be combined with the connector of FIGS. 98 to 101.

It will be appreciated that any of the headgear described above with reference to FIGS. 78 to 101 is intended to be used with any of the headgear connectors and/or user interfaces and/or headgear strap adjusters of FIGS. 1 to 77. Such a combination could comprise a useful kit of any one or more of user interface, headgear and headgear connectors and/or strap adjusters.

Unless the context clearly requires otherwise, throughout the description, the words "comprise", "comprising", and the like, are to be construed in an inclusive sense as opposed to an exclusive or exhaustive sense, that is to say, in the sense of "including, but not limited to".

Although this disclosure has been described by way of example and with reference to possible embodiments thereof, it is to be understood that modifications or improvements may be made thereto without departing from the scope of the disclosure. The disclosure may also be said broadly to consist in the parts, elements and features referred to or indicated in the specification of the application, individually or collectively, in any or all combinations of two or more of said parts, elements or features. Furthermore, where reference has been made to specific components or integers of the disclosure having known equivalents, then such equivalents are herein incorporated as if individually set forth.

Any discussion of the prior art throughout the specification should in no way be considered as an admission that such prior art is widely known or forms part of common general knowledge in the field.

The invention claimed is:

1. A headgear configured to be secured to a patient interface of a respiratory therapy system and to mount the patient interface on a user's head, the headgear comprising:
   at least one strap having a first end and a second end opposed along a longitudinal axis of the at least one strap; wherein:
      the first end of the at least one strap being configured such that the first end of the at least one strap can be looped back to form an overlapped strap portion;
      the second end of the at least one strap opposed to the first end and extending from a strap connecting region of the headgear;
      the at least one strap having an effective strap length being the distance extending between an apex of the overlapped strap portion and the strap connecting region of the headgear;
      the at least one strap comprising a strap length adjustment mechanism comprising a hook and loop fastener configured to releasably engage a portion of the at least one strap to form the overlapped strap portion, wherein a size of the overlapped strap portion can be adjusted to adjust the effective strap length by engaging the hook and loop fastener with a different portion of the headgear;
   wherein the at least one strap has a width measured in a direction perpendicular to the longitudinal axis, the hook and loop fastener comprising a strip or tab having a longitudinal axis and a width measured in a direction perpendicular to the longitudinal axis of the strip or tab, wherein the hook and loop fastener is arranged on the at least one strap such that the longitudinal axis of the strip or tab of the hook and loop fastener is inclined so as not to be aligned with the longitudinal axis of the at least one strap.

2. The headgear of claim 1, wherein the width of the strip or tab is less than 50% of the width of the at least one strap.

3. The headgear of claim 1, wherein the width of the strip or tab is less than 30% of the width of the at least one strap.

4. The headgear of claim 1, wherein the strip or tab is inclined relative to the longitudinal axis of the at least one strap at an angle between 5° and 85°, between 20° and 70°, between 30° and 60°, or between 30° and 45°.

5. The headgear of claim 1, wherein the strip or tab of the hook and loop fastener is sufficiently flexible to fold along its length to form an overlapped portion of the hook and loop fastener.

6. A headgear configured to be secured to a patient interface of a respiratory therapy system, to mount the patient interface on a user's head, the headgear comprising:
   at least one strap having a first end and a second end opposed along a longitudinal axis of the at least one strap; wherein:
   the first end of the at least one strap being configured such that the first end of the at least one strap can be looped back to form an overlapped strap portion;
   the second end of the at least one strap, opposed to the first end, extending from a strap connecting region of the headgear;
   the at least one strap having an effective strap length being the distance extending between an apex of the overlapped strap portion and the strap connecting region of the headgear;
   the at least one strap comprising a strap length adjustment mechanism comprising a hook and loop fastener arrangement configured to releasably engage a portion of the at least one strap to form the overlapped strap portion, wherein a size of the overlapped strap portion can be adjusted to adjust the effective strap length by engaging the hook and loop fastener arrangement with a different portion of the headgear;
   the hook and loop fastener arrangement comprising a plurality of discrete hook and loop fastener regions, each of which has an engaging surface and is secured along its entire length to a strap surface of the at least one strap, wherein the plurality of hook and loop fastener regions are spaced apart along the longitudinal axis of the at least one strap such that there is an exposed strap surface in a gap between each pair of the hook and loop fastener regions, wherein the engaging surface and the exposed strap surface face in a same direction, wherein the engaging surface of each of the plurality of hook and loop fastener regions comprises a first portion of the hook and loop fastener arrangement and the exposed strap surface between each pair of the hook and loop fastener regions comprises a second portion of the hook and loop fastener arrangement, the first portion configured to be releasably connectable with the second portion.

7. The headgear of claim 6, wherein the plurality of discrete hook and loop fastener regions are equispaced along the longitudinal axis of the strap.

8. The headgear of claim 6, wherein at least one of the discrete hook and loop fastener regions is a different size from another discrete hook and loop fastener region.

9. The headgear of claim 8, wherein at least one gap between a first pair of the plurality of hook and loop fastener regions is a different size from at least one other gap between a second pair of the plurality of hook and loop fastener regions that is different from the first pair.

10. The headgear of claim 6, wherein the plurality of discrete hook and loop fastener regions extend along at least 30% of the length of the strap.

11. The headgear of claim 6, wherein the plurality of discrete hook and loop fastener regions extend along at least 50% of the length of the strap.

12. The headgear of claim 6, wherein the plurality of discrete hook and loop fastener regions extend along at least 75% of the length of the strap.

\* \* \* \* \*